US010676669B2

(12) United States Patent
Goto et al.

(10) Patent No.: US 10,676,669 B2
(45) Date of Patent: Jun. 9, 2020

(54) COMPOUND HAVING NAPHTHALENE RING, LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Mayumi Goto, Chiba (JP); Sayaka Fujimori, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 22 days.

(21) Appl. No.: 16/097,269

(22) PCT Filed: Mar. 24, 2017

(86) PCT No.: PCT/JP2017/012093

§ 371 (c)(1),
(2) Date: Oct. 28, 2018

(87) PCT Pub. No.: WO2017/187859

PCT Pub. Date: Nov. 2, 2017

(65) Prior Publication Data

US 2019/0078019 A1 Mar. 14, 2019

(30) Foreign Application Priority Data

Apr. 28, 2016 (JP) ................................ 2016-090799

(51) Int. Cl.
*G02F 1/1333* (2006.01)
*C09K 19/12* (2006.01)
(Continued)

(52) U.S. Cl.
CPC .............. *C09K 19/12* (2013.01); *C07C 21/22* (2013.01); *C07C 25/24* (2013.01); *C07C 43/225* (2013.01); *C07C 69/75* (2013.01); *C07C 69/76* (2013.01); *C07C 323/09* (2013.01); *C07C 323/19* (2013.01); *C07C 323/21* (2013.01); *C07D 213/26* (2013.01); *C07D 213/30* (2013.01); *C07D 213/61* (2013.01); *C07D 239/26* (2013.01); *C07D 239/34* (2013.01); *C07D 309/04* (2013.01); *C07D 319/06* (2013.01); *C07D 401/04* (2013.01); *C07D 405/04* (2013.01); *C07D 405/06* (2013.01); *C07D 493/08* (2013.01); *C09K 19/18* (2013.01); *C09K 19/20* (2013.01); *C09K 19/30* (2013.01); *C09K 19/3003* (2013.01); *C09K 19/32* (2013.01); *C09K 19/322* (2013.01); *C09K 19/34* (2013.01); *C09K 19/3444* (2013.01);
(Continued)

(58) Field of Classification Search
CPC ........ C09K 19/12; C09K 19/18; C09K 19/20; C09K 19/30; C09K 19/3003; C09K 19/32; C09K 19/322; C09K 19/34; C09K 19/3444; C09K 19/3458; C09K 19/544; C09K 2019/3016; G02F 1/13; G02F 1/1333; C07C 21/22; C07C 25/24; C07C 43/225; C07C 69/75; C07C 69/76; C07C 323/09; C07C 323/19; C07C 323/21; C07D 213/26; C07D 213/30; C07D 213/61; C07D 239/26; C07D 239/34; C07D 309/04; C07D 319/06; C07D 401/04; C07D 405/04; C07D 405/06; C07D 493/08
USPC ..................................................... 252/299.61
See application file for complete search history.

(56) References Cited

U.S. PATENT DOCUMENTS

| | | | |
|---|---|---|---|
| 5,626,792 | A | 5/1997 | Wand et al. |
| 2010/0073621 | A1 | 3/2010 | Shimada |

(Continued)

FOREIGN PATENT DOCUMENTS

| | | |
|---|---|---|
| JP | H10291945 | 11/1998 |
| JP | H11349548 | 12/1999 |

(Continued)

OTHER PUBLICATIONS

"International Search Report (Form PCT/ISA/210) of PCT/JP2017/012093," dated May 23, 2017, with English translation thereof, pp. 1-6.

(Continued)

*Primary Examiner* — Geraldina Visconti
(74) *Attorney, Agent, or Firm* — JCIPRNET

(57) ABSTRACT

A compound represented by formula (1), a liquid crystal composition containing the compound, and a liquid crystal display device including the composition.

(1)

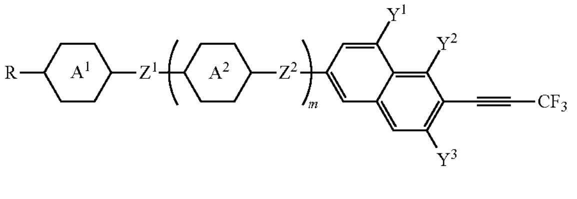

R is alkyl having 1 to 15 carbons or the like; ring $A^1$ and ring $A^2$ are independently 1,4-cyclohexylene, 1,4-phenylene or the like; $Z^1$ and $Z^2$ are independently a single bond, —COO— or the like; $Y^1$, $Y^2$ and $Y^3$ are independently hydrogen, fluorine or chlorine; and m is 0, 1 or 2.

20 Claims, No Drawings

(51) Int. Cl.

| | |
|---|---|
| ***C09K 19/18*** | (2006.01) |
| ***C09K 19/20*** | (2006.01) |
| ***G02F 1/13*** | (2006.01) |
| ***C07D 239/26*** | (2006.01) |
| ***C09K 19/30*** | (2006.01) |
| ***C07D 405/04*** | (2006.01) |
| ***C07D 401/04*** | (2006.01) |
| ***C09K 19/34*** | (2006.01) |
| ***C07D 493/08*** | (2006.01) |
| ***C07C 69/76*** | (2006.01) |
| ***C07C 323/09*** | (2006.01) |
| ***C07D 213/61*** | (2006.01) |
| ***C07D 309/04*** | (2006.01) |
| ***C07D 319/06*** | (2006.01) |
| ***C07C 43/225*** | (2006.01) |
| ***C07D 239/34*** | (2006.01) |
| ***C07C 25/24*** | (2006.01) |
| ***C07D 213/30*** | (2006.01) |
| ***C07C 69/75*** | (2006.01) |
| ***C07D 213/26*** | (2006.01) |
| ***C07C 323/21*** | (2006.01) |
| ***C07D 405/06*** | (2006.01) |
| ***C07C 323/19*** | (2006.01) |
| ***C09K 19/32*** | (2006.01) |
| ***C07C 21/22*** | (2006.01) |
| ***C09K 19/54*** | (2006.01) |

(52) U.S. Cl.
CPC ........ *C09K 19/3458* (2013.01); *C09K 19/544* (2013.01); *G02F 1/13* (2013.01); *C09K 2019/3016* (2013.01)

(56) References Cited

U.S. PATENT DOCUMENTS

| | | | |
|---|---|---|---|
| 2011/0272630 A1 | 11/2011 | Shimada et al. | |
| 2017/0107427 A1 | 4/2017 | Takahashi et al. | |
| 2019/0078019 A1* | 3/2019 | Goto .................... | C09K 19/322 |

FOREIGN PATENT DOCUMENTS

| | | |
|---|---|---|
| JP | 2000256307 | 9/2000 |
| JP | 2005047812 | 2/2005 |
| WO | 2008090780 | 7/2008 |
| WO | 2010095493 | 8/2010 |
| WO | 2015036079 | 3/2015 |
| WO | 2015190399 | 12/2015 |

OTHER PUBLICATIONS

"Search Report of Europe Counterpart Application", dated Jan. 27, 2020, pp. 1-14.

* cited by examiner

COMPOUND HAVING NAPHTHALENE RING, LIQUID CRYSTAL COMPOSITION AND LIQUID CRYSTAL DISPLAY DEVICE

CROSS-REFERENCE TO RELATED APPLICATION

This application is a 371 application of the international PCT application serial no. PCT/JP2017/012093, filed on Mar. 24, 2017, which claims the priority benefit of Japan application no. 2016-090799, filed on Apr. 28, 2016. The entirety of each of the above-mentioned patent applications is hereby incorporated by reference herein and made a part of this specification.

TECHNICAL FIELD

The invention relates to a liquid crystal compound, a liquid crystal composition and a liquid crystal display device. More specifically, the invention relates to a liquid crystal compound having a naphthalene ring, a liquid crystal composition that contains the compound and has a nematic phase, and a liquid crystal device that includes the composition.

BACKGROUND ART

A liquid crystal display device has been widely utilized in a display such as a personal computer, a television or the like. The device utilizes physical properties such as optical anisotropy and dielectric anisotropy of a liquid crystal compound. As an operating mode of the liquid crystal display device, such a mode is known as a phase change (PC) mode, a twisted nematic (TN) mode, a super twisted nematic (STN) mode, a bistable twisted nematic (BTN) mode, an electrically controlled birefringence (ECB) mode, an optically compensated bend (OCB) mode, an in-plane switching (IPS) mode, a vertical alignment (VA) mode, a fringe field switching (FFS) mode and a polymer sustained alignment (PSA) mode. In the device having the PSA mode, a liquid crystal composition containing a polymer is used. In the composition, alignment of liquid crystal molecules can further be controlled by the polymer.

In such a liquid crystal display device, a liquid crystal composition having suitable physical properties is used. In order to further improve characteristics of the device, the liquid crystal compound contained in the composition preferably has physical properties described in (1) to (8) below: (1) high stability to heat and light, (2) a high clearing point, (3) low minimum temperature of a liquid crystal phase, (4) small viscosity (η), (5) suitable optical anisotropy (Δn), (6) large dielectric anisotropy (Δε), (7) a suitable elastic constant (K), and (8) good compatibility with other liquid crystal compounds.

An effect of the physical properties of the liquid crystal compound on the characteristics of the device is as described below. A compound having the high stability to heat, light and so forth as described in (1) increases a voltage holding ratio of the device. Therefore, a service life of the device becomes long. A compound having the high clearing point as described in (2) extends a temperature range in which the device can be used. A compound having the low minimum temperature of the liquid crystal phase such as the nematic phase and a smectic phase, as described in (3), in particular, a compound having the low minimum temperature of the nematic phase, also extends the temperature range in which the device can be used. A compound having the small viscosity as described in (4) shortens a response time of the device.

A compound having the suitable optical anisotropy as described in (5), namely the compound having large optical anisotropy or small optical anisotropy is required according to a design of the device. When the response time is shortened by decreasing a cell gap of the device, the compound having the large optical anisotropy is suitable. A compound having the large dielectric anisotropy as described in (6) decreases a threshold voltage of the device. Thus, an electric power consumption of the device is decreased. On the other hand, a compound having small dielectric anisotropy shortens the response time of the device by decreasing viscosity of the composition. The compound extends the temperature range in which the device can be used by increasing the maximum temperature of the nematic phase.

With regard to (7), a compound having a large elastic constant shortens the response time of the device. A compound having a small elastic constant decreases the threshold voltage of the device. Therefore, the suitable elastic constant is required according to the characteristics to be desirably improved. A compound having the excellent compatibility with other liquid crystal compounds as described in (8) is preferred. The reason is that the physical properties of the composition are adjusted by mixing liquid crystal compounds having different physical properties.

A variety of liquid crystal compounds each having the large dielectric anisotropy have so far been synthesized. A variety of liquid crystal compounds each having the large optical anisotropy have also so far been synthesized. The reason is that good physical properties that are not found in conventional compounds are expected from a new compound. The reason is that the new compound may be occasionally provided with a suitable balance regarding at least two physical properties in the composition. Under such circumstances, desire has been expressed a compound having excellent physical properties and the suitable balance regarding the physical properties (1) to (8) described above.

Patent literature No. 1 describes, in the paragraph [0300], the compound described below.

(5.145)

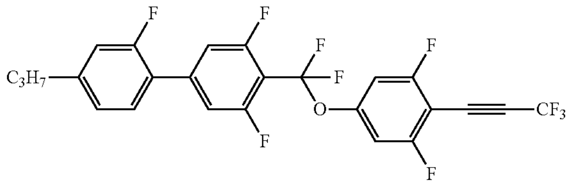

CITATION LIST

Patent Literature

Patent literature No. 1: WO 2008/090780 A.

SUMMARY OF INVENTION

Technical Problem

The invention provides a liquid crystal compound satisfying at least one of physical properties such as high stability to heat or light, a high clearing point (or high maximum temperature of a nematic phase), low minimum temperature of a liquid crystal phase, small viscosity, suitable optical anisotropy, large dielectric anisotropy, a suitable elastic constant and good compatibility with other liquid crystal compounds. The invention provides a compound having larger optical anisotropy and larger dielectric anisotropy in comparison with a similar compound. The invention further provides a liquid crystal composition that contains the compound and satisfies at least one of physical properties such as high stability to heat or light, high maximum temperature of a nematic phase, low minimum temperature of the nematic phase, small viscosity, suitable optical anisotropy, large dielectric anisotropy, large specific resistance and a suitable elastic constant. The invention further provides a liquid crystal composition having a suitable balance regarding at least two of the physical properties. The invention also provides a liquid crystal display device including the composition, and having a wide temperature range in which the device can be used, a short response time, a large voltage holding ratio, low threshold voltage, a large contrast ratio, a small flicker rate and a long service life.

Solution to Problem

The invention concerns a compound represented by formula (1), a liquid crystal composition containing the compound, and a liquid crystal display device including the composition:

(1)

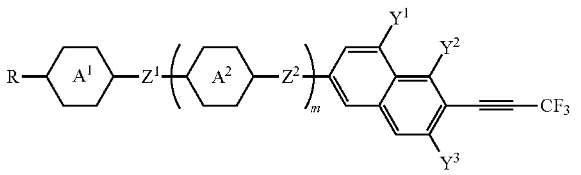

wherein, in formula (1),

R is alkyl having 1 to 15 carbons, and in the alkyl, at least one $-CH_2-$ may be replaced by $-O-$ or $-S-$, and at least one $-CH_2CH_2-$ may be replaced by $-CH=CH-$, and in the groups, at least one hydrogen may be replaced by fluorine or chlorine;

ring $A^1$ and ring $A^2$ are independently 1,4-cyclohexylene, 1,4-cyclohexenylene, 1,4-phenylene, decahydronaphthalene-2,6-diyl, 1,2,3,4-tetrahydronaphthalene-2,6-diyl, naphthalene-2,6-diyl, tetrahydropyran-2,5-diyl, 1,3-dioxane-2,5-diyl, 2,6,7-trioxabicyclo[2.2.2]octane-1,4-diyl, pyridine-2,5-diyl or pyrimidine-2,5-diyl, and in the rings, at least one hydrogen may be replaced by fluorine or chlorine;

$Z^1$ and $Z^2$ are independently a single bond, $-COO-$, $-OCO-$, $-CH_2O-$, $-OCH_2-$, $-CH_2S-$, $-SCH_2-$, $-CF_2O-$, $-OCF_2-$, $-CH_2CH_2-$, $-CH=CH-$, $-C\equiv C-$ or $-CF=CF-$;

$Y^1$, $Y^2$ and $Y^3$ are independently hydrogen, fluorine or chlorine; and m is 0, 1 or 2.

Advantageous Effects of Invention

A first advantage is to provide a liquid crystal compound satisfying at least one of physical properties such as high stability to heat or light, a high clearing point (or high maximum temperature of a nematic phase), low minimum temperature of a liquid crystal phase, small viscosity, suitable optical anisotropy, large dielectric anisotropy, a suitable elastic constant and good compatibility with other liquid crystal compounds. The invention provides a compound having larger optical anisotropy and larger dielectric anisotropy in comparison with a similar compound (see Comparative Example 1). A second advantage is to provide a liquid crystal composition that contains the compound and satisfies at least one of physical properties such as high stability to heat or light, high maximum temperature of a nematic phase, low minimum temperature of the nematic phase, small viscosity, suitable optical anisotropy, large dielectric anisotropy, large specific resistance and a suitable elastic constant. The advantage is to provide a liquid crystal composition having a suitable balance regarding at least two of the physical properties. A third advantage is to provide a liquid crystal display device including the composition, and having a wide temperature range in which the device can be used, a short response time, a large voltage holding ratio, low threshold voltage, a large contrast ratio, a small flicker rate and a long service life.

DESCRIPTION OF EMBODIMENTS

Usage of terms herein is as described below. Terms "liquid crystal compound," "liquid crystal composition" and "liquid crystal display device" may be occasionally abbreviated as "compound," "composition" and "device," respectively. "Liquid crystal compound" is a generic term for a compound having a liquid crystal phase such as a nematic phase and a smectic phase, and a compound having no liquid crystal phase but to be added for the purpose of adjusting physical properties of a composition such as maximum temperature, minimum temperature, viscosity and dielectric anisotropy. The compound has a six-membered ring such as 1,4-cyclohexylene and 1,4-phenylene, and has rod-like molecular structure. "Liquid crystal display device" is a generic term for a liquid crystal display panel and a liquid crystal display module. "Polymerizable compound" is a compound to be added for the purpose of forming a polymer in the composition.

The liquid crystal composition is prepared by mixing a plurality of liquid crystal compounds. An additive is added to the composition for the purpose of further adjusting the physical properties. The additive such as the polymerizable compound, a polymerization initiator, a polymerization inhibitor, an optically active compound, an antioxidant, an ultraviolet light absorber, a light stabilizer, a heat stabilizer, a dye and an antifoaming agent is added thereto when necessary. The liquid crystal compound and the additive are mixed in such a procedure. A proportion (content) of the liquid crystal compound is expressed in terms of weight percent (% by weight) based on the weight of the liquid crystal composition containing no additive, even after the additive is added. A proportion (amount of addition) of the additive is expressed in terms of weight percent (% by weight) based on the weight of the liquid crystal composition containing no additive. Weight parts per million (ppm) may be occasionally used. A proportion of the polymerization initiator and the polymerization inhibitor is exceptionally expressed based on the weight of the polymerizable compound.

"Clearing point" is a transition temperature between the liquid crystal phase and an isotropic phase in the liquid crystal compound. "Minimum temperature of the liquid crystal phase" is a transition temperature between a solid and the liquid crystal phase (the smectic phase, the nematic phase or the like) in the liquid crystal compound. "Maximum temperature of the nematic phase" is a transition temperature between the nematic phase and the isotropic phase in a mixture of the liquid crystal compound and a base liquid crystal or in the liquid crystal composition, and may be occasionally abbreviated as "maximum temperature." "Minimum temperature of the nematic phase" may be occasionally abbreviated as "minimum temperature." An expression "increase the dielectric anisotropy" means that a value of dielectric anisotropy positively increases in a composition having positive dielectric anisotropy, and the value of dielectric anisotropy negatively increases in a composition having negative dielectric anisotropy. An expression "having a large voltage holding ratio" means that the device has a large voltage holding ratio at room temperature and also at a temperature close to the maximum temperature in an initial stage, and the device has the large voltage holding ratio at room temperature and also at a temperature close to the maximum temperature even after the device has been used for a long period of time. In the composition or the device, the characteristics may be occasionally examined before and after an aging test (including an acceleration deterioration test).

A compound represented by formula (1) may be occasionally abbreviated as compound (1). At least one compound selected from the group of compounds represented by formula (1) may be occasionally abbreviated as compound (1). "Compound (1)" means one compound, a mixture of two compounds or a mixture of three or more compounds represented by formula (1). A same rule applies also to any other compound represented by any other formula. In formulas (1) to (15), a symbol of $A^1$, $B^1$, $C^1$ or the like surrounded by a hexagonal shape correspond to a ring such as ring $A^1$, ring $B^1$ and ring $C^1$, respectively. The hexagonal shape represents a six-membered ring such as cyclohexane or benzene. The hexagonal shape may occasionally represents a fused ring such as naphthalene or a bridged ring such as adamantane.

A symbol of terminal group $R^{11}$ is used in a plurality of compounds in chemical formulas of component compounds. In the compounds, two groups represented by two pieces of arbitrary $R^{11}$ may be identical or different. For example, in one case, $R^{11}$ of compound (2) is ethyl and $R^{11}$ of compound (3) is ethyl. In another case, $R^{11}$ of compound (2) is ethyl and $R^{11}$ of compound (3) is propyl. A same rule applies also to a symbol of $R^{12}$, $R^{13}$, $Z^{11}$ or the like. In compound (8), when i is 2, two pieces of ring $D^1$ exist. In the compound, two groups represented by two pieces of ring $D^1$ may be identical or different. When i is larger than 2, a same rule applies also to two pieces of arbitrary $D^1$. A same rule applies also to other symbols.

An expression "at least one 'A'" means that the number of 'A' is arbitrary. An expression "at least one 'A' may be replaced by 'B'" means that, when the number of 'A' is 1, a position of 'A' is arbitrary, and also when the number of 'A' is 2 or more, positions thereof can be selected without restriction. A same rule applies also to an expression "at least one 'A' is replaced by 'B'." An expression "at least one 'A' may be replaced by 'B', 'C' or 'D'" includes a case where arbitrary 'A' is replaced by 'B', a case where arbitrary 'A' is replaced by 'C', and a case where arbitrary 'A' is replaced by 'D', and also a case where a plurality of pieces of 'A' are replaced by at least two pieces of 'B', 'C' and/or 'D'. For example, "alkyl in which at least one $—CH_2—$ may be replaced by $—O—$ or $—CH{=}CH—$" includes alkyl, alkoxy, alkoxyalkyl, alkenyl, alkoxyalkenyl and alkenyloxyalkyl. In addition, a case where two pieces of consecutive $—CH_2—$ are replaced by $—O—$ to form $—O—O—$ is not preferred. In alkyl or the like, a case where $—CH_2—$ of a methyl part ($—CH_2—H$) is replaced by $—O—$ to form $—O—H$ is not preferred, either.

An expression "$R^{11}$ and $R^{12}$ are independently alkyl having 1 to 10 carbons or alkenyl having 2 to 10 carbons, and in the alkyl and the alkenyl, at least one $—CH_2—$ may be replaced by $—O—$, and in the groups, at least one hydrogen may be replaced by fluorine" may be occasionally used. In the expression, "in the groups" may be interpreted according to wording. In the expression, "the groups" means alkyl, alkenyl, alkoxy, alkenyloxy or the like. More specifically, "the groups" represents all of the groups described before the term "in the groups." The common interpretation is applied also to terms of "in the monovalent groups" or "in the divalent groups." For example, "the monovalent groups" represents all of the groups described before the term "in the monovalent groups."

Alkyl of the liquid crystal compound is straight-chain alkyl or branched-chain alkyl, but includes no cyclic alkyl. In general, straight-chain alkyl is preferred to branched-chain alkyl. A same rule applies also to a terminal group such as alkoxy and alkenyl. With regard to a configuration of 1,4-cyclohexylene, trans is preferred to cis for increasing the maximum temperature. Then, 2-fluoro-1,4-phenylene means two divalent groups described below. In a chemical formula, fluorine may be leftward (L) or rightward (R). A same rule applies also to an asymmetrical divalent group formed by removing two hydrogens from a ring, such as tetrahydropyran-2,5-diyl.

(L)

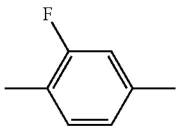

(R)

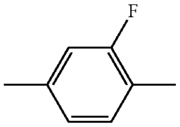

The invention includes items described below.

Item 1. A compound, represented by formula (1):

(1)

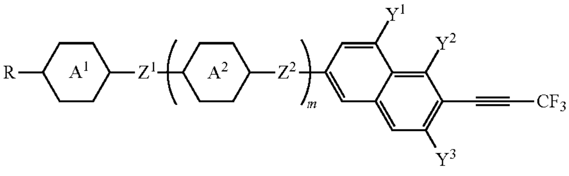

wherein, in formula (1),

R is alkyl having 1 to 15 carbons, and in the alkyl, at least one $—CH_2—$ may be replaced by $—O—$ or $—S—$, and at least one $—CH_2CH_2—$ may be replaced by $—CH{=}CH—$, and in the groups, at least one hydrogen may be replaced by fluorine or chlorine;

ring $A^1$ and ring $A^2$ are independently 1,4-cyclohexylene, 1,4-cyclohexenylene, 1,4-phenylene, tetrahydropyran-2,5- diyl, 1,3-dioxane-2,5-diyl, 2,6,7-trioxabicyclo[2.2.2]octane-1,4-diyl, naphthalene-2,6-diyl, decahydronaphthalene-2,6-diyl, 1,2,3,4-tetrahydronaphthalene-2,6-diyl, pyridine-2,5-diyl or pyrimidine-2,5-diyl, and in the rings, at least one hydrogen may be replaced by fluorine or chlorine;

$Z^1$ and $Z^2$ are independently a single bond, $—CH_2CH_2—$, —CH═CH—, —C≡C—, —COO—, —OCO—, $—CH_2O—$, $—OCH_2—$, $—CH_2S—$, $—SCH_2—$, $—CF_2O—$, $—OCF_2—$ or —CF═CF—;

$Y^1$, $Y^2$ and $Y^3$ are independently hydrogen, fluorine or chlorine; and m is 0, 1 or 2.

Item 2. The compound according to item 1, represents by formula (1A):

(1A)

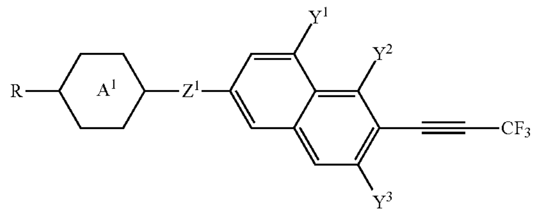

wherein, in formula (1A),

R is alkyl having 1 to 15 carbons, alkoxy having 1 to 14 carbons, alkenyl having 2 to 15 carbons, alkenyloxy having 2 to 14 carbons, alkylthio having 1 to 14 carbons or alkenylthio having 2 to 14 carbons;

$A^1$ is 1,4-cyclohexylene, 1,4-cyclohexenylene, 1,4-phenylene, 2-fluoro-1,4-phenylene, 2,6-difluoro-1,4-phenylene, tetrahydropyran-2,5-diyl, 1,3-dioxane-2,5-diyl, 2,6,7-trioxabicyclo[2.2.2]octane-1,4-diyl, pyridine-2,5-diyl, pyrimidine-2,5-diyl, naphthalene-2,6-diyl, 1-fluoronaphthalene-2,6-diyl, 1,3-difluoronaphthalene-2,6-diyl or 1,3,8-trifluoronaphthalene-2,6-diyl;

$Z^1$ is a single bond, $—CH_2CH_2—$, —CH═CH—, —C≡C—, —COO—, —OCO—, $—CH_2O—$, $—OCH_2—$, $—CH_2S—$, $—SCH_2—$, $—CF_2O—$ or $—OCF_2—$; and $Y^1$, $Y^2$ and $Y^3$ are independently hydrogen or fluorine.

Item 3. The compound according to item 1, represented by any one of formulas (1A-1) to (1A-3):

(1A-1)

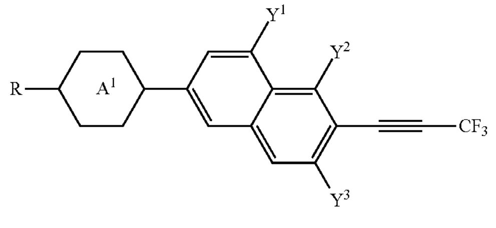

(1A-2)

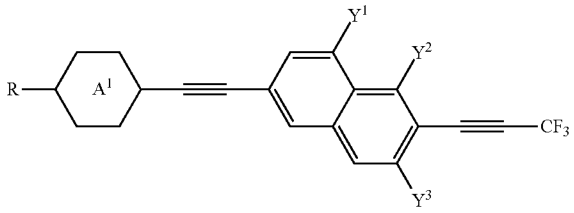

-continued (1A-3)

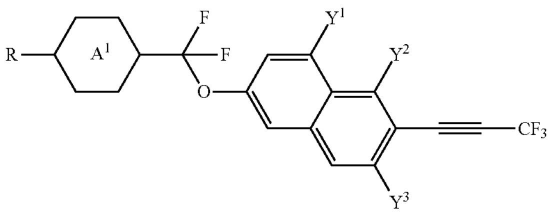

wherein, in formulas (1A-1) to (1A-3),

R is alkyl having 1 to 15 carbons, alkoxy having 1 to 14 carbons, alkenyl having 2 to 15 carbons or alkenyloxy having 2 to 14 carbons;

ring $A^1$ is 1,4-cyclohexylene, 1,4-phenylene, 2-fluoro-1,4-phenylene, 2,6-difluoro-1,4-phenylene, 1,3-dioxane-2,5-diyl, 2,6,7-trioxabicyclo[2.2.2]octane-1,4-diyl, pyridine-2,5-diyl, pyrimidine-2,5-diyl, naphthalene-2,6-diyl, 1-fluoronaphthalene-2,6-diyl, 1,3-difluoronaphthalene-2,6-diyl or 1,3,8-trifluoronaphthalene-2,6-diyl; and $Y^1$, $Y^2$ and $Y^3$ are independently hydrogen or fluorine.

Item 4. The compound according to item 1, represented by any one of formulas (1A-4) to (1A-15):

(1A-4)

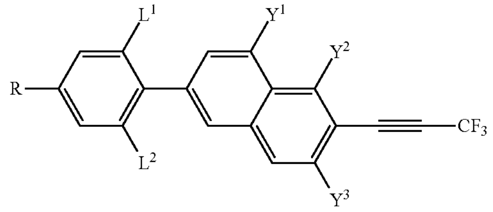

(1A-5)

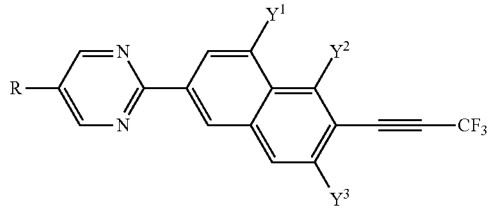

(1A-6)

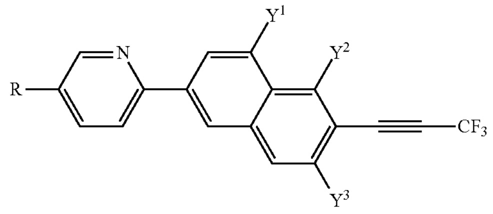

(1A-7)

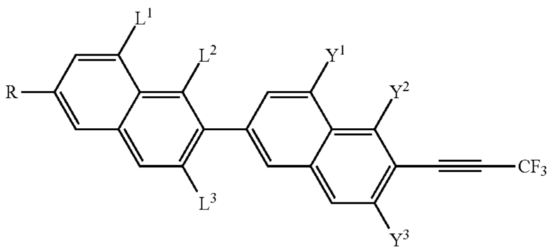

-continued (1A-8)

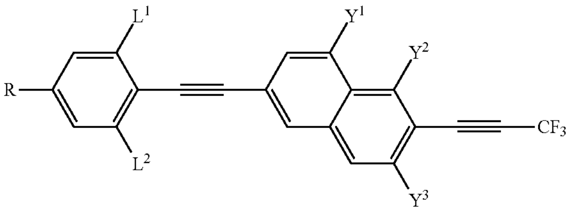

(1A-9)

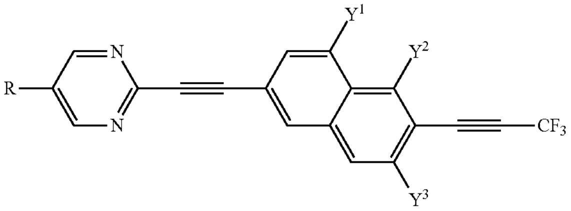

(1A-10)

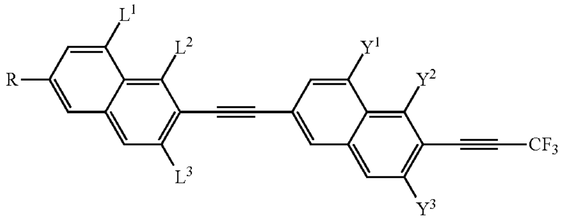

(1A-11)

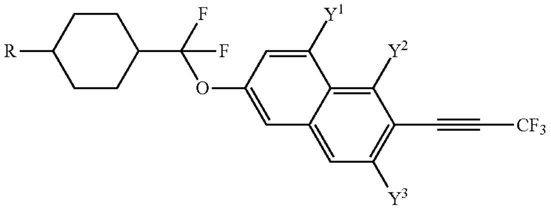

(1A-12)

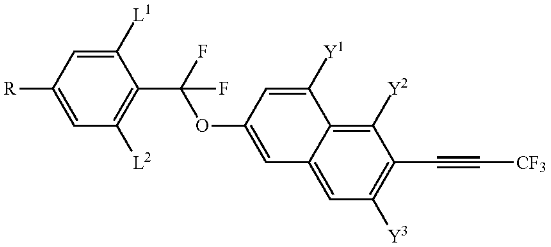

(1A-13)

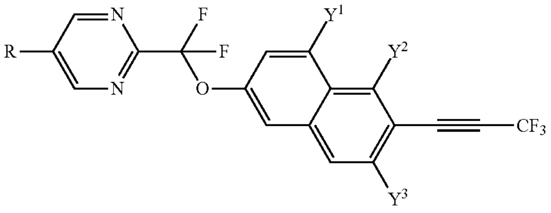

-continued (1A-14)

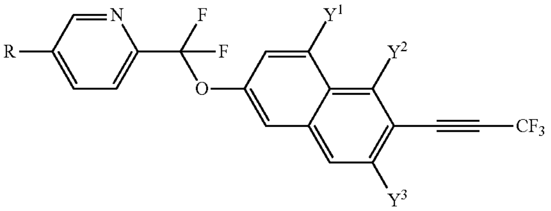

(1A-15)

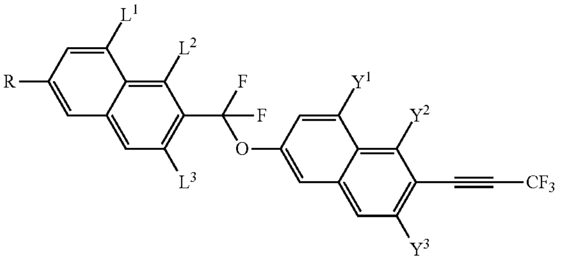

wherein, in formulas (1A-4) to (1A-15),

R is alkyl having 1 to 10 carbons, alkoxy having 1 to 9 carbons, alkenyl having 2 to 10 carbons or alkenyloxy having 2 to 9 carbons; and $Y^1$, $Y^2$, $Y^3$, $L^1$, $L^2$ and $L^3$ are independently hydrogen or fluorine.

Item 5. The compound according to item 1, represented by formula (1B):

(1B)

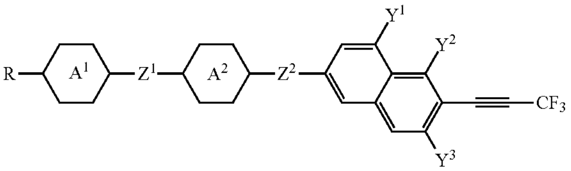

wherein, in formula (1B),

R is an alkyl having 1 to 15 carbons, alkoxy having 1 to 14 carbons, alkenyl having 2 to 15 carbons, alkenyloxy having 2 to 14 carbons, alkylthio having 1 to 14 carbons or alkenylthio having 2 to 14 carbons;

ring $A^1$ is 1,4-cyclohexylene, 1,4-cyclohexenylene, 1,4-phenylene, 2-fluoro-1,4-phenylene, 2,6-difluoro-1,4-phenylene, tetrahydropyran-2,5-diyl, 1,3-dioxane-2,5-diyl, 2,6,7-trioxabicyclo[2.2.2]octane-1,4-diyl, pyridine-2,5-diyl, pyrimidine-2,5-diyl, naphthalene-2,6-diyl, 1-fluoronaphthalene-2,6-diyl, 1,3-difluoronaphthalene-2,6-diyl or 1,3,8-trifluoronaphthalene-2,6-diyl; and ring $A^2$ is 1,4-phenylene, 2-fluoro-1,4-phenylene, 2,6-difluoro-1,4-phenylene, pyridine-2,5-diyl, pyrimidine-2,5-diyl, naphthalene-2,6-diyl, 1-fluoronaphthalene-2,6-diyl, 1,3-difluoronaphthalene-2,6-diyl or 1,3,8-trifluoronaphthalene-2,6-diyl;

$Z^1$ and $Z^2$ are independently a single bond, $-CH_2CH_2-$, $-CH{=}CH-$, $-C{\equiv}C-$, $-COO-$, $-OCO-$, $-CH_2O-$, $-OCH_2-$, $-CH_2S-$, $-SCH_2-$, $-CF_2O-$ or $-OCF_2-$; and $Y^1$, $Y^2$ and $Y^3$ are independently hydrogen or fluorine.

Item 6. The compound according to item 1, represented by any one of formulas (1B-1) to (1B-5):

(1B-1)

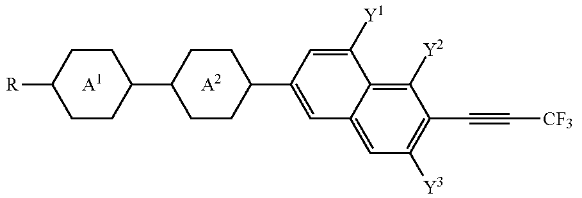

(1B-2)

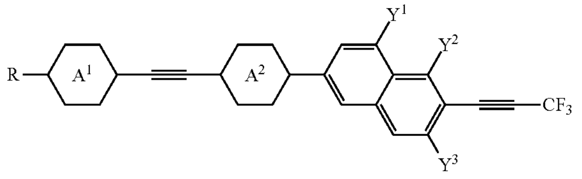

(1B-3)

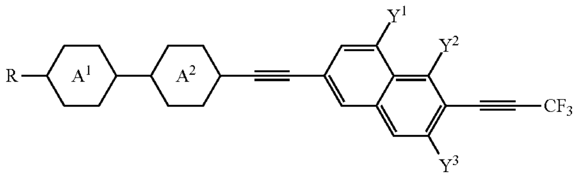

(1B-4)

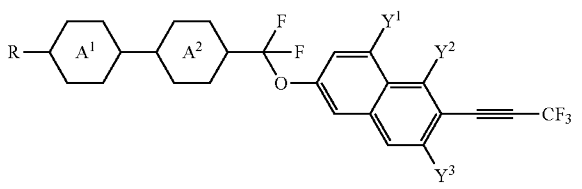

-continued (1B-5)

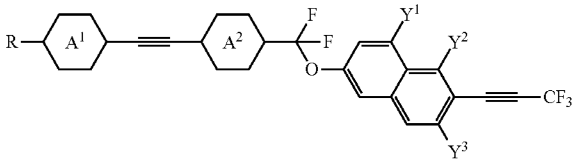

wherein, in formulas (1B-1) to (1B-5),

R is an alkyl having 1 to 15 carbons, alkoxy having 1 to 14 carbons, alkenyl having 2 to 15 carbons or alkenyloxy having 2 to 14 carbons;

ring $A^1$ is 1,4-cyclohexylene, 1,4-phenylene, 2-fluoro-1,4-phenylene, 2,6-difluoro-1,4-phenylene, 1,3-dioxane-2,5-diyl, pyridine-2,5-diyl, pyrimidine-2,5-diyl, naphthalene-2,6-diyl, 1-fluoronaphthalene-2,6-diyl, 1,3-difluoronaphthalene-2,6-diyl or 1,3,8-trifluoronaphthalene-2,6-diyl; and ring $A^2$ is 1,4-phenylene, 2-fluoro-1,4-phenylene, 2,6-difluoro-1,4-phenylene, naphthalene-2,6-diyl, 1-fluoronaphthalene-2,6-diyl, 1,3-difluoronaphthalene-2,6-diyl or 1,3,8-trifluoronaphthalene-2,6-diyl; and $Y^1$, $Y^2$ and $Y^3$ are independently hydrogen or fluorine.

Item 7. The compound according to item 1, represented by any one of formulas (1B-6) to (1B-31):

(1B-6)

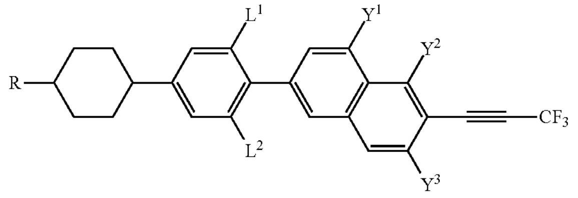

(1B-7)

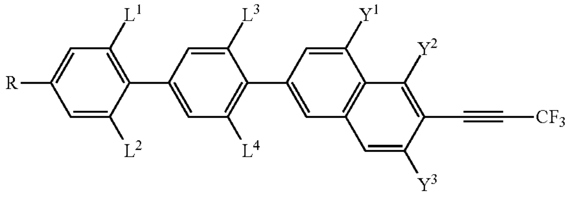

(1B-8)

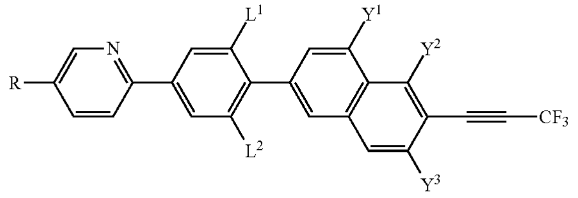

(1B-9)

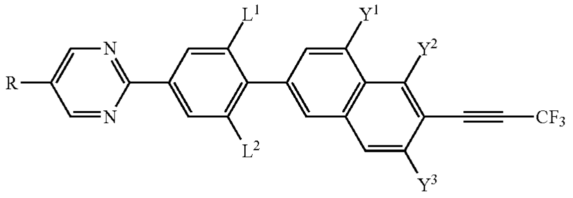

(1B-10)

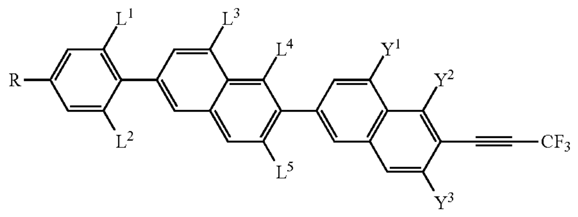

(1B-11)

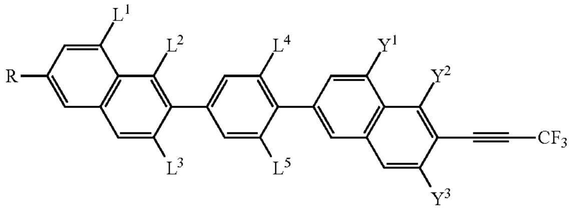

-continued
(1B-12)
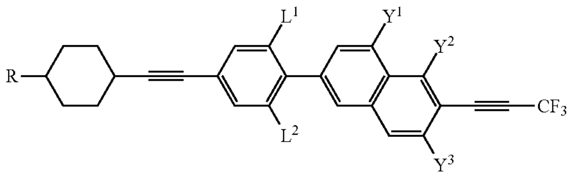
(1B-13)
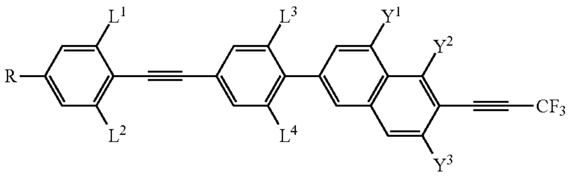
(1B-14)
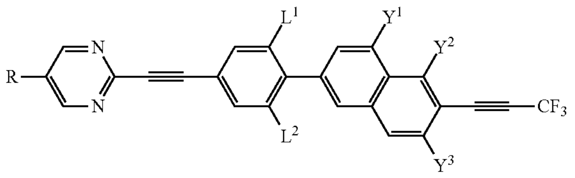
(1B-15)
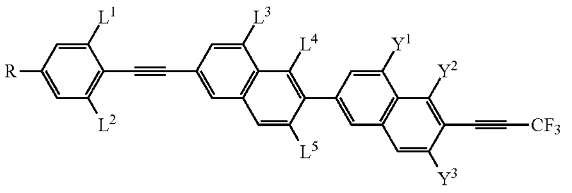
(1B-16)
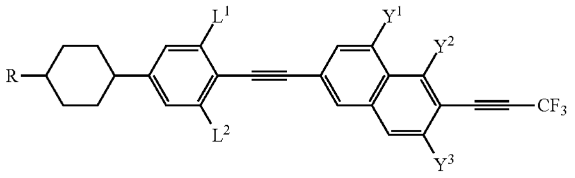
(1B-17)
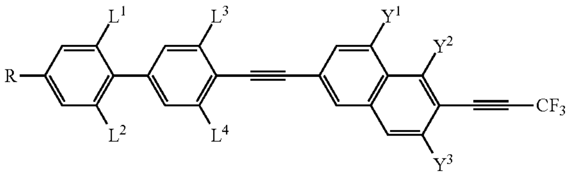
(1B-18)
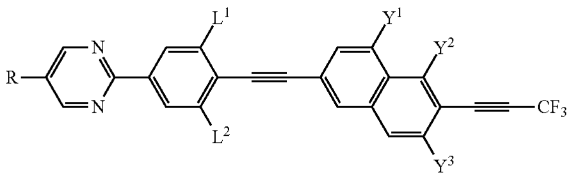
(1B-19)
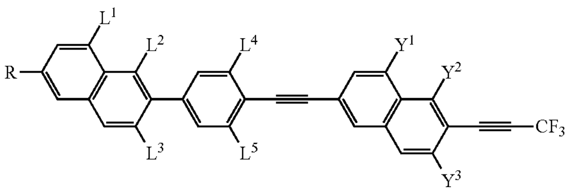
(1B-20)
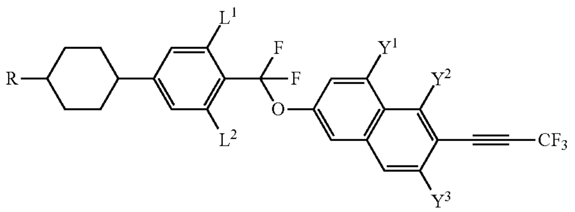
(1B-21)
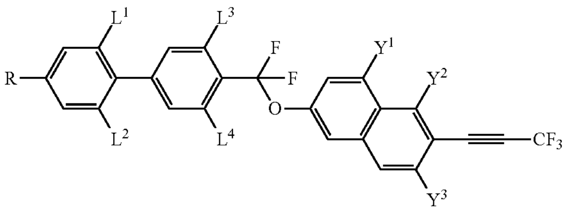
(1B-22)
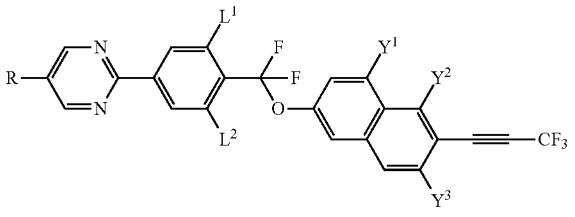
(1B-23)
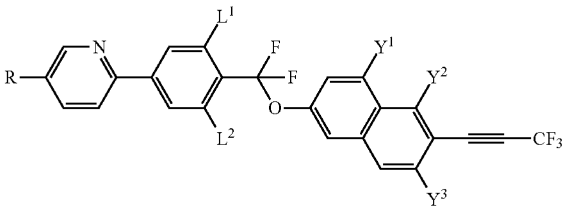
(1B-24)
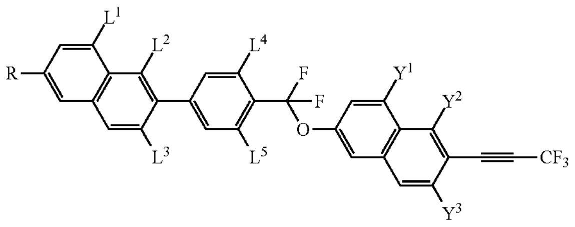
(1B-25)
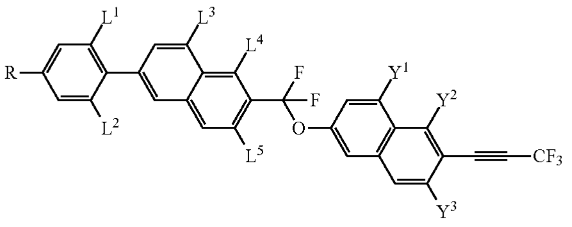

-continued (1B-26)

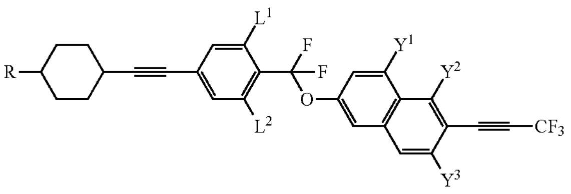

(1B-27)

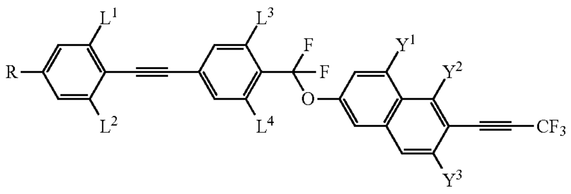

(1B-28)

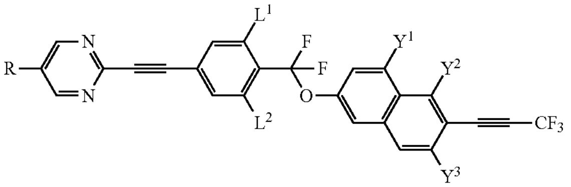

(1B-29)

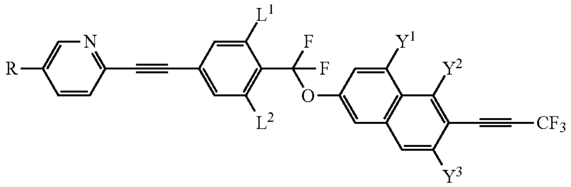

(1B-30)

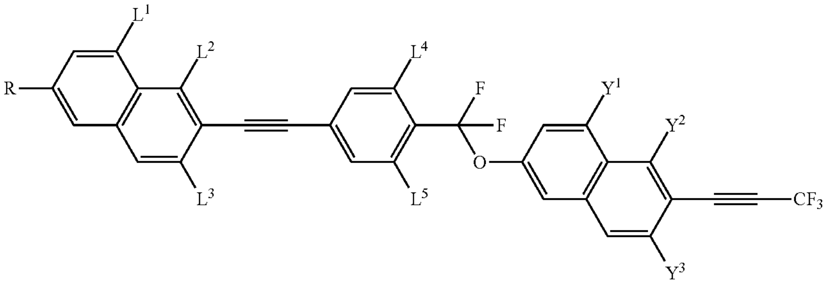

(1B-31)

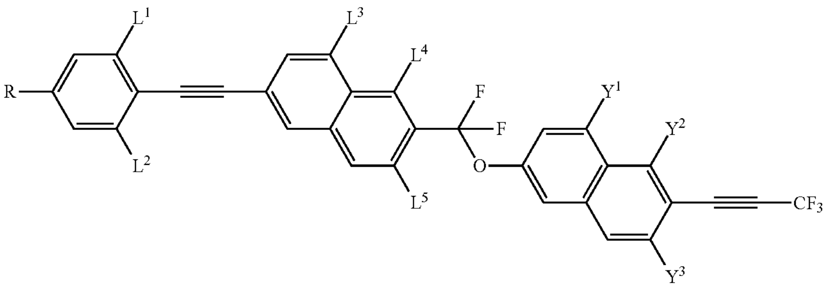

wherein, in formulas (1B-6) to (1B-31),

R is alkyl having 1 to 10 carbons, alkoxy having 1 to 9 carbons, alkenyl having 2 to 10 carbons or alkenyloxy having 2 to 9 carbons; and $Y^1$, $Y^2$, $Y^3$, $L^1$, $L^2$, $L^3$, $L^4$ and $L^5$ are independently hydrogen or fluorine.

Item 8. The compound according to item 1, represented by formula (1C):

(1C)

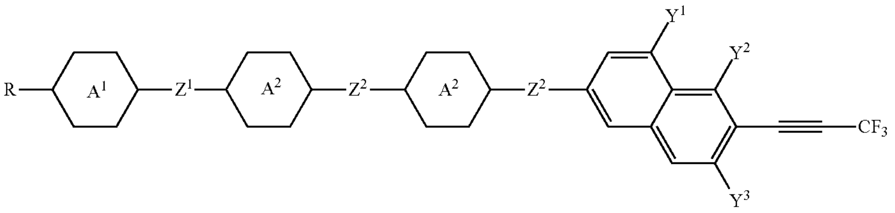

wherein, in formula (1C),

R is alkyl having 1 to 15 carbons, alkoxy having 1 to 14 carbons, alkenyl having 2 to 15 carbons, alkenyloxy having 2 to 14 carbons, alkylthio having 1 to 14 carbons or alkenylthio having 2 to 14 carbons;

ring $A^1$ is 1,4-cyclohexylene, 1,4-cyclohexenylene, 1,4-phenylene, 2-fluoro-1,4-phenylene, 2,6-difluoro-1,4-phenylene, tetrahydropyran-2,5-diyl, 1,3-dioxane-2,5-diyl, 2,6,7-trioxabicyclo[2.2.2]octane-1,4-diyl, pyridine-2,5-diyl, pyrimidine-2,5-diyl, naphthalene-2,6-diyl, 1-fluoronaphthalene-2,6-diyl, 1,3-difluoronaphthalene-2,6-diyl or 1,3,8-trifluoronaphthalene-2,6-diyl, and ring $A^2$ is 1,4-cyclohexylene, 1,4-cyclohexenylene, 1,4-phenylene, 2-fluoro-1,4-phenylene, 2,6-difluoro-1,4-phenylene, pyridine-2,5-diyl, naphthalene-2,6-diyl, pyrimidine-2,5-diyl, 1-fluoronaphthalene-2,6-diyl, 1,3-difluoronaphthalene-2,6-diyl or 1,3,8-trifluoronaphthalene-2,6-diyl;

$Z^1$ and $Z^2$ are independently a single bond, $—CH_2CH_2—$, —CH—CH—, —C≡C—, —COO—, —OCO—, $—CH_2O—$, $—OCH_2—$, $—CH_2S—$, $—SCH_2—$, $—CF_2O—$ or $—OCF_2—$; and $Y^1$, $Y^2$ and $Y^3$ are independently hydrogen or fluorine.

Item 9. The compound according to item 1 or 8, represented by any one of formulas (1C-1) to (1C-6):

(1C-1)

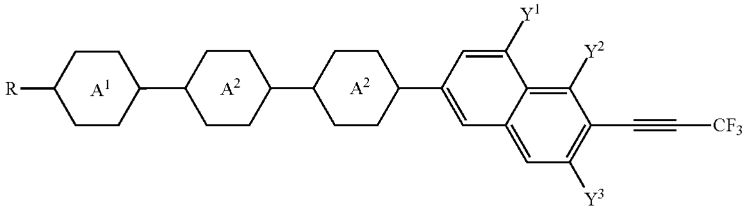

(1C-2)

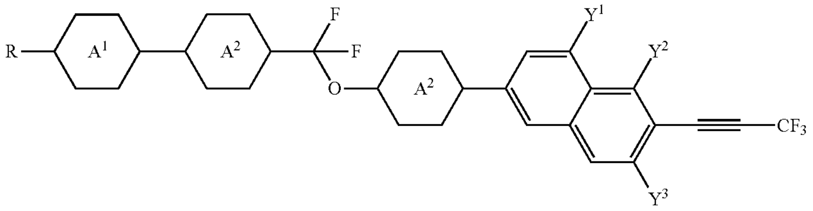

(1C-3)

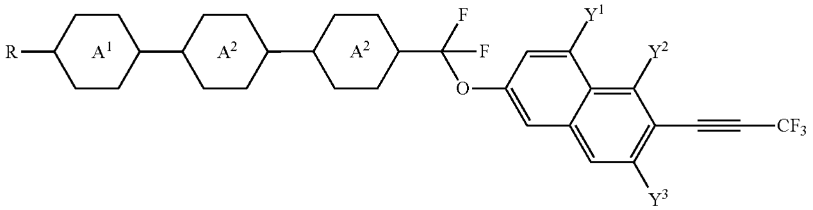

(1C-4)

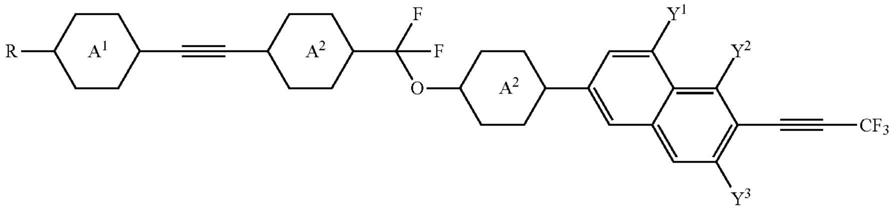

(1C-5)

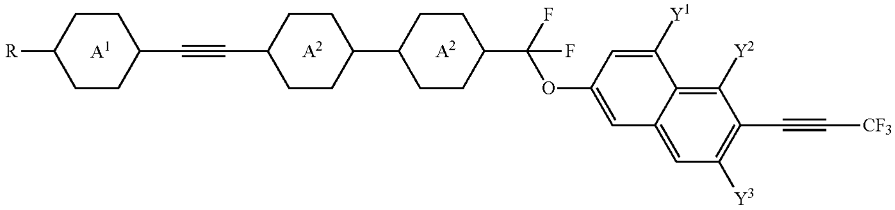

(1C-6)

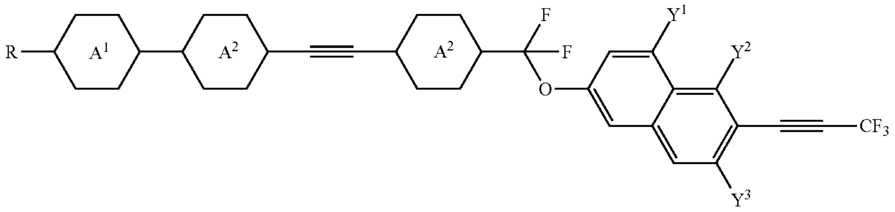

wherein, in formulas (1C-1) to (1C-6),

R is alkyl having 1 to 15 carbons, alkoxy having 1 to 14 carbons, alkenyl having 2 to 15 carbons or alkenyloxy having 2 to 14 carbons;

ring $A^1$ is 1,4-cyclohexylene, 1,4-phenylene, 2-fluoro-1,4-phenylene, 2,6-difluoro-1,4-phenylene, 1,3-dioxane-2,5-diyl, pyridine-2,5-diyl, pyrimidine-2,5-diyl, naphthalene-2,6-diyl, 1-fluoronaphthalene-2,6-diyl, 1,3-difluoronaphthalene-2,6-diyl or 1,3,8-trifluoronaphthalene-2,6-diyl, and ring $A^2$ is 1,4-cyclohexylene, 1,4-phenylene, 2-fluoro-1,4-phenylene, 2,6-difluoro-1,4-phenylene, naphthalene-2,6-diyl, 1-fluoronaphthalene-2,6-diyl, 1,3-difluoronaphthalene-2,6-diyl or 1,3,8-trifluoronaphthalene-2,6-diyl; and $Y^1$, $Y^2$ and $Y^3$ are independently hydrogen or fluorine.

Item 10. The compound according to item 1, represented by any one of formulas (1C-7) to (1C-32):

(1C-7)

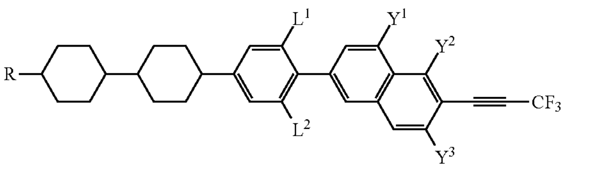

(1C-8)

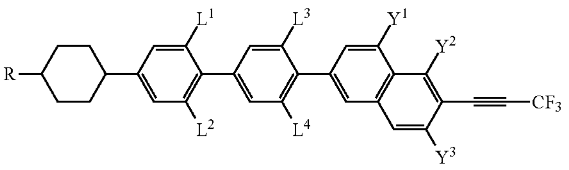

(1C-9)

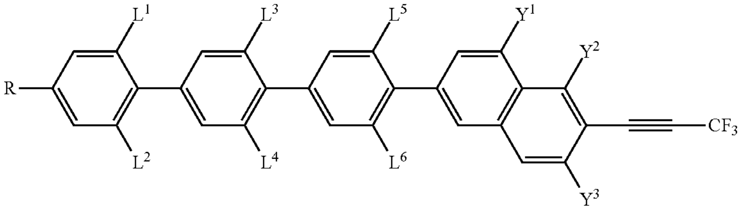

(1C-10)

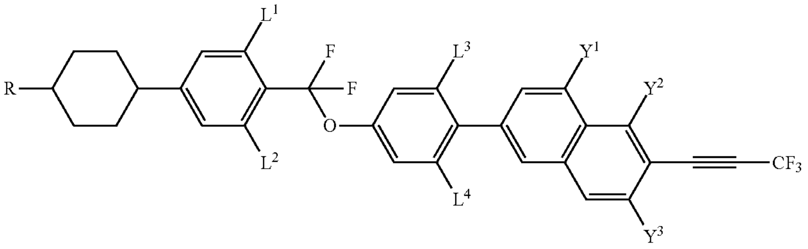

(1C-11)

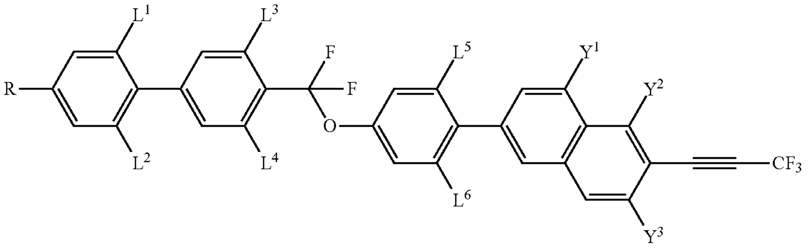

(1C-12)

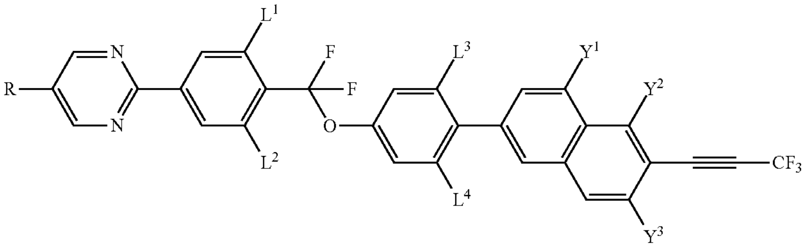

-continued
(1C-13)
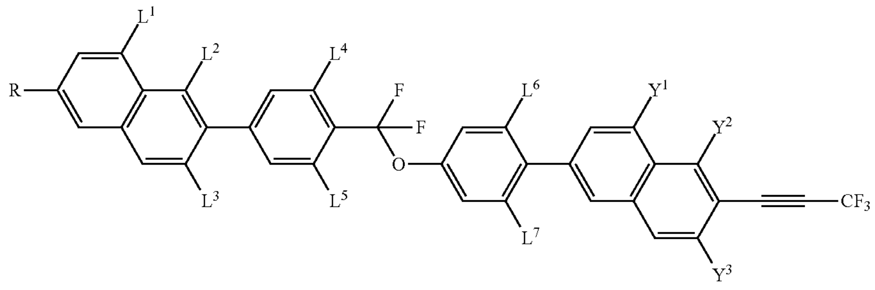
(1C-14)
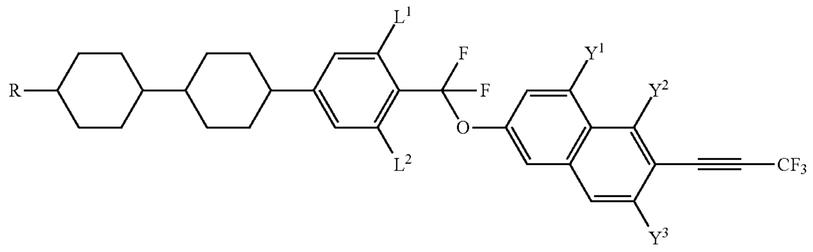
(1C-15)
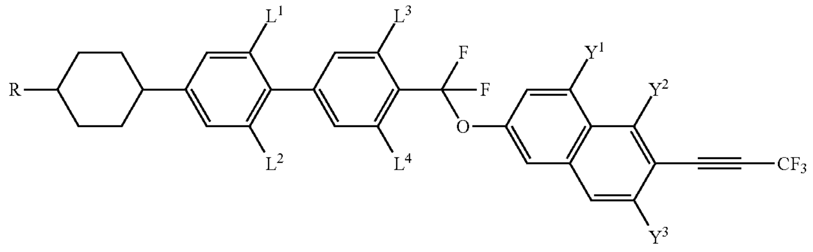
(1C-16)
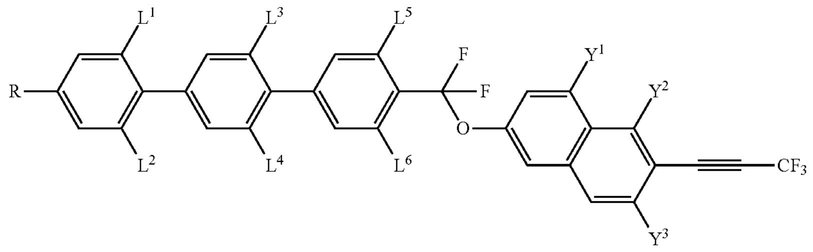
(1C-17)
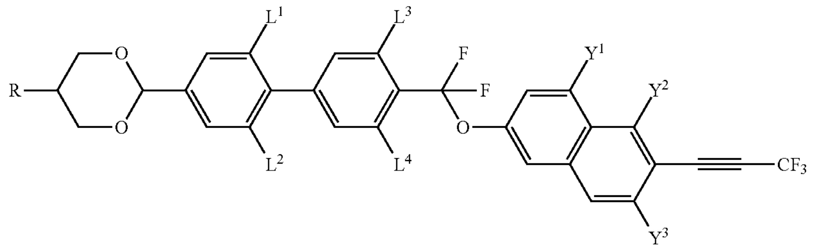
(1C-18)
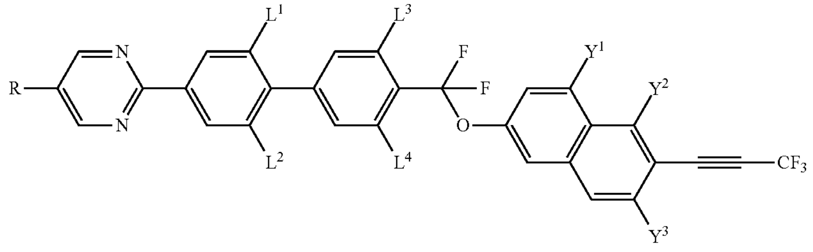

-continued
(1C-19)
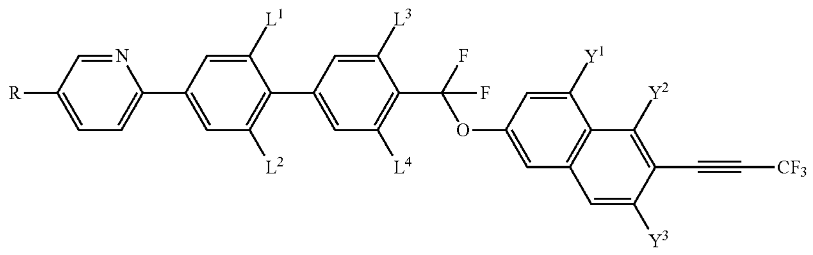
(1C-20)
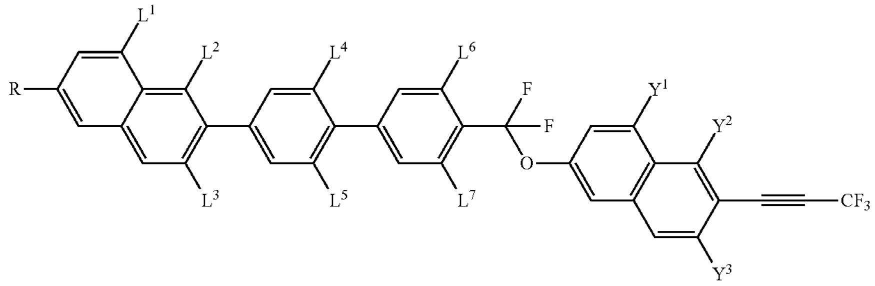
(1C-21)
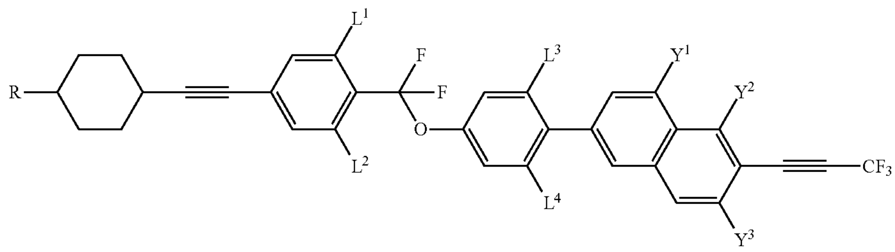
(1C-22)
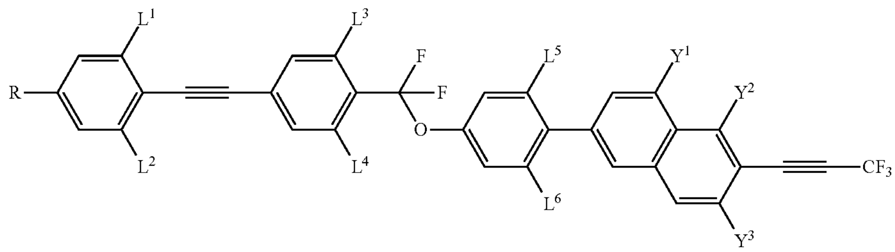
(1C-23)
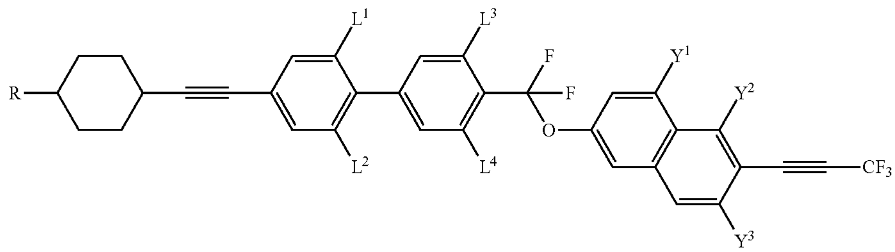
(1C-24)
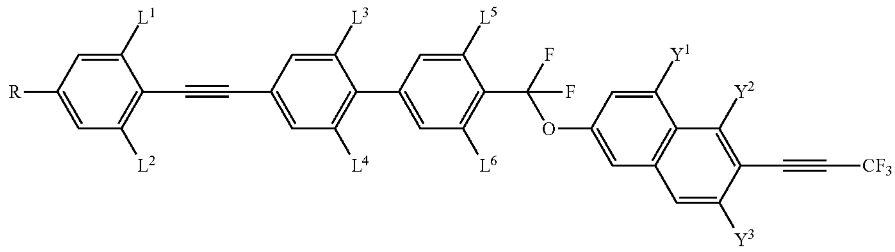

-continued
(1C-25)
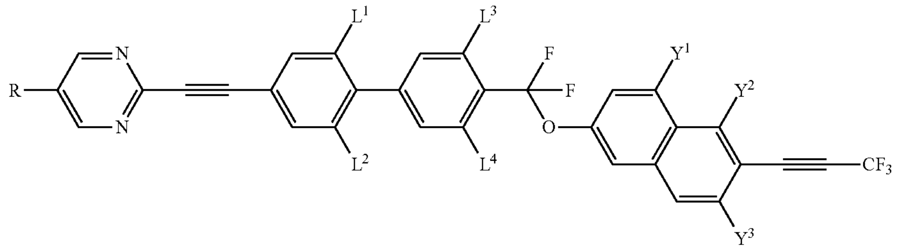
(1C-26)
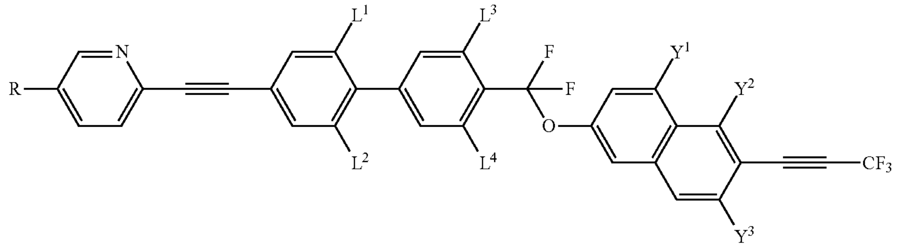
(1C-27)
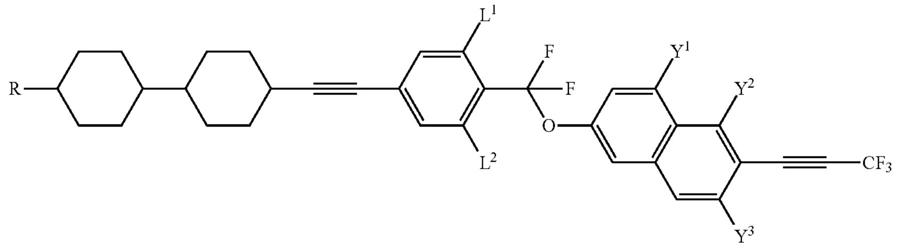
(1C-28)
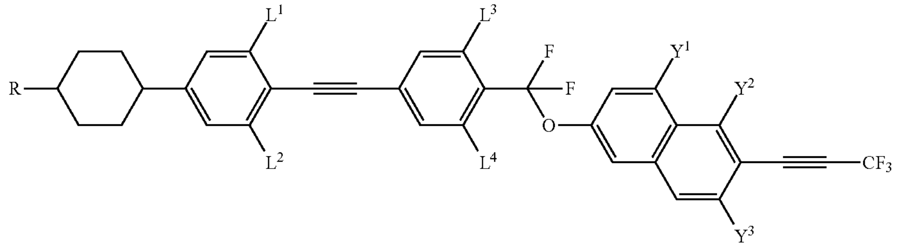
(1C-29)
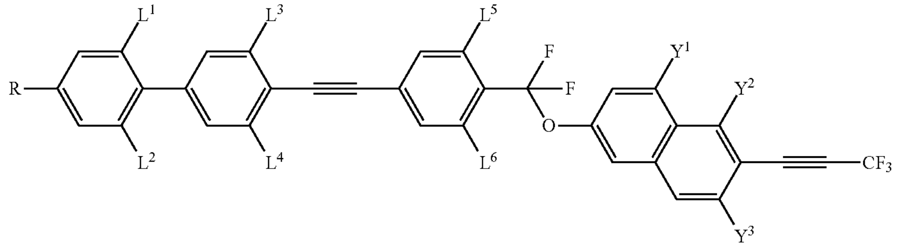
(1C-30)
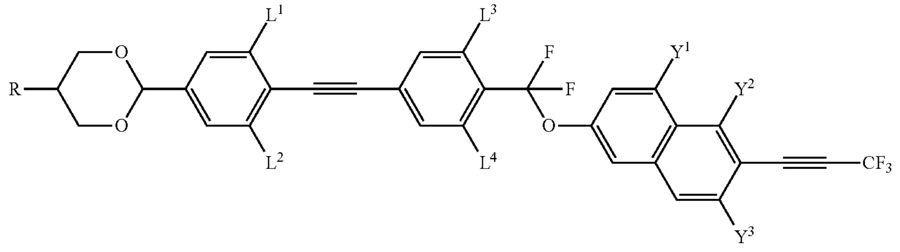

-continued
(1C-31)
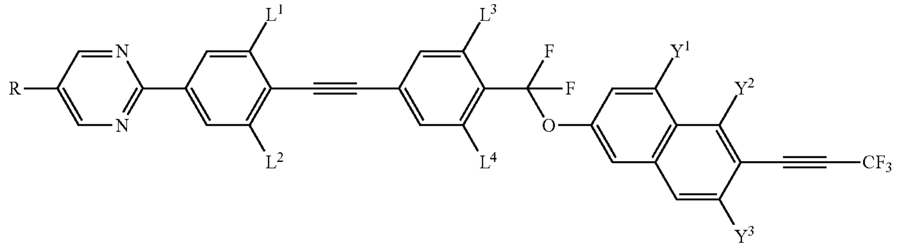
(1C-32)
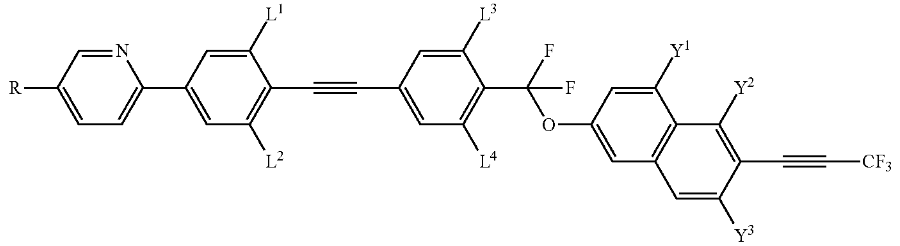
wherein, in formulas (1C-7) to (1C-32),
R is alkyl having 1 to 10 carbons, alkoxy having 1 to 9 carbons, alkenyl having 2 to 10 carbons or alkenyloxy having 2 to 9 carbons; and
$Y^1$, $Y^2$, $Y^3$, $L^1$, $L^2$, $L^3$, $L^4$, $L^5$, $L^6$ and $L^7$ are independently hydrogen or fluorine.
Item 11. The compound according to item 1, represented by any one of formulas (1A-12), (1B-21) to (1B-23), (1B-27), (1C-15) to (1C-19), (1C-22), (1C-24) and (1C-29):
(1A-12)
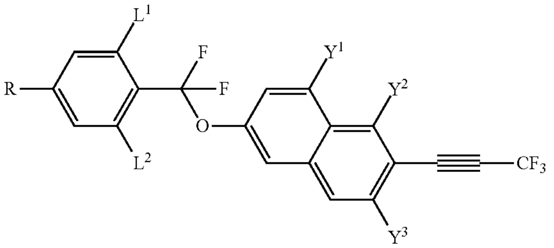
(1B-21)
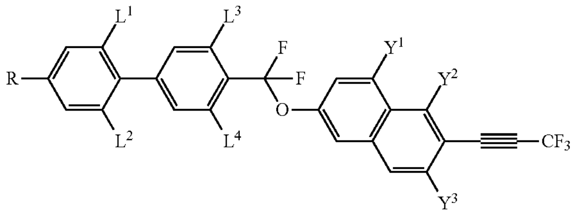
(1B-22)
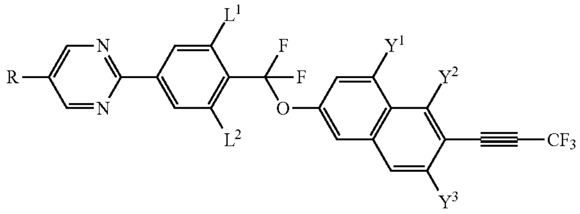
-continued
(1B-23)
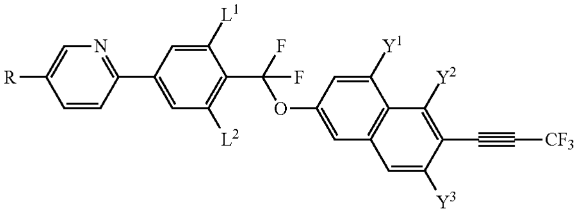
(1B-27)
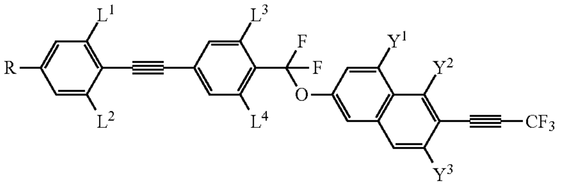
(1C-15)
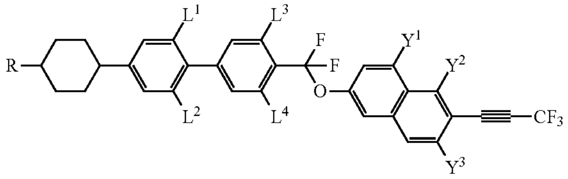
(1C-16)
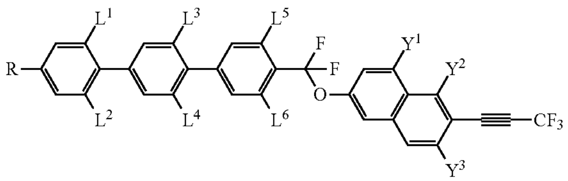

-continued (1C-17)

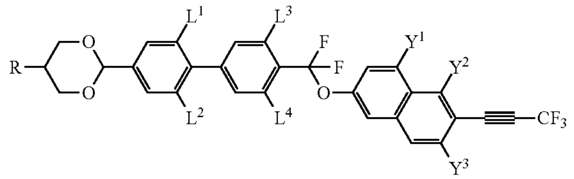

(1C-18)

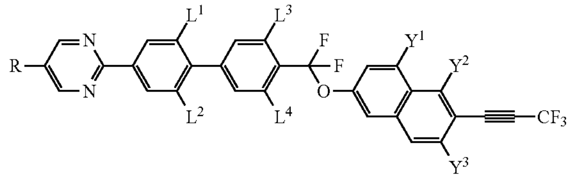

(1C-19)

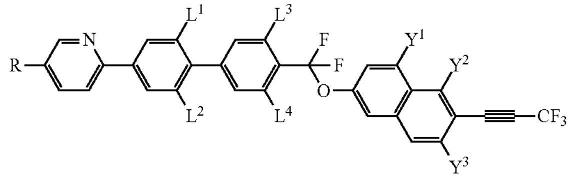

(1C-22)

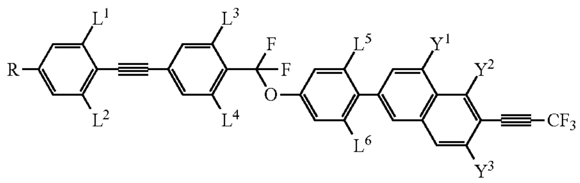

(1C-24)

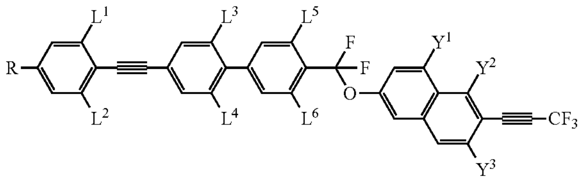

(1C-29)

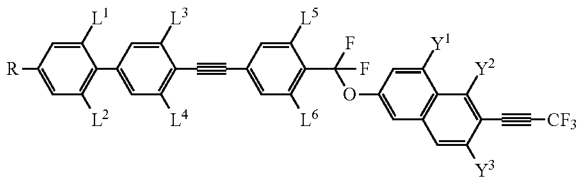

wherein, in formulas (1A-12), (1B-21) to (1B-23), (1B-27), (1C-15) to (1C-19), (1C-22), (1C-24) and (1C-29), R is alkyl having 1 to 10 carbons, alkoxy having 1 to 9 carbons, alkenyl having 2 to 10 carbons, alkenyloxy having 2 to 9 carbons, alkylthio having 1 to 9 carbons or alkenylthio having 2 to 9 carbons; and $Y^1$, $Y^2$, $Y^3$, $L^1$, $L^2$, $L^3$, $L^4$, $L^5$ and $L^6$ are independently hydrogen or fluorine.

Item 12. The compound according to item 11, wherein, in formulas (1A-12), (1B-21) to (1B-23), (1B-27), (1C-15) to (1C-19), (1C-22), (1C-24) and (1C-29), R is alkyl having 1 to 10 carbons, alkoxy having 1 to 9 carbons or alkenyl having 2 to 10 carbons; and $Y^2$, $Y^3$, $L^1$, $L^2$, $L^3$, $L^4$, $L^5$ and $L^6$ are independently hydrogen or fluorine.

Item 13. A liquid crystal composition, containing at least one compound according to any one of items 1 to 12.

Item 14. The liquid crystal composition according to item 13, further containing at least one compound selected from the group of compounds represented by formulas (2) to (4):

(2)

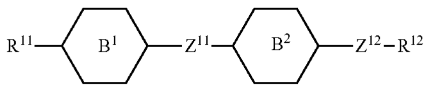

(3)

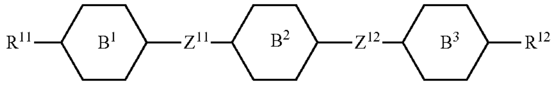

(4)

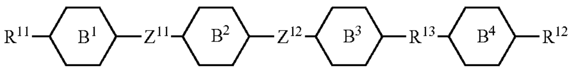

wherein, in formulas (2) to (4), $R^{11}$ and $R^{12}$ are independently alkyl having 1 to 10 carbons or alkenyl having 2 to 10 carbons, and in the alkyl and the alkenyl, at least one —$CH_2$— may be replaced by —O—, and in the groups, at least one hydrogen may be replaced by fluorine;

ring $B^1$, ring $B^2$, ring $B^3$ and ring $B^4$ are independently 1,4-cyclohexylene, 1,4-phenylene, 2-fluoro-1,4-phenylene, 2,5-difluoro-1,4-phenylene or pyrimidine-2,5-diyl; and $Z^{11}$, $Z^{12}$ and $Z^{13}$ are independently a single bond, —COO—, —$CH_2CH_2$—, —CH═CH— or —C≡C—.

Item 15. The liquid crystal composition according to item 13 or 14, further containing at least one compound selected from the group of compounds represented by formulas (5) to (7):

(5)

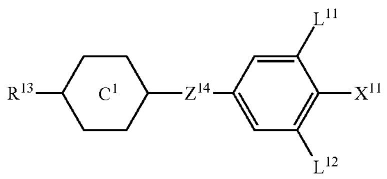

(6)

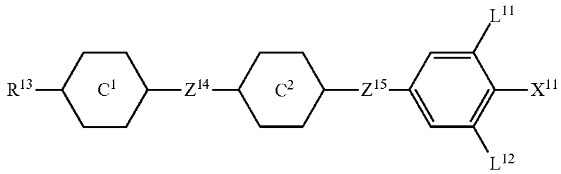

(7)

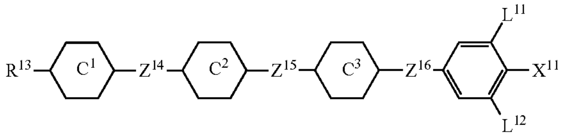

wherein, in formulas (5) to (7), $R^{13}$ is alkyl having 1 to 10 carbons or alkenyl having 2 to 10 carbons, and in the alkyl and the alkenyl, at least one —$CH_2$— may be replaced by —O—, and in the groups, at least one hydrogen may be replaced by fluorine;

$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;

ring $C^1$, ring $C^2$ and ring $C^3$ are independently 1,4-cyclohexylene, 1,4-phenylene, 1,4-phenylene in which at least one hydrogen is replaced by fluorine, tetrahydropyran-2,5-diyl, 1,3-dioxane-2,5-diyl or pyrimidine-2,5-diyl;

$Z^{14}$, $Z^{15}$ and $Z^{16}$ are independently a single bond, —COO—, —OCO—, —$CH_2O$—, —$OCH_2$—, —$CF_2O$—, —$OCF_2$—, —$CH_2CH_2$—, —CH═CH—, —C≡C— or —$(CH_2)_4$—; and $L^{11}$ and $L^{12}$ are independently hydrogen or fluorine.

Item 16. The liquid crystal composition according to any one of items 13 to 15, further containing at least one compound selected from the group of compounds represented by formula (8):

(8)

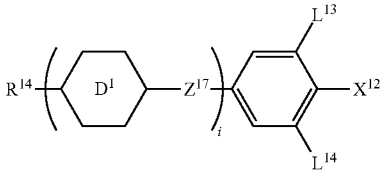

wherein, in formula (8), $R^{14}$ is alkyl having 1 to 10 carbons or alkenyl having 2 to 10 carbons, and in the alkyl and the alkenyl, at least one —$CH_2$— may be replaced by —O—, and in the groups, at least one hydrogen may be replaced by fluorine;

$X^{12}$ is —C≡N or —C≡C—C≡N;

ring D1 is 1,4-cyclohexylene, 1,4-phenylene, 1,4-phenylene in which at least one hydrogen is replaced by fluorine, tetrahydropyran-2,5-diyl, 1,3-dioxane-2,5-diyl or pyrimidine-2,5-diyl;

$Z^{17}$ is a single bond, —COO—, —OCO—, —$CH_2O$—, —$OCH_2$—, —$CF_2O$—, —$OCF_2$—, —$CH_2CH_2$— or —C≡C—;

$L^{13}$ and $L^{14}$ are independently hydrogen or fluorine; and i is 1, 2, 3 or 4.

Item 17. The liquid crystal composition according to any one of items 13 to 16: further containing at least one compound selected from the group of compounds represented by formulas (9) to (15):

(9)

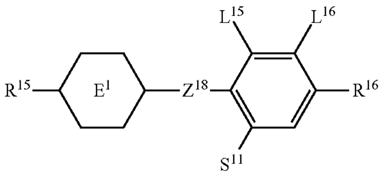

(10)

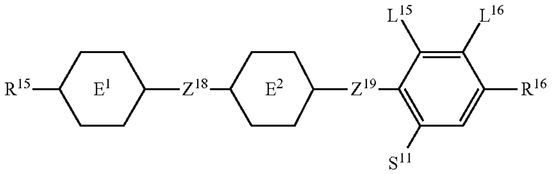

(11)

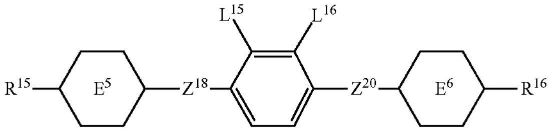

(12)

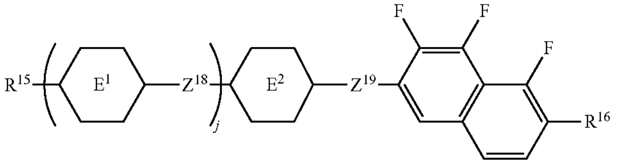

(13)

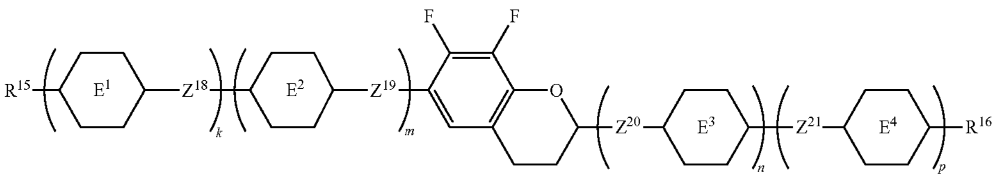

-continued (14)

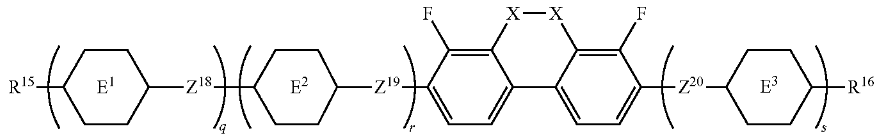

(15)

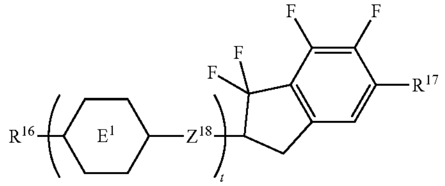

wherein, in formulas (9) to (15), $R^{15}$, $R^{16}$ and $R^{17}$ are independently alkyl having 1 to 10 carbons or alkenyl having 2 to 10 carbons, and in the alkyl and the alkenyl, at least one —$CH_2$— may be replaced by —O—, and in the groups, at least one hydrogen may be replaced by fluorine, and $R^{17}$ may be hydrogen or fluorine;

ring $E^1$, ring $E^2$, ring $E^3$ and ring $E^4$ are independently 1,4-cyclohexylene, 1,4-cyclohexenylene, 1,4-phenylene, 1,4-phenylene in which at least one of hydrogen is replaced by fluorine, tetrahydropyran-2,5-diyl or decahydronaphthalene-2,6-diyl;

ring $E^5$ and ring $E^6$ are independently 1,4-cyclohexylene, 1,4-cyclohexenylene, 1,4-phenylene, tetrahydropyran-2,5-diyl or decahydronaphthalene-2,6-diyl;

$Z^{18}$, $Z^{19}$, $Z^{20}$ and $Z^{21}$ are independently a single bond, —COO—, —OCO—, —$CH_2O$—, —$OCH_2$—, —$CF_2O$—, —$OCF_2$—, —$CH_2CH_2$—, —$CF_2OCH_2CH_2$— or —$OCF_2CH_2CH_2$—;

$L^{15}$ and $L^{16}$ are independently fluorine or chlorine;

$S^{11}$ is hydrogen or methyl;

X is —CHF— or —$CF_2$—; and j, k, m, n, p, q, r and s are independently 0 or 1, a sum of k, m, n and p is 1 or 2, a sum of q, r and s is 0, 1, 2 or 3, and t is 1, 2 or 3.

Item 18. A liquid crystal display device, including the liquid crystal composition according to any one of items 13 to 17.

Item 19. The liquid crystal display device according to item 18, wherein the liquid crystal composition according to any one of items 13 to 17 is encapsulated.

Item 20. The liquid crystal display device according to item 18, wherein the liquid crystal composition according to any one of items 13 to 17 is used in a lens to be utilized in switching between 2D and 3D.

The invention further includes the following items: (a) the composition, further containing one, two or at least three additives selected from the group of a polymerizable compound, a polymerization initiator, a polymerization inhibitor, an optically active compound, an antioxidant, an ultraviolet light absorber, a light stabilizer, a heat stabilizer, a dye and an antifoaming agent; (b) the liquid crystal composition, wherein a maximum temperature of a nematic phase is 70° C. or higher, an optical anisotropy (measured at 25° C.) at a wavelength of 589 nanometers is 0.07 or more, and a dielectric anisotropy (measured at 25° C.) at a frequency of 1 kHz is 2 or more; and (c) the liquid crystal display device, wherein an operating mode in the liquid crystal display device is a TN mode, an ECB mode, an OCB mode, an IPS mode, a VA mode, an FFS mode or an FPA mode, and a driving mode in the liquid crystal display device is an active matrix (AM) mode.

An aspect of compound (1), a synthesis method of compound (1), the liquid crystal composition and the liquid crystal display device will be described in the order.

1. Aspect of Compound (1)

Compound (1) of the invention has a structure of “naphthalene ring-triple bond between carbons-$CF_3$”. Compound (1) has a feature of having larger optical anisotropy and larger dielectric anisotropy in comparison with a similar compound (see Comparative Example 1). Preferred examples of compound (1) will be described. Preferred examples of terminal group R, ring A, bonding group Z and substituent Y in compound (1) apply also to a subordinate formula of formula (1) of compound (1). In compound (1), physical properties can be arbitrarily adjusted by suitably combining the groups. Compound (1) may contain a larger amount of isotope such as $^2H$ (deuterium) and $^{13}C$ than the amount of natural abundance because no significant difference exists in the physical properties of the compound. In addition, definitions of symbols of compound (1) are as described in item 1.

(1)

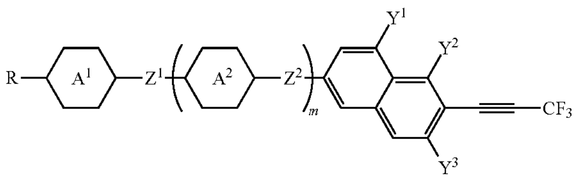

In formula (1), R is alkyl having 1 to 15 carbons, and in the alkyl, at least one —$CH_2$— may be replaced by —O— or —S—, and at least one —$CH_2CH_2$— may be replaced by —CH=CH—, and in the groups, at least one hydrogen may be replaced by fluorine or chlorine.

Examples of R are alkyl, alkoxy, alkoxyalkyl, alkoxyalkoxy, alkenyl, alkenyloxy, alkenyloxyalkyl, alkoxyalkenyl, alkylthio, alkylthio alkyl, alkenylthio, alkenylthioalkyl and alkylthioalkenyl. In addition, alkylthio is represented by —SR, in which R is alkyl.

Preferred R is alkyl, alkoxy, alkoxyalkyl, alkoxyalkoxy, alkenyl, alkenyloxy, alkenyloxyalkyl or alkoxyalkenyl. Further preferred R is alkyl, alkoxy, alkoxyalkyl, alkenyl or alkenyloxy. Particularly preferred R is alkyl or alkenyl. Most preferred R is alkyl. In the groups, at least one hydrogen may be replaced by fluorine or chlorine. In the groups, at least one hydrogen may be preferably replaced by fluorine.

Preferred alkyl is $—CH_3$, $—C_2H_5$, $—C_3H_7$, $—C_4H_9$, $—C_5H_{11}$, $—C_6H_{13}$ or $—C_7H_{15}$.

Preferred alkoxy is $—OCH_3$, $—OC_2H_5$, $—OC_3H_7$, $—OC_4H_9$, $—OC_5H_{11}$, $—OC_6H_{13}$ or $—OC_7H_{15}$.

Preferred alkoxyalkyl is $—CH_2OCH_3$, $—CH_2OC_2H_5$, $—CH_2OC_3H_7$, $—(CH_2)_2—OCH_3$, $—(CH_2)_2—OC_2H_5$, $—(CH_2)_2—OC_3H_7$, $—(CH_2)_3—OCH_3$, $—(CH_2)_4—OCH_3$ or $—(CH_2)_5—OCH_3$.

Preferred alkenyl is $—CH{=}CH_2$, $—CH{=}CHCH_3$, $—CH_2CH{=}CH_2$, $—CH{=}CHC_2H_5$, $—CH_2CH{=}CHCH_3$, $—(CH_2)_2—CH{=}CH_2$, $—CH{=}CHC_3H_7$, $—CH_2CH{=}CHC_2H_5$, $—(CH_2)_2—CH{=}CHCH_3$ or $—(CH_2)_3—CH{=}CH_2$.

Preferred alkenyloxy is $—OCH_2CH{=}CH_2$, $—OCH_2CH{=}CHCH_3$ or $—OCH_2CH{=}CHC_2H_5$.

Preferred examples of alkyl in which at least one hydrogen is replaced by fluorine are fluoromethyl, 2-fluoroethyl, 3-fluoropropyl, 4-fluorobutyl, 5-fluoropentyl, 6-fluorohexyl, 7-fluoroheptyl or 8-fluorooctyl. Further preferred examples are 2-fluoroethyl, 3-fluoropropyl, 4-fluorobutyl or 5-fluoropentyl for increasing the dielectric anisotropy.

Preferred examples of alkenyl in which at least one hydrogen is replaced by fluorine are 2,2-difluorovinyl, 3,3-difluoro-2-propenyl, 4,4-difluoro-3-butenyl, 5,5-difluoro-4-pentenyl or 6,6-difluoro-5-hexenyl. Further preferred examples are 2,2-difluorovinyl or 4,4-difluoro-3-butenyl for decreasing the viscosity.

Preferred R is $—CH_3$, $—C_2H_5$, $—C_3H_7$, $—C_4H_9$, $—C_5H_{11}$, $—C_6H_{13}$, $—OCH_3$, $—OC_2H_5$, $—OC_3H_7$, $—OC_4H_9$, $—OC_5H_{11}$, $—CH_2OCH_3$, $—CH{=}CH_2$, $—CH{=}CHCH_3$, $—(CH_2)_2—CH{=}CH_2$, $—CH_2CH{=}CHC_2H_5$, $—(CH_2)_2—CH{=}CHCH_3$, $—OCH_2CH{=}CH_2$, $—OCH_2CH{=}CHCH_3$ or $—OCH_2CH{=}CHC_2H_5$. Further preferred R is $—C_3H_7$, $—C_4H_9$, $—C_5H_{11}$, $—C_6H_{13}$, $—(CH_2)_2—CH{=}CH_2$ or $—(CH_2)_2—CH{=}CHCH_3$.

When R has the straight chain, a temperature range of the liquid crystal phase is wide, and the viscosity is small. When R has the branched chain, the compatibility with other liquid crystal compounds is good. A compound in which R is optically active is useful as a chiral dopant. A reverse twisted domain to be generated in the liquid crystal display device can be prevented by adding the compound to the composition. A compound in which R is not optically active is useful as a component of the composition. When R is alkenyl, a preferred configuration depends on a position of a double bond. Δn alkenyl compound having the preferred configuration has low viscosity, high maximum temperature or a wide temperature range of the liquid crystal phase.

A preferred configuration of $—CH{=}CH—$ in the alkenyl depends on a position of a double bond. In alkenyl having the double bond in an odd-numbered position, such as $—CH{=}CHCH_3$, $—CH{=}CHC_2H_5$, $—CH{=}CHC_3H_7$, $—CH{=}CHC_4H_9$, $—C_2H_4CH{=}CHCH_3$ and $—C_2H_4CH{=}CHC_2H_5$, a trans configuration is preferred. In alkenyl having the double bond in an even-numbered position, such as $—CH_2CH{=}CHCH_3$, $—CH_2CHCHC_2H_5$ and $—CH_2CHCHC_3H_7$, a cis configuration is preferred. The alkenyl compound having the preferred configuration has high clearing point or a wide temperature range of the liquid crystal phase. A detailed description is found in Mol. Cryst. Liq. Cryst., 1985, 131, 109 and Mol. Cryst. Liq. Cryst., 1985, 131 and 327.

In formula (1), ring $A^1$ and ring $A^2$ are independently 1,4-cyclohexylene, 1,4-cyclohexenylene, 1,4-phenylene, decahydronaphthalene-2,6-diyl, 1,2,3,4-tetrahydronaphthalene-2,6-diyl, naphthalene-2,6-diyl, tetrahydropyran-2,5-diyl, 1,3-dioxane-2,5-diyl, 2,6,7-trioxabicyclo[2.2.2]octane-1,4-diyl, pyridine-2,5-diyl or pyrimidine-2,5-diyl, and in the rings, at least one hydrogen may be replaced by fluorine or chlorine.

Preferred examples of 1,4-phenylene in which at least one hydrogen is replaced by fluorine or chlorine are group (A1) to group (A19). Further preferred examples are group (A1), group (A2), group (A5), group (A6) and group (A7). Particularly preferred examples are group (A1) or group (A5).

A1

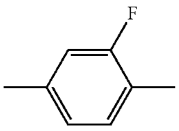

A2

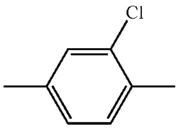

A3

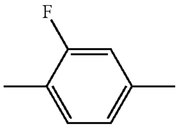

A4

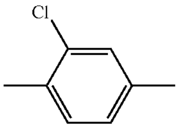

A5

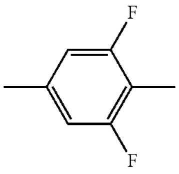

A6

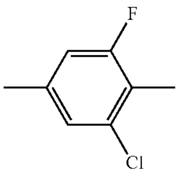

A7

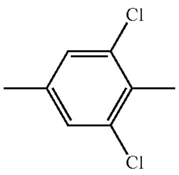

A8

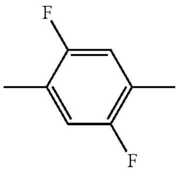

-continued
A9
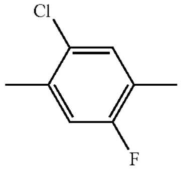
A10
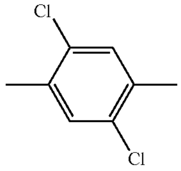
A11
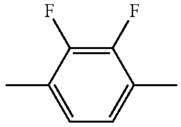
A12
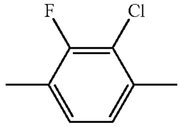
A13
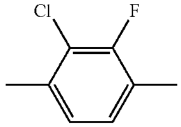
A14
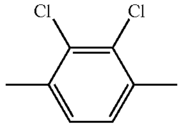
A15
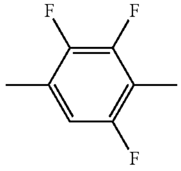
A16
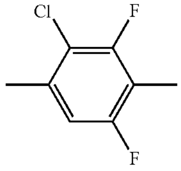
A17
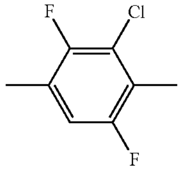
-continued
A18
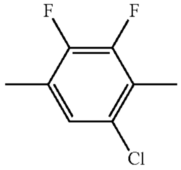
A19
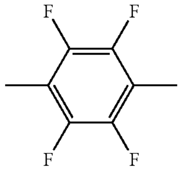
Preferred examples of naphthalene-2,6-diyl in which at least one hydrogen is replaced by fluorine or chlorine are group (A20) to group (A31). Further preferred examples are group (A20), group (A22), group (A24), group (A25) and group (A28). Particularly preferred examples are group (A20), group (A25) or group (A28).
A20
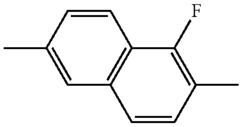
A21
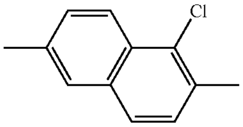
A22
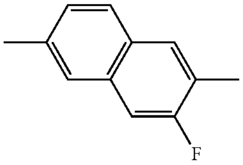
A23
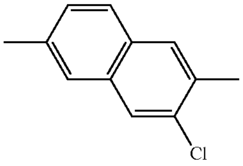
A24
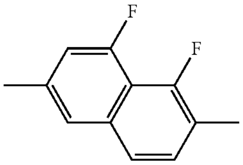
A25
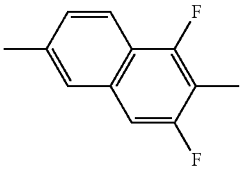

-continued

A26

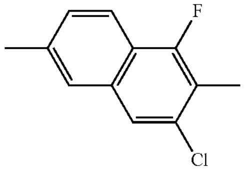

A27

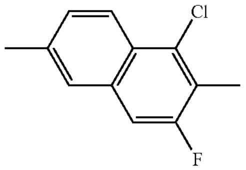

A28

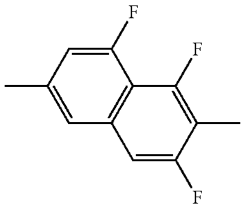

A29

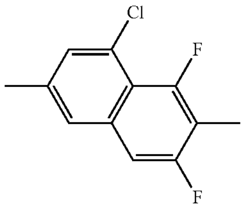

A30

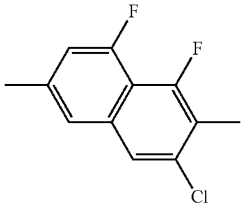

A31

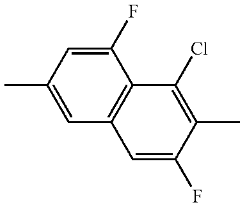

Preferred ring $A^1$ or ring $A^2$ is 1,4-cyclohexylene, 1,4-phenylene, naphthalene-2,6-diyl, tetrahydropyran-2,5-diyl, 1,3-dioxane-2,5-diyl or pyrimidine-2,5-diyl. In the rings, at least one hydrogen may be replaced by fluorine. Further preferred ring $A^1$ or ring $A^2$ is 1,4-cyclohexylene, 1,4-phenylene, 2-fluoro-1,4-phenylene, 2,6-difluoro-1,4-phenylene or tetrahydropyran-2,5-diyl. Particularly preferred ring $A^1$ or ring $A^2$ is 1,4-cyclohexylene or 1,4-phenylene.

When ring $A^1$ or ring $A^2$ is 1,4-cyclohexylene, the clearing point is high, and the viscosity is small. When ring $A^1$ or ring $A^2$ is 1,4-phenylene, or 1,4-phenylene in which at least one hydrogen is replaced by fluorine, the optical anisotropy is large and an orientation order parameter is comparatively large. When ring $A^1$ or ring $A^2$ is 1,4-phenylene in which at least one hydrogen is replaced by fluorine, the dielectric anisotropy is large.

In formula (1), $Z^1$ and $Z^2$ are independently a single bond, —COO—, —OCO—, —$CH_2O$—, —$OCH_2$—, —$CH_2S$—, —$SCH_2$—, —$CF_2O$—, —$OCF_2$—, —$CH_2CH_2$—, —CH═CH—, —C≡C— or —CF═CF—.

Preferred $Z^1$ or $Z^2$ is a single bond, —COO—, —OCO—, —$CH_2O$—, —$OCH_2$—, —$CF_2O$—, —$OCF_2$—, —$CH_2CH_2$— or —C≡C—. Preferred $Z^1$ or $Z^2$ is also a single bond, —COO—, —OCO—, —$CH_2S$—, —$SCH_2$—, —$CF_2O$—, —$OCF_2$—, —$CH_2CH_2$— or —C≡C—. Further preferred $Z^1$ or $Z^2$ is a single bond, —COO—, —$CH_2O$—, —$CF_2O$— or —C≡C—. Particularly preferred $Z^1$ or $Z^2$ is a single bond.

When $Z^1$ or $Z^2$ is a single bond, chemical stability is high, and the viscosity is small. When $Z^1$ or $Z^2$ is —$CF_2O$—, the viscosity is small, dielectric anisotropy is large, and maximum temperature is high.

In formula (1), $Y^1$, $Y^2$ and $Y^3$ are independently hydrogen, fluorine or chlorine. Preferred $Y^1$, $Y^2$ and $Y^3$ are a combination of hydrogen or fluorine. Preferred $Y^1$, $Y^2$ and $Y^3$ are a combination of fluorine and fluorine. When $Y^1$, $Y^2$ and $Y^3$ are a combination of hydrogen and fluorine, the dielectric anisotropy is large. When $Y^1$, $Y^2$ and $Y^3$ are a combination of fluorine and fluorine, the dielectric anisotropy is particularly large.

In formula (1), m is 0, 1 or 2. When a fused ring such as naphthalene ring is counted as a monocyclic ring, compound (1) has a bicyclic ring to a tetracyclic ring. Preferred m is 0 from a viewpoint of small viscosity or good compatibility. Preferred m is 1 or 2 from a viewpoint of high maximum temperature.

Preferred compound (1) is described in item 2 or the like. Compounds (1B-26) to (1B-31) and (1C) are preferred from a viewpoint of high clearing point and large optical anisotropy. Compounds (1B-20) to (1B-25) are preferred from a viewpoint of large optical anisotropy and good compatibility.

2. Synthesis of Compound (1)

A synthetic method of compound (1) will be described. Compound (1) can be prepared by suitably combining methods in synthetic organic chemistry. A method for introducing a required terminal group, ring and bonding group into a starting material is described in books such as "Organic Syntheses" (John Wiley & Sons, Inc.), "Organic Reactions" (John Wiley & Sons, Inc.), "Comprehensive Organic Synthesis" (Pergamon Press) and "New Experimental Chemistry Course (Shin Jikken Kagaku Koza in Japanese)" (Maruzen Co., Ltd.).

2-1. Formation of Bonding Group Z

First, a scheme is shown with regard to a method for forming bonding groups $Z^1$ or $Z^2$. Next, reactions described in the scheme in methods (1) to (11) will be described. In the scheme, $MSG^1$ (or $MSG^2$) is a monovalent organic group having at least one ring. The monovalent organic groups represented by a plurality of $MSG^1$ (or $MSG^2$) used in the scheme may be identical or different. Compounds (1A) to (1J) correspond to compound (1).

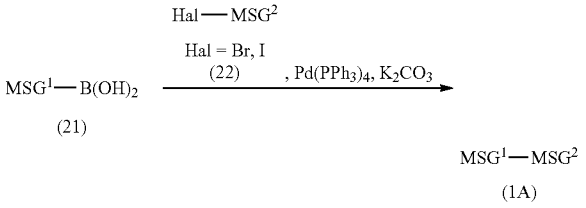

-continued

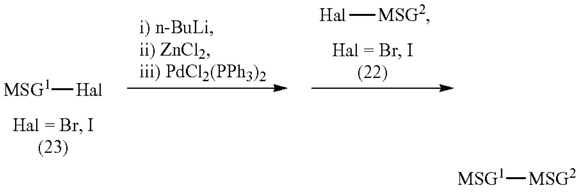

(23) (22) (1A)

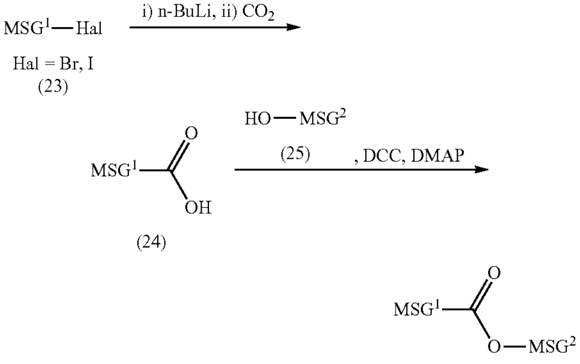

(23) (25) (24) (1B)

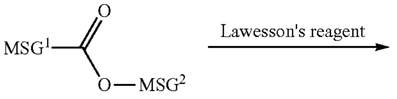

(1B)

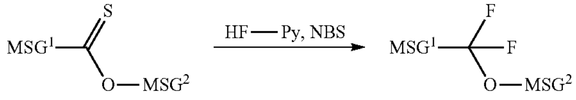

(26) (1C)

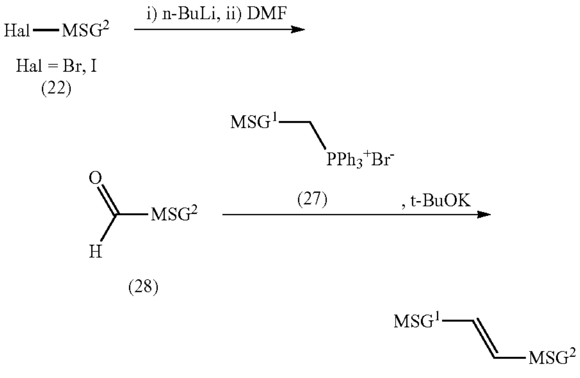

(22) (27) (28) (1D)

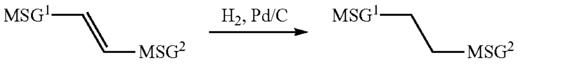

(1D) (1E)

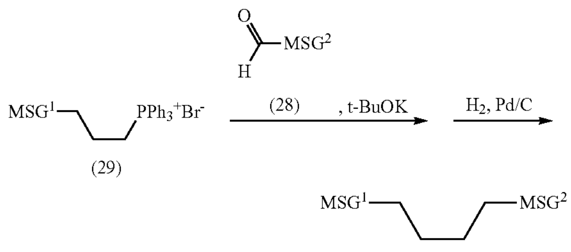

(28) (29) (1F)

-continued

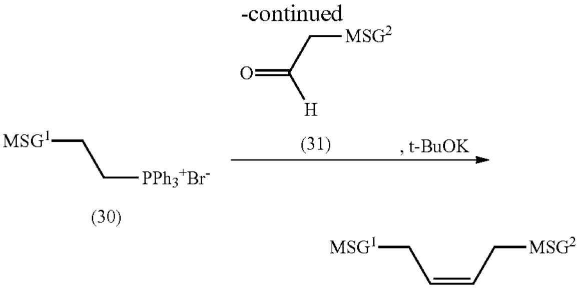

(31) (30) (1G)

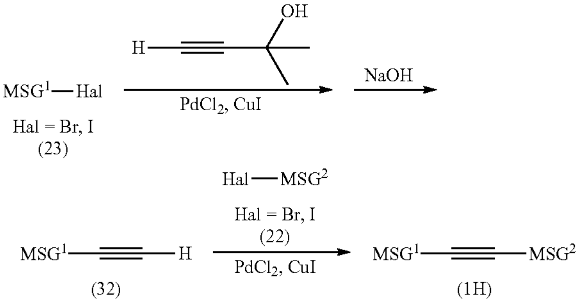

(23) (22) (32) (1H)

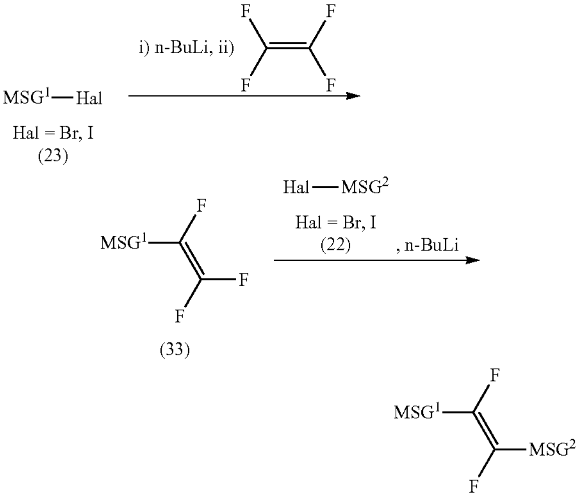

(23) (22) (33) (1I)

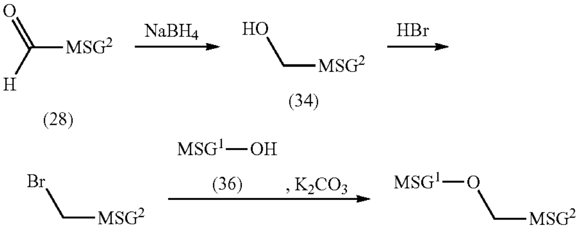

(28) (34) (36) (35) (1J)

(1) Formation of a Single Bond

Compound (1A) is prepared by allowing aryl boronic acid (21) prepared according to a publicly-known method to react with halide (22), in the presence of carbonate and a catalyst such as tetrakis(triphenylphosphine)palladium. Compound (1A) is also prepared by allowing halide (23) prepared according to a publicly-known method to react with n-butyllithium and subsequently with zinc chloride, and further with halide (22) in the presence of a catalyst such as dichlorobis(triphenylphosphine)palladium.

(2) Formation of —COO—

Carboxylic acid (24) is obtained by allowing halide (23) to react with n-butyllithium and subsequently with carbon dioxide. Compound (1B) is prepared by dehydration of compound (25) prepared according to a publicly-known method and carboxylic acid (24) in the presence of 1,3-dicyclohexylcarbodiimide (DCC) and 4-dimethylaminopyridine (DMAP).

(3) Formation of $—CF_2O—$

Thionoester (26) is obtained by treating compound (1B) with a thiation reagent such as Lawesson's reagent. Compound (1C) is prepared by fluorinating thionoester (26) with a hydrogen fluoride-pyridine complex and N-bromosuccinimide (NBS). Refer to M. Kuroboshi et al., Chem. Lett., 1992, 827. Compound (1C) is also prepared by fluorinating thionoester (26) with (diethylamino) sulfur trifluoride (DAST). Refer to W. H. Bunnelle et al., J. Org. Chem. 1990, 55, 768. The bonding group can also be formed according to the method described in Peer. Kirsch et al., Angew. Chem. Int. Ed. 2001, 40, 1480.

(4) Formation of —CH═CH—

Phosphorus ylide is generated by treating phosphonium salt (27) prepared according to a publicly-known method with a base such as potassium t-butoxide. Compound (1D) is prepared by allowing the phosphorus ylide to react with aldehyde (28). A cis isomer may be formed depending on reaction conditions, and therefore the cis isomer is isomerized into a trans isomer according to a publicly-known method when necessary.

(5) Formation of $—CH_2CH_2—$

Compound (1E) is prepared by hydrogenating compound (1D) in the presence of a catalyst such as palladium on carbon.

(6) Formation of $—(CH_2)_4—$

A compound having $—(CH_2)_2—CH═CH—$ is obtained by using phosphonium salt (29) in place of phosphonium salt (27) according to the method in method (4). Compound (1F) is prepared by performing catalytic hydrogenation of the compound obtained.

(7) Formation of $—CH_2CH═CHCH_2—$

Compound (1G) is prepared by using phosphonium salt (30) in place of phosphonium salt (27) and aldehyde (31) in place of aldehyde (28) according to the method of method (4). A trans isomer may be formed depending on reaction conditions, and therefore the trans isomer is isomerized into a cis isomer according to a publicly-known method when necessary.

(8) Formation of —C≡C—

Compound (32) is obtained by allowing halide (23) to react with 2-methyl-3-butyn-2-ol in the presence of a catalyst of dichloropalladium and copper halide, and then performing deprotection under basic conditions. Compound (1H) is prepared by allowing compound (32) to react with halide (22) in the presence of the catalyst of dichloropalladium and copper halide.

(9) Formation of —CF═CF—

Compound (33) is obtained by treating halide (23) with n-butyllithium and then allowing the treated halide to react with tetrafluoroethylene. Compound (11) is prepared by treating halide (22) with n-butyllithium, and then allowing the treated halide to react with compound (33).

(10) Formation of $—OCH_2—$

Compound (34) is obtained by reducing aldehyde (28) with a reducing agent such as sodium borohydride. Bromide (35) is obtained by brominating compound (34) with hydrobromic acid or the like. Compound (1J) is prepared by allowing bromide (35) to react with compound (36) in the presence of a base such as potassium carbonate.

(11) Formation of $—CF_2CF_2—$

A compound having $—(CF_2)_2—$ is obtained by fluorinating diketone (—COCO—) with sulfur tetrafluoride, in the presence of a hydrogen fluoride catalyst, according to a method described in J. Am. Chem. Soc., 2001, 123, 5414.

(12) Formation of $—CH_2S—$

Compound (1K) is prepared by allowing bromide (35) to react with compound (37) in the presence of a base such as potassium carbonate.

2-2. Formation of Ring $A^1$ and Ring $A^2$

With regard to a ring such as 1,4-cyclohexylene, 1,4-phenylene, 2-fluoro-1,4-phenylene and 2,6-difluoro-1,4-phenylene, a starting material is commercially available or formation method thereof is well known. With regard to the formation of tetrahydropyran-2,5-diyl, see paragraphs from [0084] to [0107] in JP 2013-241397 A. With regard to the formation of 1,3-dioxane-2,5-diyl, see paragraphs from [0096] to [0119] in JP 2009-132927 A. With regard to the formation of pyrimidine-2,5-diyl and pyridine-2,5-diyl, see paragraphs from [0086] to [0094] in WO 2010/047260 A.

2-3. Method for Preparing Compound (1)

An example of a method for preparing compound (1) is as described below. An example of a method for preparing compound (50) in which $Z^2$ is $CF_2O$ and $Y^1$ is hydrogen in compound (1B) is as described below. Acid chloride (42) is obtained by allowing commercially available carboxylic acid (41) to react with oxalyl chloride. Ketone (43) is obtained by allowing acid chloride (42) to react with ethylene in the presence of aluminum chloride. Phenol (44) is obtained by allowing ketone (43) to react with hydrobromic acid in the presence of N-bromosuccinimide (NBS). Compound (46) is obtained by allowing phenol (44) to react with compound (45) that can be prepared by a publicly-known method in the presence of tetrabutylammonium bromide (TBAB) and potassium carbonate. Compound (47) is obtained by allowing compound (46) to react with BuLi and subsequently with iodine. Compound (48) is obtained by allowing compound (47) to react with trimethylsilyl acetylene in the presence of $Pd(PPh_3)_2Cl_2$ and copper iodide. Compound (49) is obtained by allowing compound (48) to react with potassium carbonate. Compound (50) is prepared by allowing compound (49) to react with $TMSCF_3$ in the presence of copper iodide, tetramethylethylenediamine (TMEDA) and potassium carbonate. In the compounds, symbols such as $R^1$ and ring $A^1$ are defined in a manner identical with the symbols described in item 1.

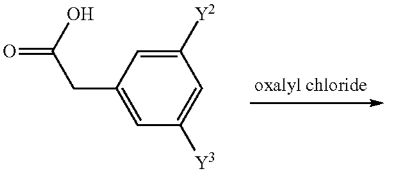

(41)

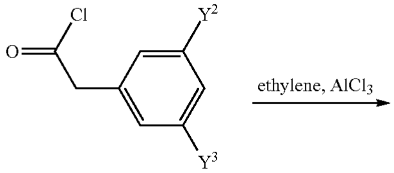

(42)

-continued

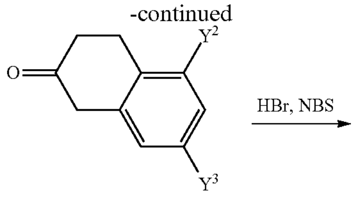

(43)

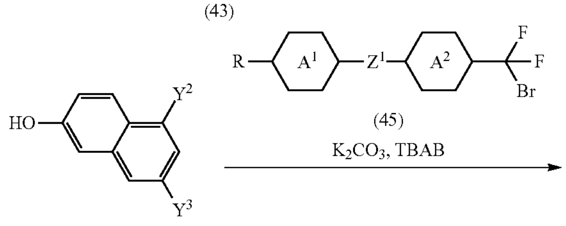

(44)

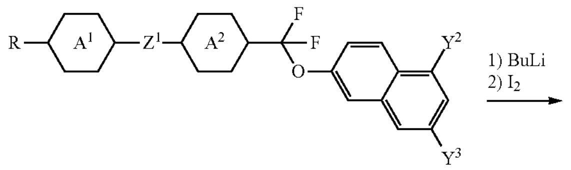

(46)

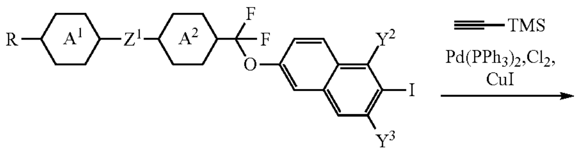

(47)

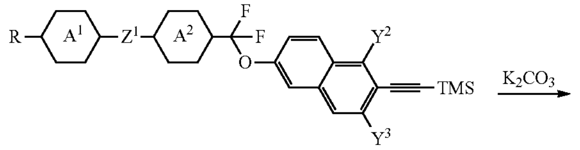

(48)

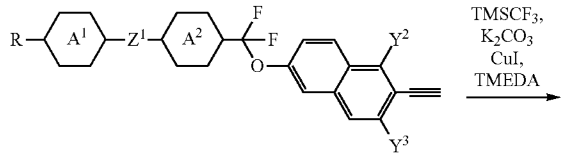

(49)

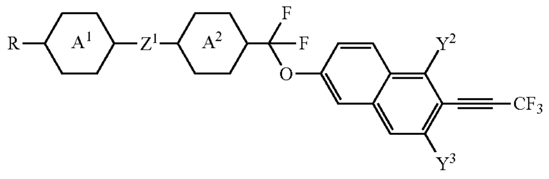

(50)

3. Liquid Crystal Composition 3-1. Component Compound

A liquid crystal composition of the invention will be described. The composition contains at least one compound (1) as component A. The composition may contain two, three or more compounds (1). A component in the composition may be only compound (1). In order to develop excellent physical properties, the composition preferably contains at least one of compounds (1) in the range of 1% by weight to 99% by weight. In a composition having positive dielectric anisotropy, a preferred content of compound (1) is in the range of 5% by weight to 60% by weight. In a composition having negative dielectric anisotropy, a preferred content of compound (1) is 30% by weight or less.

TABLE 1

Dielectric anisotropy of component compounds

| Component in composition | Component compound | Dielectric anisotropy |
|---|---|---|
| Component A | Compound (1) | Positively large |
| Component B | Compound (2) to Compound (4) | Small |
| Component C | Compound (5) to Compound (7) | Positively large |
| Component D | Compound (8) | Positively large |
| Component E | Compound (9) to Compound (15) | Negatively large |

The composition contains compound (1) as component A, and further preferably contains a liquid crystal compound selected from components B, C, D and E described in Table 1. When the composition is prepared, components B, C, D and E are preferably selected by taking into account the positive or negative dielectric anisotropy and magnitude of the dielectric anisotropy. The composition may contain a liquid crystal compound different from compounds (1) to (15). The composition may not contain such a liquid crystal compound.

Component B includes a compound in which two terminal groups are alkyl or the like. Preferred examples of component B include compounds (2-1) to (2-11), compounds (3-1) to (3-19) and compounds (4-1) to (4-8). In the compounds, $R^{11}$ and $R^{12}$ are independently alkyl having 1 to 10 carbons or alkenyl having 2 to 10 carbons, and in the alkyl and the alkenyl, at least one $—CH_2—$ may be replaced by —O—, and in the groups, at least one hydrogen may be replaced by fluorine.

(2-1)

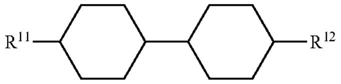

(2-2)

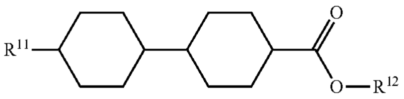

(2-3)

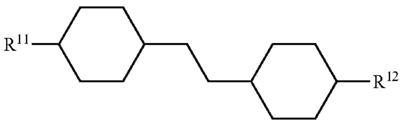

(2-4)

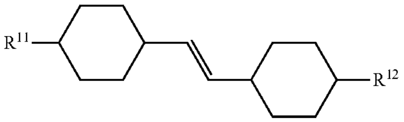

(2-5)

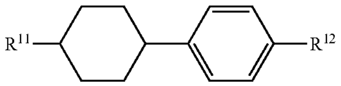

(2-6)

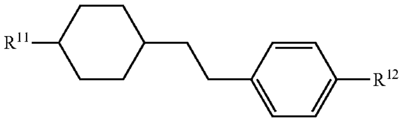

-continued
(2-7)
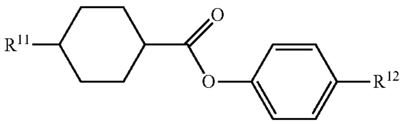
(2-8)
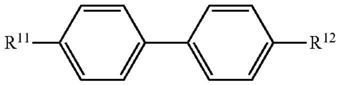
(2-9)
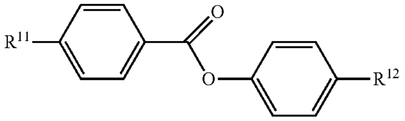
(2-10)
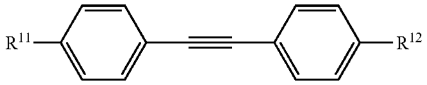
(2-11)
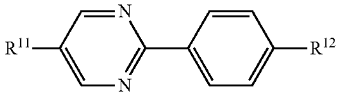
(3-1)
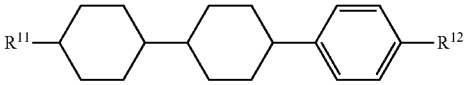
(3-2)
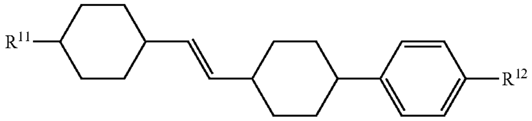
(3-3)
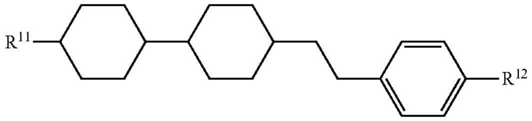
(3-4)
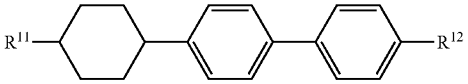
(3-5)
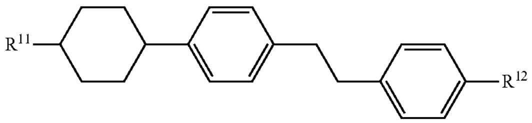
(3-6)
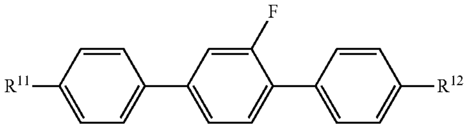
(3-7)
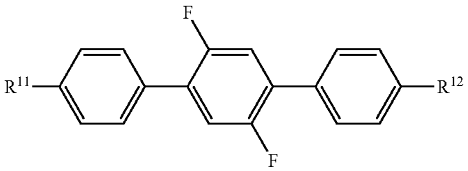
-continued
(3-8)
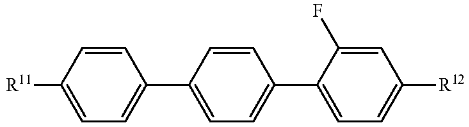
(3-9)
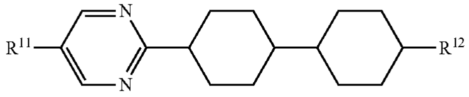
(3-10)
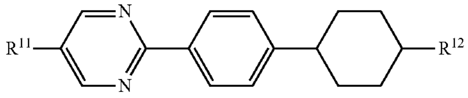
(3-11)
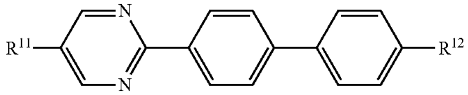
(3-12)
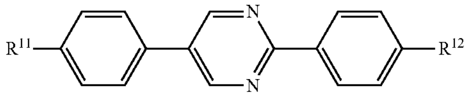
(3-13)
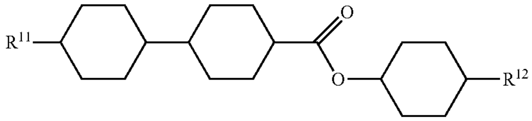
(3-14)
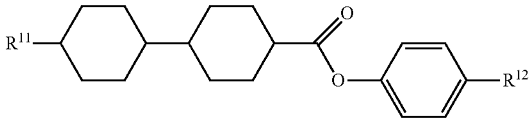
(3-15)
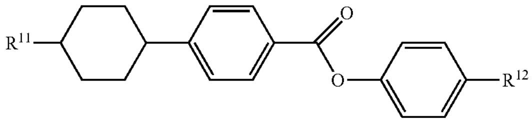
(3-16)
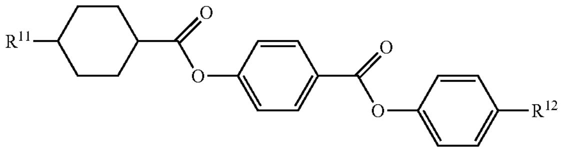
(3-17)
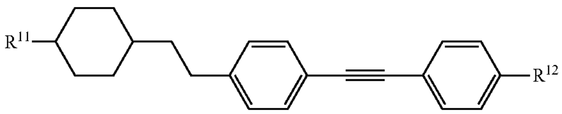
(3-18)
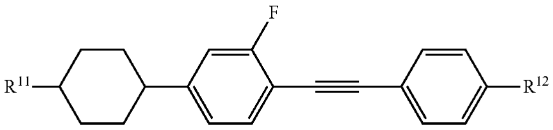

-continued (3-19)

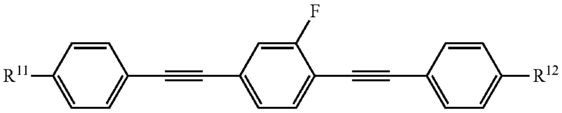

(4-1)

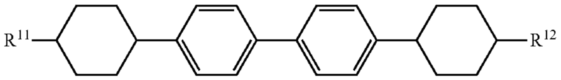

(4-2)

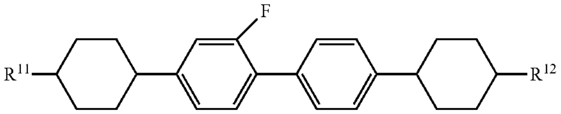

(4-3)

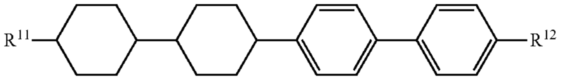

(4-4)

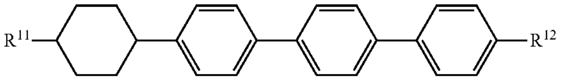

(4-5)

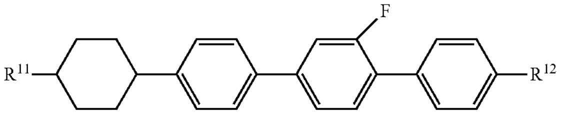

(4-6)

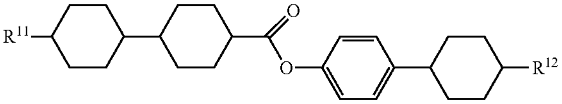

(4-7)

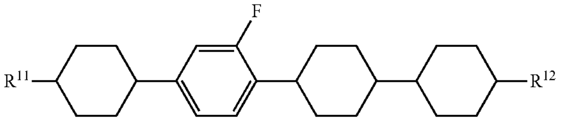

(4-8)

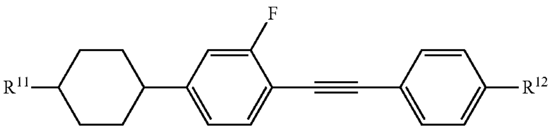

Component B has small dielectric anisotropy. Component B is close to neutrality. Compound (2) is effective in decreasing the viscosity or adjusting the optical anisotropy. Compounds (3) and (4) are effective in extending the temperature range of the nematic phase by increasing the maximum temperature, or in adjusting the optical anisotropy.

As a content of component B is increased, the viscosity of the composition is decreased, but the dielectric anisotropy is decreased. Thus, as long as a desired value of threshold voltage of a device is met, the content is preferably as large as possible. When a composition for the IPS mode, the VA mode or the like is prepared, the content of component B is preferably 30% by weight or more, and further preferably 40% by weight or more, based on the weight of the liquid crystal composition.

Component C is a compound having a halogen-containing group or a fluorine-containing group at a right terminal. Preferred examples of component C include compounds (5-1) to (5-16), compounds (6-1) to (6-113) and compounds (7-1) to (7-58). In the compounds, $R^{13}$ is alkyl having 1 to 10 carbons or alkenyl having 2 to 10 carbons, and in the alkyl and the alkenyl, at least one $—CH_2—$ may be replaced by —O—, and in the groups, at least one hydrogen may be replaced by fluorine. $X^{11}$ is fluorine, chlorine, $—OCF_3$, $—OCHF_2$, $—CF_3$, $—CHF_2$, $—CH_2F$, $—OCF_2CHF_2$ or $—OCF_2CHFCF_3$.

(5-1)

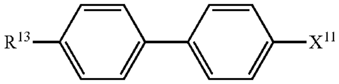

(5-2)

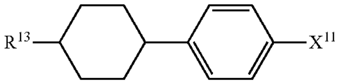

(5-3)

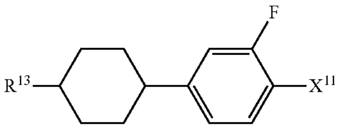

(5-4)

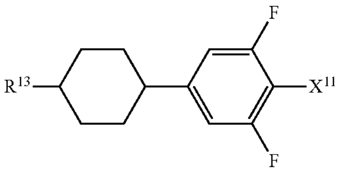

(5-5)

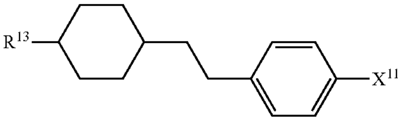

(5-6)

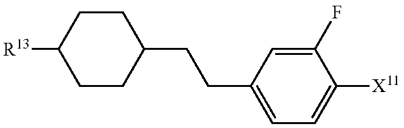

(5-7)

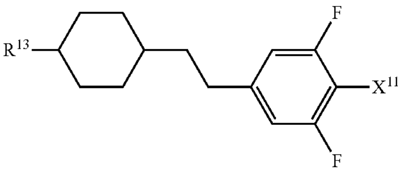

(5-8)

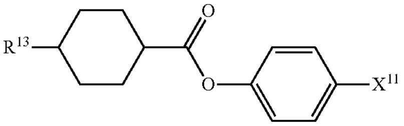

(5-9)

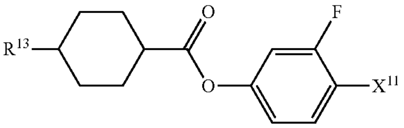

-continued
(5-10)
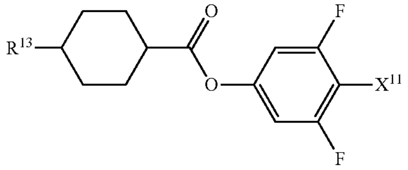
(5-11)
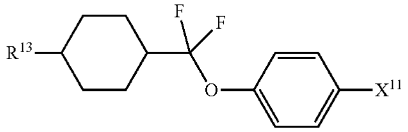
(5-12)
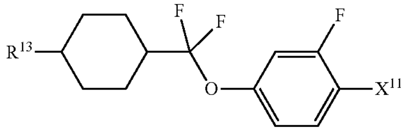
(5-13)
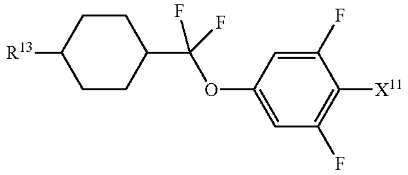
(5-14)
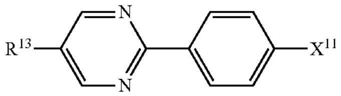
(5-15)
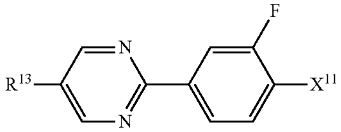
(5-16)
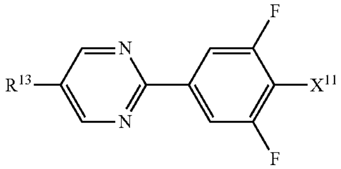
(6-1)
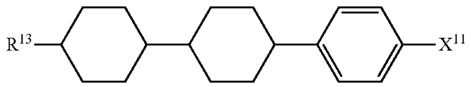
(6-2)
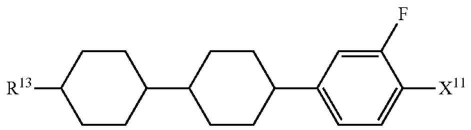
(6-3)
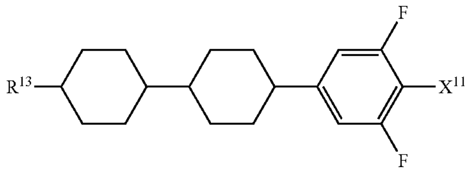
-continued
(6-4)
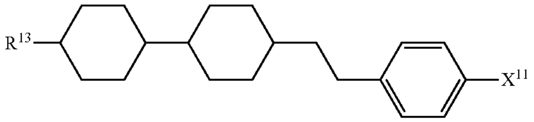
(6-5)
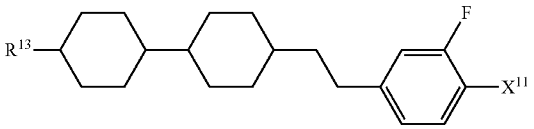
(6-6)
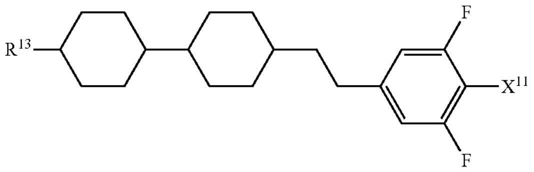
(6-7)
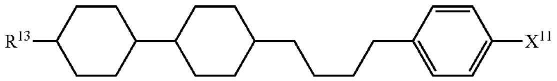
(6-8)
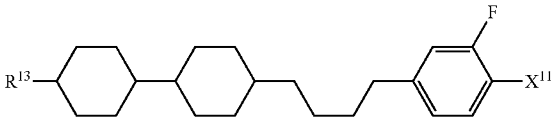
(6-9)
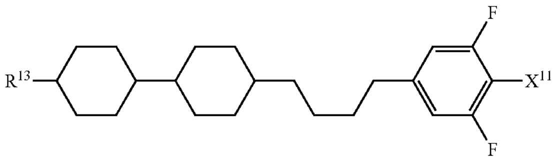
(6-10)
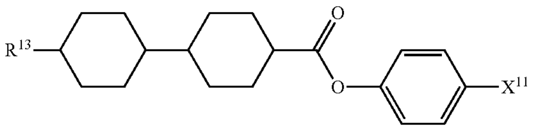
(6-11)
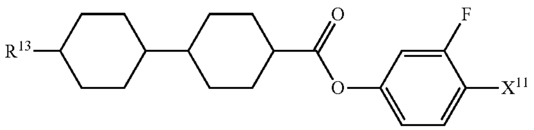
(6-12)
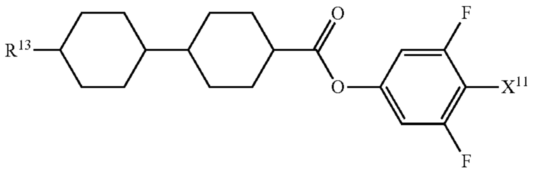
(6-13)
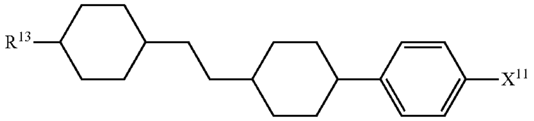

-continued
(6-14)
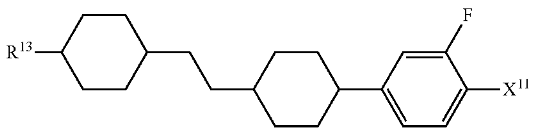
(6-15)
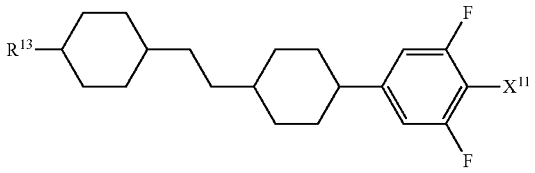
(6-16)
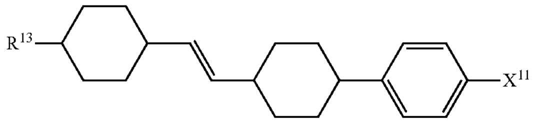
(6-17)
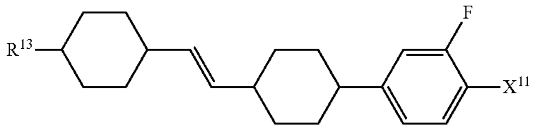
(6-18)
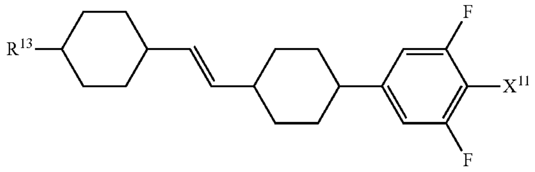
(6-19)
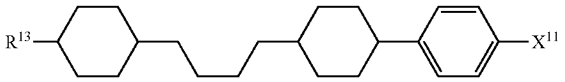
(6-20)
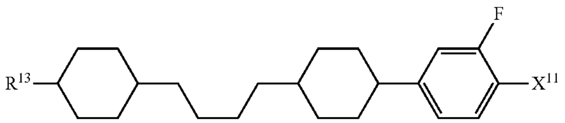
(6-21)
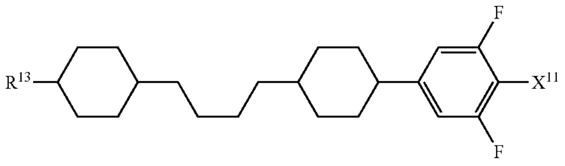
(6-22)
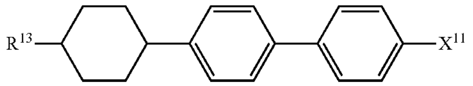
(6-23)
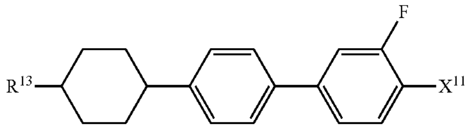
-continued
(6-24)
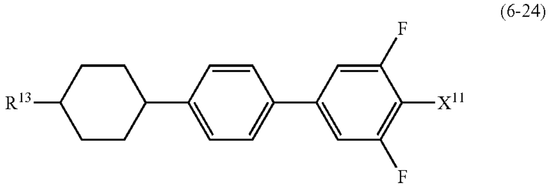
(6-25)
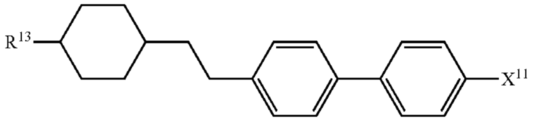
(6-26)
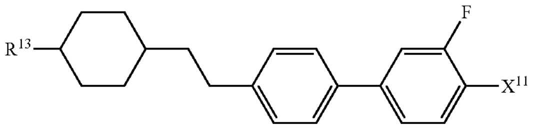
(6-27)
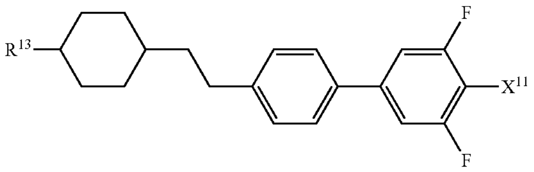
(6-28)
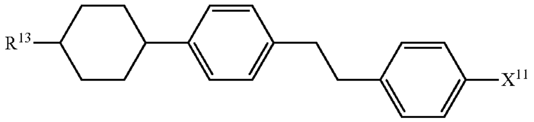
(6-29)
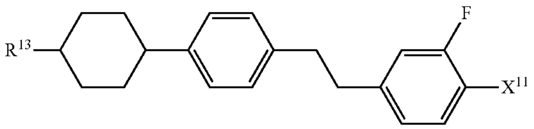
(6-30)
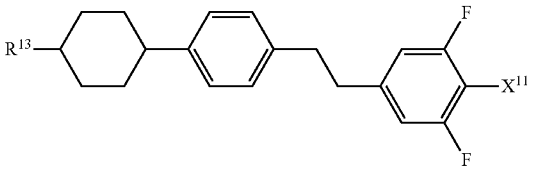
(6-31)
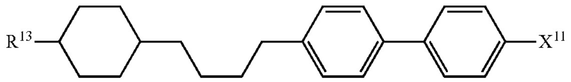
(6-32)
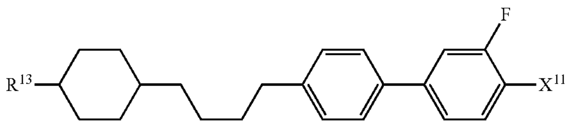

-continued
(6-33)
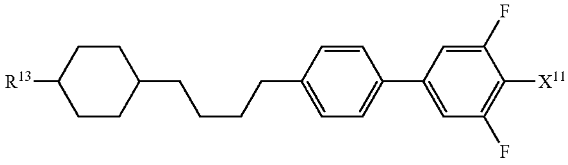
(6-34)
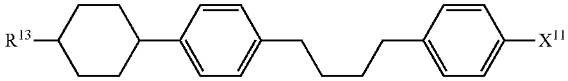
(6-35)
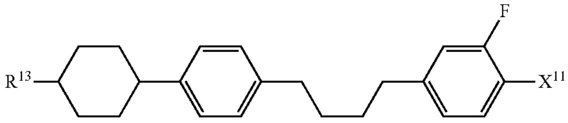
(6-36)
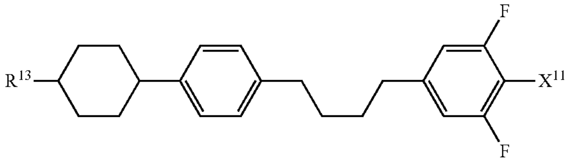
(6-37)
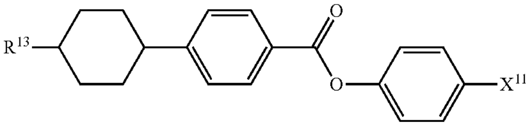
(6-38)
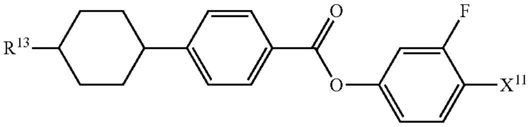
(6-39)
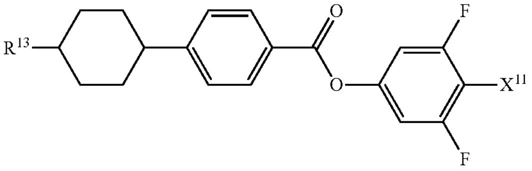
(6-40)
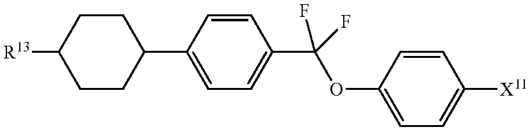
(6-41)
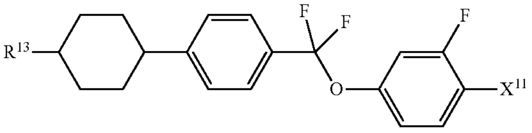
-continued
(6-42)
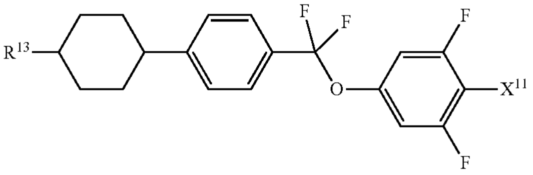
(6-43)
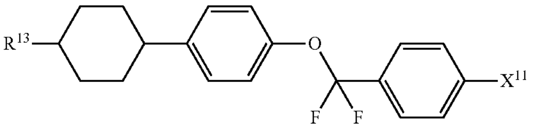
(6-44)
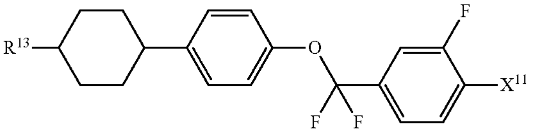
(6-45)
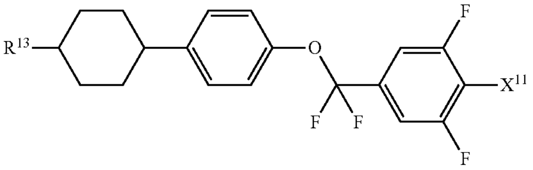
(6-46)
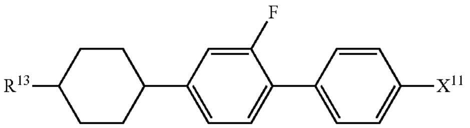
(6-47)
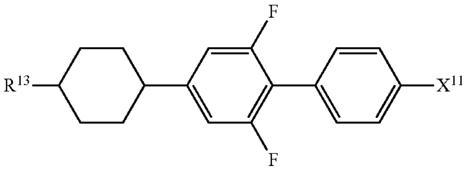
(6-48)
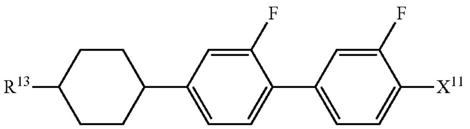
(6-49)
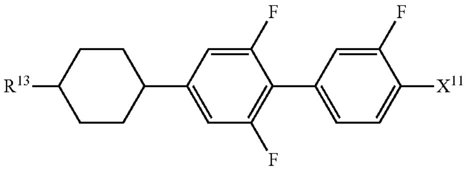
(6-50)
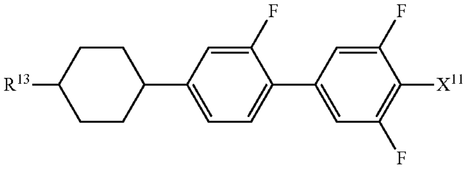

(6-51)
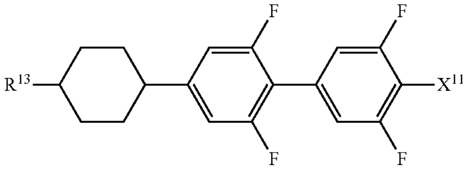
(6-52)
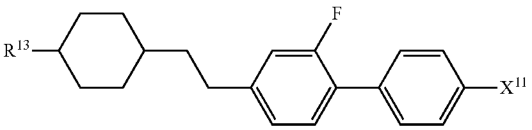
(6-53)
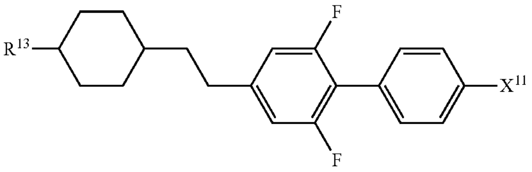
(6-54)
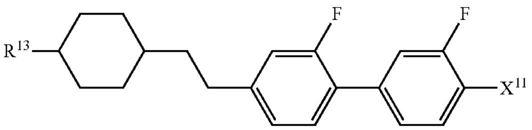
(6-55)
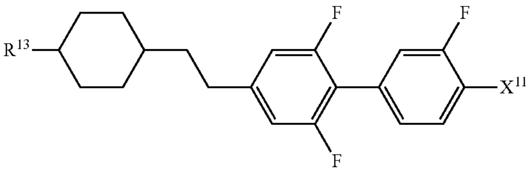
(6-56)
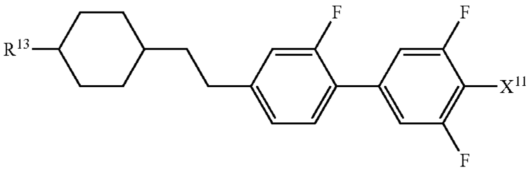
(6-57)
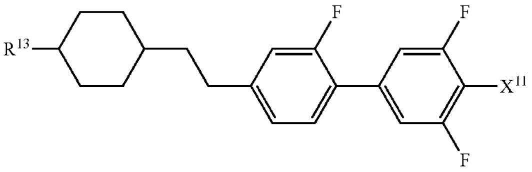
(6-58)
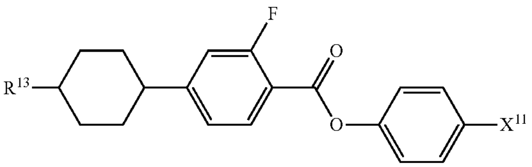
(6-59)
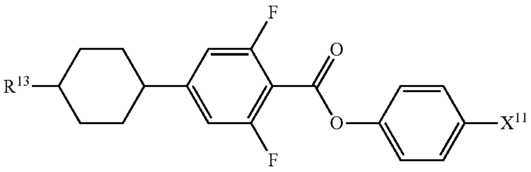
(6-60)
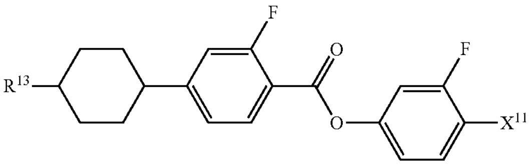
(6-61)
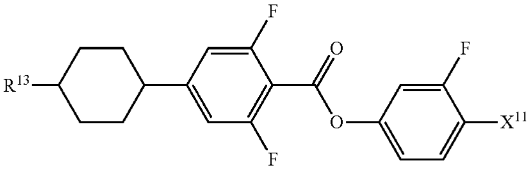
(6-62)
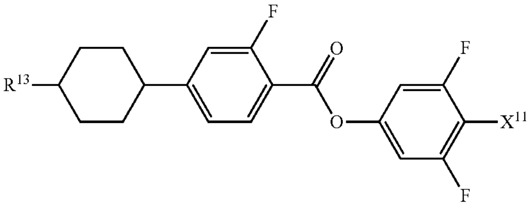
(6-63)
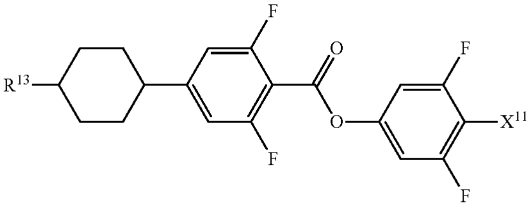
(6-64)
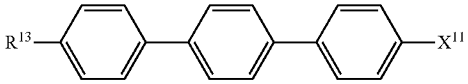
(6-65)
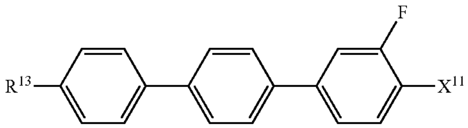
(6-66)
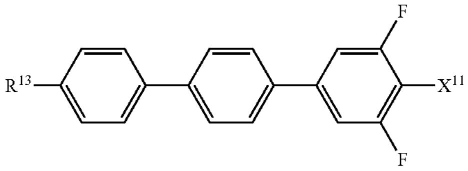
(6-67)
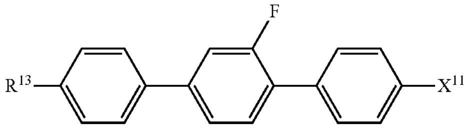

-continued
(6-68)
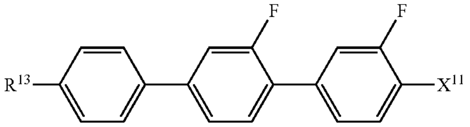
(6-69)
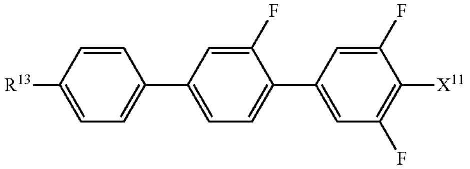
(6-70)
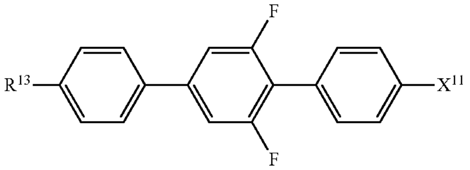
(6-71)
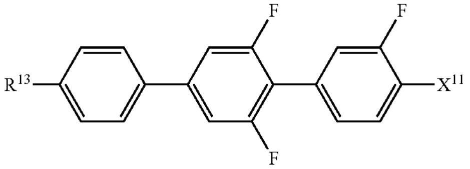
(6-72)
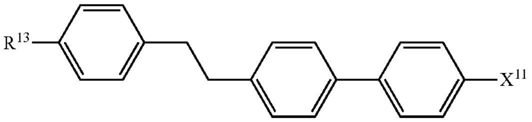
(6-73)
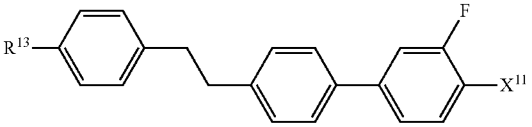
(6-74)
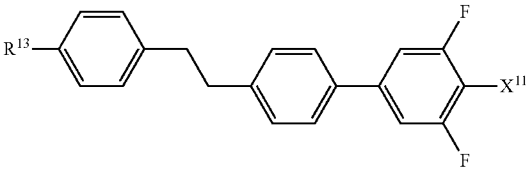
(6-75)
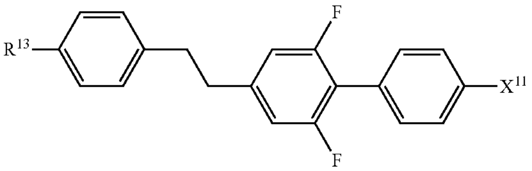
(6-76)
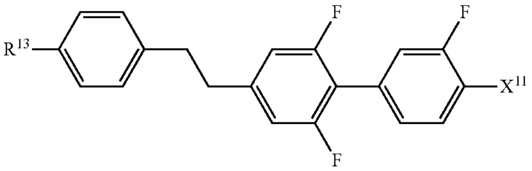
-continued
(6-77)
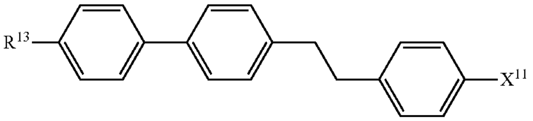
(6-78)
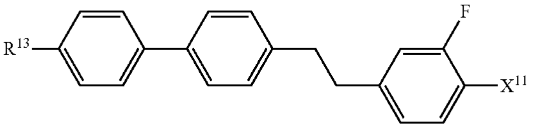
(6-79)
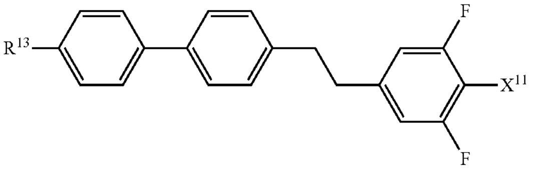
(6-80)
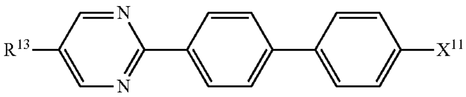
(6-81)
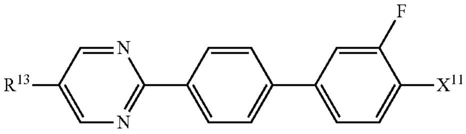
(6-82)
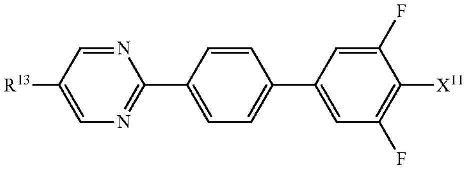
(6-83)
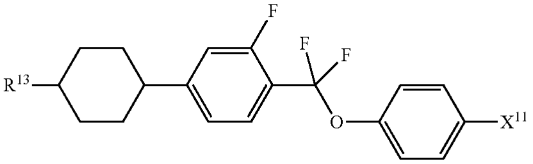
(6-84)
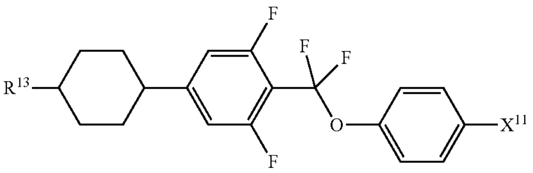
(6-85)
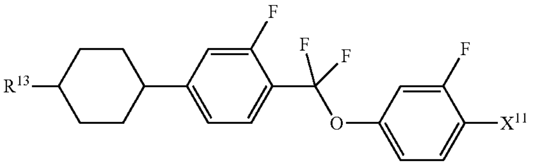

-continued
(6-86)
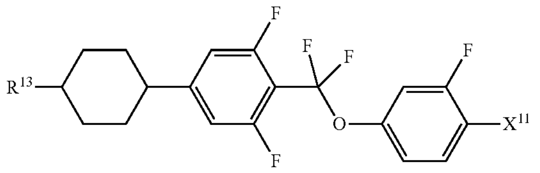
(6-87)
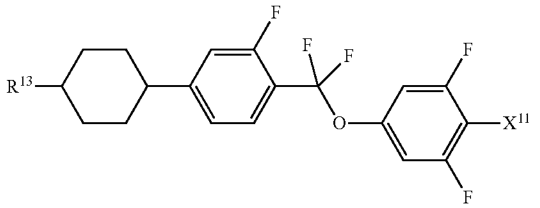
(6-88)
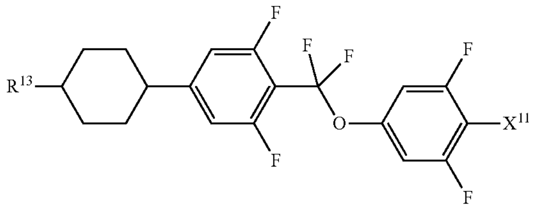
(6-89)
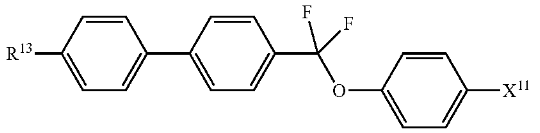
(6-90)
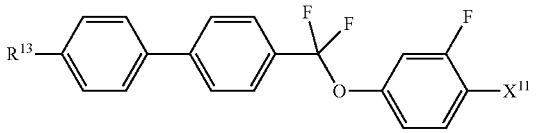
(6-91)
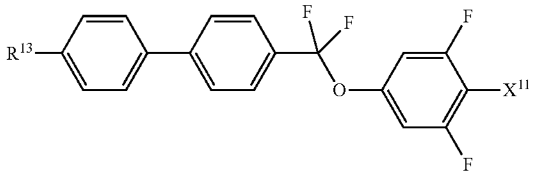
(6-92)
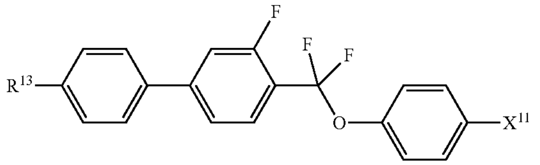
(6-93)
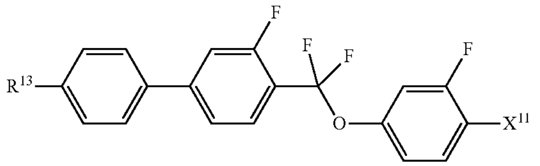
-continued
(6-94)
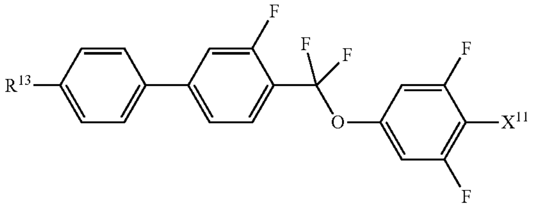
(6-95)
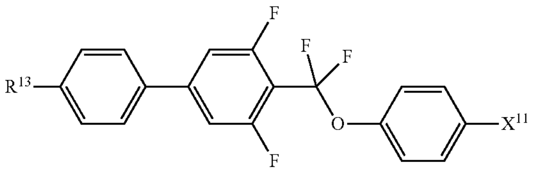
(6-96)
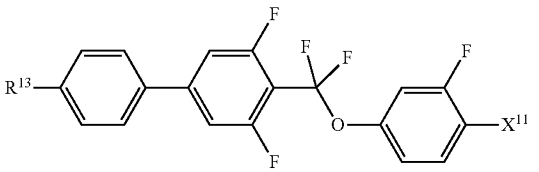
(6-97)
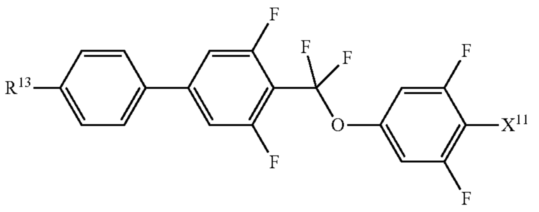
(6-98)
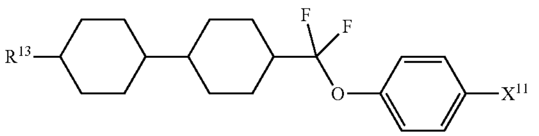
(6-99)
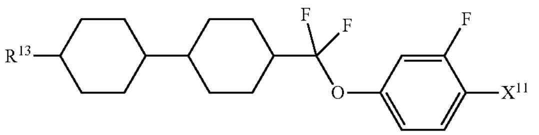
(6-100)
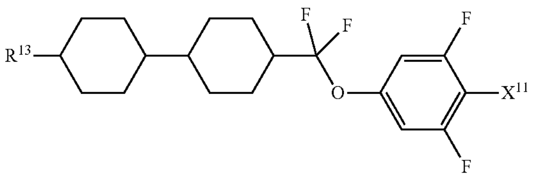
(6-101)
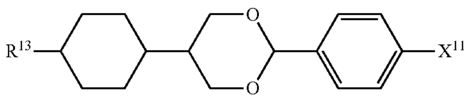

-continued
(6-102)
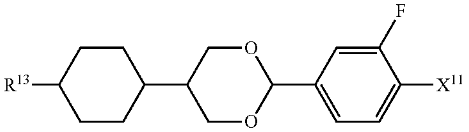
(6-103)
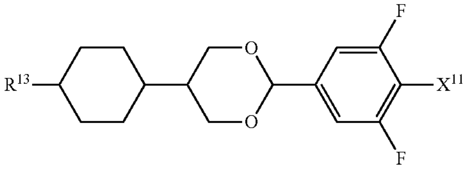
(6-104)
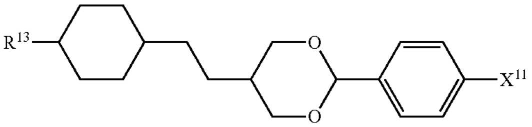
(6-105)
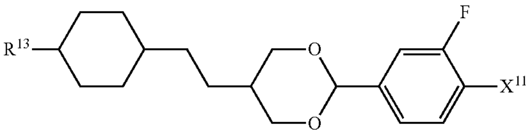
(6-106)
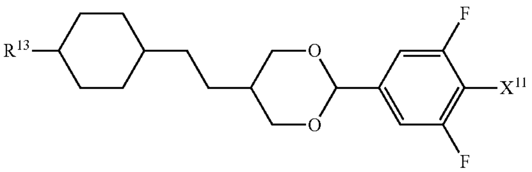
(6-107)
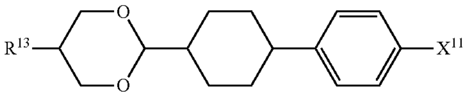
(6-108)
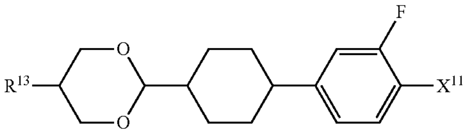
(6-109)
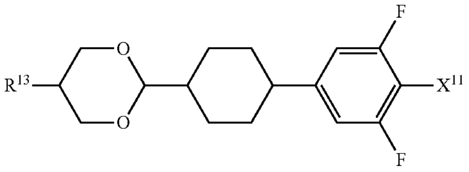
(6-110)
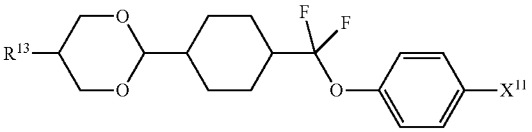
(6-111)
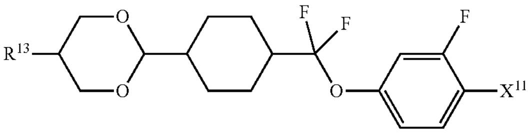
-continued
(6-112)
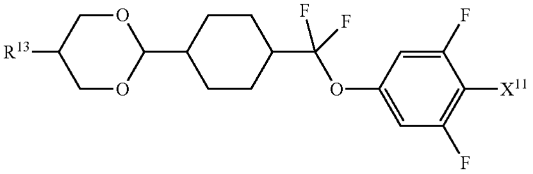
(6-113)
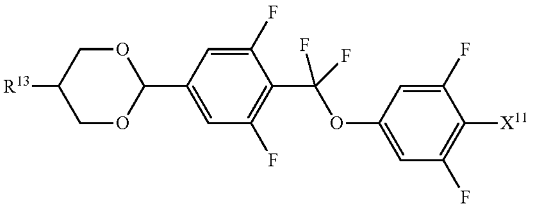
(7-1)
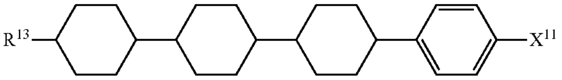
(7-2)
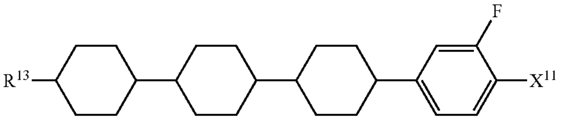
(7-3)
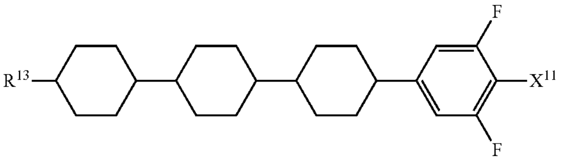
(7-4)
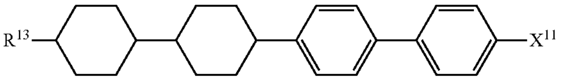
(7-5)
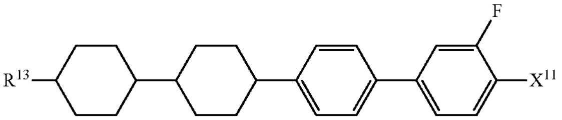
(7-6)
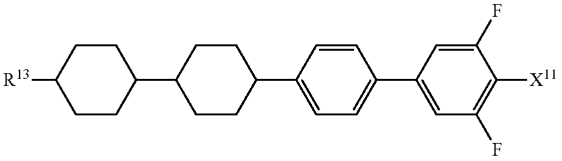
(7-7)
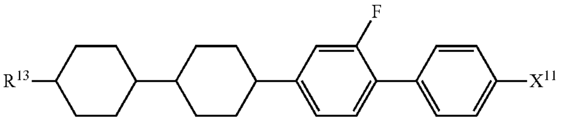

-continued
(7-8)
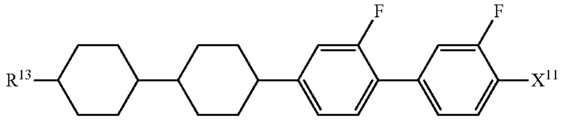
(7-9)
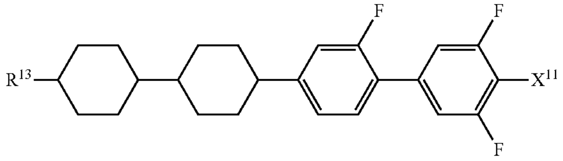
(7-10)
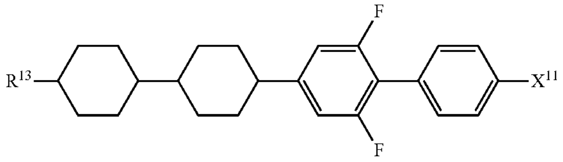
(7-11)
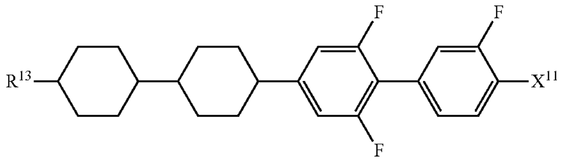
(7-12)
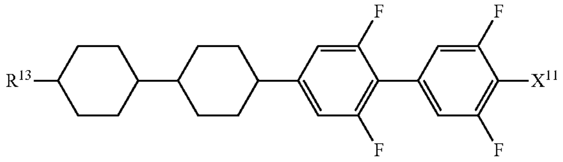
(7-13)
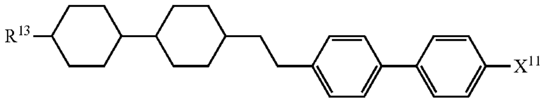
(7-14)
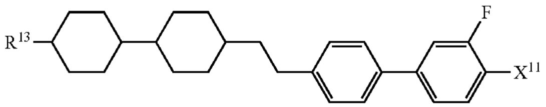
(7-15)
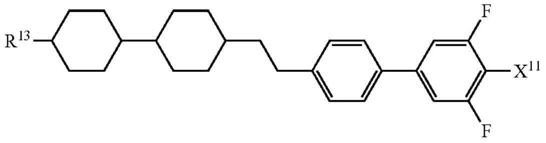
(7-16)
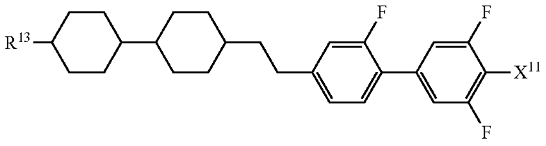
-continued
(7-17)
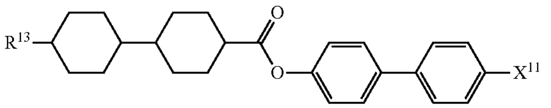
(7-18)
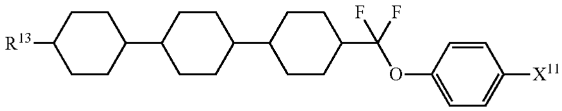
(7-19)
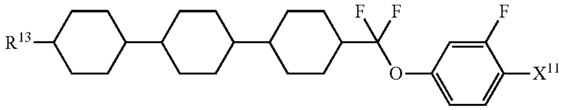
(7-20)
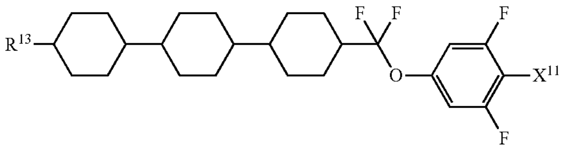
(7-21)
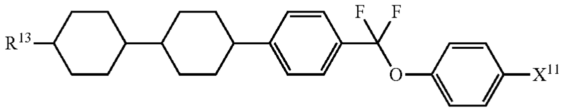
(7-22)
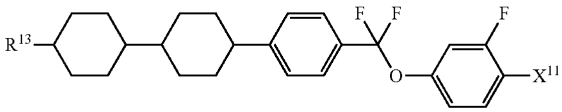
(7-23)
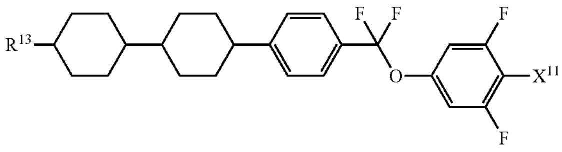
(7-24)
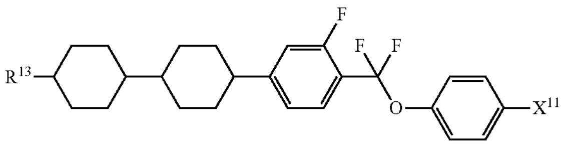
(7-25)
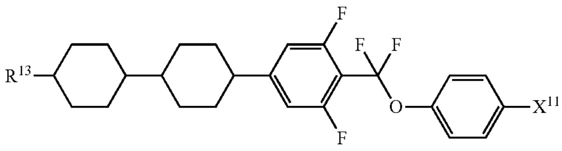
(7-26)
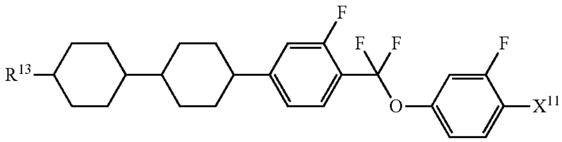

-continued
(7-27)
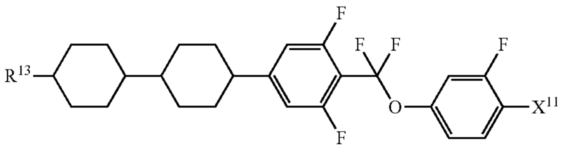
(7-28)
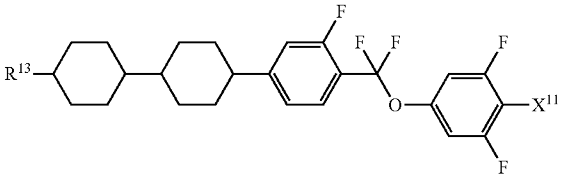
(7-29)
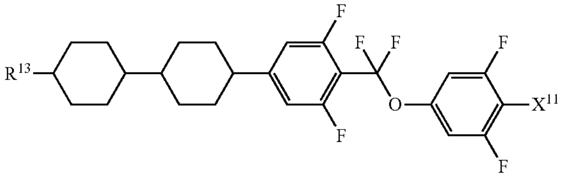
(7-30)
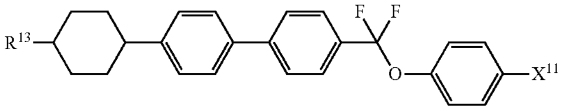
(7-31)
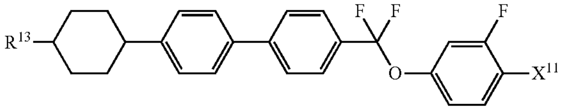
(7-32)
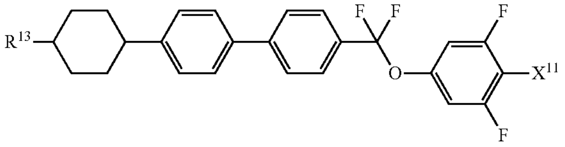
(7-33)
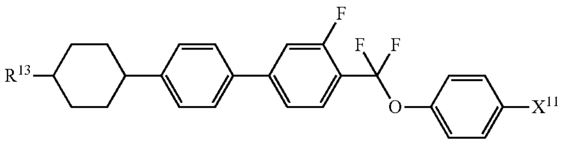
(7-34)
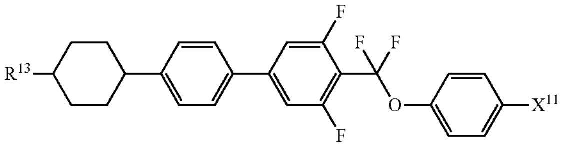
(7-35)
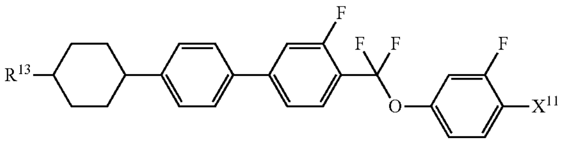
-continued
(7-36)
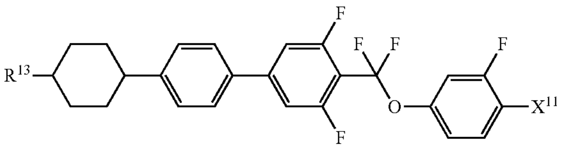
(7-37)
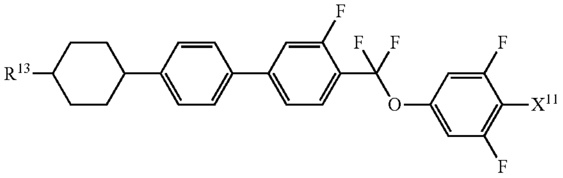
(7-38)
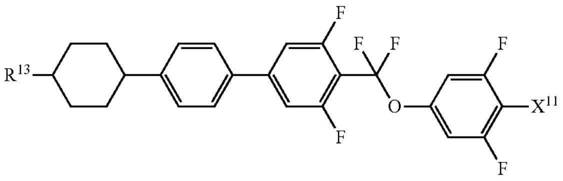
(7-39)
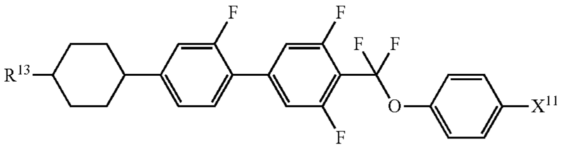
(7-40)
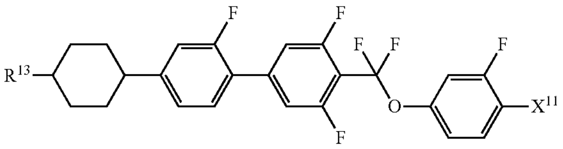
(7-41)
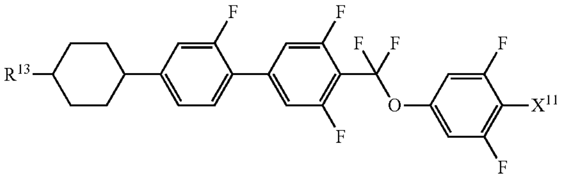
(7-42)
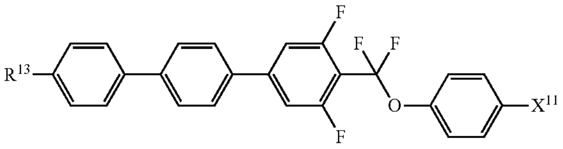
(7-43)
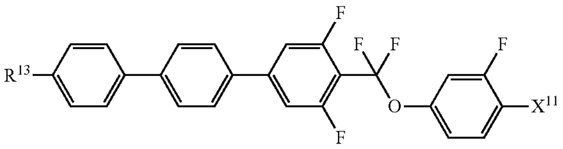

-continued (7-44)

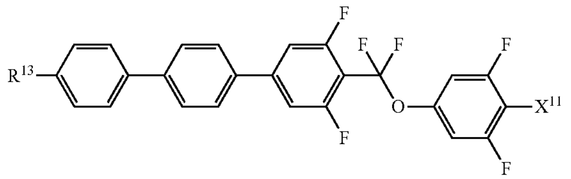

(7-45)

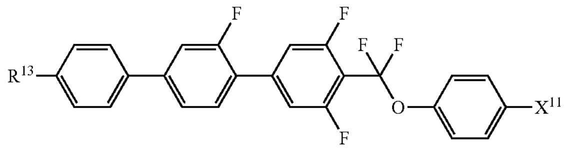

(7-46)

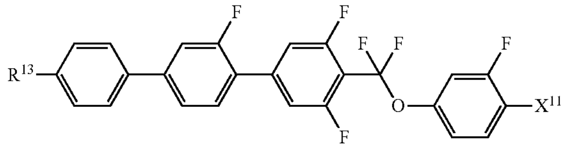

(7-47)

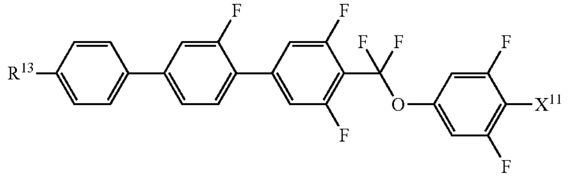

(7-48)

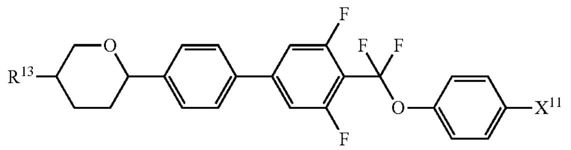

(7-49)

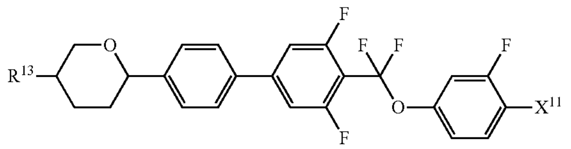

(7-50)

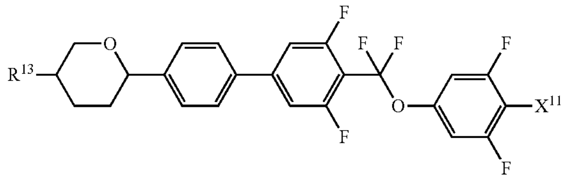

(7-51)

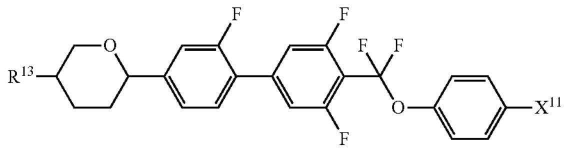

-continued (7-52)

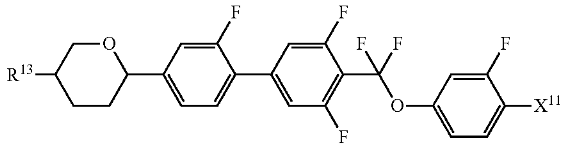

(7-53)

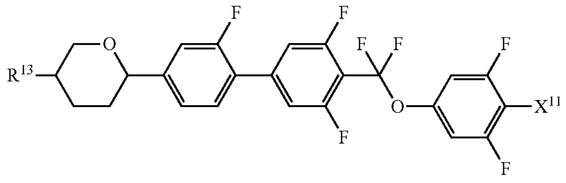

(7-54)

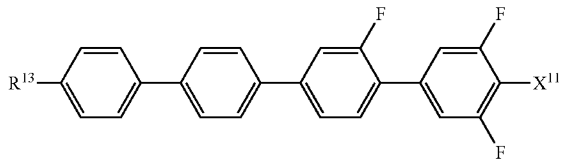

(7-55)

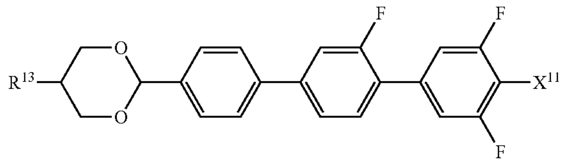

(7-56)

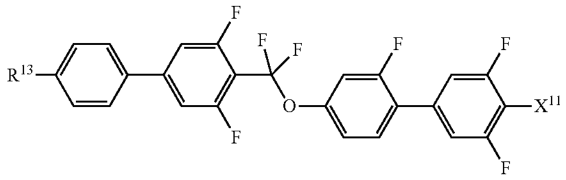

(7-57)

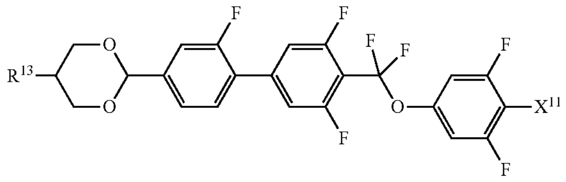

(7-58)

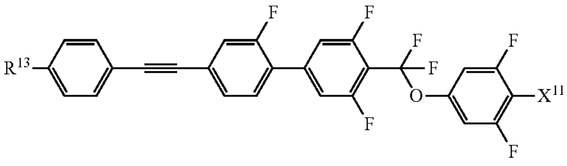

Component C has positive dielectric anisotropy, and significantly satisfactory stability to heat or light, and therefore is used when a composition for the IPS mode, the FFS mode, the OCB mode or the like is prepared. A content of component C is suitably in the range of 1% by weight to 99% by weight, preferably in the range of 10% by weight to 97% by weight, and further preferably in the range of 40% by weight to 95% by weight, based on the weight of the liquid crystal composition. When component C is added to a composition having negative dielectric anisotropy, the content of component C is preferably 30% by weight or less. Addition of component C allows adjustment of the elastic constant of the composition and adjustment of a voltage-transmittance curve of the device.

Component D is compound (8) in which a right terminal group is —C≡N or —C≡C—C≡N. Preferred examples of component D include compounds (8-1) to (8-64). In the compounds, $R^{14}$ is alkyl having 1 to 10 carbons or alkenyl having 2 to 10 carbons, and in the alkyl and the alkenyl, at least one —$CH_2$— may be replaced by —O—, and in the groups, at least one hydrogen may be replaced by fluorine. $X^{12}$ is —C≡N or —C≡C—C≡N.

(8-1)

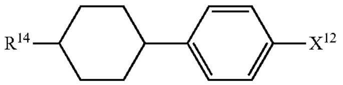

(8-2)

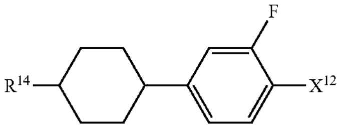

(8-3)

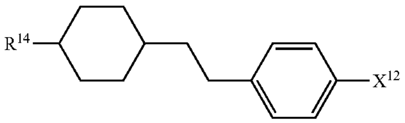

(8-4)

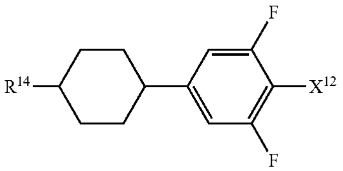

(8-5)

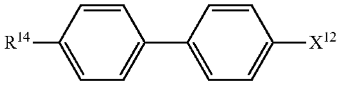

(8-6)

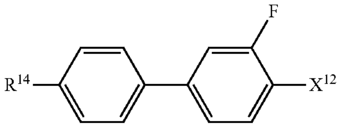

(8-7)

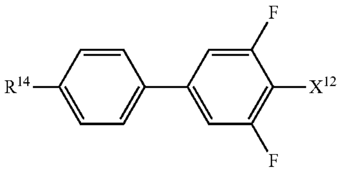

(8-8)

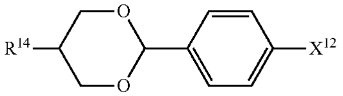

(8-9)

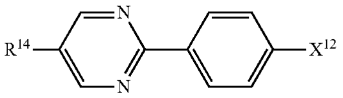

-continued (8-10)

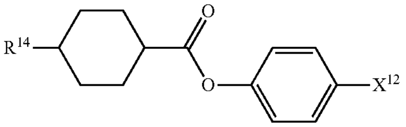

(8-11)

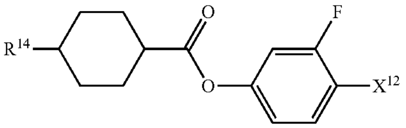

(8-12)

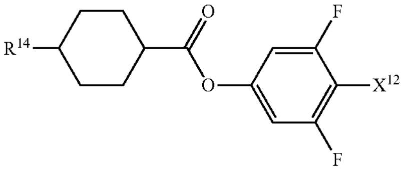

(8-13)

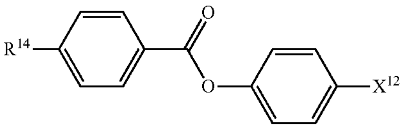

(8-14)

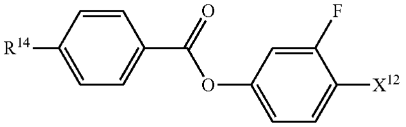

(8-15)

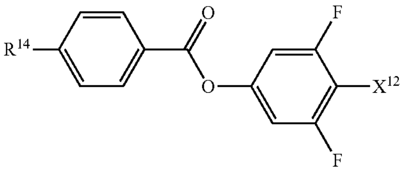

(8-16)

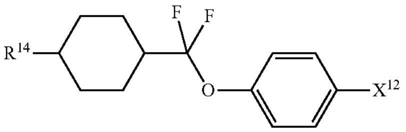

(8-17)

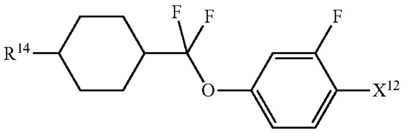

(8-18)

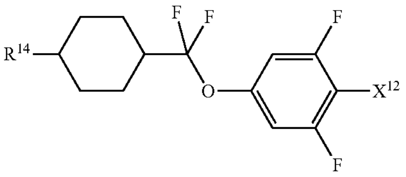

(8-19)

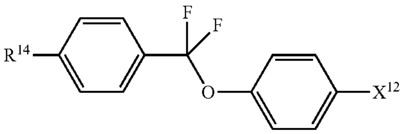

-continued
(8-20)
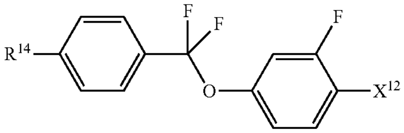
(8-21)
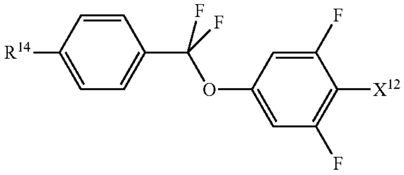
(8-22)
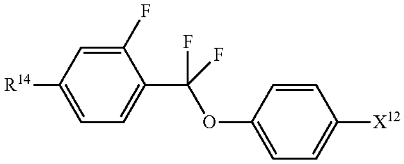
(8-23)
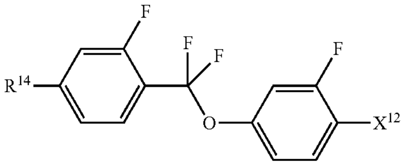
(8-24)
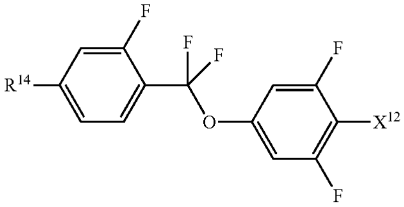
(8-25)
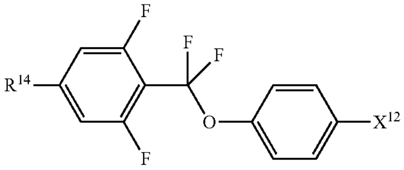
(8-26)
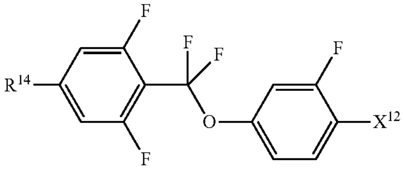
(8-27)
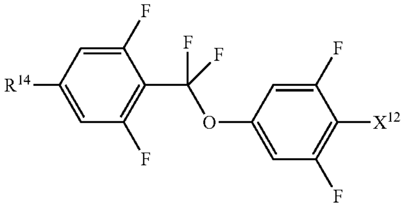
(8-28)
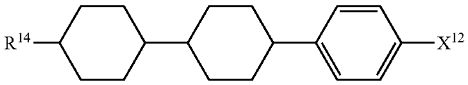
-continued
(8-29)
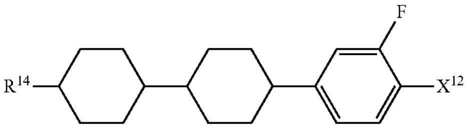
(8-30)
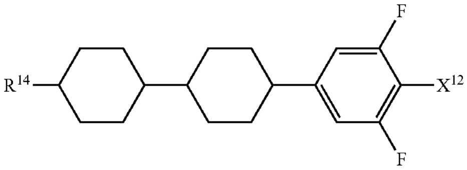
(8-31)
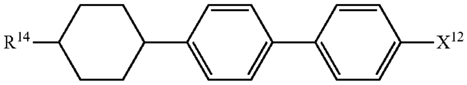
(8-32)
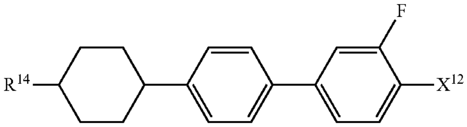
(8-33)
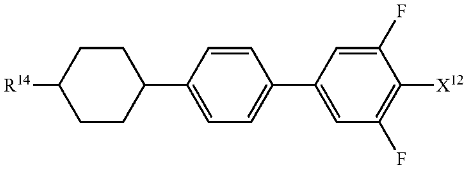
(8-34)
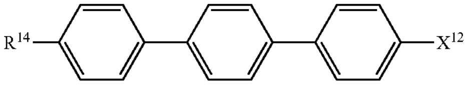
(8-35)
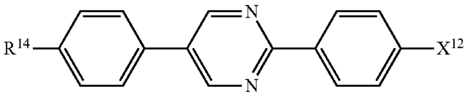
(8-36)
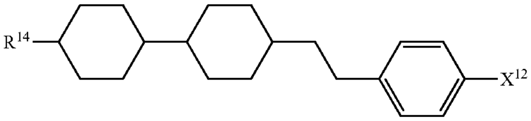
(8-37)
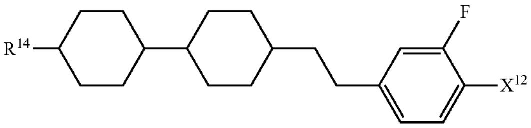
(8-38)
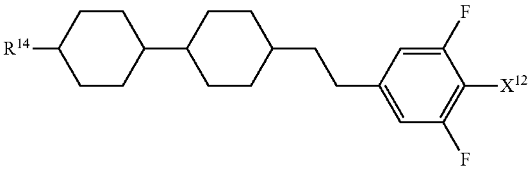

-continued
(8-39)
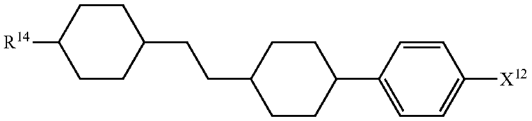
(8-40)
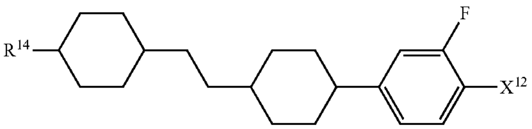
(8-41)
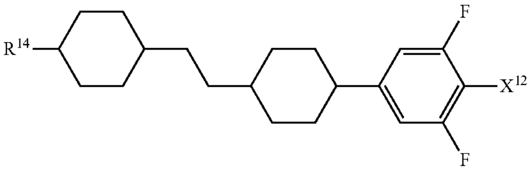
(8-42)
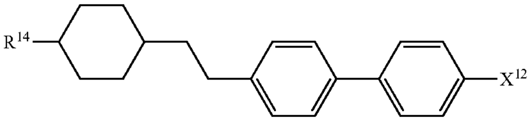
(8-43)
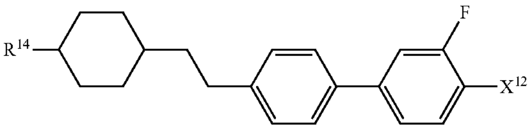
(8-44)
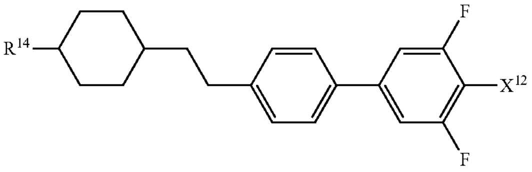
(8-45)
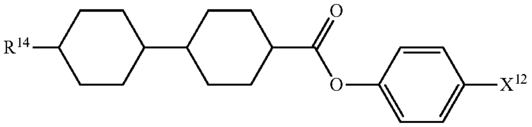
(8-46)
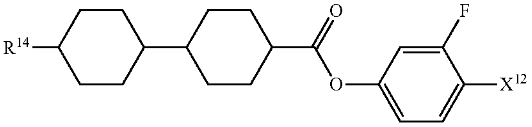
(8-47)
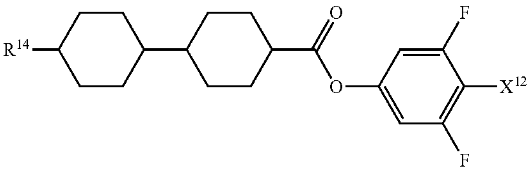
-continued
(8-48)
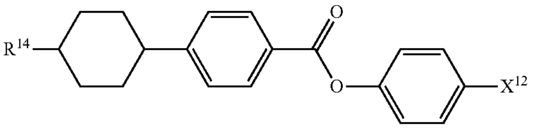
(8-49)
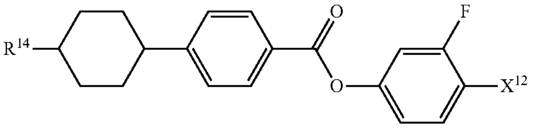
(8-50)
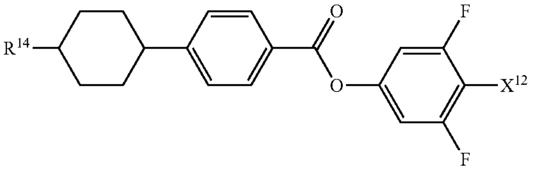
(8-51)
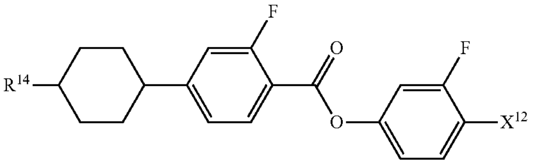
(8-52)
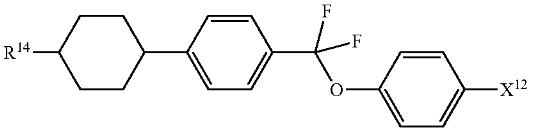
(8-53)
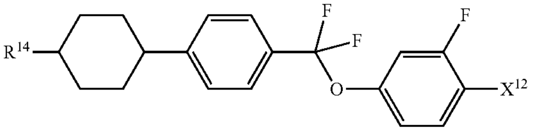
(8-54)
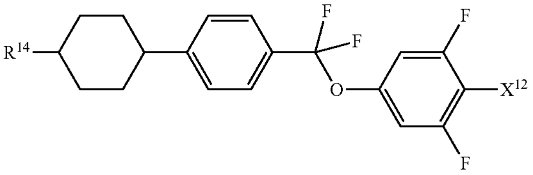
(8-55)
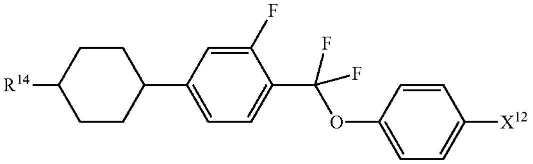
(8-56)
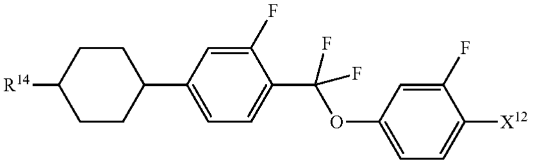

-continued (8-57)

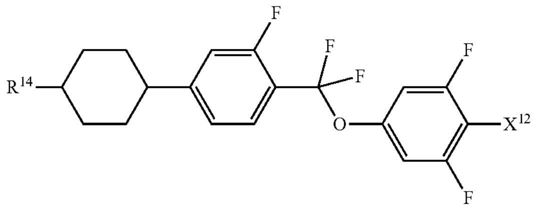

(8-58)

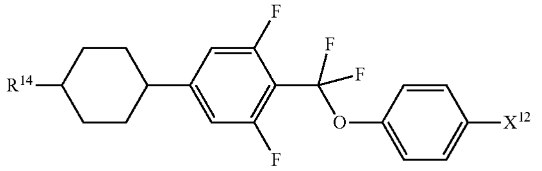

(8-59)

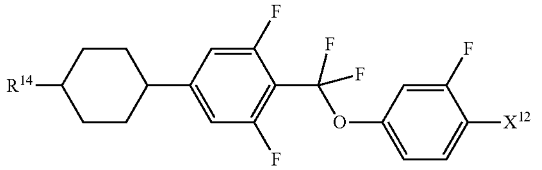

(8-60)

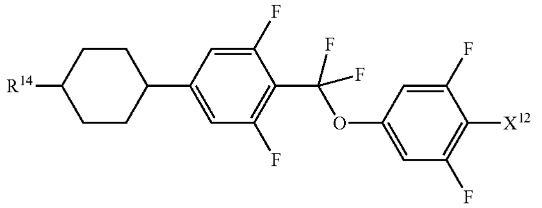

(8-61)

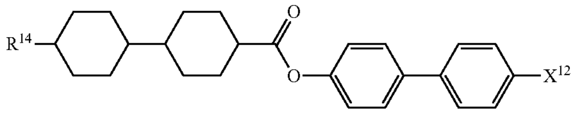

(8-62)

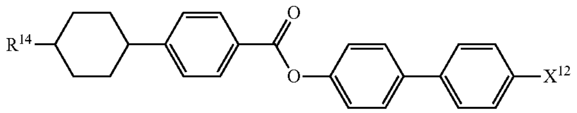

(8-63)

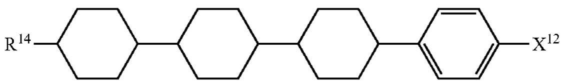

(8-64)

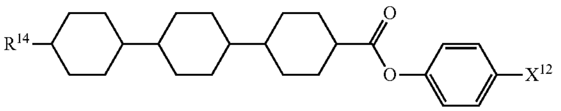

Component D has positive dielectric anisotropy and a value thereof is large, and therefore is used when a composition for the TN mode or the like is prepared. Addition of component D can increase the dielectric anisotropy of the composition. Component D is effective in extending the temperature range of the liquid crystal phase, adjusting the viscosity or adjusting the optical anisotropy. Component D is also useful for adjustment of the voltage-transmittance curve of the device.

When the composition for the TN mode or the like is prepared, a content of component D is suitably in the range of 1% by weight to 99% by weight, preferably in the range of 10% by weight to 97% by weight, and further preferably in the range of 40% by weight to 95% by weight, based on the weight of the liquid crystal composition. When component D is added to a composition having negative dielectric anisotropy, the content of component D is preferably 30% by weight or less. Addition of component D allows adjustment of the elastic constant of the composition and adjustment of the voltage-transmittance curve of the device.

Component E includes compounds (9) to (15). The compounds have phenylene in which hydrogen in lateral positions are replaced by two halogens, such as 2,3-difluoro-1,4-phenylene. Preferred examples of component E include compounds (9-1) to (9-8), compounds (10-1) to (10-17), compound (11-1), compounds (12-1) to (12-3), compounds (13-1) to (13-11), compounds (14-1) to (14-3) and compounds (15-1) to (15-3). In the compounds, $R^{15}$, $R^{16}$ and $R^{17}$ are independently alkyl having 1 to 10 carbons or alkenyl having 2 to 10 carbons, and in the alkyl and the alkenyl, at least one $-CH_2-$ may be replaced by $-O-$, and in the groups, at least one hydrogen may be replaced by fluorine, and $R^{17}$ may be hydrogen or fluorine.

(9-1)

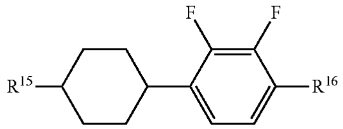

(9-2)

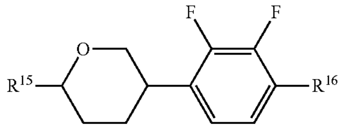

(9-3)

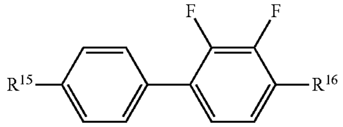

(9-4)

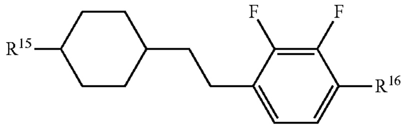

(9-5)

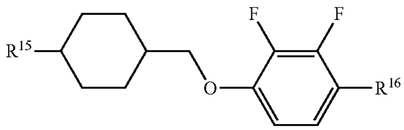

(9-6)

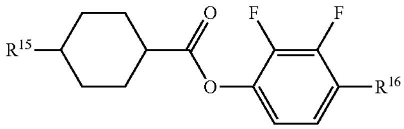

(9-7)

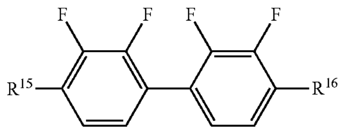

-continued
(9-8)
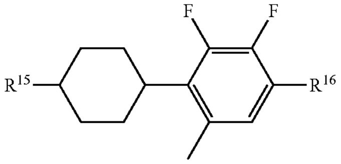
(10-1)
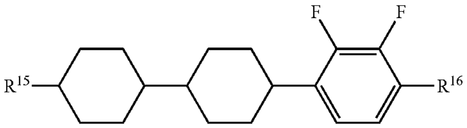
(10-2)
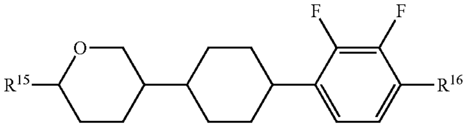
(10-3)
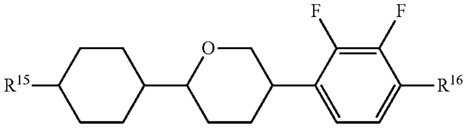
(10-4)
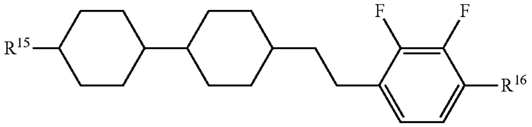
(10-5)
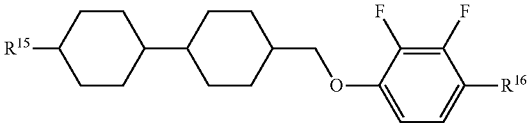
(10-6)
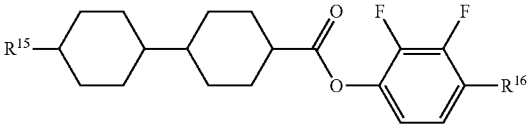
(10-7)
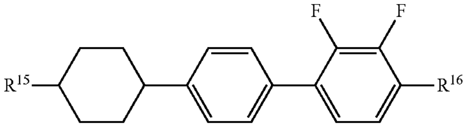
(10-8)
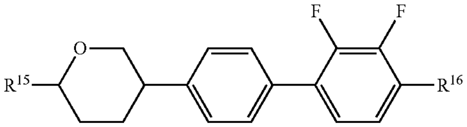
(10-9)
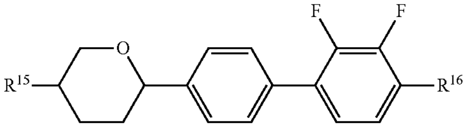
-continued
(10-10)
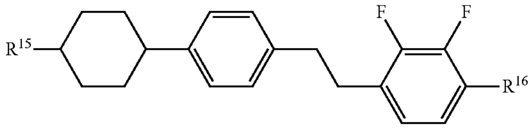
(10-11)
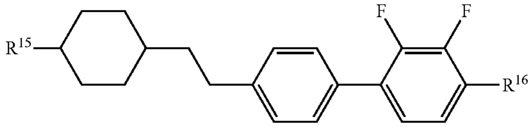
(10-12)
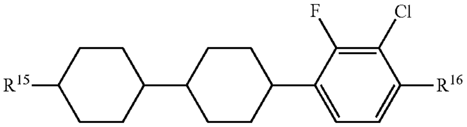
(10-13)
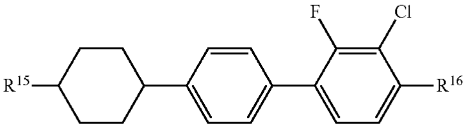
(10-14)
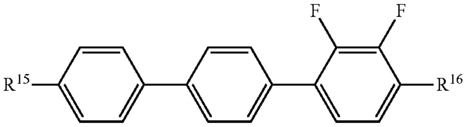
(10-15)
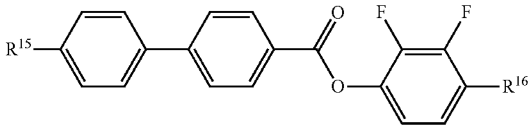
(10-16)
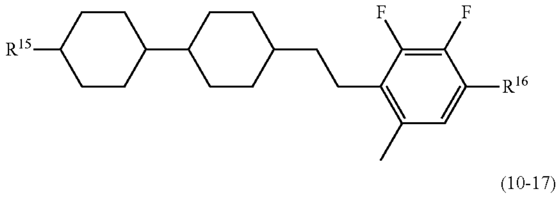
(10-17)
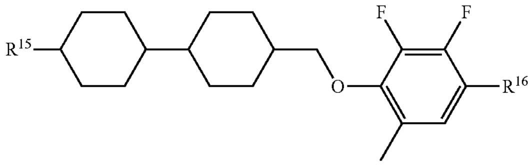
(11-1)
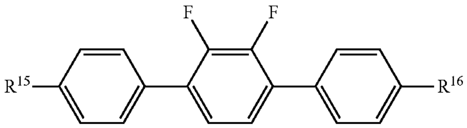
(12-1)
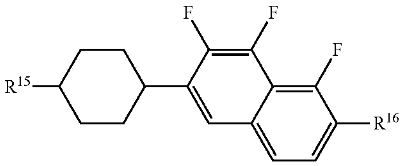

-continued
(12-2)
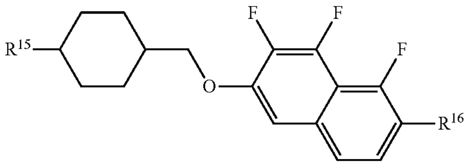
(12-3)
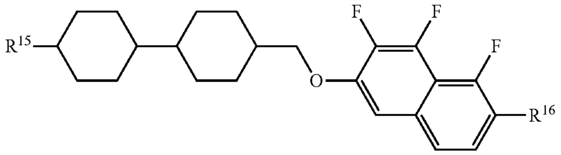
(13-1)
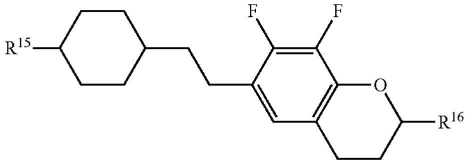
(13-2)
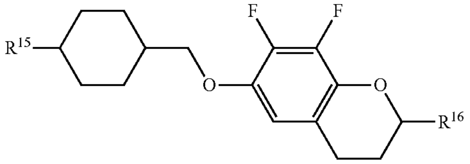
(13-3)
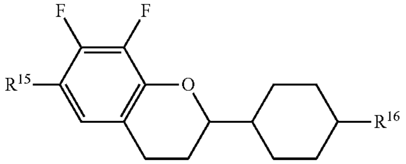
(13-4)
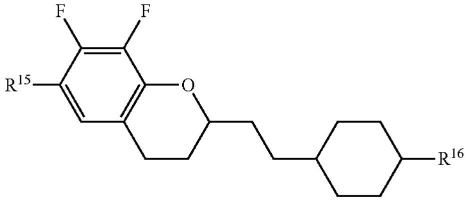
(13-5)
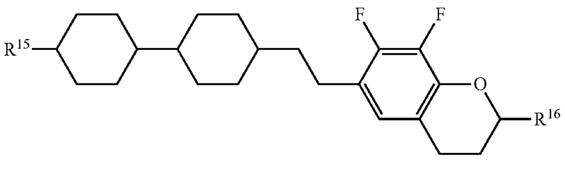
(13-6)
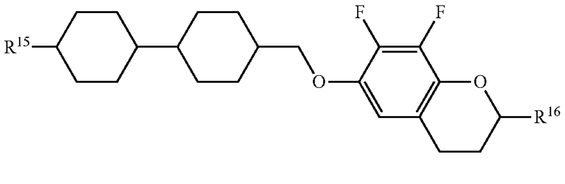
-continued
(13-7)
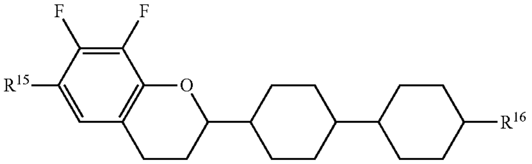
(13-8)
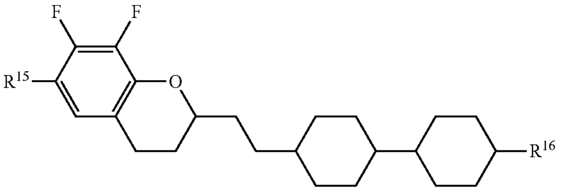
(13-9)
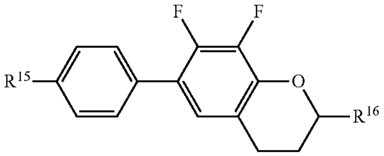
(13-10)
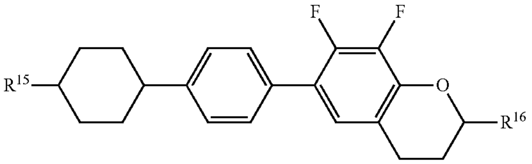
(13-11)
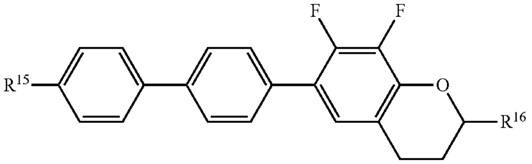
(14-1)
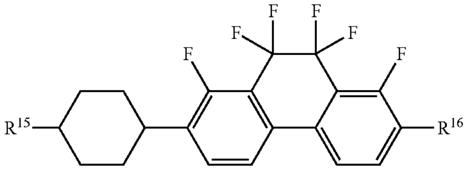
(14-2)
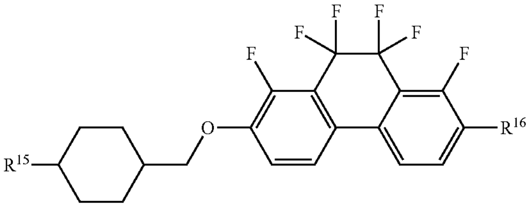
(14-3)
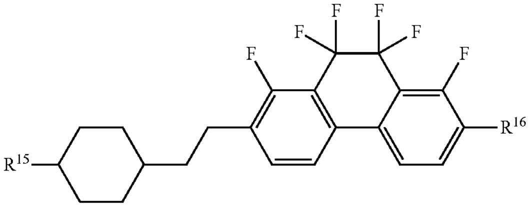

-continued (15-1)

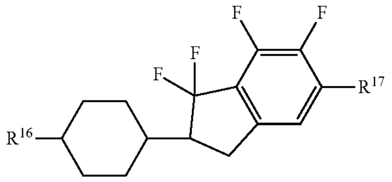

(15-2)

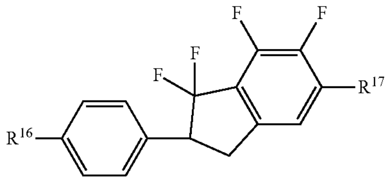

(15-3)

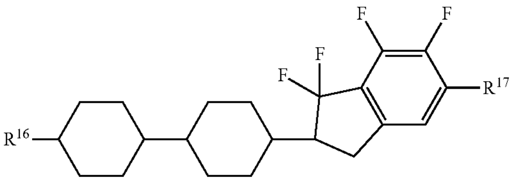

Component E has negatively large dielectric anisotropy. Component E is used when a composition for the IPS mode, the VA mode, the PSA mode or the like is prepared. As a content of component E is increased, the dielectric anisotropy of the composition is negatively increased, but the viscosity is increased. Thus, as long as a desired value of threshold voltage of the device is met, the content is preferably as small as possible. When the dielectric anisotropy at a degree of −5 is taken into account, the content is preferably 40% by weight or more in order to allow a sufficient voltage driving.

Among types of component E, compound (9) is a bicyclic compound, and therefore is effective in decreasing the viscosity, adjusting the optical anisotropy or increasing the dielectric anisotropy. Compounds (10) and (11) are a tricyclic compound, and therefore are effective in increasing the maximum temperature, the optical anisotropy or the dielectric anisotropy. Compounds (12) to (15) are effective in increasing the dielectric anisotropy.

When a composition for the IPS mode, the VA mode, the PSA mode or the like is prepared, the content of component E is preferably 40% by weight or more, and further preferably in the range of 50% by weight to 95% by weight, based on the weight of the liquid crystal composition. When component E is added to a composition having positive dielectric anisotropy, the content of component E is preferably 30% by weight or less. Addition of component E allows adjustment of the elastic constant of the composition and adjustment of the voltage-transmittance curve of the device.

A liquid crystal composition satisfying at least one of physical properties such as high stability to heat or light, high maximum temperature, low minimum temperature, small viscosity, suitable optical anisotropy (more specifically, large optical anisotropy or small optical anisotropy), large dielectric anisotropy, large specific resistance and a suitable elastic constant (more specifically, a large elastic constant or a small elastic constant) can be prepared by suitably combining components B, C, D and E with compound (1). A device including such a composition has a wide temperature range in which the device can be used, a short response time, a large voltage holding ratio, low threshold voltage, a large contrast ratio, a small flicker rate and a long service life.

If the device is used for a long period of time, a flicker may be occasionally generated on a display screen. A flicker rate (%) can be represented by a formula: (|luminance upon applying positive voltage−luminance upon applying negative voltage|/average luminance)×100. In a device having the flicker rate in the range of 0% to 1%, the flicker is hard to be generated on the display screen even if the device is used for a long period of time. The flicker is associated with image persistence, and is presumed to be generated according to a difference in electric potential between a positive frame and a negative frame in driving the device at an alternating current. The composition containing compound (1) is also useful for reducing generation of the flicker.

3-2. Additive

A liquid crystal composition is prepared according to a publicly-known method. For example, the component compounds are mixed and dissolved in each other by heating. According to an application, an additive may be added to the composition. Specific examples of the additives include the polymerizable compound, the polymerization initiator, the polymerization inhibitor, the optically active compound, the antioxidant, the ultraviolet light absorber, the light stabilizer, the heat stabilizer, the dye and the antifoaming agent. Such additives are well known to those skilled in the art, and described in literature.

In a liquid crystal display device having the polymer sustained alignment (PSA) mode, the composition contains a polymer. The polymerizable compound is added for the purpose of forming the polymer in the composition. The polymerizable compound is polymerized by irradiation with ultraviolet light while voltage is applied between electrodes, and thus the polymer is formed in the composition. A suitable pretilt is achieved by the method, and therefore the device in which a response time is shortened and the image persistence is improved is prepared.

Preferred examples of the polymerizable compound include acrylate, methacrylate, a vinyl compound, a vinyloxy compound, propenyl ether, an epoxy compound (oxirane, oxetane) and vinyl ketone. Further preferred examples include a compound having at least one acryloyloxy, and a compound having at least one methacryloyloxy. Still further preferred examples also include a compound having both acryloyloxy and methacryloyloxy.

Still further preferred examples include compounds (M-1) to (M-18). In the compounds, $R^{25}$ to $R^{31}$ are independently hydrogen or methyl; $R^{32}$, $R^{33}$ and $R^{34}$ are independently hydrogen or alkyl having 1 to 5 carbons, and at least one of $R^{32}$, $R^{33}$ and $R^{34}$ is alkyl having 1 to 5 carbons; v, w and x are independently 0 or 1; and u and v are independently an integer from 1 to 10. $L^{21}$ to $L^{26}$ are independently hydrogen or fluorine; and $L^{27}$ and $L^{28}$ are independently hydrogen, fluorine or methyl.

(M-1)
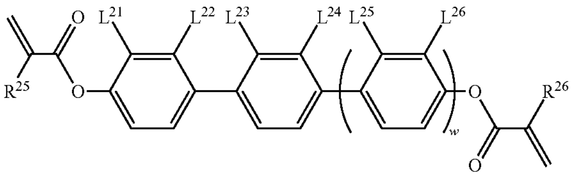
(M-2)
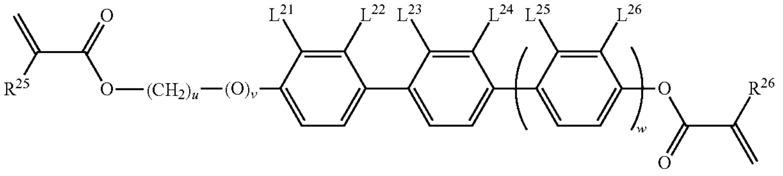
(M-3)
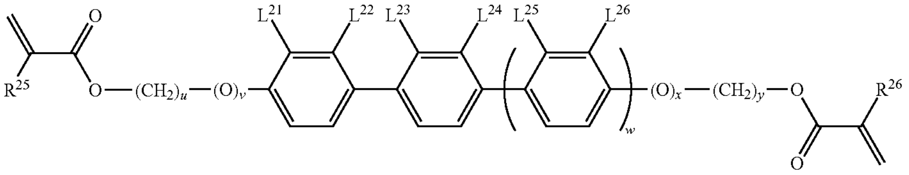
(M-4)
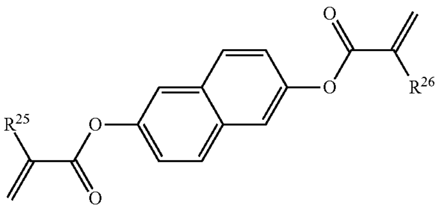
(M-5)
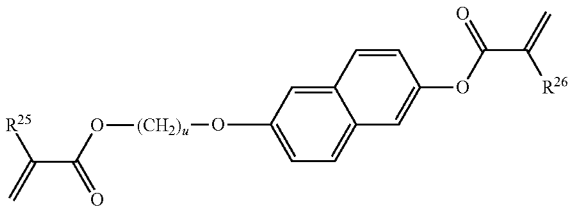
(M-6)
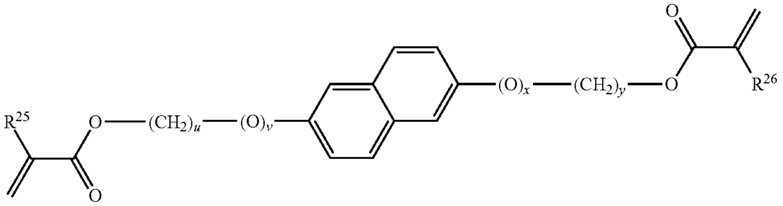
(M-7)
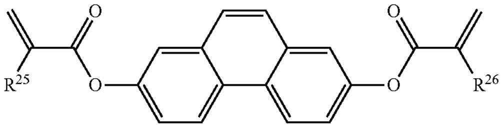
(M-8)
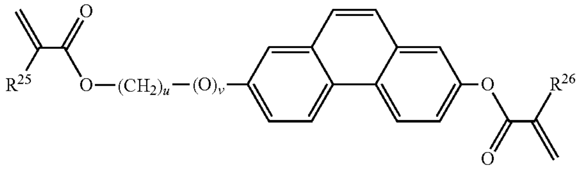
(M-9)
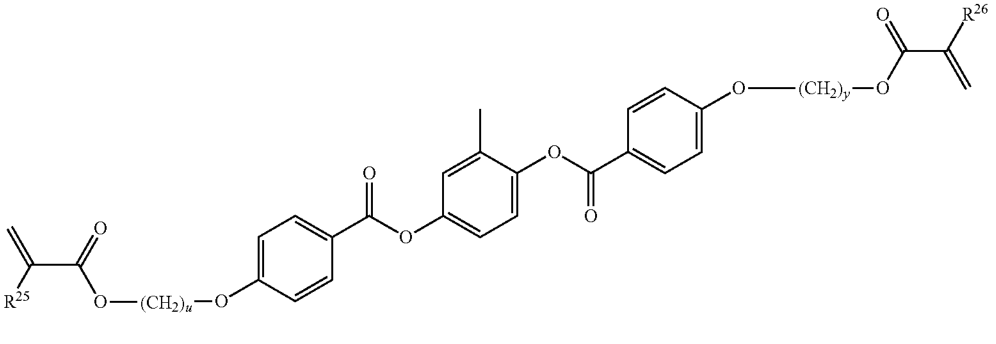

-continued
(M-10)
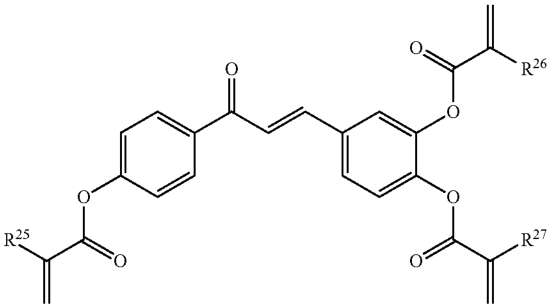
(M-11)
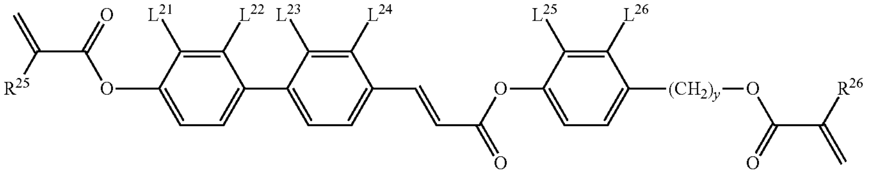
(M-12)
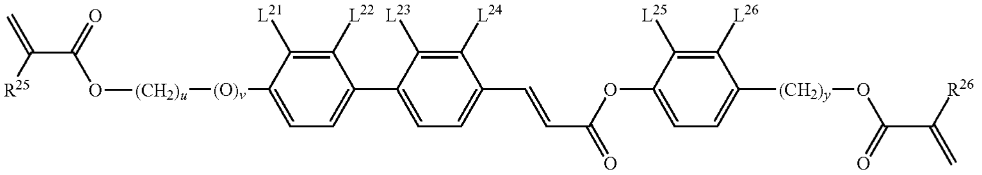
(M-13)
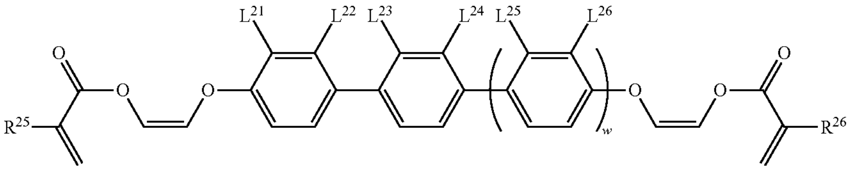
(M-14)
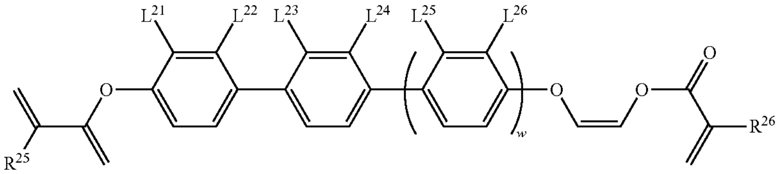
(M-15)
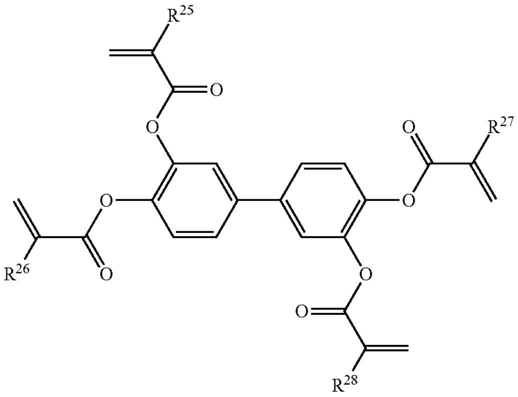
(M-16)
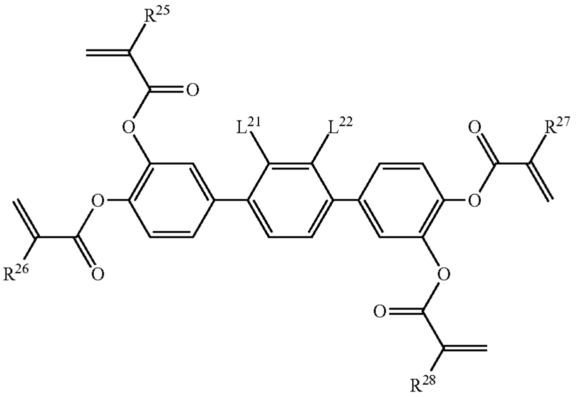

-continued (M-17)

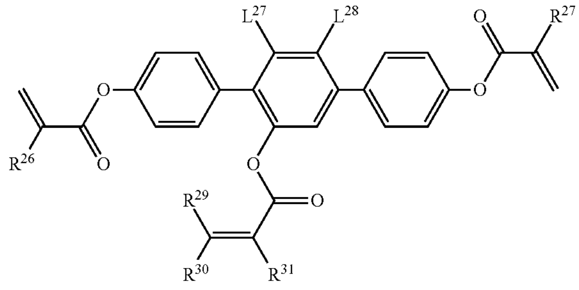

(M-18)

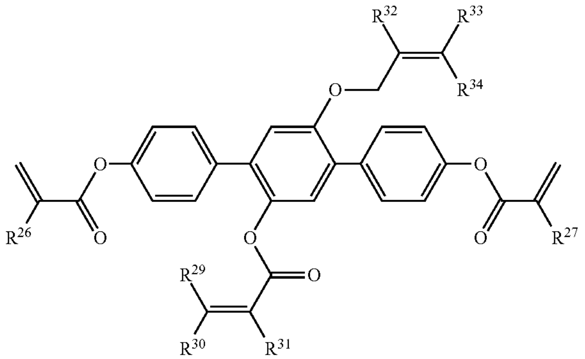

The polymerizable compound can be rapidly polymerized by adding the polymerization initiator. Δn amount of a remaining polymerizable compound can be reduced by optimizing reaction conditions. Examples of a photoradical polymerization initiator include TPO, 1173 and 4265 from Darocur series of BASF SE, and 184, 369, 500, 651, 784, 819, 907, 1300, 1700, 1800, 1850 and 2959 from Irgacure series thereof.

Additional examples of the photoradical polymerization initiator include 4-methoxyphenyl-2,4-bis(trichloromethyl) triazine, 2-(4-butoxystyryl)-5-trichloromethyl-1,3,4-oxadiazole, 9-phenylacridine, 9,10-benzphenazine, a benzophenone-Michler's ketone mixture, a hexaarylbiimidazole-mercaptobenzimidazole mixture, 1-(4-isopropylphenyl)-2-hydroxy-2-methylpropane-1-one, benzyl dimethyl ketal, 2-methyl-1-[4-(methylthio)phenyl]-2-morpholinopropane-1-one, a mixture of 2,4-diethylxanthone and methyl p-dimethylaminobenzoate, and a mixture of benzophenone and methyltriethanolamine.

After the photoradical polymerization initiator is added to the liquid crystal composition, polymerization can be performed by irradiation with ultraviolet light while an electric field is applied. However, an unreacted polymerization initiator or a decomposition product of the polymerization initiator may cause poor display such as image persistence in the device. In order to prevent such an event, photopolymerization may be performed with no addition of the polymerization initiator. A preferred wavelength of irradiation light is in the range of 150 nanometers to 500 nanometers. A further preferred wavelength is in the range of 250 nanometers to 450 nanometers, and a most preferred wavelength is in the range of 300 nanometers to 400 nanometers.

Upon storing the polymerizable compound, the polymerization inhibitor may be added thereto for preventing polymerization. The polymerizable compound is ordinarily added to the composition without removing the polymerization inhibitor. Examples of the polymerization inhibitor include hydroquinone, a hydroquinone derivative such as methylhydroquinone, 4-t-butylcatechol, 4-methoxyphenol and phenothiazine.

The optically active compound is effective in inducing helical structure in liquid crystal molecules to give a required twist angle, thereby preventing a reverse twist. A helical pitch can be adjusted by adding the optically active compound thereto. Two or more optically active compounds may be added for the purpose of adjusting temperature dependence of the helical pitch. Specific examples of a preferred optically active compound include compounds (Op-1) to (Op-18) described below. In compound (Op-18), ring J is 1,4-cyclohexylene or 1,4-phenylene, and $R^{28}$ is alkyl having 1 to 10 carbons. Asterisk mark (*) represents asymmetrical carbon.

(Op-1)

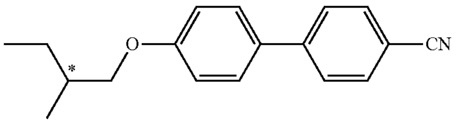

(Op-2)

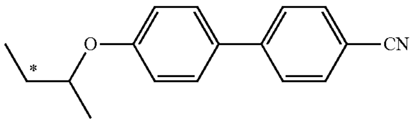

(Op-3)

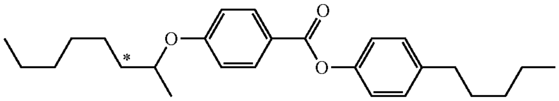

(Op-4)

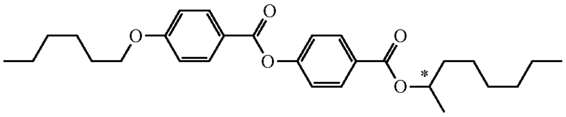

(Op-5)

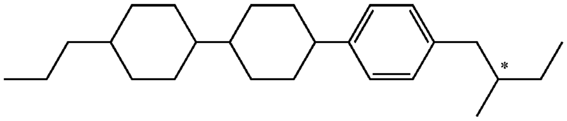

(Op-6)

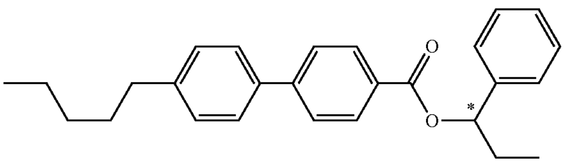

(Op-7)

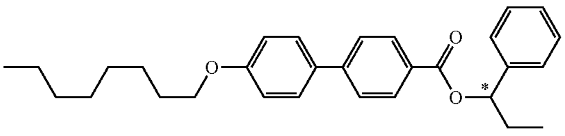

-continued (Op-8)

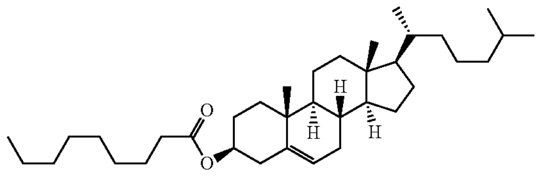

(Op-9)

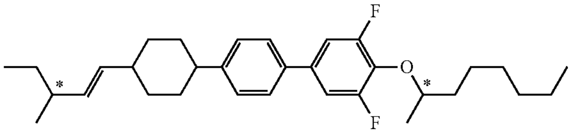

(Op-10)

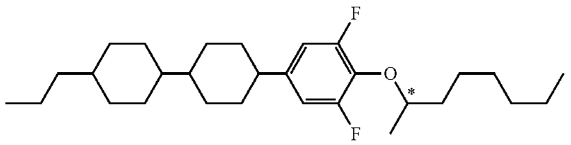

(Op-11)

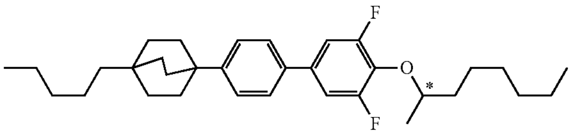

(Op-12)

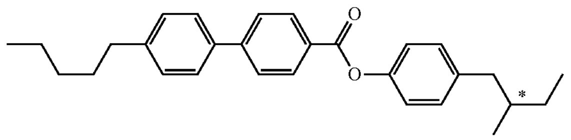

(Op-13)

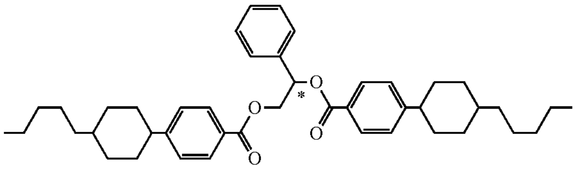

(Op-14)

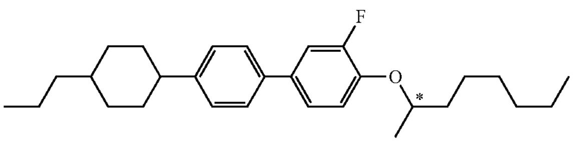

(Op-15)

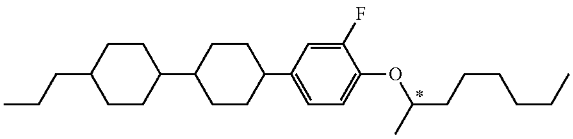

(Op-16)

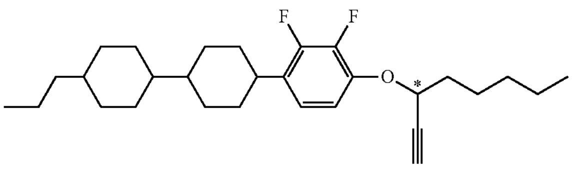

-continued (Op-17)

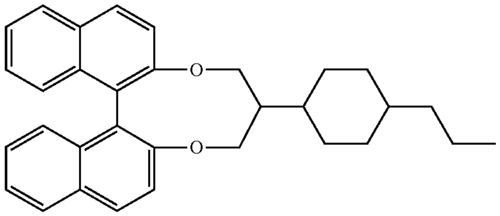

(Op-18)

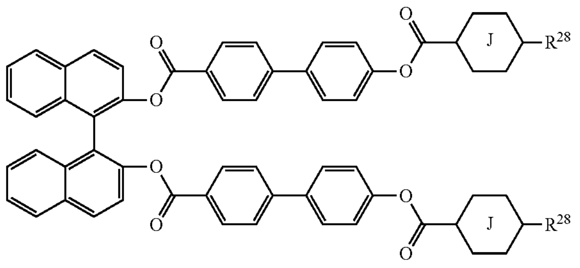

The antioxidant is effective for maintaining the large voltage holding ratio. Preferred examples of the antioxidant include compounds (AO-1) and (AO-2) described below; and Irganox 415, Irganox 565, Irganox 1010, Irganox 1035, Irganox 3114 and Irganox 1098 (trade names; BASF SE). The ultraviolet light absorber is effective for preventing a decrease of the maximum temperature. Preferred examples of the ultraviolet light absorber include a benzophenone derivative, a benzoate derivative and a triazole derivative, and specific examples include compounds (AO-3) and (AO-4) described below; Tinuvin 329, Tinuvin P, Tinuvin 326, Tinuvin 234, Tinuvin 213, Tinuvin 400, Tinuvin 328 and Tinuvin 99-2 (trade names; BASF SE); and 1,4-diazabicyclo [2.2.2]octane (DABCO).

The light stabilizer such as an amine having steric hindrance is preferred for maintaining the large voltage holding ratio. Preferred examples of the light stabilizer include compounds (AO-5), (AO-6) and (AO-7) described below; Tinuvin 144, Tinuvin 765 and Tinuvin 770DF (trade names; BASF SE); and LA-77Y and LA-77G (trade names; ADEKA Corporation). The heat stabilizer is also effective for maintaining the large voltage holding ratio, and specific preferred examples include Irgafos 168 (trade name; BASF SE). A dichroic dye such as an azo dye or an anthraquinone dye is added to the composition to be adapted for a device having a guest host (GH) mode. The antifoaming agent is effective for preventing foam formation. Preferred examples of the antifoaming agent include dimethyl silicone oil and methylphenyl silicone oil.

(AO-1)

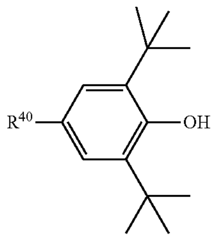

-continued (AO-2)

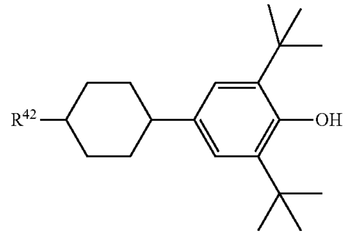

(AO-3)

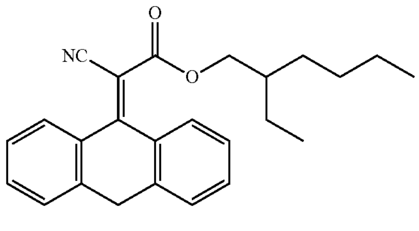

(AO-4)

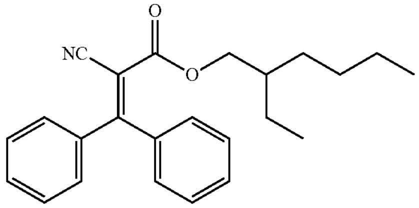

(AO-5)

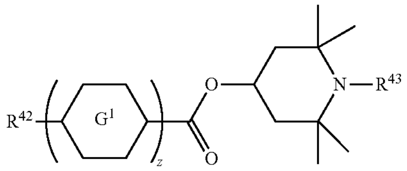

(AO-6)

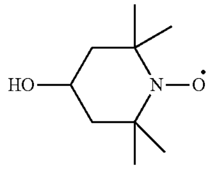

(AO-7)

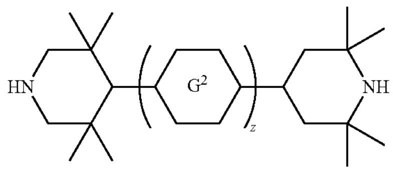

In compound (AO-1), $R^{40}$ is alkyl having 1 to 20 carbons, alkoxy having 1 to 20 carbons, —$COOR^{41}$ or —$CH_2CH_2COOR^{41}$, in which $R^{41}$ is alkyl having 1 to 20 carbons. In compounds (AO-2) and (AO-5), $R^{42}$ is alkyl having 1 to 20 carbons. In compound (AO-5), $R^{43}$ is hydrogen, methyl or O. (oxygen radical); and ring $G^1$ is 1,4-cyclohexylene or 1,4-phenylene; in compound (AO-7), ring $G^2$ is 1,4-cyclohexylene, 1,4-phenylene, or 1,4-phenylene in which at least one hydrogen is replaced by fluorine; and in compounds (AO-5) and (AO-7), z is 1, 2 or 3.

4. Liquid Crystal Display Device

The liquid crystal composition can be used in a liquid crystal display device having an operating mode such as the PC mode, the TN mode, the STN mode, the OCB mode and the PSA mode, and driven by an active matrix mode. The composition can also be used in a liquid crystal display device having the operating mode such as the PC mode, the TN mode, the STN mode, the OCB mode, the VA mode and the IPS mode, and driven by a passive matrix mode. The devices can be applied to any of a reflective type, a transmissive type and a transflective type.

The composition is also suitable for a nematic curvilinear aligned phase (NCAP) device, and the composition is microencapsulated herein. The composition can also be used in a polymer dispersed liquid crystal display device (PDLCD), a polymer network liquid crystal display device (PNLCD) or a nano capsule-dispersed liquid crystal display device. In the compositions, a large amount of polymerizable compound is added. On the other hand, when a proportion of the polymerizable compound is 10% by weight or less based on the weight of the liquid crystal composition, the liquid crystal display device having the PSA mode is prepared. A preferred proportion is in the range of 0.1% by weight to 2% by weight based thereon. A further preferred proportion is in the range of 0.2% by weight to 1.0% by weight based thereon. The device having the PSA mode can be driven by the driving mode such as the active matrix mode and the passive matrix mode. Such devices can be applied to any of the reflective type, the transmissive type and the transflective type.

The liquid crystal composition is suitable also for a liquid crystal display device having a capability of stereoscopic display. In a liquid crystal lens mode, a gradient refractive index lens is combined with an ordinary liquid crystal display device. When the composition is put in the lens and voltage is applied thereto, a distribution is caused in a refractive index in the composition. Thus, a lens effect is developed, and an image is displayed in three dimensions (3D). When no voltage is applied thereto, the image is displayed in two dimensions (2D). Accordingly, switching between 2D and 3D can be performed by electrically turning on or turning off the gradient refractive index lens.

EXAMPLES

1. Example of Compound (1)

The invention will be described in greater detail by way of Examples. The Examples each is a typical example, and therefore the invention is not limited by the Examples. The invention includes a mixture of a composition in Use Example 1 and a composition in Use Example 2. The invention also includes a mixture in which at least two compositions in Use Examples are mixed. Compound (1) was prepared according to procedures described below. The thus prepared compound was identified by methods such as an NMR analysis. Physical properties of a compound and a composition, and characteristics of a device were measured by methods described below.

NMR analysis: For measurement, DRX-500 made by Bruker BioSpin Corporation was used. In $^{1}H$-NMR measurement, a sample was dissolved in a deuterated solvent such as $CDCl_3$, and measurement was carried out under conditions of room temperature, 500 MHz and 16 times of accumulation. Tetramethylsilane was used as an internal standard. In $^{19}F$-NMR measurement, $CFCl_3$ was used as an internal standard, and measurement was carried out under conditions of 24 times of accumulation. In explaining nuclear magnetic resonance spectra obtained, s, d, t, q, quin, sex and m stand for a singlet, a doublet, a triplet, a quartet, a quintet, a sextet and a multiplet, and br being broad, respectively.

Gas chromatographic analysis: For measurement, GC-2010 Gas Chromatograph made by Shimadzu Corporation was used. As a column, a capillary column DB-1 (length 60 m, bore 0.25 mm, film thickness 0.25 μm) made by Agilent Technologies, Inc. was used. As a carrier gas, helium (1 mL/minute) was used. A temperature of a sample vaporizing chamber and a temperature of a detector (FID) were set to 300° C. and 300° C., respectively. A sample was dissolved in acetone and prepared to be a 1 weight % solution, and then 1 microliter of the solution obtained was injected into the sample vaporizing chamber. As a recorder, GC Solution System made by Shimadzu Corporation or the like was used.

HPLC analysis: For measurement, Prominence (LC-20AD; SPD-20A) made by Shimadzu Corporation was used. As a column, YMC-Pack ODS-A (length 150 mm, bore 4.6 mm, particle diameter 5 μm) made by YMC Co., Ltd. was used. As an eluate, acetonitrile and water were appropriately mixed and used. As a detector, a UV detector, an RI detector, a CORONA detector or the like was appropriately used. When the UV detector was used, a detection wavelength was set to 254 nanometers. A sample was dissolved in acetonitrile and prepared to be a 0.1 weight % solution, and then 1 microliter of the solution was introduced into a sample chamber. As a recorder, C-R7Aplus made by Shimadzu Corporation was used.

Ultraviolet-Visible spectrophotometry: For measurement, PharmaSpec UV-1700 made by Shimadzu Corporation was used. A detection wavelength was adjusted in the range of 190 nanometers to 700 nanometers. A sample was dissolved in acetonitrile and prepared to be a 0.01 mmol/L solution, and measurement was carried out by putting the solution in a quartz cell (optical path length: 1 cm).

Sample for measurement: Upon measuring phase structure and a transition temperature (a clearing point, a melting point, a polymerization starting temperature or the like), the compound itself was used as a sample. Upon measuring physical properties such as maximum temperature of a nematic phase, viscosity, optical anisotropy and dielectric anisotropy, a mixture of the compound and a base liquid crystal was used as a sample.

Extrapolation method: When the sample prepared by mixing the compound with the base liquid crystal was used, an extrapolated value was calculated according to the following equation and the calculated value was described: [extrapolated value]=(100×[measured value of a sample]−[% by weight of a base liquid crystal]×[measured value of the base liquid crystal])/[% by weight of a compound].

Base liquid crystal (A): When the dielectric anisotropy of the compound was zero or positive, base liquid crystal (A) described below was used. A proportion of each component was expressed in terms of weight percent (% by weight).

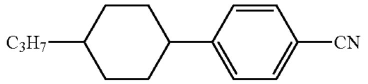
24%

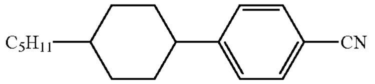
36%

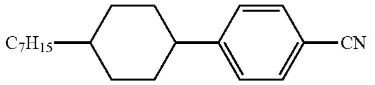
25%

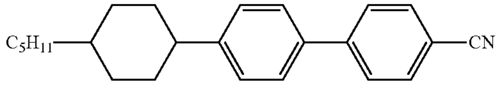
15%

A ratio of the compound to base liquid crystal (A) was adjusted to (15% by weight: 85% by weight). When crystals (or a smectic phase) precipitated at 25° C. at the ratio, a ratio of the compound to base liquid crystal (A) was changed in the order of (10% by weight: 90% by weight), (5% by weight: 95% by weight) and (1% by weight: 99% by weight), and the physical properties of the sample were measured at a ratio at which no crystal (or no smectic phase) precipitated at 25° C. In addition, unless otherwise noted, the ratio of the compound to base liquid crystal (A) was (15% by weight: 85% by weight).

Base liquid crystal (B): Base liquid crystal (B) containing the fluorine-based compound described below as a component may be occasionally used. A proportion of components in base liquid crystal (B) was expressed in terms of weight percent (% by weight).

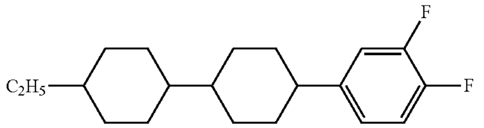 [SMILES: CCC1CCC(C2CCC(c3ccc(F)c(F)c3)CC2)CC1]
16.67% (i-1)

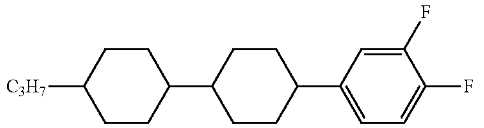
16.67% (i-2)

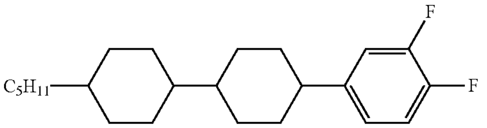
16.67% (i-3)

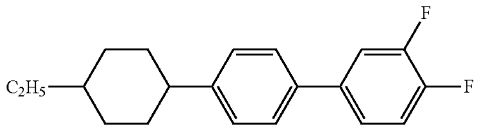 [SMILES: CCC1CCC(c2ccc(-c3ccc(F)c(F)c3)cc2)CC1]
6.25% (i-4)

-continued

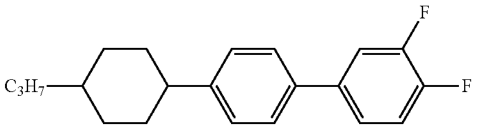
6.25% (i-5)

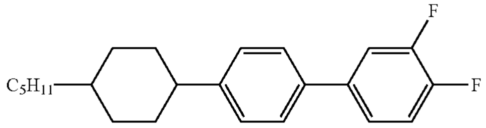
12.50% (i-6)

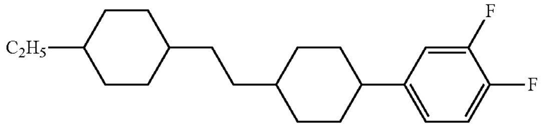
10.00% (i-7)

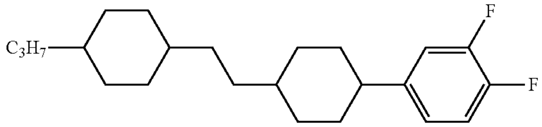
5.00% (i-8)

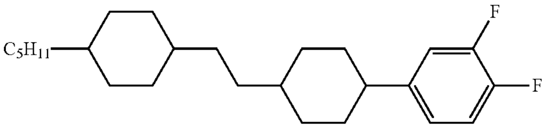
10.00% (i-9)

A ratio of the compound to base liquid crystal (B) was adjusted to (20% by weight: 80% by weight). When crystals (or a smectic phase) precipitated at 25° C. at the ratio, a ratio of the compound to the base liquid crystal was changed in the order of (15% by weight: 85% by weight), (10% by weight: 90% by weight), (5% by weight: 95% by weight), and (1% by weight: 99% by weight), and the physical properties of the sample were measured at a ratio at which no crystal (or no smectic phase) precipitated at 25° C. In addition, unless otherwise noted, the ratio of the compound to base liquid crystal (B) was (20% by weight: 80% by weight).

Measuring method: Physical properties were measured according to methods described below. Most of the methods are described in the Standard of Japan Electronics and Information Technology Industries Association (JEITA) discussed and established in JEITA (JEITA ED-2521B). A modification of the methods were also used. No thin film transistor (TFT) was attached to a TN device used for measurement.

(1) Phase structure: A sample was placed on a hot plate in a melting point apparatus (FP-52 Hot Stage made by Mettler-Toledo International Inc.) equipped with a polarizing microscope. A state of phase and a change thereof were observed with the polarizing microscope while the sample was heated at a rate of 3° C. per minute, and a kind of the phase was specified.

(2) Transition temperature (° C.): For measurement, a differential scanning calorimeter, Diamond DSC System, made by PerkinElmer, Inc., or a high sensitivity differential scanning calorimeter, X-DSC7000, made by SII NanoTechnology Inc. was used. A sample was heated and then cooled at a rate of 3° C. per minute, and a starting point of an endothermic peak or an exothermic peak caused by a phase change of the sample was determined by extrapolation, and thus a transition temperature was determined. A melting point and a polymerization starting temperature of a compound were also measured using the apparatus. Temperature at which a compound undergoes transition from a solid to a liquid crystal phase such as the smectic phase and the nematic phase may be occasionally abbreviated as “minimum temperature of the liquid crystal phase.” Temperature at which the compound undergoes transition from the liquid crystal phase to liquid may be occasionally abbreviated as “clearing point.”

A crystal was expressed as C. When the crystals were distinguishable into two kinds, each of the crystals was expressed as $C_1$ or $C_2$. The smectic phase or the nematic phase was expressed as S or N. When a phase was distinguishable such as smectic A phase, smectic B phase, smectic C phase and smectic F, the phase was expressed as $S_A$, $S_B$, $S_C$ and $S_F$, respectively. A liquid (isotropic) was expressed as I. A transition temperature was expressed as “C 50.0 N 100.0 I,” for example. The expression indicates that a transition temperature from the crystals to the nematic phase is 50.0° C., and a transition temperature from the nematic phase to the liquid is 100.0° C.

(3) Compatibility of compound: Samples in which the base liquid crystal and the compound were mixed for proportions of the compounds to be 20% by weight, 15% by weight, 10% by weight, 5% by weight, 3% by weight or 1% by weight were prepared. The samples were put in a glass vials, and kept in freezers at −20° C. or −30° C. for a predetermined period of time. Whether a nematic phase of the samples was maintained or crystals (or a smectic phase) precipitated was observed. Conditions on which the nematic phase was maintained were used as a measure of the compatibility. Proportions of the compounds and each temperature in the freezers may be occasionally changed when necessary.

(4) Maximum temperature of nematic phase ($T_{NI}$ or NI; ° C.): A sample was placed on a hot plate in a melting point apparatus equipped with a polarizing microscope, and heated at a rate of 1° C. per minute. Temperature when part of the sample began to change from a nematic phase to an isotropic liquid was measured. When the sample was a mixture of compound (1) and the base liquid crystal, the maximum temperature was expressed in terms of a symbol $T_{NI}$. The value was calculated using the extrapolation method described above. When the sample was a mixture of compound (1) and a compound selected from compounds (2) to (15), the measured value was expressed in terms of a symbol NI. A maximum temperature of the nematic phase may be occasionally abbreviated as "maximum temperature."

(5) Minimum temperature of nematic phase ($T_C$; ° C.): Samples each having a nematic phase were put in glass vials and kept in freezers at temperatures of 0° C., −10° C., −20° C., −30° C. and −40° C. for 10 days, and then liquid crystal phases were observed. For example, when the sample was maintained in the nematic phase at −20° C. and changed to crystals or a smectic phase at −30° C., TC was expressed as $T_C < −20°$ C. A minimum temperature of the nematic phase may be occasionally abbreviated as "minimum temperature."

(6) Viscosity (bulk viscosity; η; measured at 20° C.; mPa·s): For measurement, a cone-plate (E type) rotational viscometer made by Tokyo Keiki Inc. was used.

(7) Viscosity (rotational viscosity; γ1; measured at 25° C.; mPa·s): Measurement was carried out according to a method described in M. Imai et al., Molecular Crystals and Liquid Crystals, Vol. 259, p. 37 (1995). A sample was put in a TN device in which a twist angle was 0 degrees and a distance (cell gap) between two glass substrates was 5 micrometers. Voltage was applied stepwise to the device from 16 V to 19.5 V at an increment of 0.5 V. After a period of 0.2 second with no voltage application, voltage was repeatedly applied under conditions of only one rectangular wave (rectangular pulse; 0.2 second) and no voltage application (2 seconds). A peak current and a peak time of transient current generated by the applied voltage were measured. A value of rotational viscosity was obtained from the measured values and equation (8) on page 40 of the paper presented by M. Imai et al. A value of dielectric anisotropy required for the calculation was determined using the device by which the rotational viscosity was measured and by a method described below.

(8) Optical anisotropy (refractive index anisotropy; measured at 25° C.; Δn): Measurement was carried out by an Abbe refractometer with a polarizing plate mounted on an ocular, using light at a wavelength of 589 nanometers. A surface of a main prism was rubbed in one direction, and then a sample was added dropwise onto the main prism. A refractive index (n∥) was measured when a direction of polarized light was parallel to a direction of rubbing. A refractive index (n⊥) was measured when the direction of polarized light was perpendicular to the direction of rubbing. A value of optical anisotropy (Δn) was calculated from an equation: Δn=n∥−n⊥.

(9) Dielectric anisotropy (Δε; measured at 25° C.): A sample was put in a TN device in which a distance (cell gap) between two glass substrates was 9 micrometers and a twist angle was 80 degrees. Sine waves (10 V, 1 kHz) were applied to the device, and after 2 seconds, a dielectric constant (ε∥) of liquid crystal molecules in a major axis direction was measured. Sine waves (0.5 V, 1 kHz) were applied to the device, and after 2 seconds, a dielectric constant (ε⊥) of liquid crystal molecules in a minor axis direction was measured. A value of dielectric anisotropy was calculated from an equation: Δε=ε∥−ε⊥.

(10) Elastic constant (K; measured at 25° C.; pN): For measurement, HP4284A LCR Meter made by Yokogawa-Hewlett-Packard Co. was used. A sample was put in a horizontal alignment device in which a distance (cell gap) between two glass substrates was 20 micrometers. An electric charge from 0 V to 20 V was applied to the device, and electrostatic capacity (C) and applied voltage (V) were measured. The measured values were fitted to equation (2.98) and equation (2.101) on page 75 of "Liquid Crystal Device Handbook (Ekisho Debaisu Handobukku in Japanese; Nikkan Kogyo Shimbun, Ltd.)," and values of $K_{11}$ and $K_{33}$ were obtained from equation (2.99). Next, $K_{22}$ was calculated using the previously determined values of $K_{11}$ and $K_{33}$ in equation (3.18) on page 171. Elastic constant K was expressed in terms of a mean value of the thus determined $K_{11}$, $K_{22}$ and $K_{33}$.

(11) Threshold voltage (Vth; measured at 25° C.; V): For measurement, an LCD-5100 luminance meter made by Otsuka Electronics Co., Ltd. was used. A light source was a halogen lamp. A sample was put in a normally white mode TN device in which a distance (cell gap) between two glass substrates was 0.45/Δn (μm) and a twist angle was 80 degrees. A voltage (32 Hz, rectangular waves) to be applied to the device was stepwise increased from 0 V to 10 V at an increment of 0.02 V. On the occasion, the device was irradiated with light from a direction perpendicular to the device, and an amount of light transmitted through the device was measured. A voltage-transmittance curve was prepared, in which the maximum amount of light corresponds to 100% transmittance and the minimum amount of light corresponds to 0% transmittance. A threshold voltage is expressed in terms of voltage at 90% transmittance.

(12) Voltage holding ratio (VHR-1; measured at 25° C.; %): A TN device used for measurement had a polyimide alignment film, and a distance (cell gap) between two glass substrates was 5 micrometers. A sample was put in the device, and then the device was sealed with an ultraviolet-curable adhesive. The device was charged by applying a pulse voltage (60 microseconds at 5 V) at 25° C. A decaying voltage was measured for 16.7 milliseconds with a high-speed voltmeter, and area A between a voltage curve and a horizontal axis in a unit cycle was determined. Area B is an area without decay. A voltage holding ratio is expressed in terms of a percentage of area A to area B.

(13) Voltage holding ratio (VHR-2; measured at 80° C.; %): A voltage holding ratio was measured according to the method described above except that the voltage holding ratio was measured at 80° C. in place of 25° C. The results obtained were expressed in terms of a symbol VHR-2.

(14) Specific resistance (ρ; measured at 25° C.; Ωcm): Into a vessel equipped with electrodes, 1.0 milliliter of sample was injected. A direct current voltage (10 V) was applied to the vessel, and a direct current after 10 seconds was measured. Specific resistance was calculated from the following equation: (specific resistance)={(voltage)×(electric capacity of a vessel)}/{(direct current)×(dielectric constant of vacuum)}.

(15) Response time (i; measured at 25° C.; ms): For measurement, an LCD-5100 luminance meter made by Otsuka Electronics Co., Ltd. was used. A light source was a halogen lamp. A low-pass filter was set to 5 kHz. A sample was put in a normally white mode TN device in which a distance (cell gap) between two glass substrates was 5.0 micrometers and a twist angle was 80 degrees. A voltage (rectangular waves; 60 Hz, 5 V, 0.5 second) was applied to the device. On the occasion, the device was irradiated with light from a direction perpendicular to the device, and an amount of light transmitted through the device was measured. The maximum amount of light corresponds to 100% transmittance, and the minimum amount of light corresponds to 0% transmittance. A rise time (τr; millisecond) was expressed in terms of time required for a change from 90% transmittance to 10% transmittance. A fall time (τf; millisecond) was expressed in terms of time required for a change from 10% transmittance to 90% transmittance. A response time was expressed by a sum of the rise time and the fall time thus determined.

(16) Flicker rate (measured at 25° C.; %): For measurement, 3298F Multimedia Display Tester made by Yokogawa Electric Corporation was used. A light source was LED. A sample was put in a normally black mode FFS device in which a distance (cell gap) between two glass substrates was 3.5 micrometers, and a rubbing direction was anti-parallel. The device was sealed with an ultraviolet-curable adhesive. Voltage was applied to the device, and a voltage having a maximum amount of light transmitted through the device was measured. A sensor part was brought close to the device while the voltage was applied, and a flicker rate displayed thereon was read.

Raw material: Solmix (registered tradename) A-11 is a mixture of ethanol (85.5%), methanol (13.4%) and isopropanol (1.1%), and was purchased from Japan Alcohol Trading Co., Ltd.

Synthesis Example 1

Synthesis of Compound (No. 290)

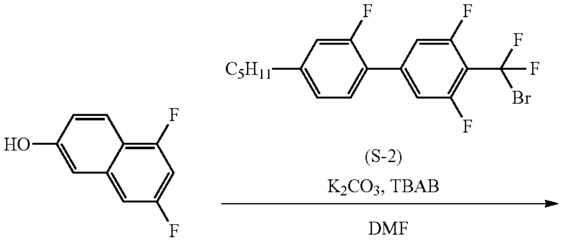

(S-1)

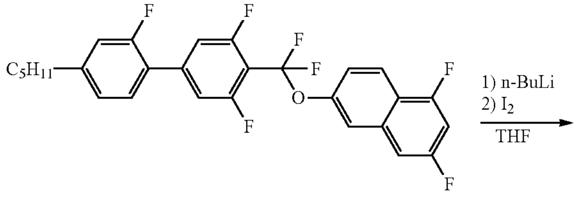

(S-3)

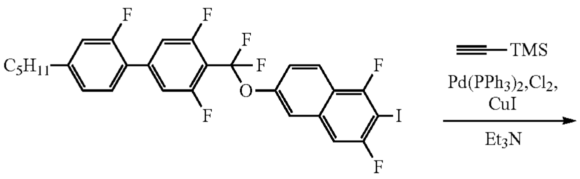

(S-4)

-continued

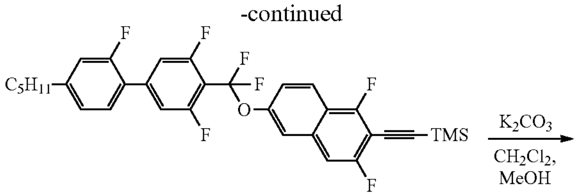

(S-5)

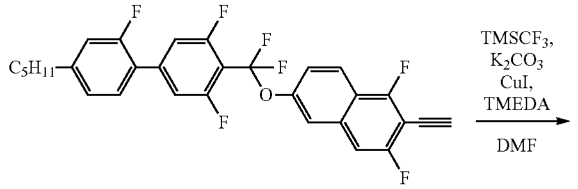

(S-6)

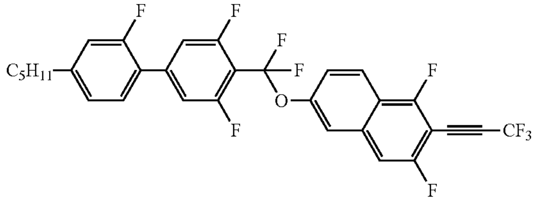

(No. 290)

First Step

Under a nitrogen atmosphere, compound (S-1) (1.75 g, 9.71 mmol) prepared by a publicly-known method, compound (S-2) (3.96 g, 9.71 mmol), potassium carbonate (2.82 g, 20.4 mmol), tetrabutylammonium bromide (0.157 g, 0.49 mmol) and DMF (20 mL) were put in a reaction vessel, and the resulting mixture was heated to 90° C. and stirred for 3 hours. The resulting reaction mixture was poured into water, and an aqueous layer was subjected to extraction with toluene. Combined organic layers were washed with water, and dried over anhydrous magnesium sulfate. The solution was concentrated under reduced pressure, and the residue was purified by silica gel chromatography (heptane:ethyl acetate=10:1 in a volume ratio) to obtain compound (S-3) (3.77 g, yield: 76.6%).

Second Step

Under a nitrogen atmosphere, compound (S-3) (3.77 g, 7.44 mmol) and THF (60 mL) were put in a reaction vessel, and the resulting mixture was cooled to −70° C. Thereto, n-BuLi (1.55 M; n-hexane solution; 5.04 mL) was slowly added dropwise, and after dropwise addition, the resulting mixture was stirred for 1 hour while being maintained at −70° C. Next, a THF solution (10 mL) of iodine (2.27 g, 8.93 mmol) was slowly added dropwise thereto, and after dropwise addition, the resulting mixture was warmed to room temperature, further stirred at room temperature for 12 hours. The resulting reaction mixture was poured into water, and an aqueous layer was subjected to extraction with ethyl acetate. Combined organic layers were washed with water, and dried over anhydrous magnesium sulfate. The solution was concentrated under reduced pressure, and the residue was purified by silica gel chromatography (heptane:ethyl acetate=10:1 in a volume ratio) to obtain compound (S-4) (4.03 g, yield: 85.6%).

Third Step

Under a nitrogen atmosphere, compound (S-4) (4.03 g, 6.37 mmol), trimethylsilyl acetylene (0.97 mL, 7.01 mmol), $Pd(PPh_3)_2Cl_2$ (0.447 g, 0.64 mmol), copper iodide (0.121 g, 0.64 mmol) and triethylamine (60 mL) were put in a reaction vessel, and the resulting mixture was stirred at room temperature for 2 hours. The resulting reaction mixture was poured into water, and an aqueous layer was subjected to extraction with toluene. Combined organic layers were washed with water, and dried over anhydrous magnesium sulfate. The solution was concentrated under reduced pressure, and the residue was purified by silica gel column chromatography (heptane:toluene=10:1 in a volume ratio) to obtain compound (S-5) (3.33 g, yield: 86.7%).

Fourth Step

Under a nitrogen atmosphere, compound (S-5) (3.33 g, 5.53 mmol), dichloromethane (16 mL) and methanol (20 mL) were put in a reaction vessel, and the resulting mixture was stirred at room temperature. Thereto, potassium carbonate (0.916 g, 6.63 mmol) was added little by little, and the resulting mixture was stirred at room temperature for 6 hours. The resulting reaction mixture was poured into water, and an aqueous layer was subjected to extraction with toluene. Combined organic layers were washed with water, and dried over anhydrous magnesium sulfate. The solution was concentrated under reduced pressure, and the residue was purified by silica gel column chromatography (heptane: toluene=5:1 in a volume ratio) to obtain compound (S-6) (2.62 g, yield: 89.4%).

Fifth Step

Under an air atmosphere, copper iodide (1.27 g, 6.64 mmol), potassium carbonate (1.84 g, 13.3 mmol), TMEDA (1.00 mL, 6.64 mmol) and DMF (20 mL) were put in a reaction vessel, and the resulting mixture was stirred at room temperature for 15 minutes. Thereto, a Ruppert reagent (1.32 mL, 8.86 mmol) was added, and the resulting mixture was stirred at room temperature for 5 minutes, and then cooled to 0° C. Thereto, a DMF solution (20 mL) of compound (S-6) (2.35 g, 4.43 mmol) and a Ruppert reagent (1.32 mL, 8.86 mmol) in which the solution was cooled to 00° C. were added, and the resulting mixture was stirred for 30 minutes while being maintained at 00° C. Then, the resulting mixture was warmed to room temperature, and further stirred at room temperature for 12 hours. The resulting reaction mixture was poured into water, and an aqueous layer was subjected to extraction with toluene. Combined organic layers were washed with water, and dried over anhydrous magnesium sulfate. The solution was concentrated under reduced pressure, and the residue was purified by silica gel column chromatography (heptane:toluene=20:1 in a volume ratio). The resulting material was further purified by recrystallization from a mixed solvent of IPA:ethyl acetate=5:1 (volume ratio) to obtain compound (No. 290) (0.82 g, yield: 27.8%).

$^1$H-NMR (ppm; $CDCl_3$): δ 8.11 (d, J=9.1 Hz, 1H), 7.72 (s, 1H), 7.51 (dd, J=9.15 Hz, J=1.85 Hz, 1H), 7.38-7.30 (m, 2H), 7.22 (d, J=10.9 Hz, 2H), 7.09-6.99 (m, 2H), 2.65 (t, J=7.60 Hz, 2H), 1.70-1.60 (m, 2H), 1.40-1.30 (m, 4H), 0.91 (t, J=6.70 Hz, 3H).

Transition temperature: C 64.7 $S_A$ 112 I. Maximum temperature ($T_{NI}$)=72.4° C.; Dielectric anisotropy (Δε)=56.6; Optical anisotropy (Δn)=0.210.

Synthesis Example 2

Synthesis of Compound (No. 614)

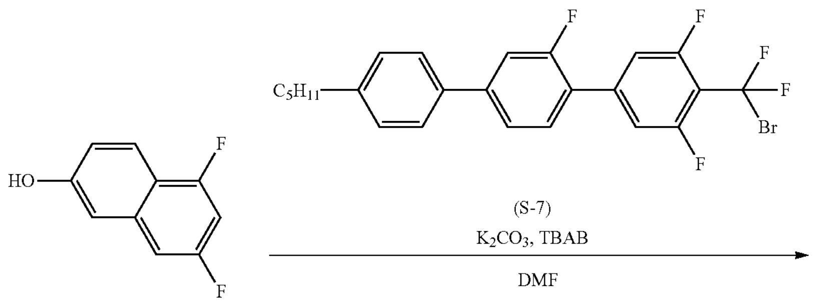

(S-1)

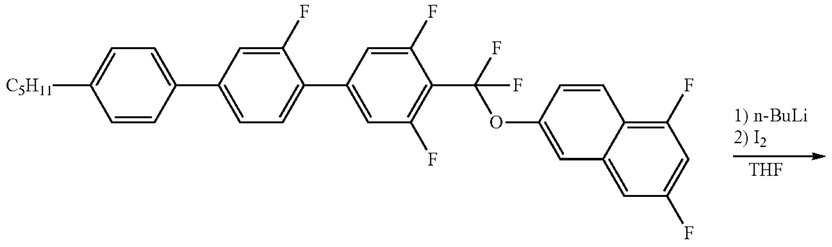

(S-8)

-continued

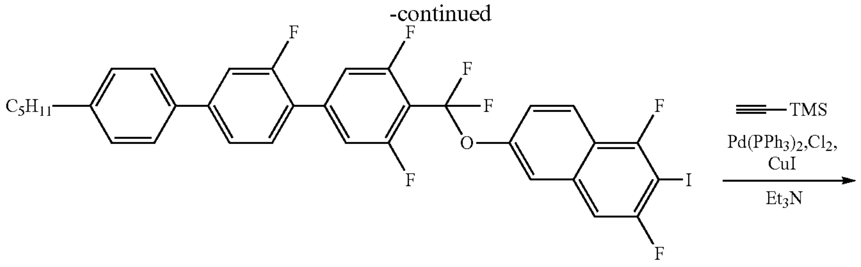

(S-9)

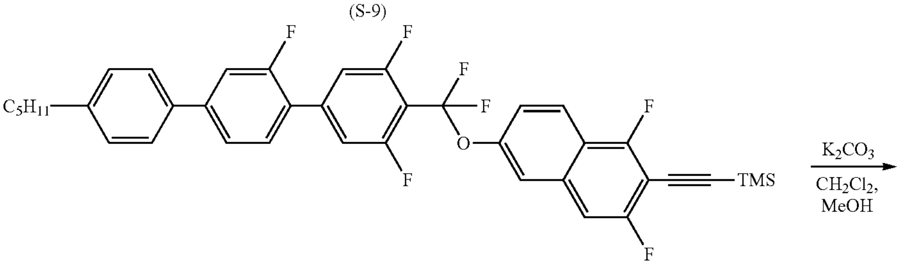

(S-10)

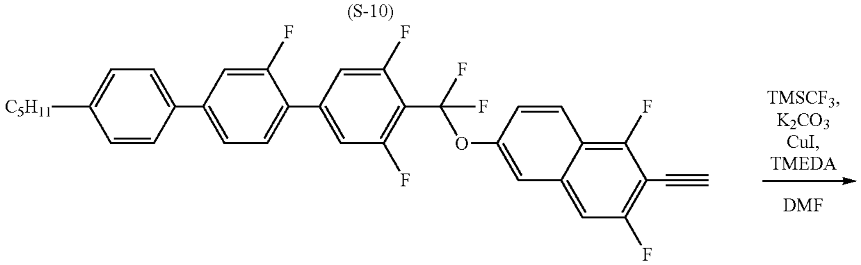

(S-11)

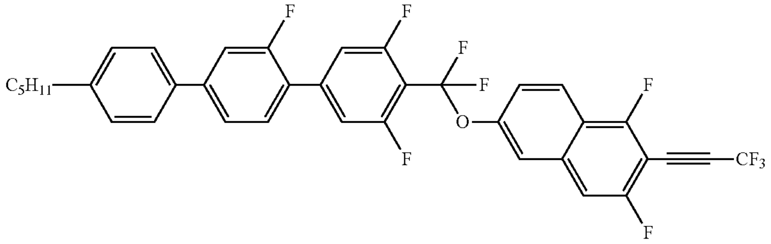

(No. 614)

First Step

Under a nitrogen atmosphere, compound (S-1) (1.83 g, 10.2 mmol) prepared by a publicly-known method, compound (S-7) (4.91 g, 10.2 mmol), potassium carbonate (2.95 g, 21.3 mmol), tetrabutylammonium bromide (0.164 g, 0.51 mmol) and DMF (50 mL) were put in a reaction vessel, and the resulting mixture was heated to 90° C. and stirred for 5.5 hours. The resulting reaction mixture was poured into water, and an aqueous layer was subjected to extraction with toluene. Combined organic layers were washed with water, and dried over anhydrous magnesium sulfate. The solution was concentrated under reduced pressure, and the residue was purified by silica gel column chromatography (heptane: toluene=10:1 in a volume ratio) to obtain compound (S-8) (3.51 g, yield: 59%).

Second Step

A synthesis was made in a manner similar to Synthesis Example 1 to obtain compound (S-9) (7.19 g, yield: 89.4%).

Third Step

A synthesis was made in a manner similar to Synthesis Example 1 to obtain compound (S-10) (6.89 g, yield: 100%).

Fourth Step

A synthesis was made in a manner similar to Synthesis Example 1 to obtain compound (S-11) (5.79 g, yield: 94.0%).

Fifth Step

A synthesis was made in a manner similar to Synthesis Example 1 to obtain compound (No. 614) (2.22 g, yield: 38.7%).

$^1$H-NMR (ppm; $CDCl_3$): δ 8.12 (d, J=9.2 Hz, 1H), 7.73 (s, 1H), 7.56-7.46 (m, 5H), 7.42 (d, J=12.5 Hz, 1H), 7.36 (d, J=9.4 Hz, 1H), 7.32-7.24 (m, 4H), 2.67 (t, J=7.60 Hz, 2H), 1.70-1.62 (m, 2H), 1.41-1.30 (m, 4H), 0.91 (t, J=6.85 Hz, 3H).

A sample having a ratio of the compound to the base liquid crystal (5% by weight: 95% by weight) was used for measurement of the maximum temperature, the optical anisotropy and the dielectric anisotropy.

Transition temperature: C 102 $S_A$ 205 N 212 I.

Maximum temperature ($T_{NI}$)=158° C.; dielectric anisotropy (Δε)=52.1; optical anisotropy (Δn)=0.297.

Synthesis Example 3
Synthesis of Compound (No. 518)
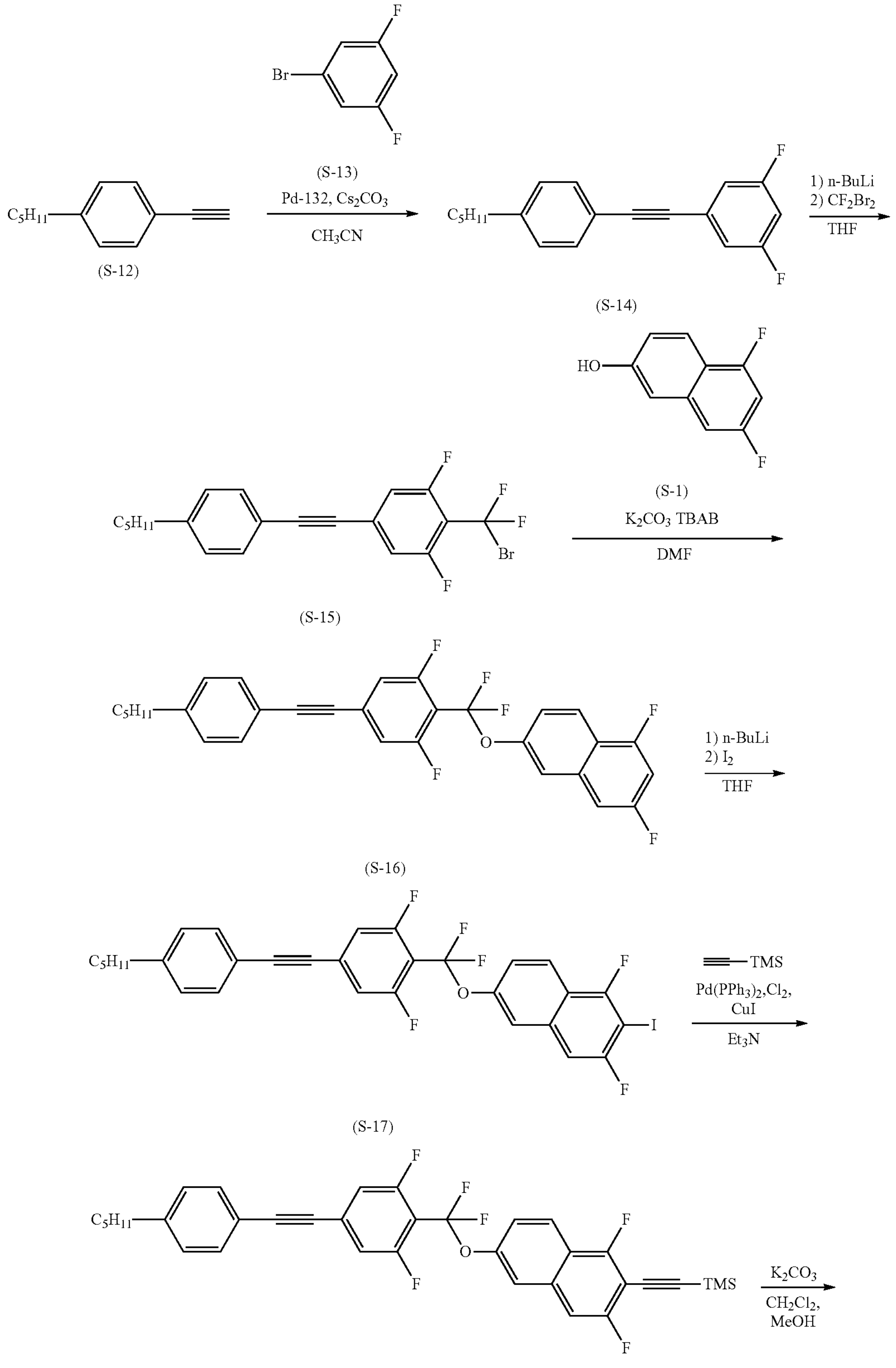
(S-12)
(S-14)
(S-15)
(S-16)
(S-17)
(S-18)

-continued

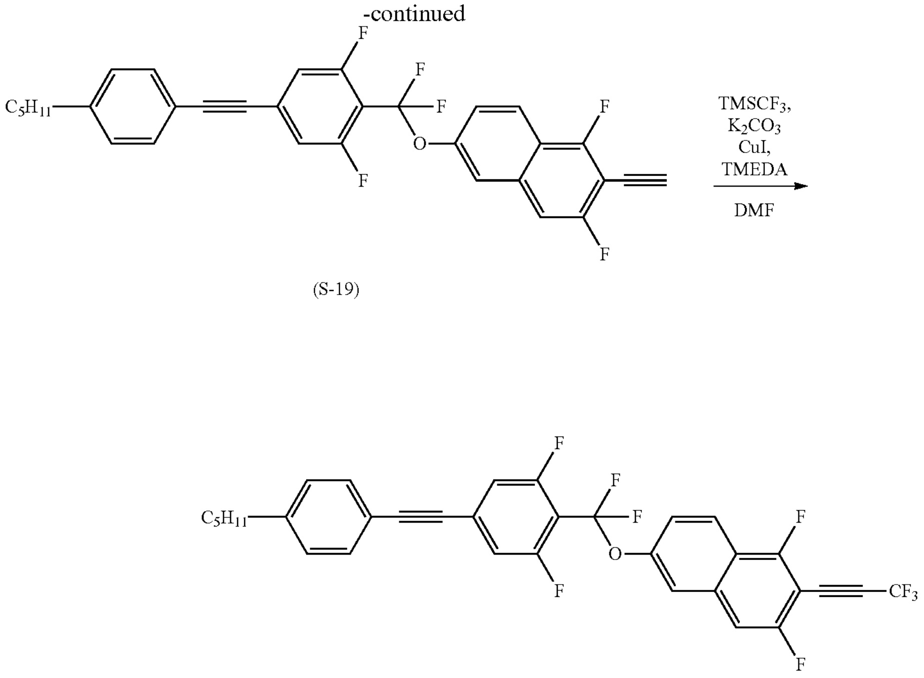

(S-19)

(No. 518)

First Step

Under a nitrogen atmosphere, compound (S-12) (10.7 g, 62.2 mmol), compound (S-13) (10.0 g, 51.8 mmol), Pd-132 (0.367 g, 0.518 mmol), cesium carbonate (33.8 g, 103 mmol) and acetonitrile (215 mL) were put in a reaction vessel, and the resulting mixture was refluxed under heating for 5 hours. The resulting reaction mixture was poured into water, and an aqueous layer was subjected to extraction with toluene. Combined organic layers were washed with an aqueous solution of ammonium chloride and water, and dried over anhydrous magnesium sulfate. The solution was concentrated under reduced pressure, and the residue was purified by silica gel column chromatography (heptane) to obtain compound (S-14) (12.9 g, yield: 87.8%).

Second Step

Under a nitrogen atmosphere, compound (S-14) (12.9 g, 45.4 mmol) and THF (100 mL) were put in a reaction vessel, and the resulting mixture was cooled to −70° C. Thereto, n-BuLi (1.64 M; n-hexane solution; 29.1 mL) was slowly added dropwise, and after dropwise addition, the resulting mixture was stirred for 1 hour while being maintained at −70° C. Next, a THF solution (15 mL) of dibromodifluoromethane (10.5 g, 49.9 mmol) was slowly added dropwise thereto, and after dropwise addition, the resulting mixture was stirred for 1 hour while being maintained at −70° C. Then, the resulting mixture was warmed to room temperature, and further stirred at room temperature for 1 hour. The resulting reaction mixture was poured into water, and an aqueous layer was subjected to extraction with ethyl acetate. Combined organic layers were washed with water, and dried over anhydrous magnesium sulfate. The solution was concentrated under reduced pressure, and the residue was purified by silica gel chromatography (heptane) to obtain compound (S-15) (13.7 g, yield: 73.1%).

Third Step

A synthesis was made in a manner similar to Synthesis Example 2 to obtain compound (S-16) (5.49 g, yield: 38.0%).

Fourth Step

A synthesis was made in a manner similar to Synthesis Example 1 to obtain compound (S-17) (4.18 g, yield: 61.4%).

Fifth Step

A synthesis was made in a manner similar to Synthesis Example 1 to obtain compound (S-18) (5.08 g, yield: 100%).

Sixth Step

A synthesis was made in a manner similar to Synthesis Example 1 to obtain compound (S-19) (4.30 g, yield: 88.4%).

Seventh Step

A synthesis was made in a manner similar to Synthesis Example 1 to obtain compound (No. 518) (0.85 g, yield: 19.8%).

$^1$H-NMR (ppm; $CDCl_3$): δ 8.11 (d, J=9.10 Hz, 1H), 7.69 (s, 1H), 7.50-7.43 (m, 3H), 7.35 (d, J=9.35 Hz, 1H), 7.19 (d, J=8.15 Hz, 2H), 7.13 (d, J=9.55 Hz, 2H), 2.63 (t, J=7.60 Hz, 2H), 1.67-1.58 (m, 2H), 1.39-1.27 (m, 4H), 0.90 (t, J=6.80 Hz, 3H).

Transition temperature: C 92.0 $S_A$ 117 N 133 I.

Maximum temperature ($T_{NI}$)=109° C.; Dielectric anisotropy (Δε)=56.1; optical anisotropy (Δn)=0.264.

Synthesis Example 4
Synthesis of Compound (No. 520)
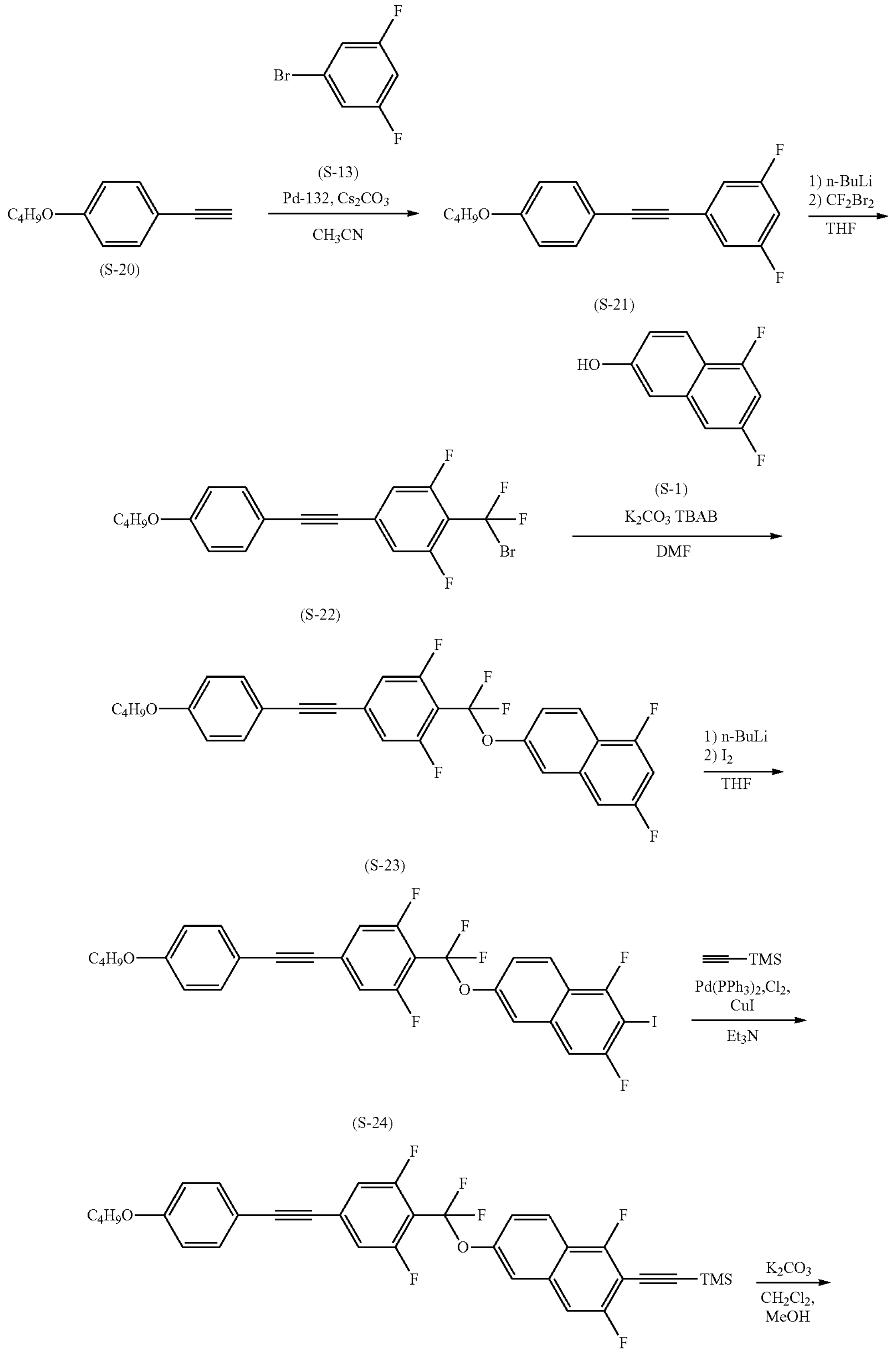
(S-20)
(S-21)
(S-22)
(S-23)
(S-24)
(S-25)

-continued

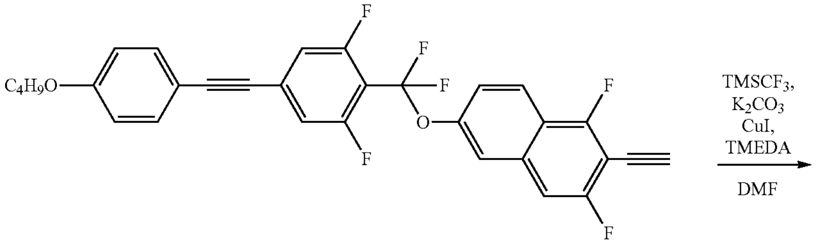

(S-26)

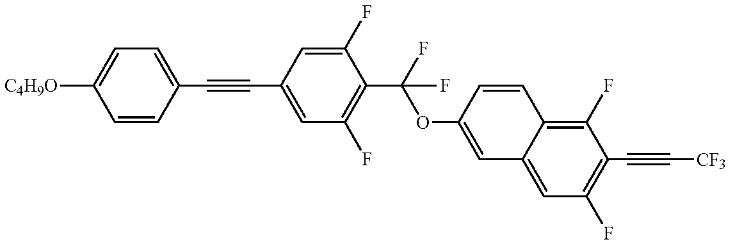

(No. 520)

First Step

A synthesis was made in a manner similar to Synthesis Example 3 to obtain compound (S-21) (11.5 g, yield: 83%).

Second Step

A synthesis was made in a manner similar to Synthesis Example 3 to obtain compound (S-22) (22.5 g, yield: 98%).

Third Step

A synthesis was made in a manner similar to Synthesis Example 2 to obtain compound (S-23) (8.84 g, yield: 42%).

Fourth Step

A synthesis was made in a manner similar to Synthesis Example 1 to obtain compound (S-24) (8.40 g, yield: 70%).

Fifth Step

A synthesis was made in a manner similar to Synthesis Example 1 to obtain compound (S-25) (6.40 g, yield: 79%).

Sixth Step

A synthesis was made in a manner similar to Synthesis Example 1 to obtain compound (S-26) (5.29 g, yield: 93%).

Seventh Step

A synthesis was made in a manner similar to Synthesis Example 1 to obtain compound (No. 520) (1.71 g, yield: 28%).

$^1$H-NMR (ppm; $CDCl_3$): δ 8.10 (d, J=9.10 Hz, 1H), 7.69 (s, 1H), 7.50-7.43 (m, 3H), 7.34 (d, J=9.40 Hz, 1H), 7.10 (d, J=9.60 Hz, 2H), 6.91-6.87 (m, 2H), 3.99 (t, J=6.55 Hz, 2H), 1.82-1.76 (m, 2H), 1.54-1.47 (m, 2H), 0.99 (t, J=7.45 Hz, 3H).

A sample having a ratio of the compound to the base liquid crystal (5% by weight: 95% by weight) was used for measurement of maximum temperature, optical anisotropy and dielectric anisotropy.

Transition temperature: C 129 $S_A$ 161 N 165 I.

Maximum temperature ($T_{NI}$)=134° C.; dielectric anisotropy (Δε)=57.7; optical anisotropy (Δn)=0.277.

Comparative Example 1

Comparison of Physical Properties

As a comparative compound, compound (C-1) described below was selected. The reason is that compound (C-1) is different from a compound of the invention in that compound (C-1) has a benzene ring in place of a naphthalene ring. Compound (C-1) was prepared in a manner similar to Synthesis Example 1 by using compound (S-50) prepared by a publicly-known method as a starting material.

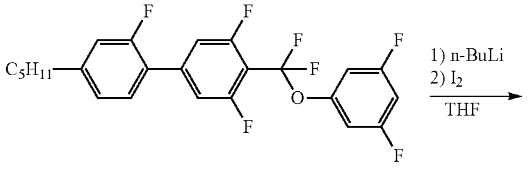

(S-50)

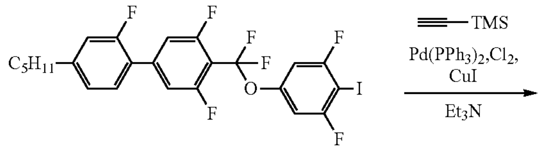

(S-51)

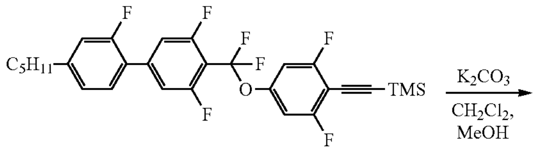

(S-52)

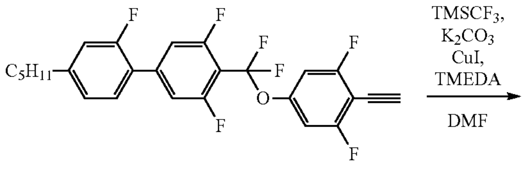

(S-53)

-continued

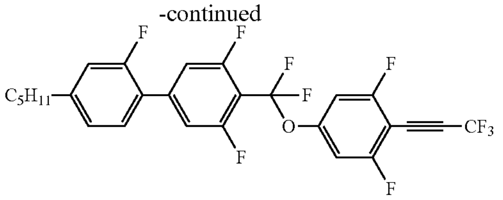

(C-1)

$^1$H-NMR (ppm; $CDCl_3$): δ 7.33 (t, J=8.00 Hz, 1H), 7.22 (d, J=10.9 Hz, 2H), 7.09-7.05 (m, 1H), 7.04-7.00 (m, 1H), 6.97 (d, J=7.95 Hz, 2H), 2.65 (t, J=7.60 Hz, 2H), 1.69-1.60 (m, 2H), 1.40-1.30 (m, 4H), 0.91 (t, J=6.75 Hz, 3H).

Transition temperature: C 52.9 I. Maximum temperature ($T_{NI}$)=14.4° C.; dielectric anisotropy (Δε)=48.1; optical anisotropy (Δn)=0.157.

TABLE 2

Physical properties of compound (No. 290) and comparative compound (C-1)

| Compound | Maximum temperature ($T_{NI}$) | Dielectric anisotropy (Δε) | Optical anisotropy (Δn) |
| --- | --- | --- | --- |
| 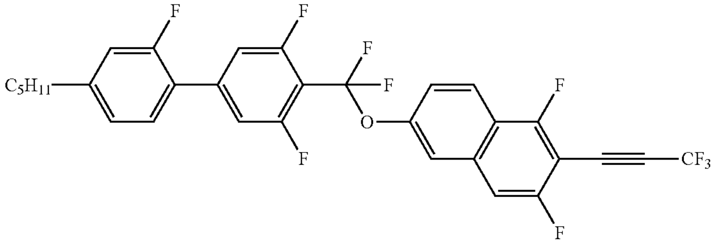 (No. 290) | 72.4° C. | 56.57 | 0.2103 |
| 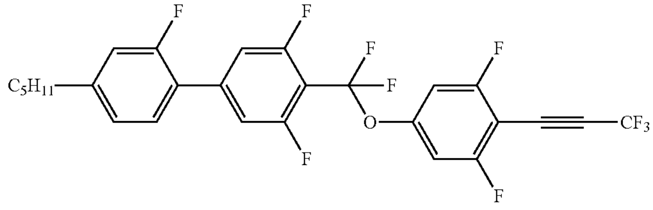 (C-1) | 14.4° C. | 48.10 | 0.1570 |

Physical properties of compound (No. 290) obtained by Synthesis Example 1 and comparative compound (C-1) are summarized in Table 2. From Table 2, compound (No. 290) was found to be satisfactory in view of high maximum temperature, large dielectric anisotropy, and large optical anisotropy.

2. Synthesis of Compound (1)

Compound (1) is prepared according to "2. Synthesis of compound (1)" and Synthesis Examples as described above. Specific examples of such a compound include compounds (No. 1) to (No. 120), compounds (No. 130) to (No. 539) and compounds (No. 550) to (No. 679) described below.

(No.1)
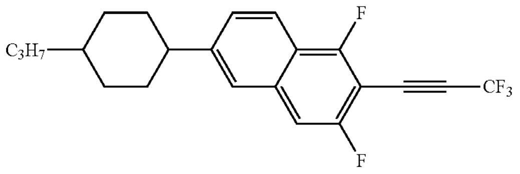
(No.2)
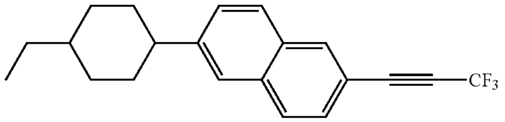
(No.3)
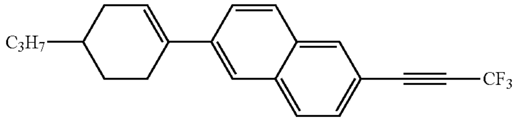
(No.4)
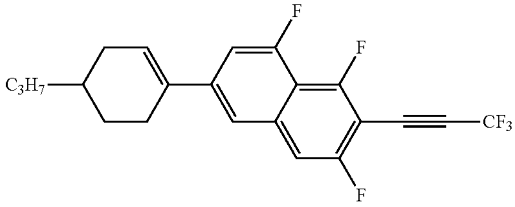
(No.5)
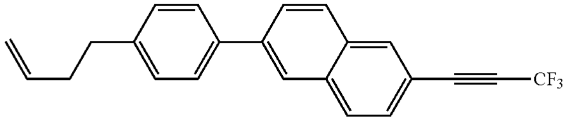
(No.6)
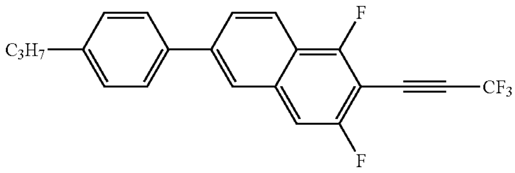
(No.7)
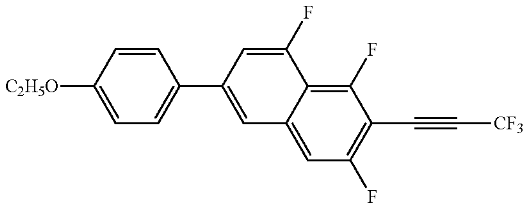
(No.8)
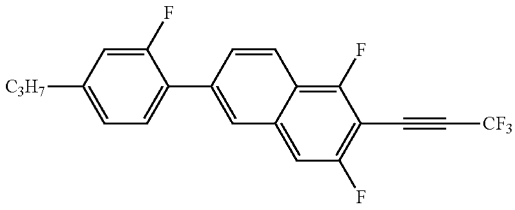
(No.9)
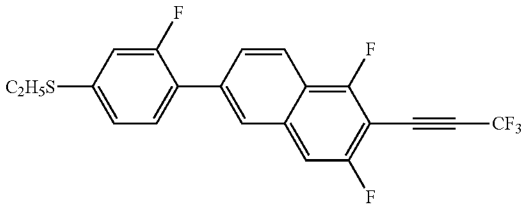
(No.10)
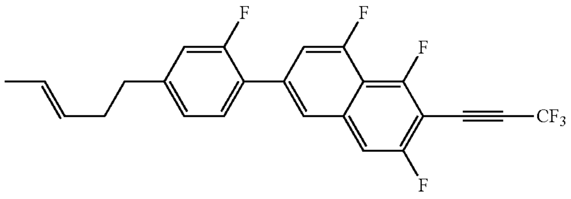
(No.11)
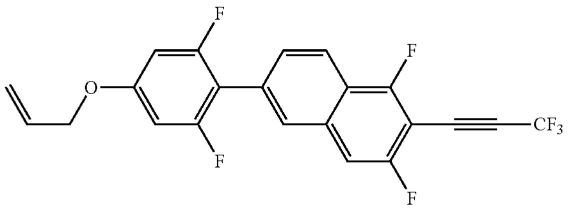
(No.12)
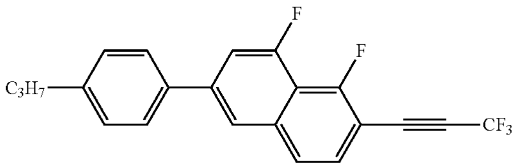
(No.13)
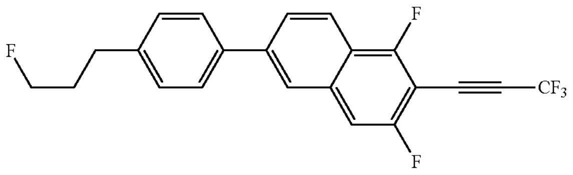
(No.14)
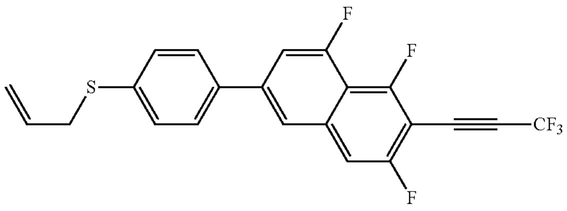

-continued
(No.15)
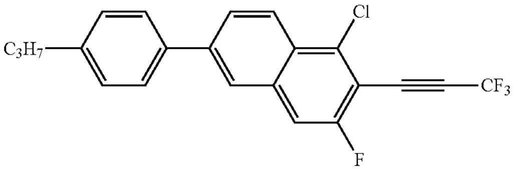
(No.16)
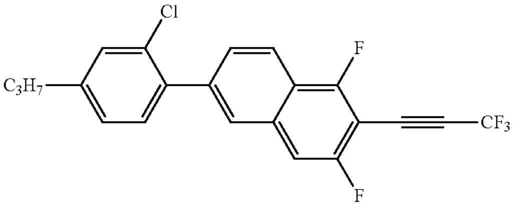
(No.17)
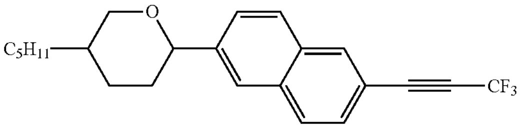
(No.18)
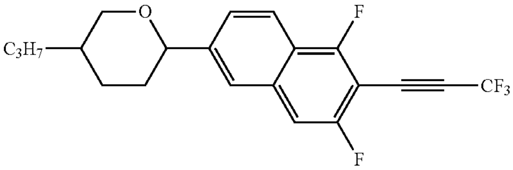
(No.19)
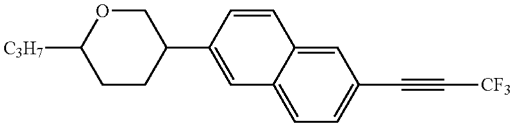
(No.20)
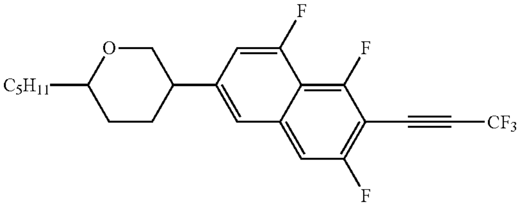
(No.21)
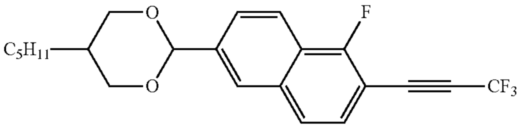
(No.22)
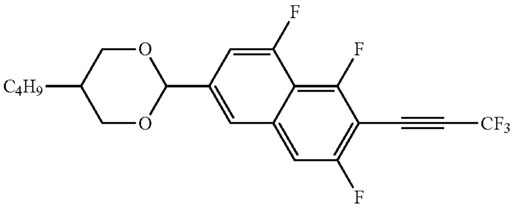
(No.23)
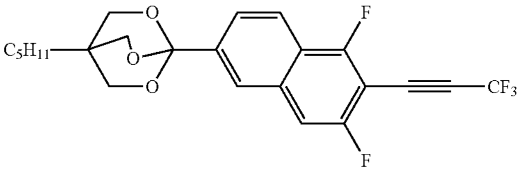
(No.24)
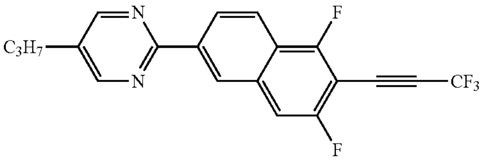
(No.25)
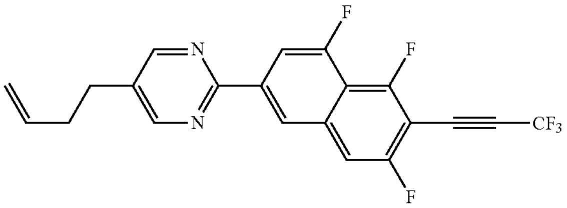
(No.26)
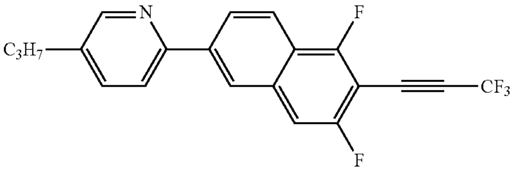
(No.27)
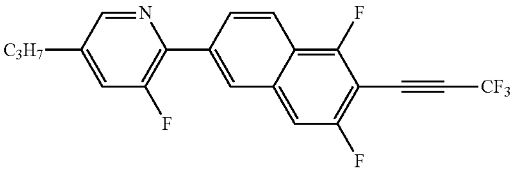
(No.28)
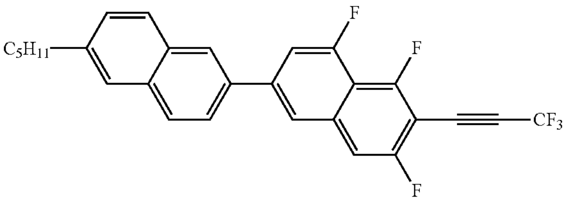

-continued
(No.29)
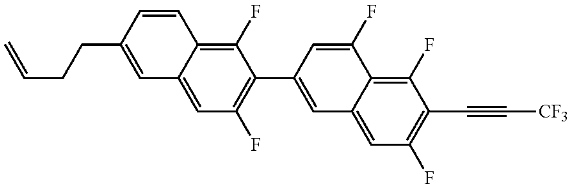
(No.30)
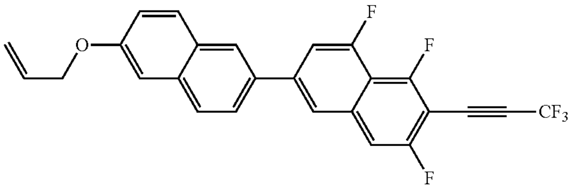
(No.31)
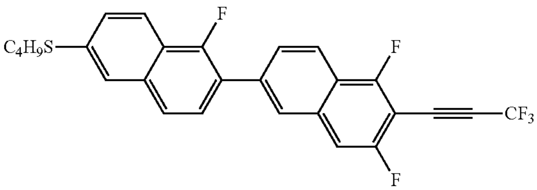
(No.32)
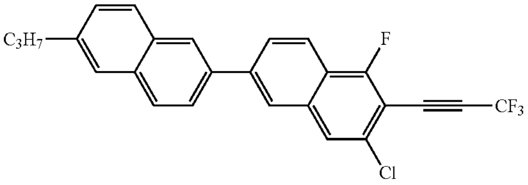
(No.33)
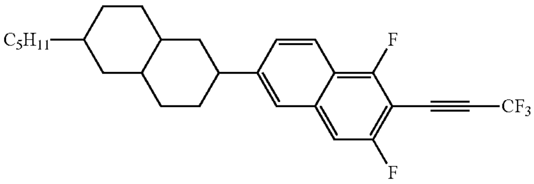
(No.34)
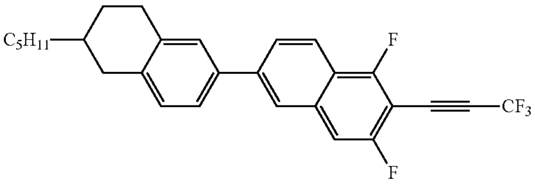
(No.35)
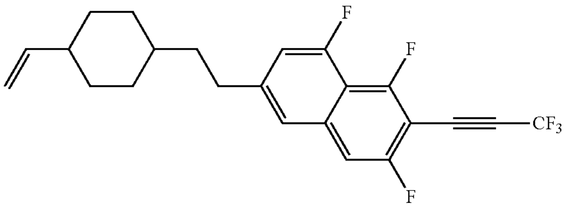
(No.36)
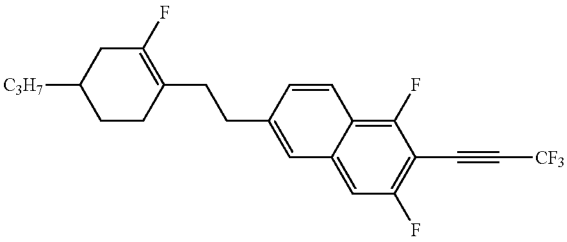
(No.37)
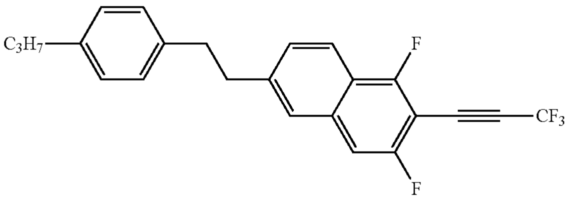
(No.38)
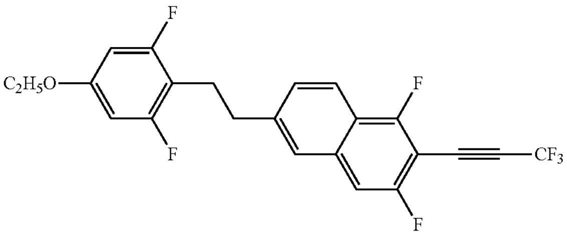
(No.39)
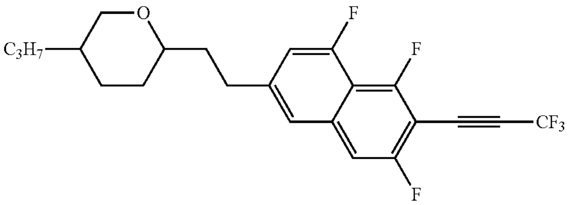
(No.40)
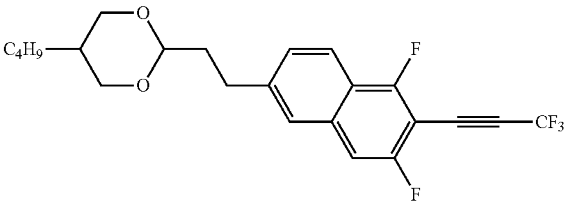

-continued
(No.41)
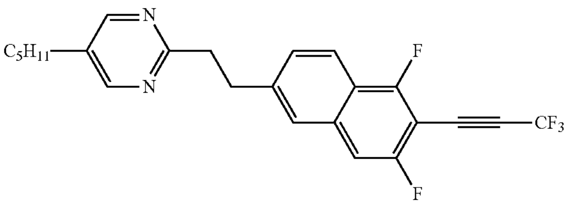
(No.42)
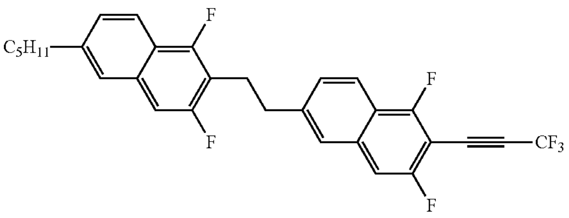
(No.43)
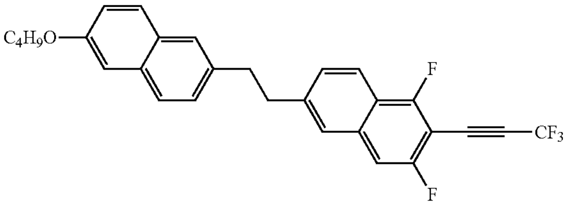
(No.44)
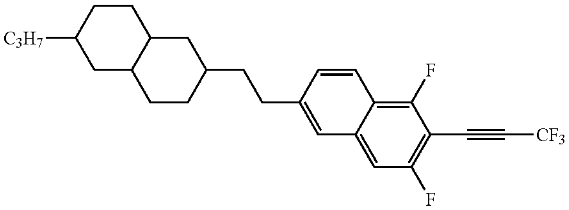
(No.45)
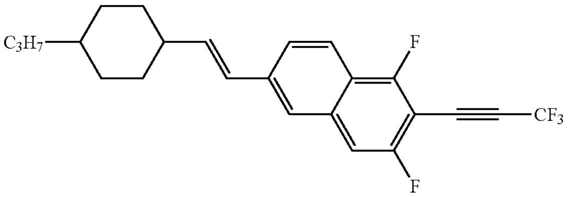
(No.46)
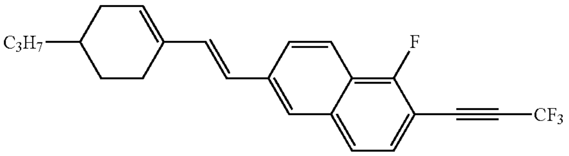
(No.47)
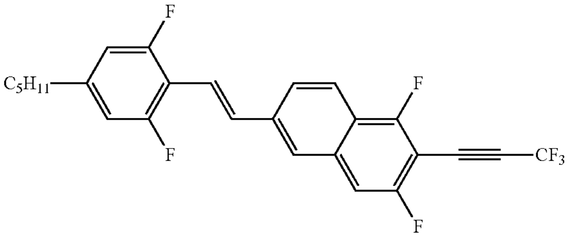
(No.48)
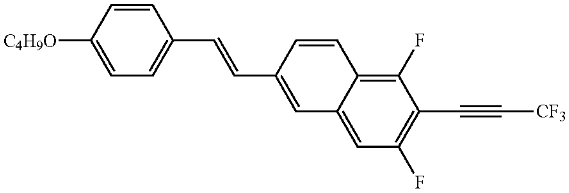
(No.49)
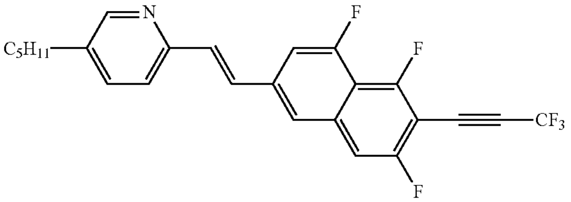
(No.50)
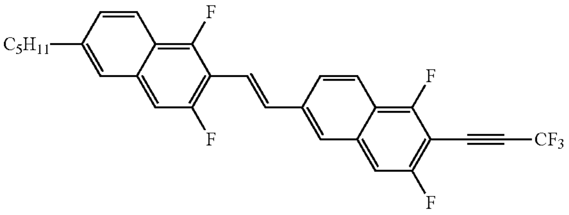
(No.51)
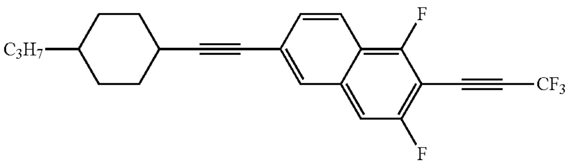
(No.52)
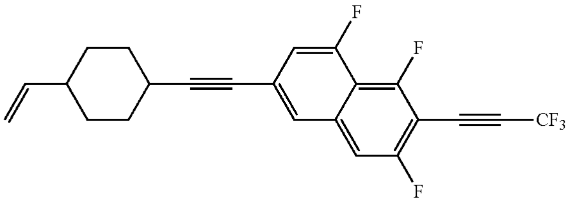
(No.53)
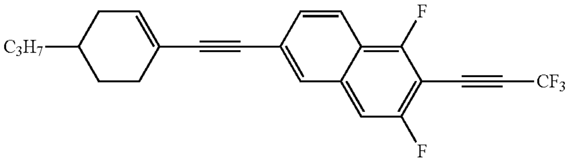
(No.54)
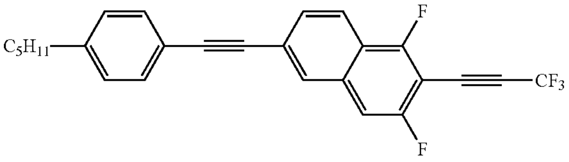

-continued
(No.55)
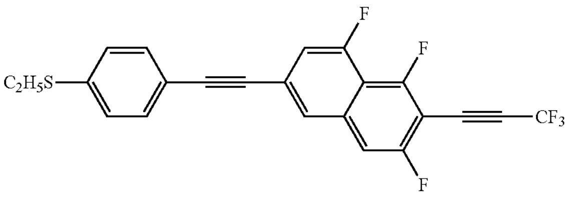
(No.56)
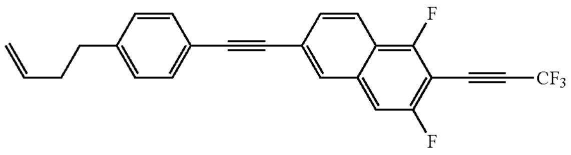
(No.57)
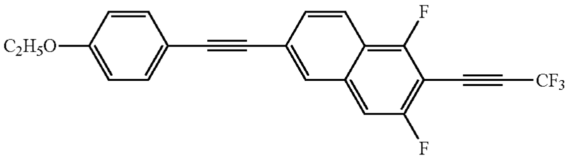
(No.58)
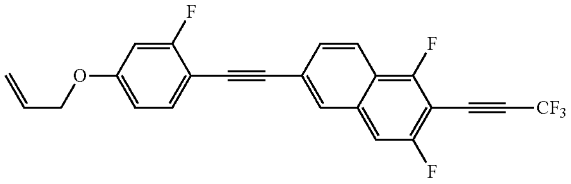
(No.59)
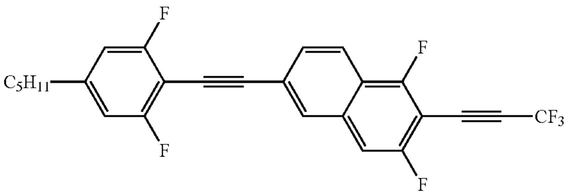
(No.60)
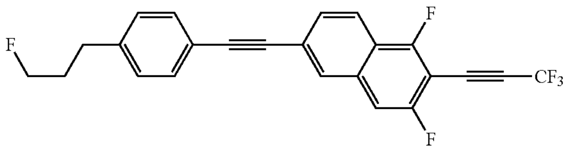
(No.61)
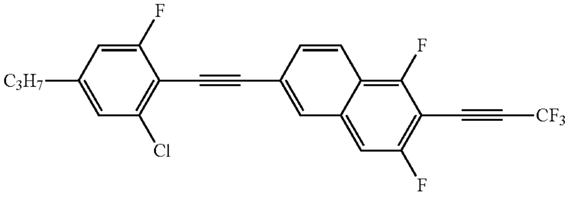
(No.62)
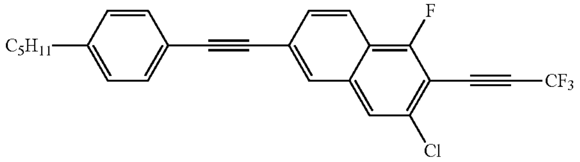
(No.63)
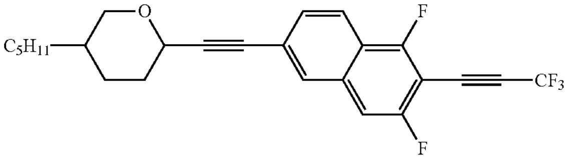
(No.64)
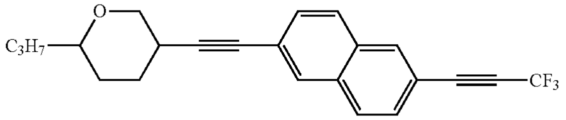
(No.65)
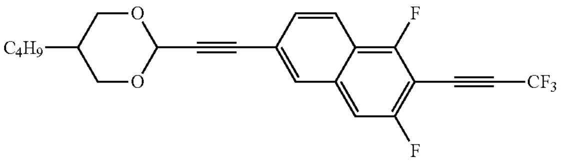
(No.66)
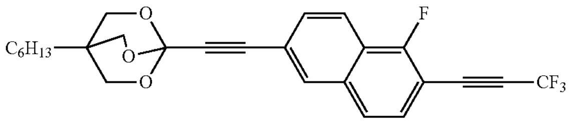
(No.67)
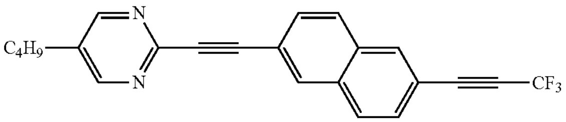
(No.68)
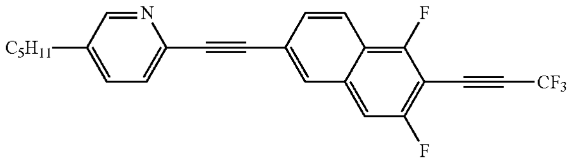

-continued
(No.69)
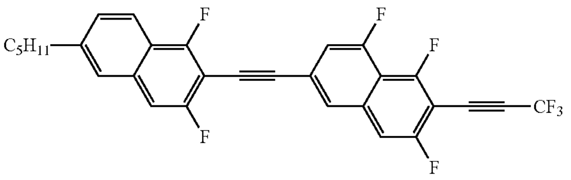
(No.70)
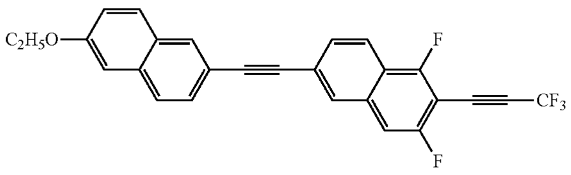
(No.71)
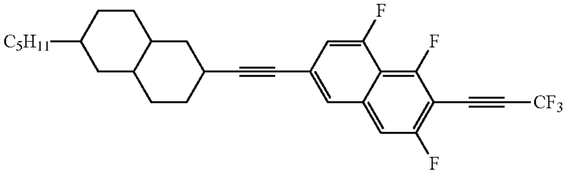
(No.72)
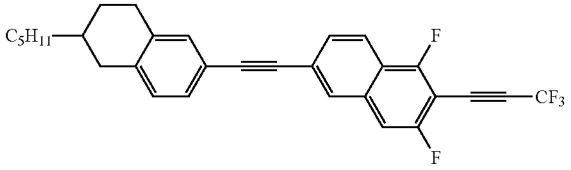
(No.73)
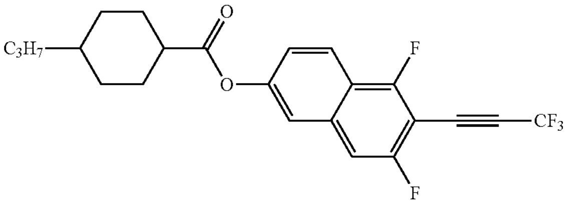
(No.74)
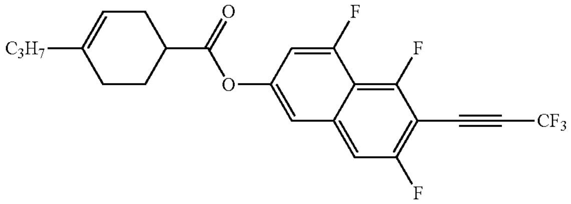
(No.75)
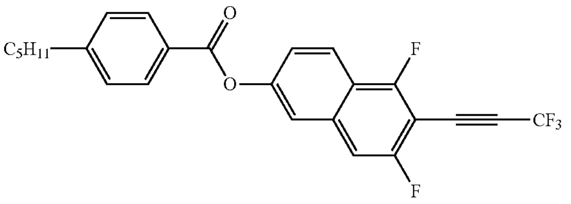
(No.76)
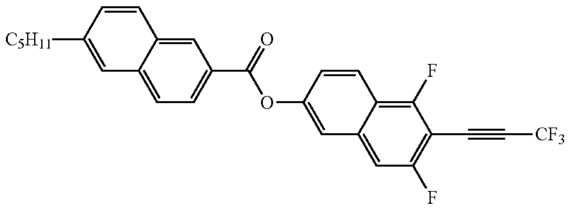
(No.77)
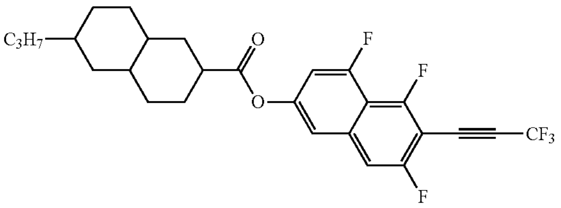
(No.78)
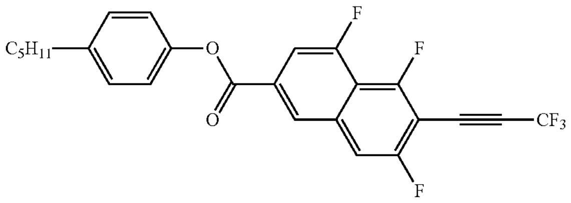
(No.79)
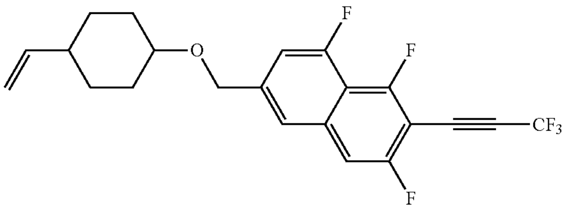
(No.80)
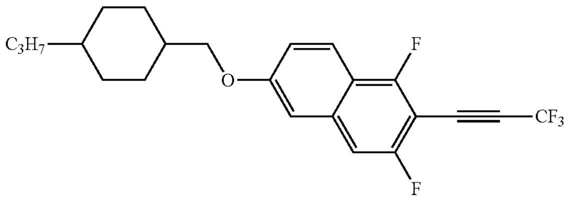
(No.81)
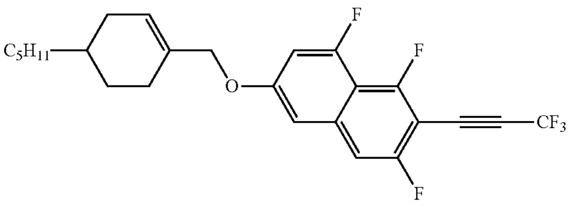
(No.82)
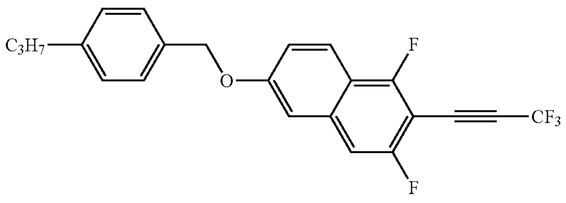

-continued
(No.83)
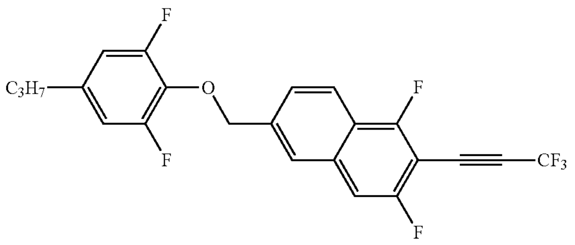
(No.84)
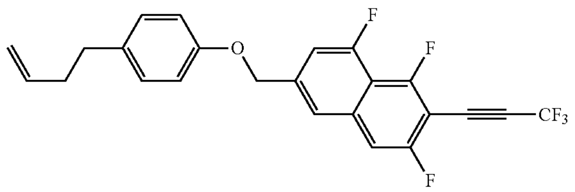
(No.85)
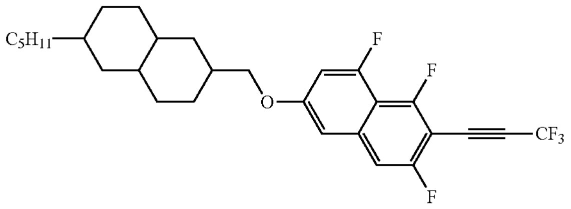
(No.86)
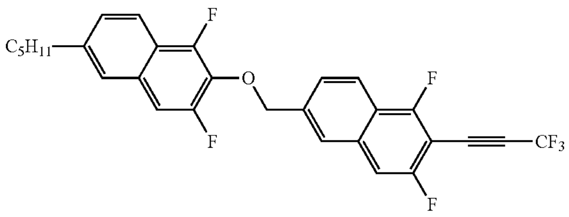
(No.87)
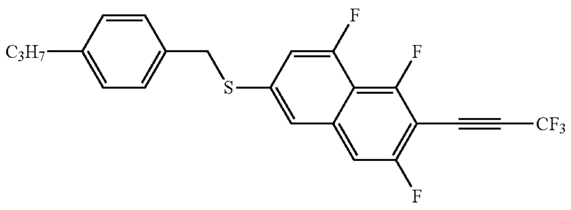
(No.88)
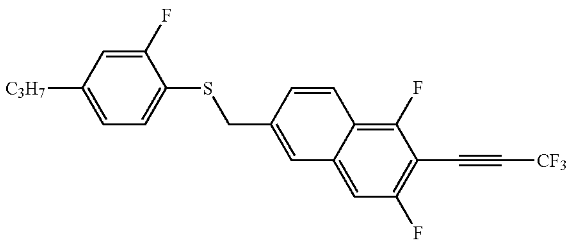
(No.89)
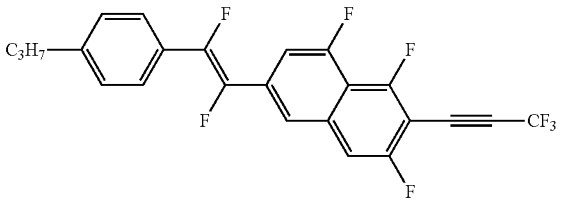
(No.90)
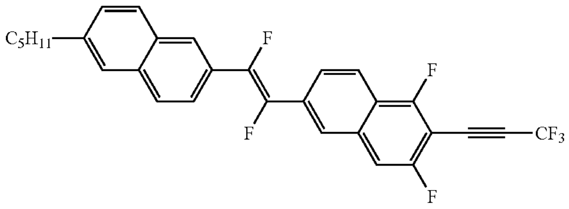
(No.91)
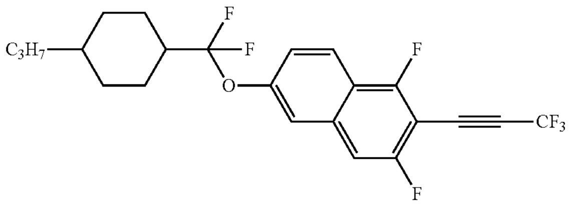
(No.92)
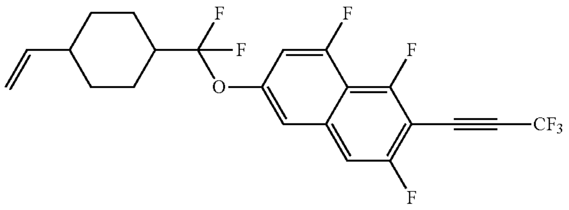
(No.93)
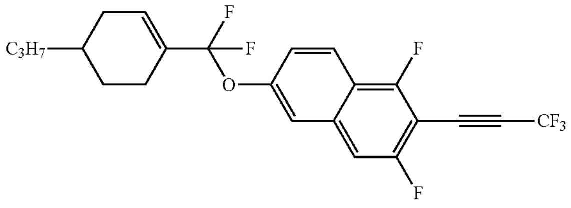
(No.94)
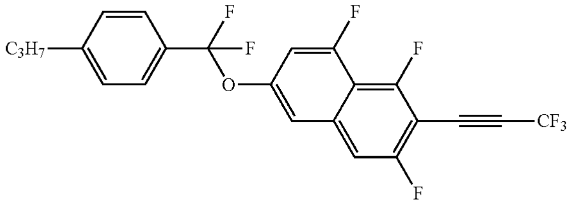

-continued
(No.95)
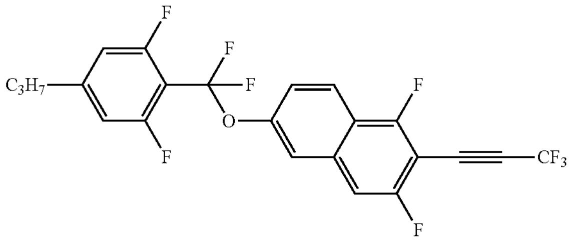
(No.96)
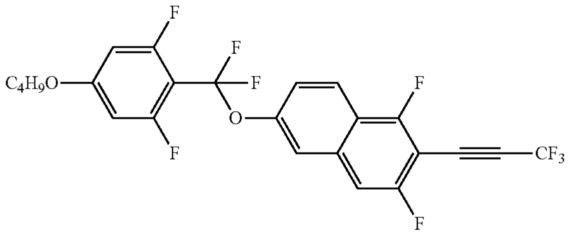
(No.97)
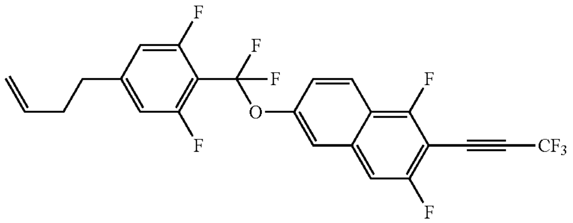
(No.98)
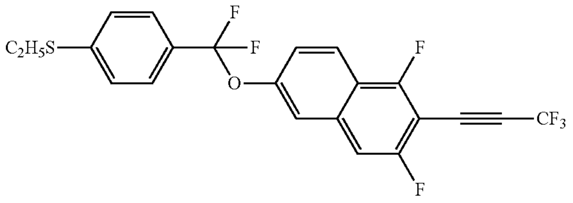
(No.99)
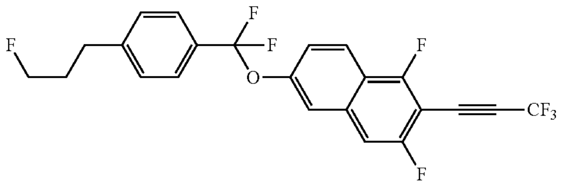
(No.100)
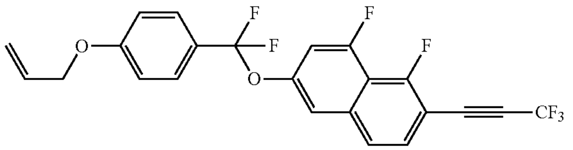
(No.101)
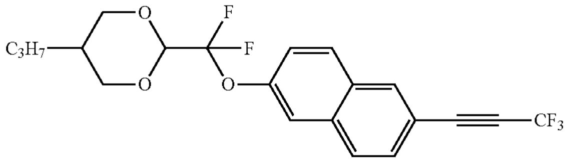
(No.102)
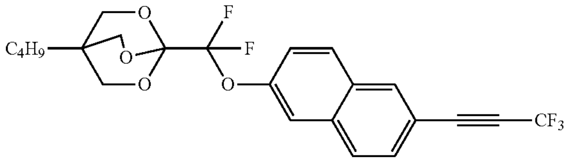
(No.103)
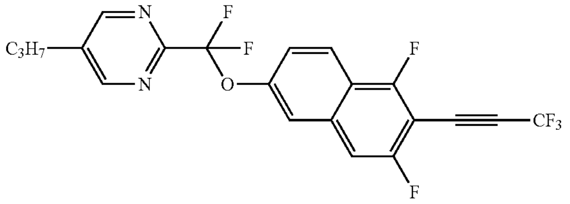
(No.104)
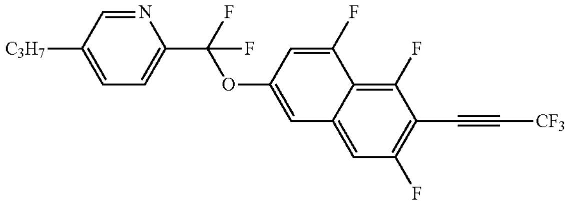
(No.105)
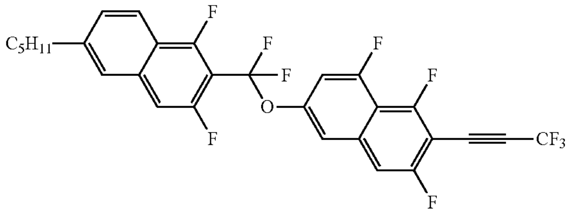
(No.106)
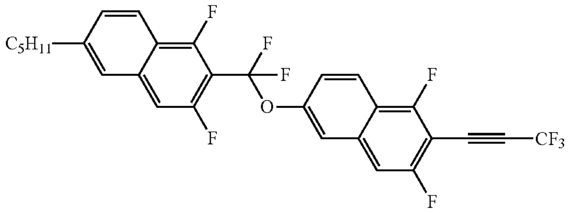
(No.107)
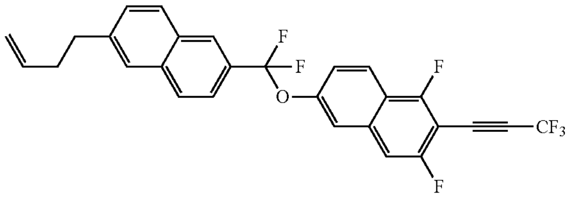
(No.108)
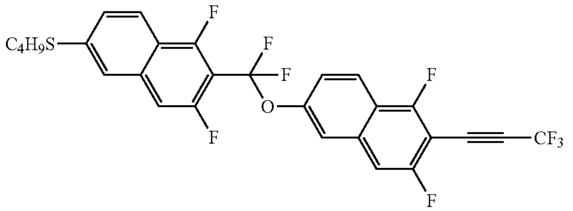

-continued
(No.109)
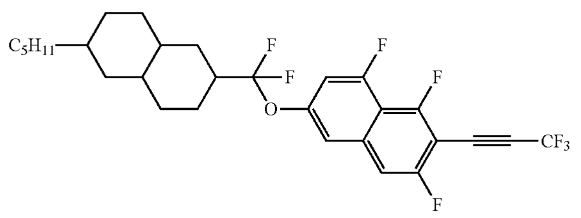
(No.110)
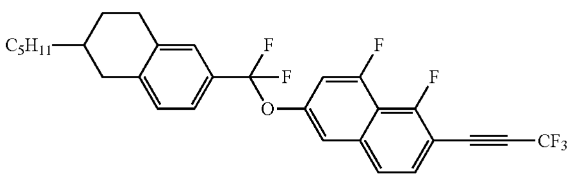
(No.111)
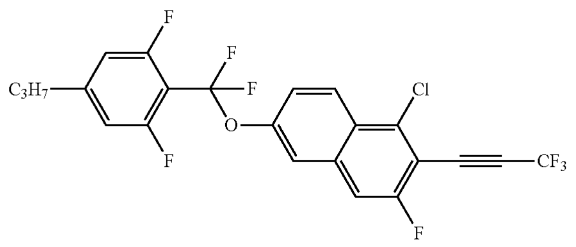
(No.112)
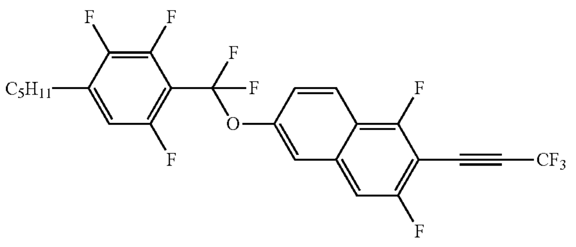
(No.113)
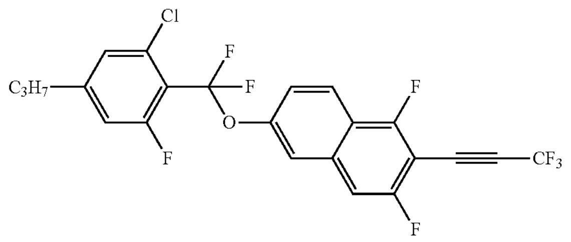
(No.114)
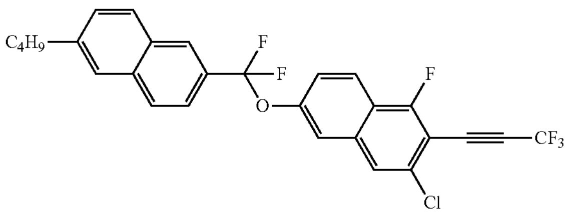
(No.115)
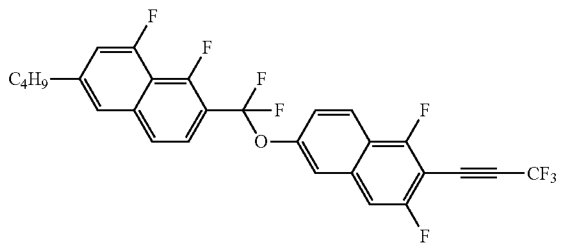
(No.116)
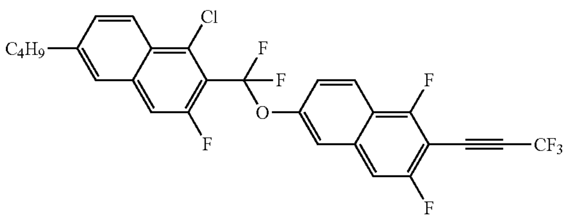
(No.117)
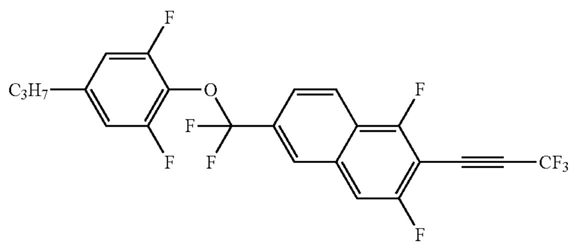
(No.118)
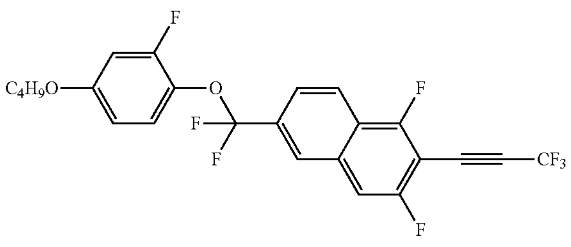
(No.119)
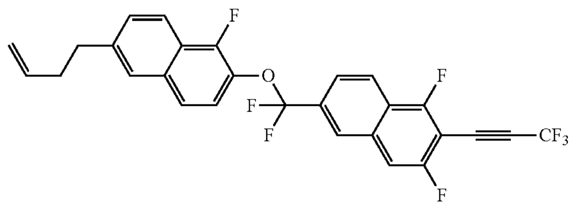
(No.120)
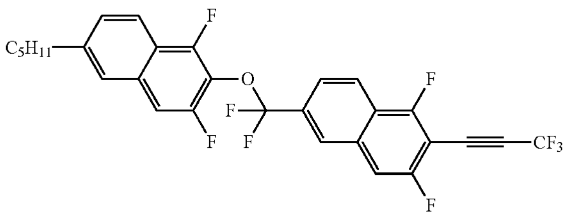

-continued
(No.130)
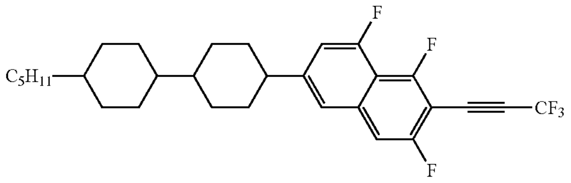
(No.131)
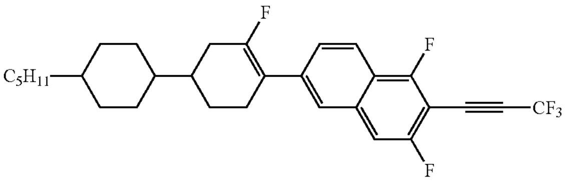
(No.132)
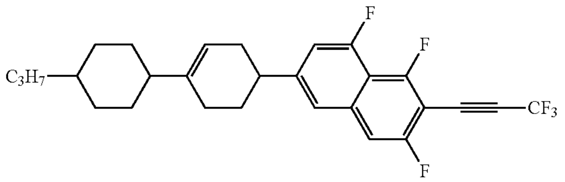
(No.133)
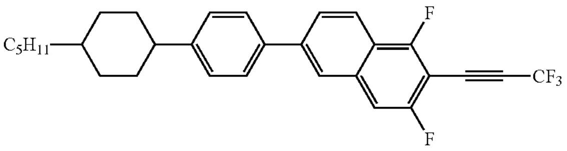
(No.134)
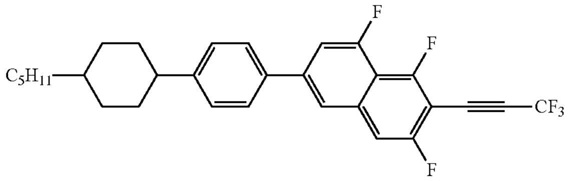
(No.135)
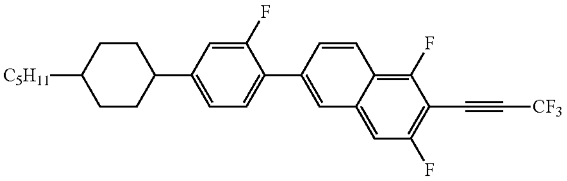
(No.136)
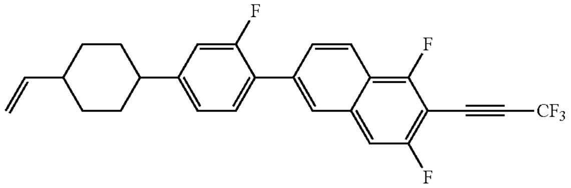
(No.137)
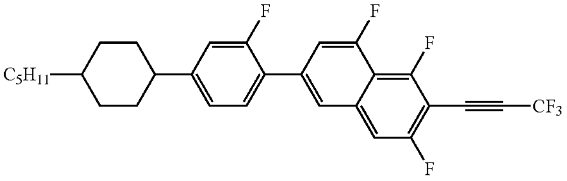
(No.138)
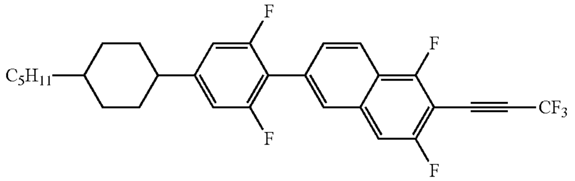
(No.139)
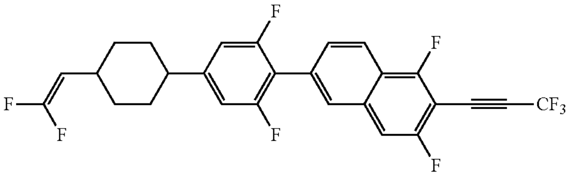
(No.140)
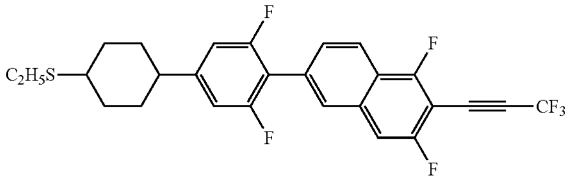
(No.141)
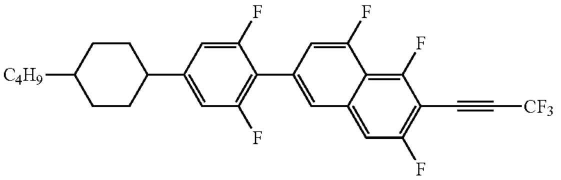
(No.142)
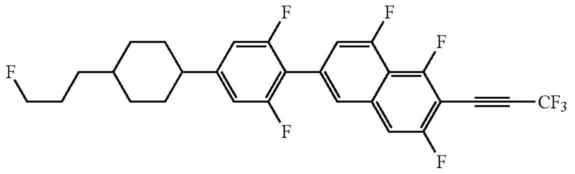
(No.143)
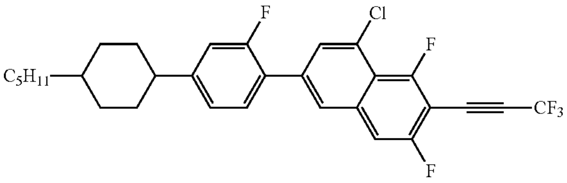

-continued
(No.144)
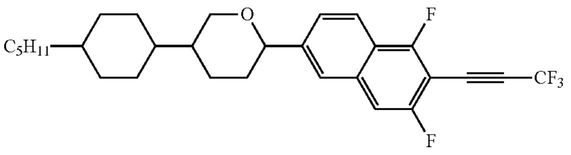
(No.145)
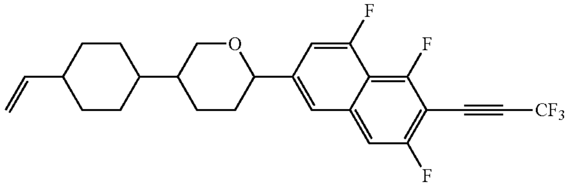
(No.146)
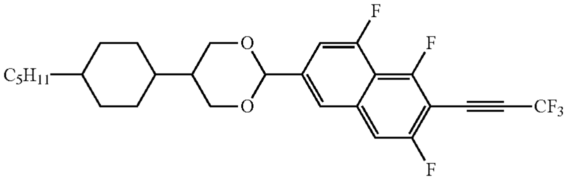
(No.147)
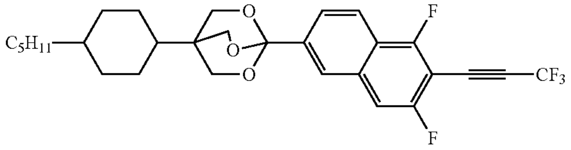
(No.148)
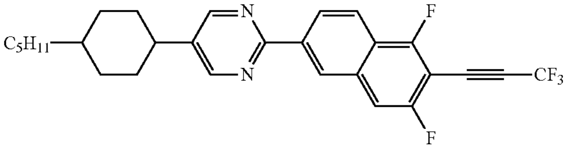
(No.149)
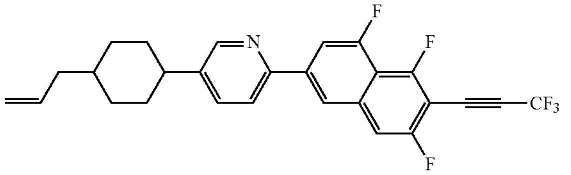
(No.150)
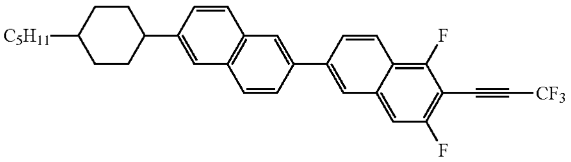
(No.151)
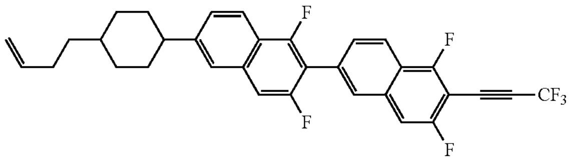
(No.152)
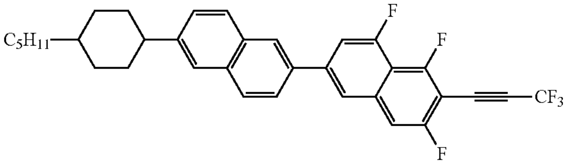
(No.153)
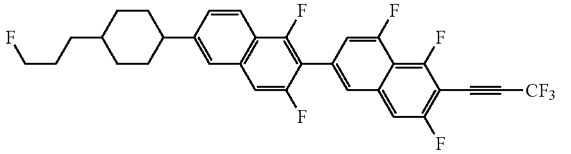
(No.154)
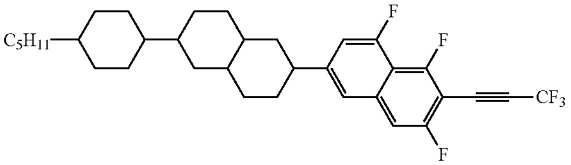
(No.155)
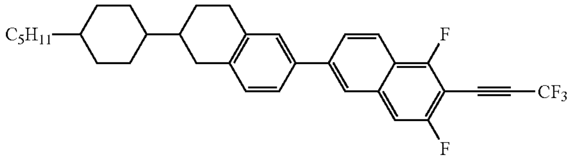
(No.156)
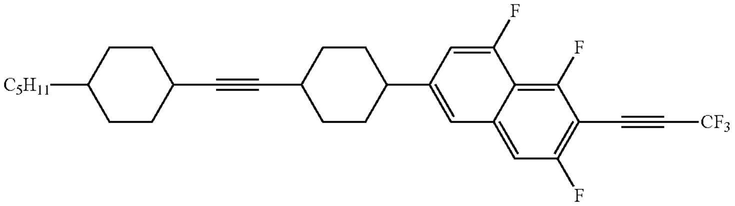
(No.157)
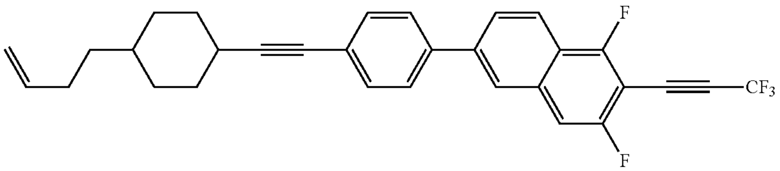

-continued
(No.158)
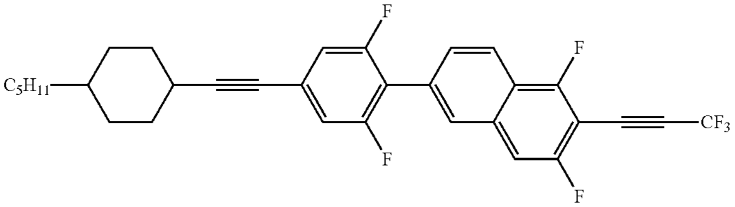
(No.159)
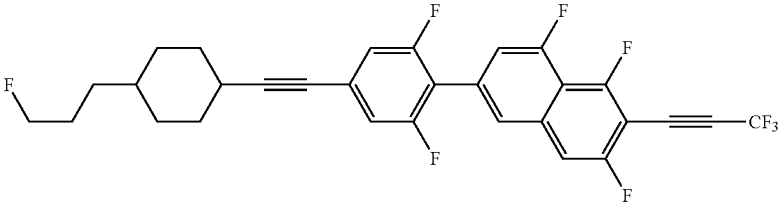
(No.160)
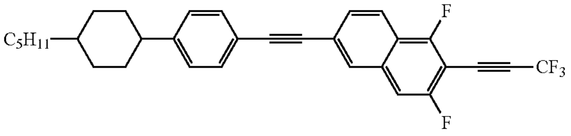
(No.161)
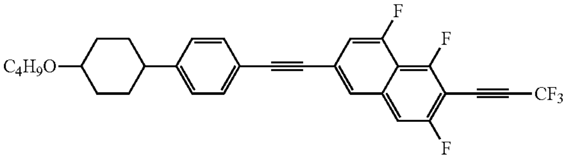
(No.162)
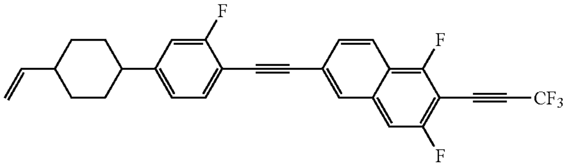
(No.163)
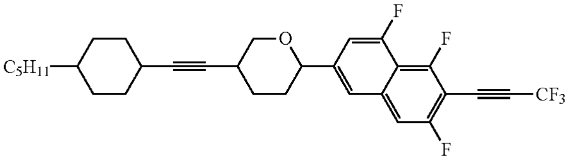
(No.164)
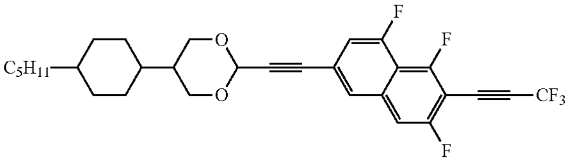
(No.165)
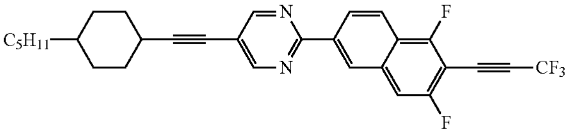
(No.166)
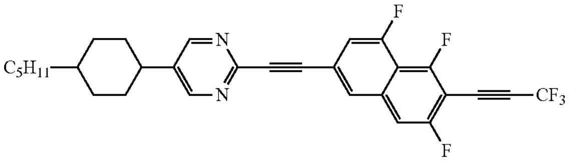
(No.167)
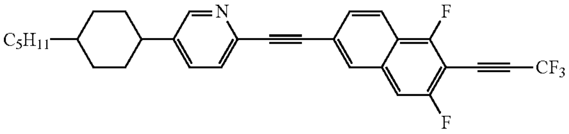
(No.168)
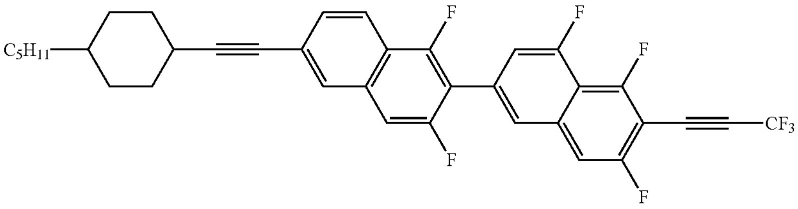
(No.169)
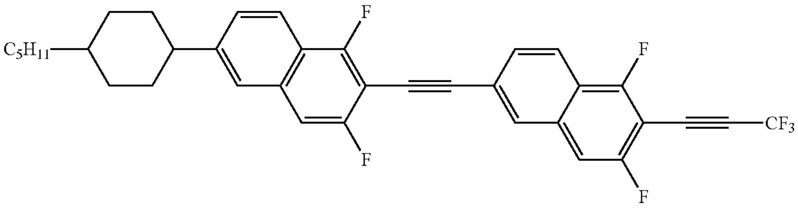

-continued
(No.170)
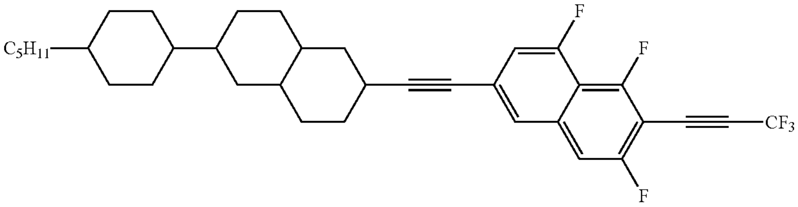
(No.171)
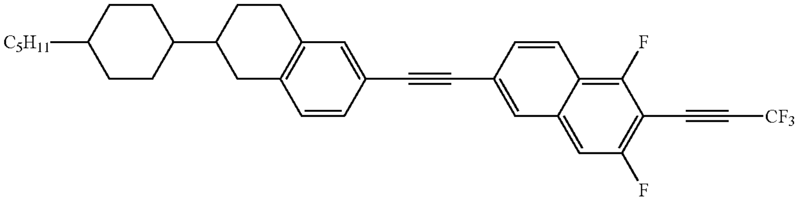
(No.172)
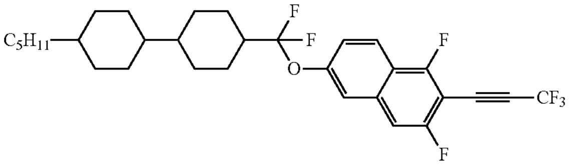
(No.173)
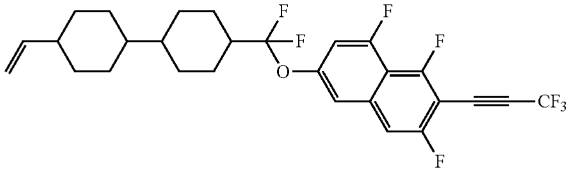
(No.174)
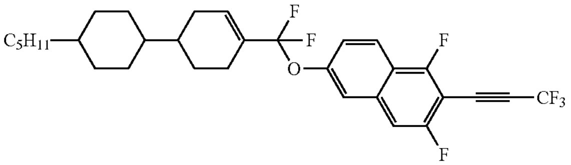
(No.175)
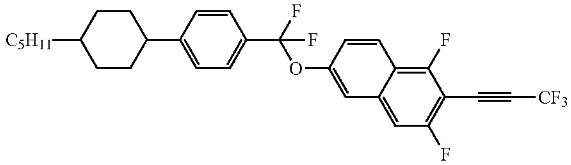
(No.176)
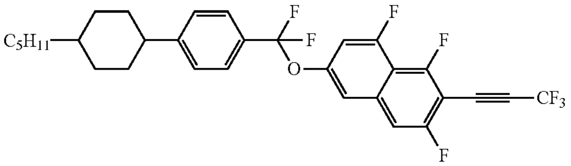
(No.177)
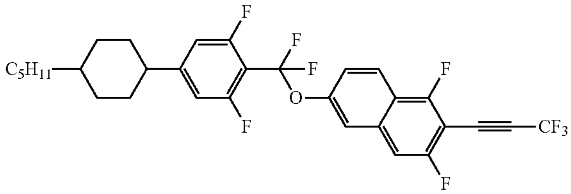
(No.178)
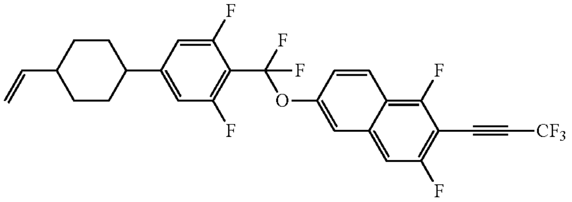
(No.179)
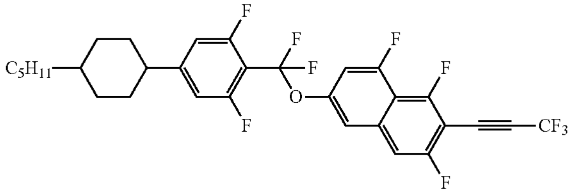
(No.180)
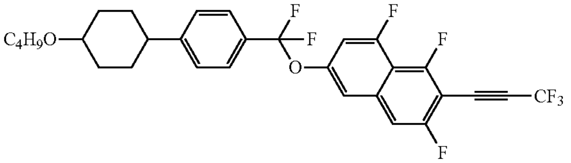
(No.181)
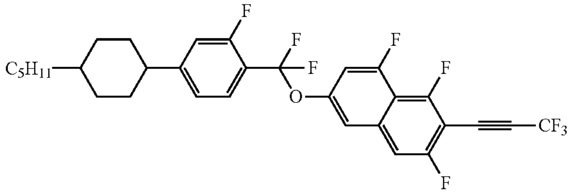

-continued
(No.182)
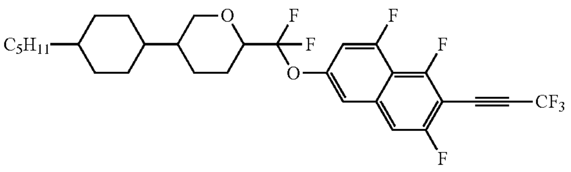
(No.183)
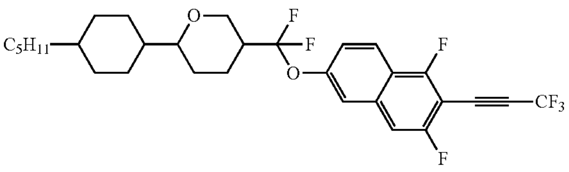
(No.184)
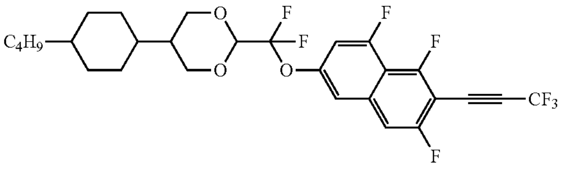
(No.185)
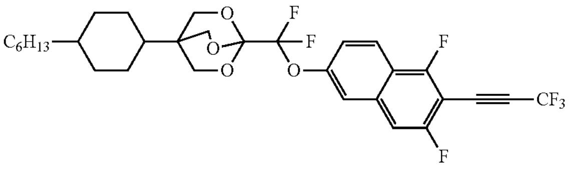
(No.186)
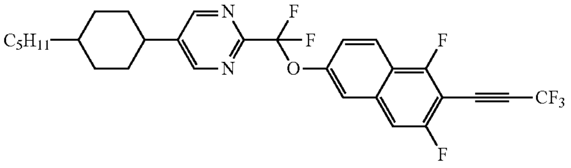
(No.187)
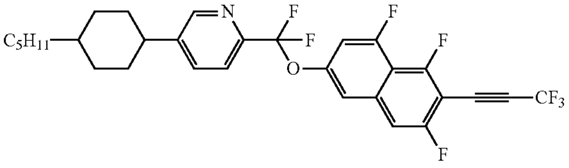
(No.188)
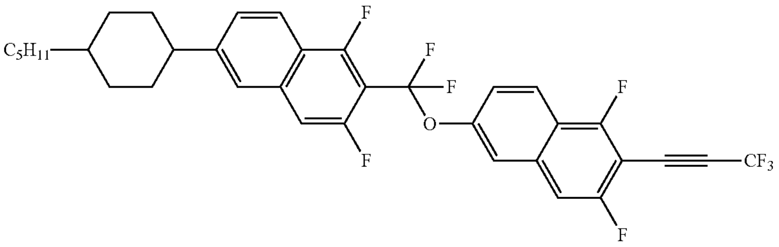
(No.189)
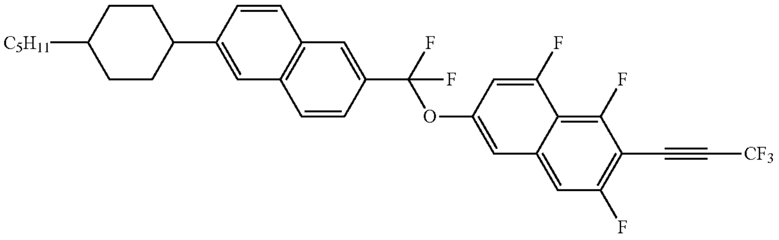
(No.190)
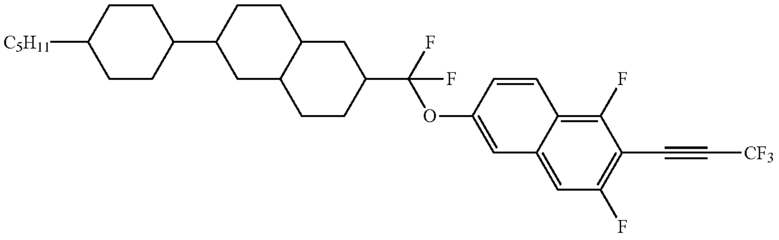
(No.191)
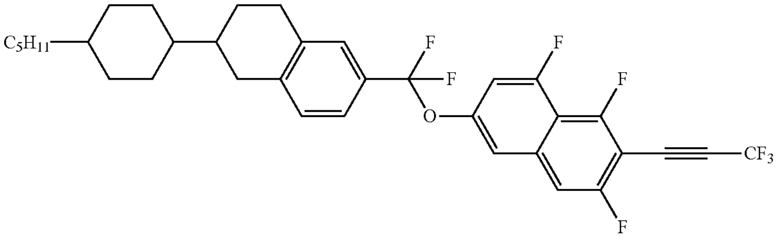

-continued
(No.192)
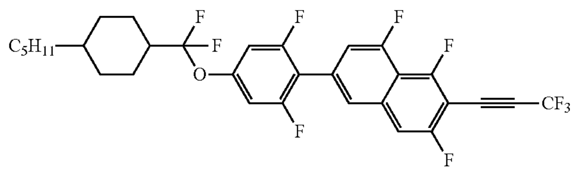
(No.193)
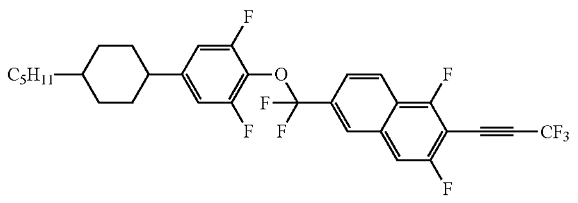
(No.194)
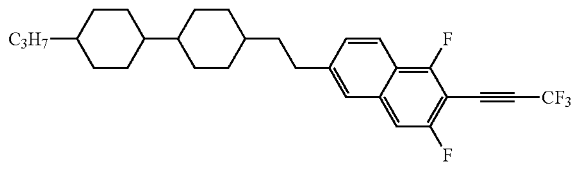
(No.195)
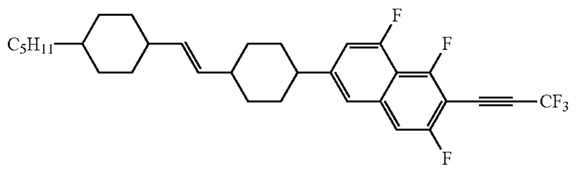
(No.196)
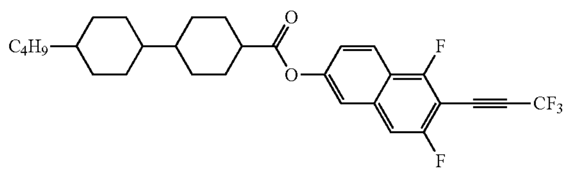
(No.197)
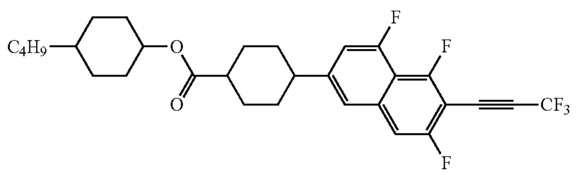
(No.198)
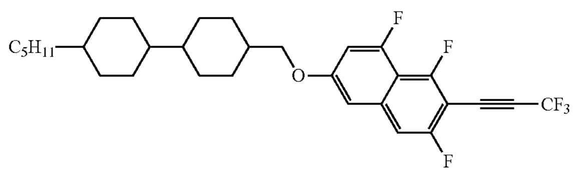
(No.199)
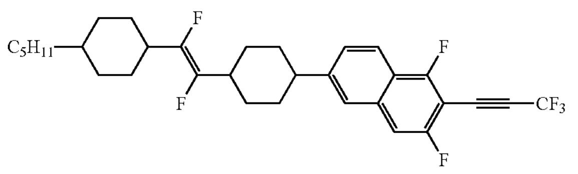
(No.200)
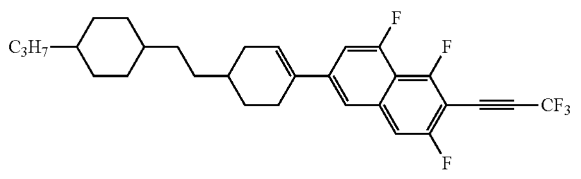
(No.201)
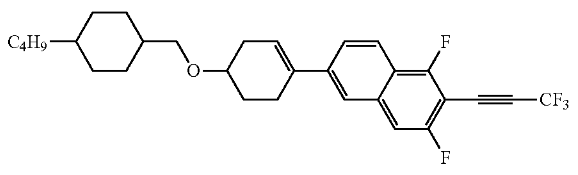
(No.202)
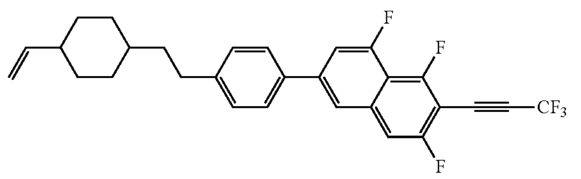
(No.203)
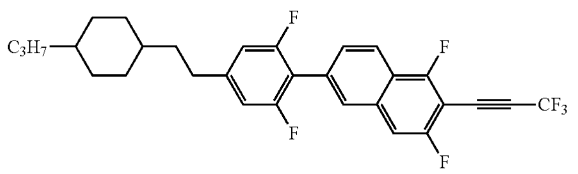
(No.204)
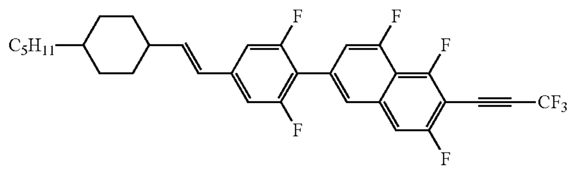
(No.205)
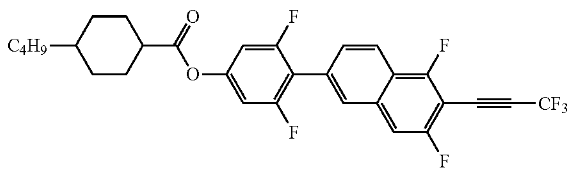
(No.206)
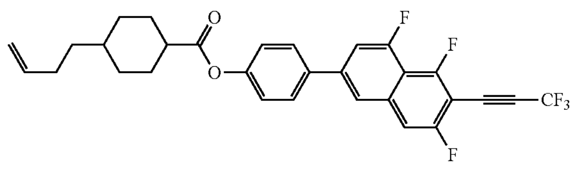
(No.207)
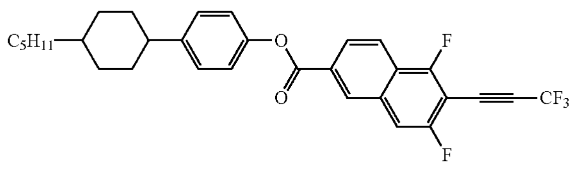

-continued
(No.208)
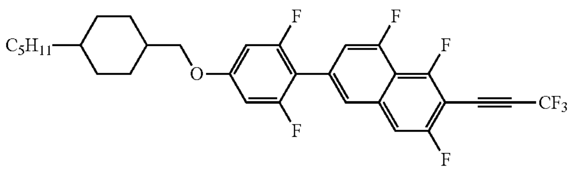
(No.209)
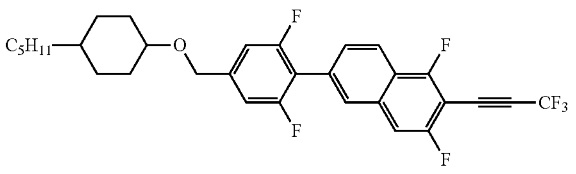
(No.210)
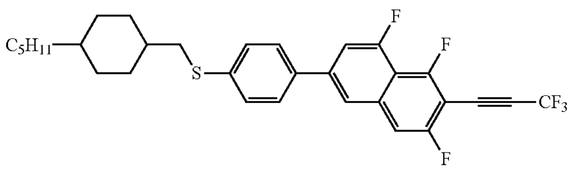
(No.211)
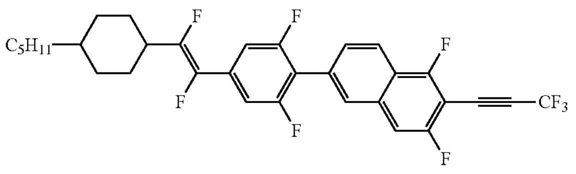
(No.212)
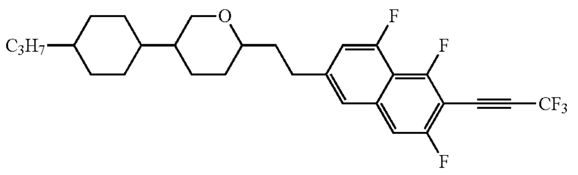
(No.213)
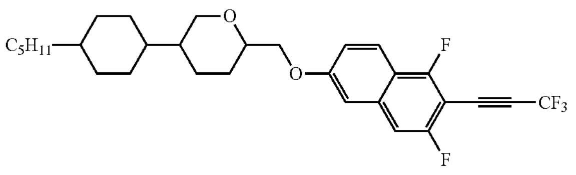
(No.214)
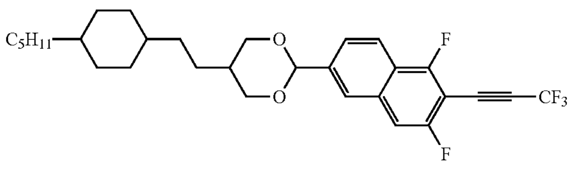
(No.215)
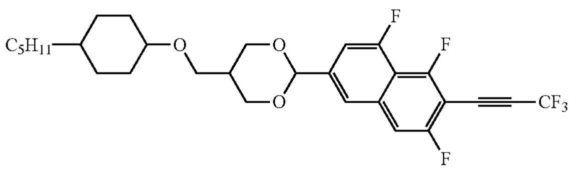
(No.216)
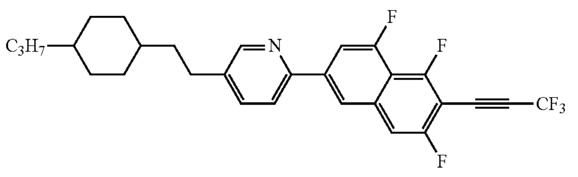
(No.217)
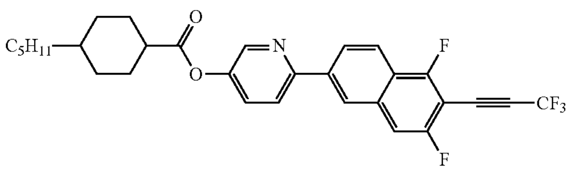
(No.218)
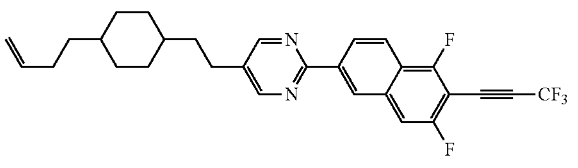
(No.219)
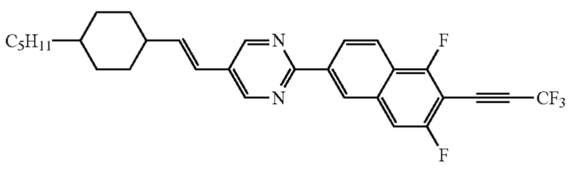
(No.220)
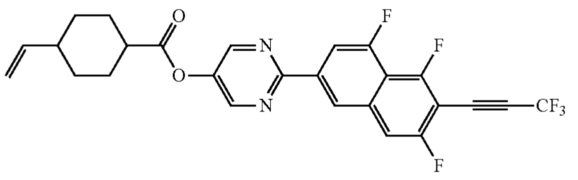
(No.221)
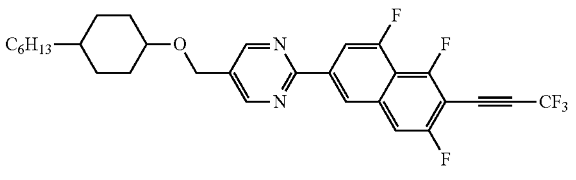
(No.222)
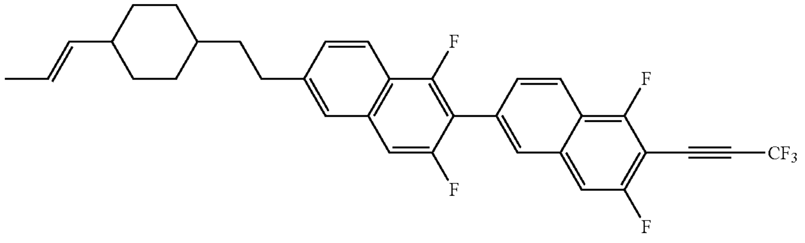

-continued
(No.223)
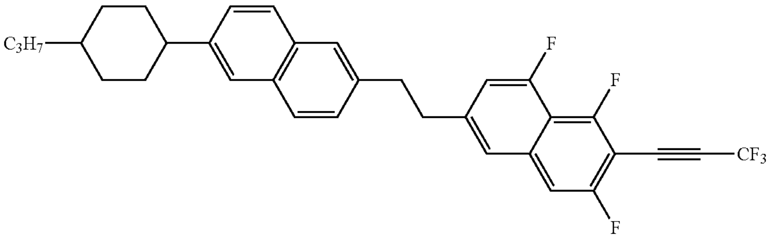
(No.224)
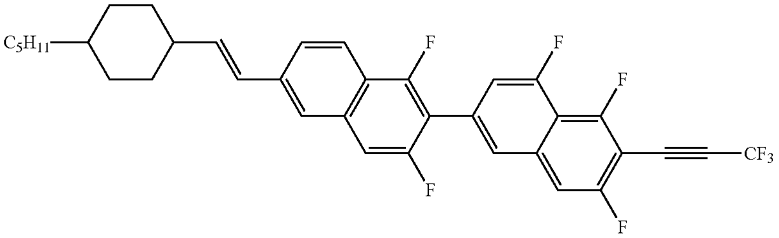
(No.225)
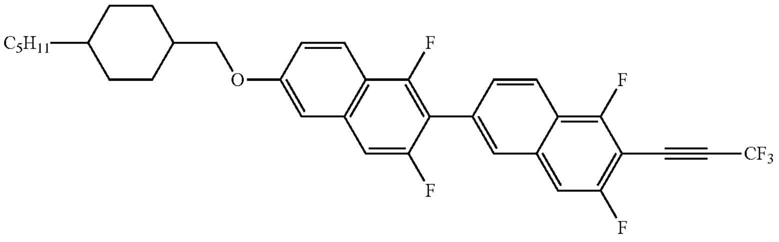
(No.226)
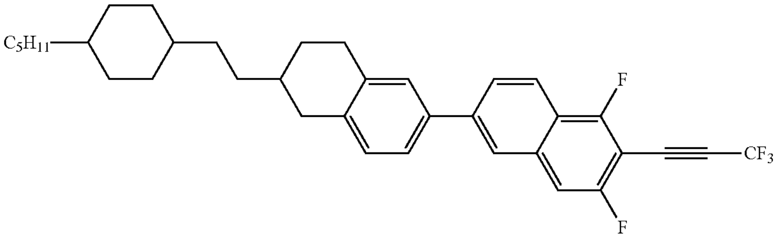
(No.227)
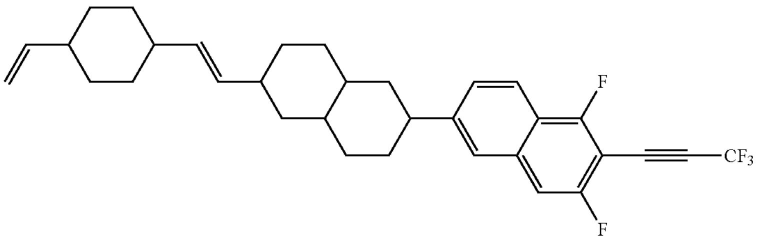
(No.228)
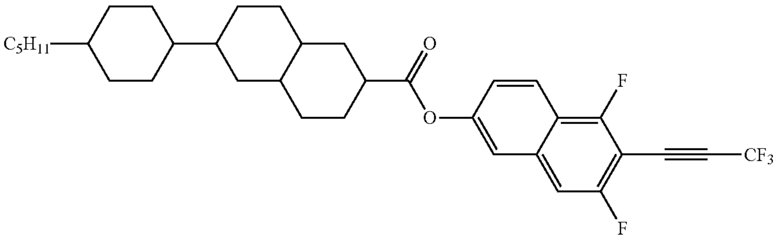

-continued
(No.229)
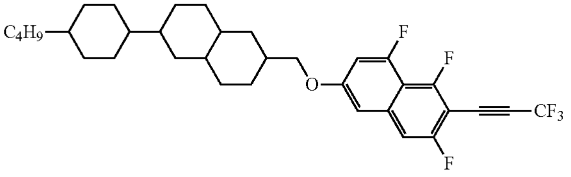
(No.230)
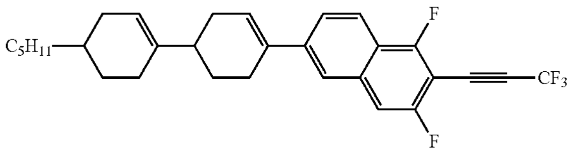
(No.231)
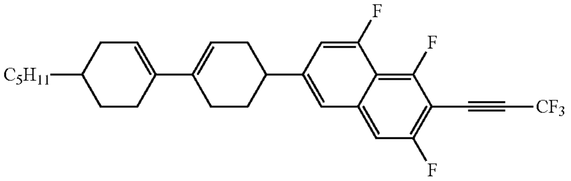
(No.232)
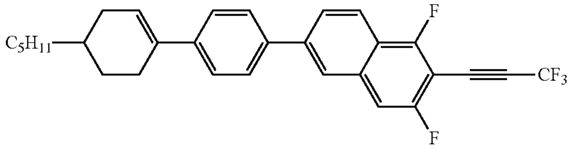
(No.233)
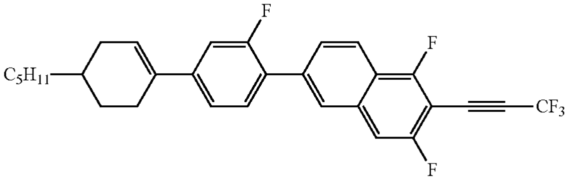
(No.234)
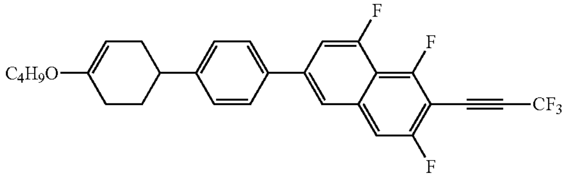
(No.235)
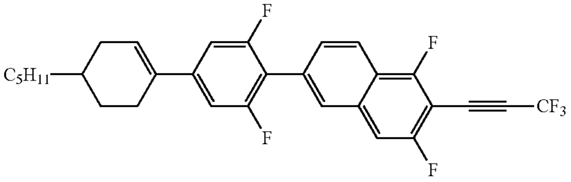
(No.236)
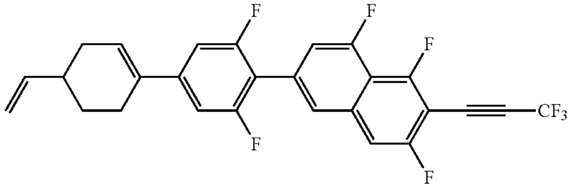
(No.237)
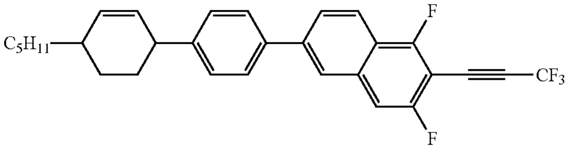
(No.238)
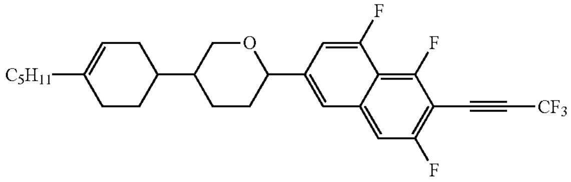
(No.239)
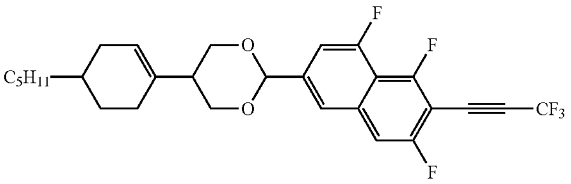
(No.240)
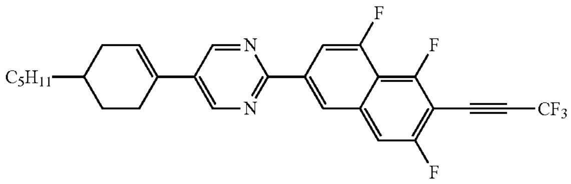
(No.241)
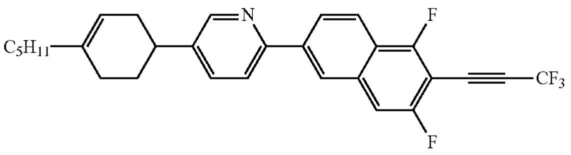
(No.242)
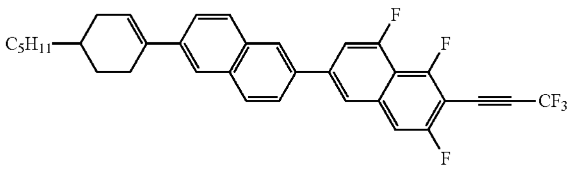

-continued
(No.243)
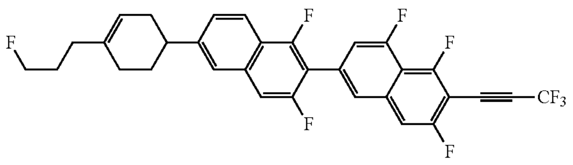
(No.244)
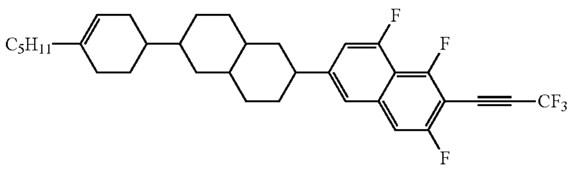
(No.245)
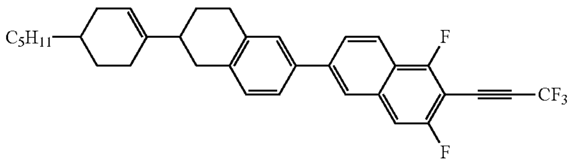
(No.246)
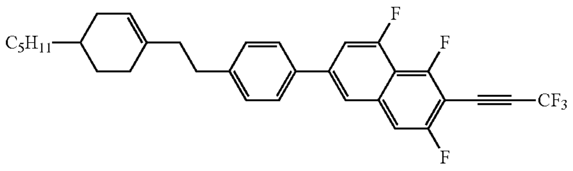
(No.247)
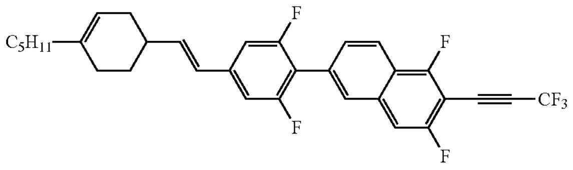
(No.248)
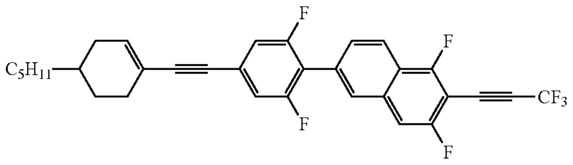
(No.249)
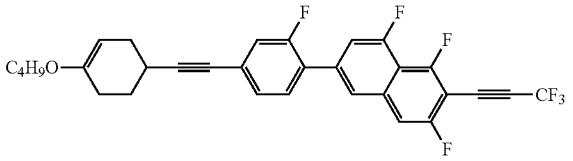
(No.250)
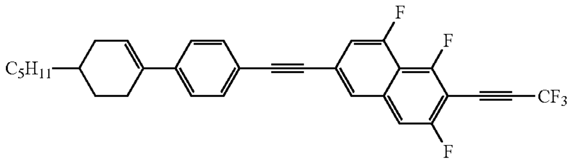
(No.251)
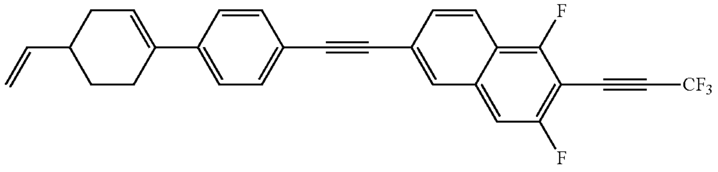
(No.252)
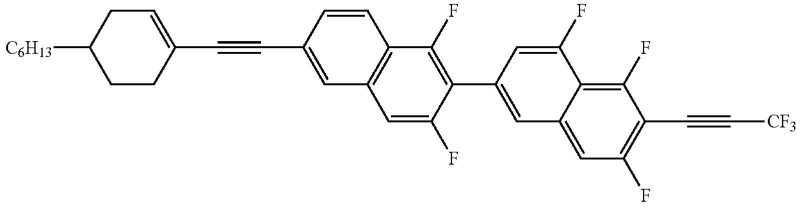
(No.253)
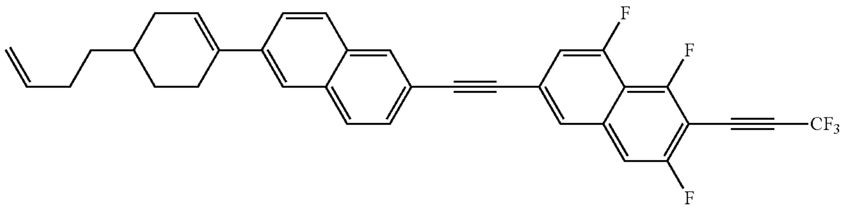
(No.254)
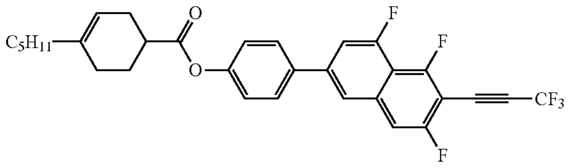
(No.255)
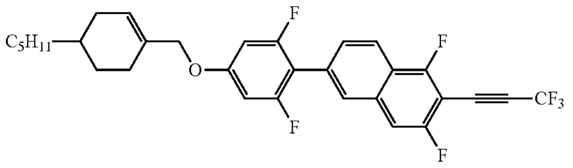

-continued
(No.256)
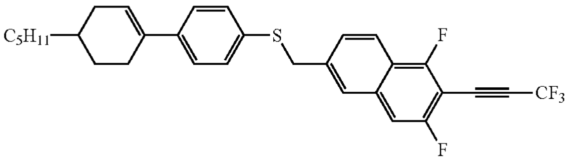
(No.257)
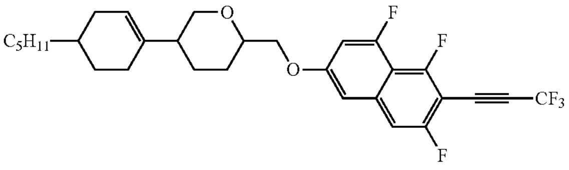
(No.258)
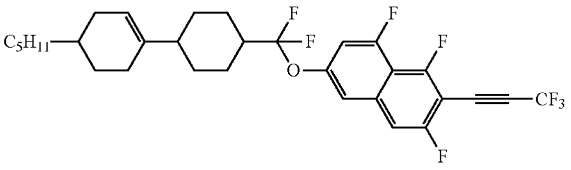
(No.259)
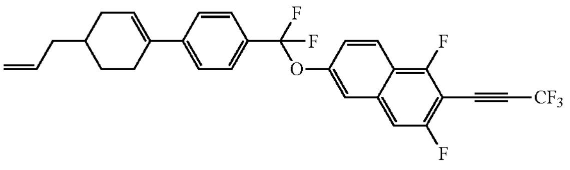
(No.260)
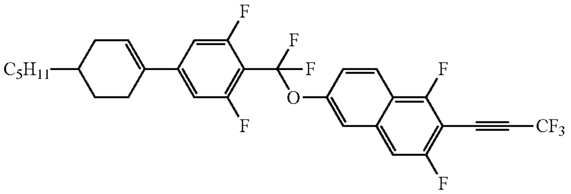
(No.261)
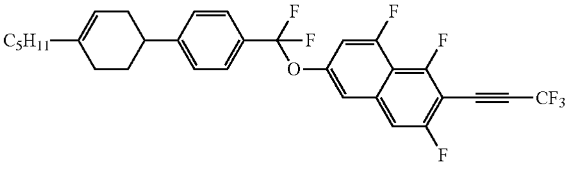
(No.262)
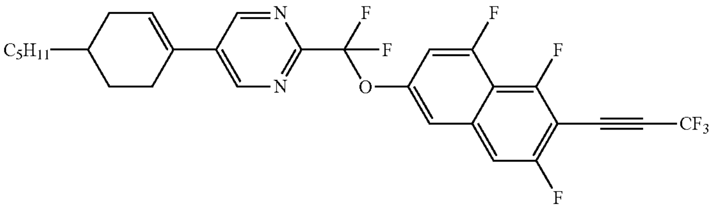
(No.263)
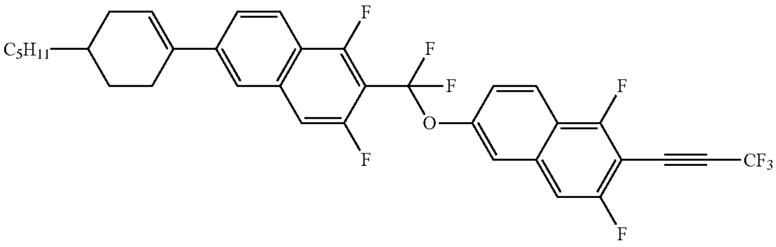
(No.264)
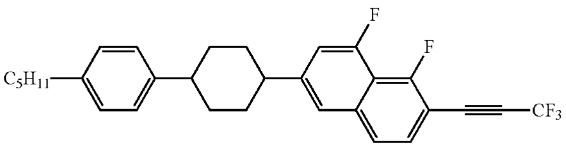
(No.265)
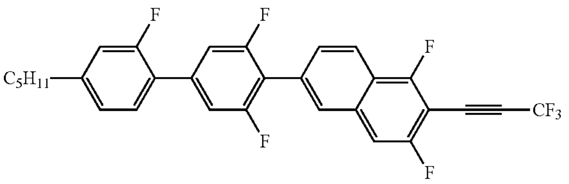
(No.266)
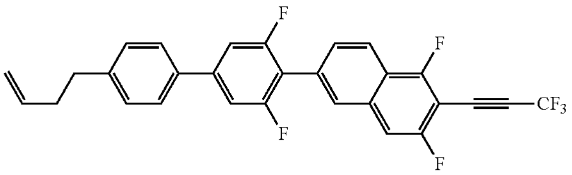
(No.267)
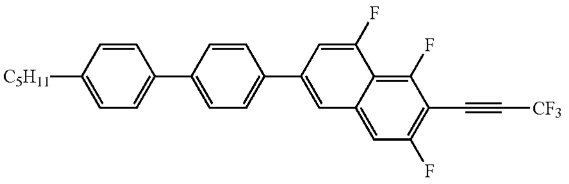

-continued
(No.268)
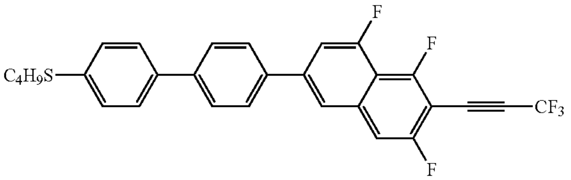
(No.269)
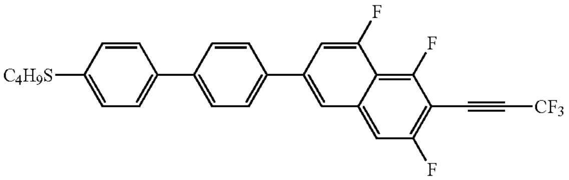
(No.270)
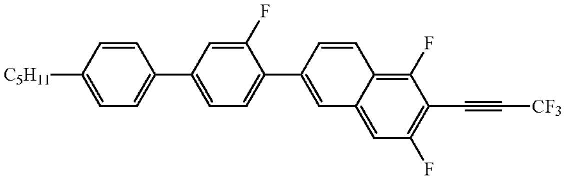
(No.271)
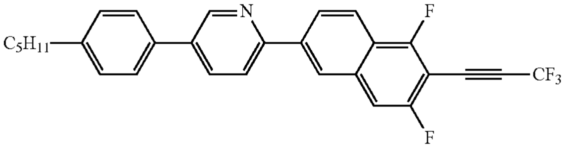
(No.272)
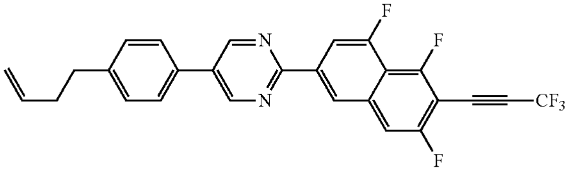
(No.273)
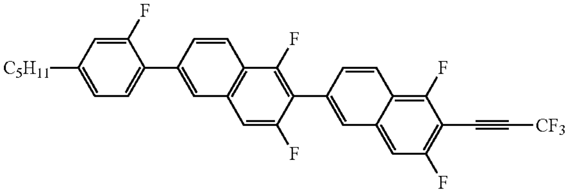
(No.274)
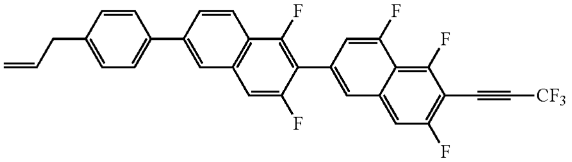
(No.275)
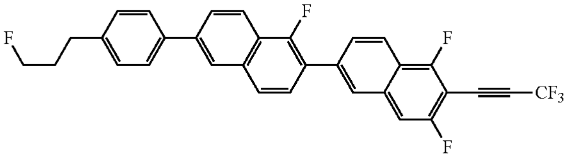
(No.276)
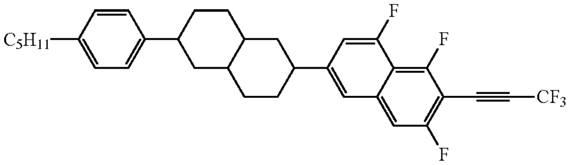
(No.277)
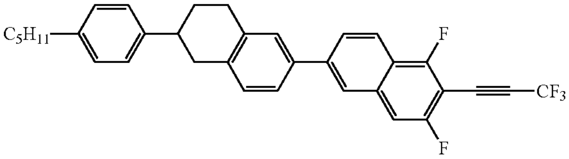
(No.278)
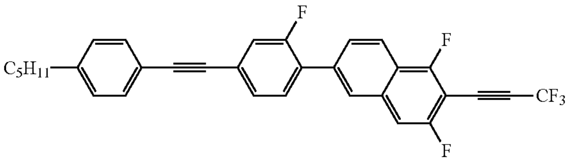
(No.279)
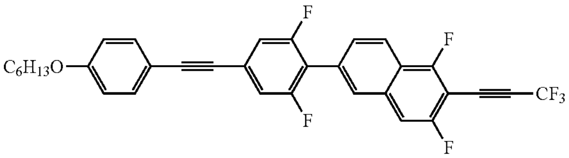
(No.280)
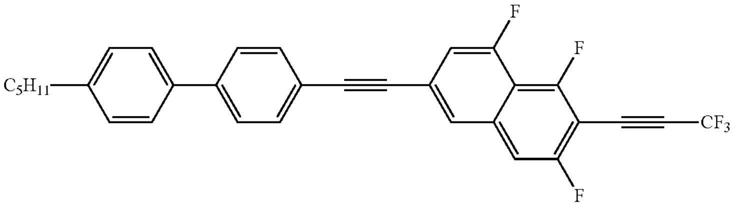

-continued
(No.281)
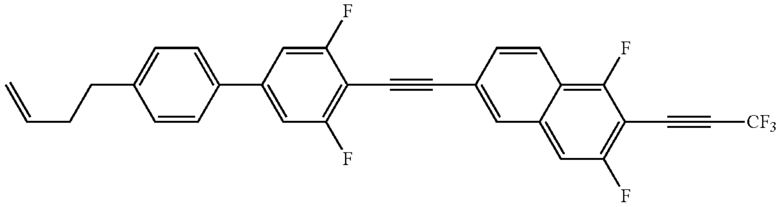
(No.282)
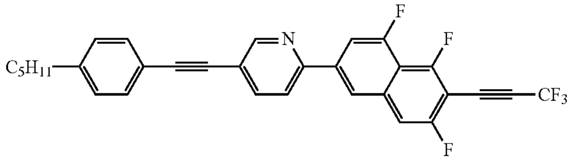
(No.283)
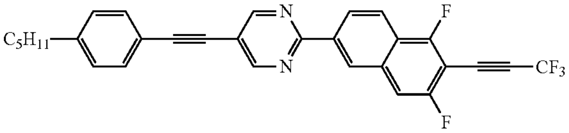
(No.284)
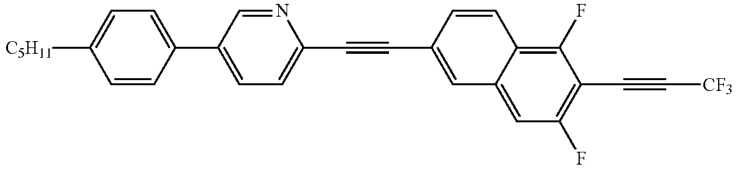
(No.285)
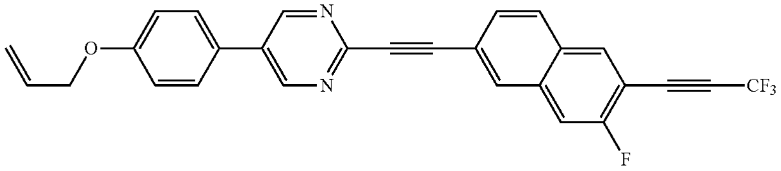
(No.286)
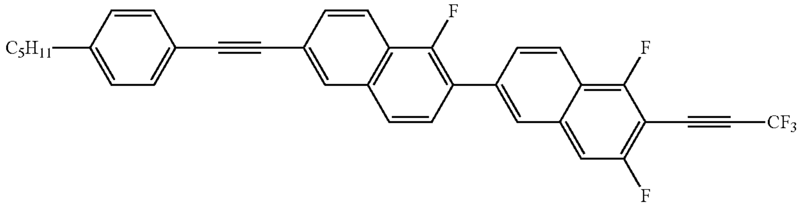
(No.287)
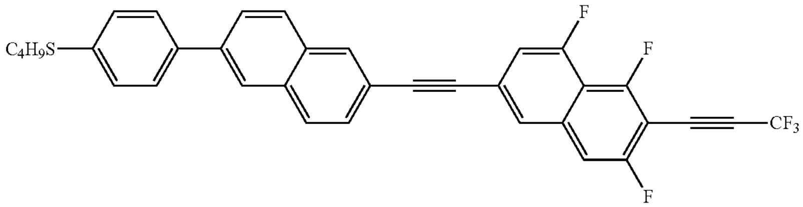
(No.288)
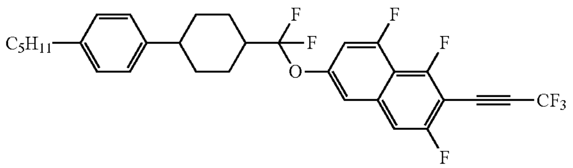
(No.289)
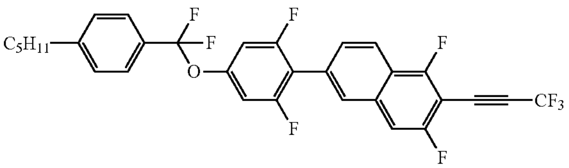

-continued
(No.290)
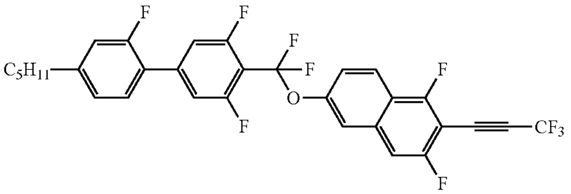
C 64.7 $S_A$ 112 I
$T_{NI}$ = 72.4° C., Δε = 56.6, Δn = 0.210
(No.291)
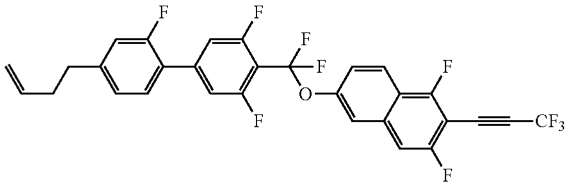
(No.292)
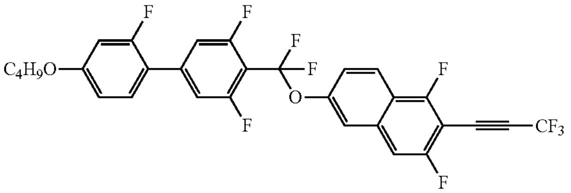
(No.293)
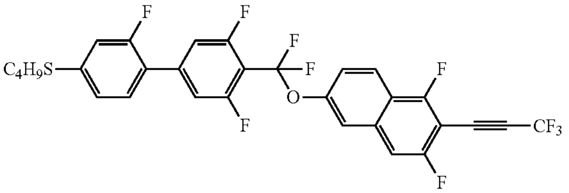
(No.294)
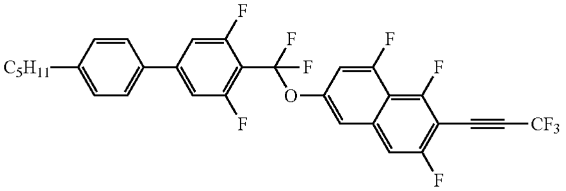
(No.295)
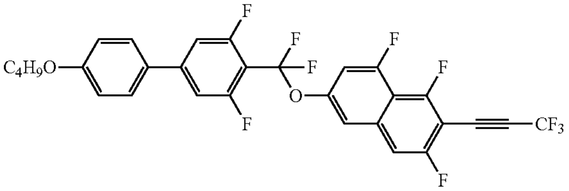
(No.296)
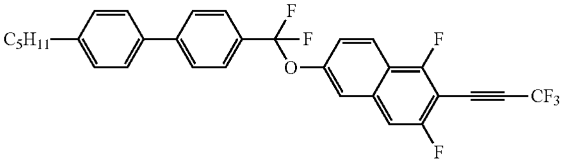
(No.297)
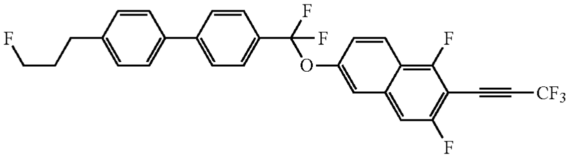
(No.298)
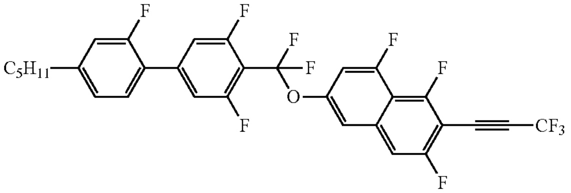
(No.299)
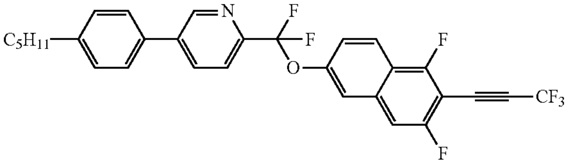
(No.300)
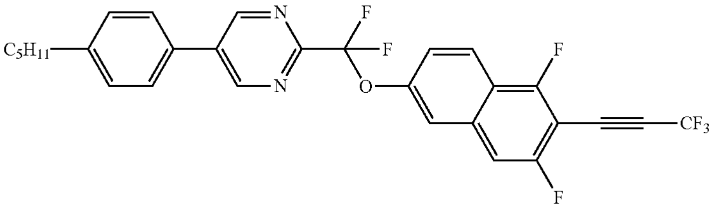
(No.301)
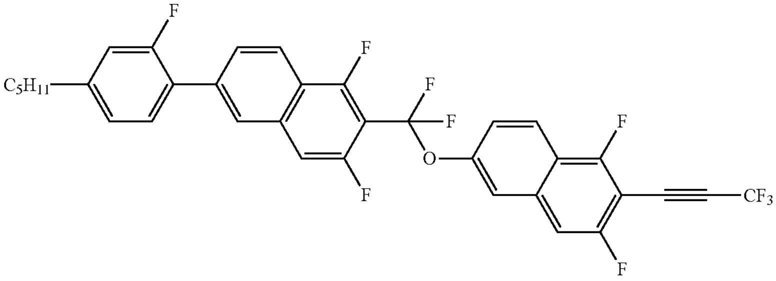

-continued
(No.302)
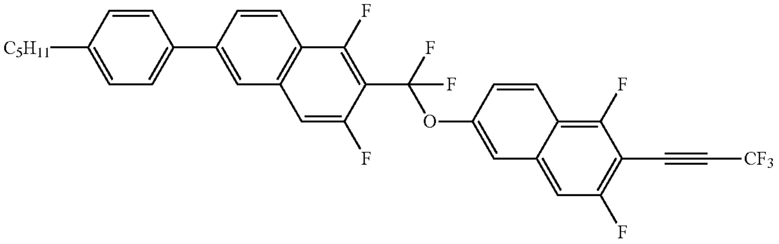
(No.303)
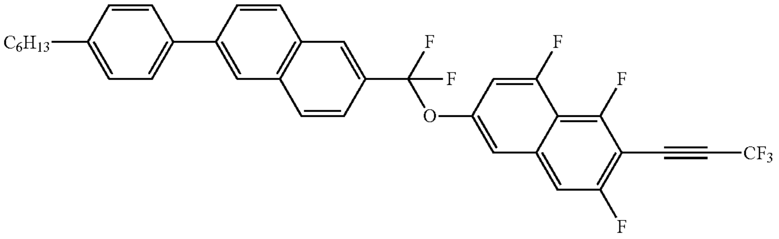
(No.304)
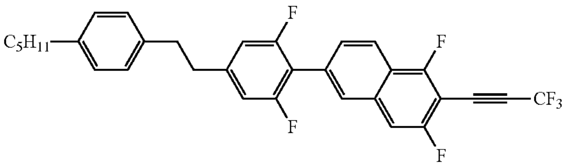
(No.305)
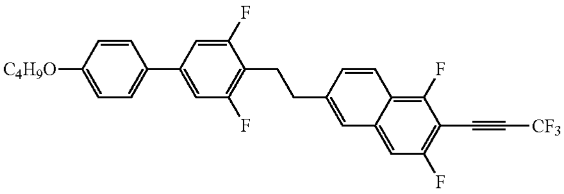
(No.306)
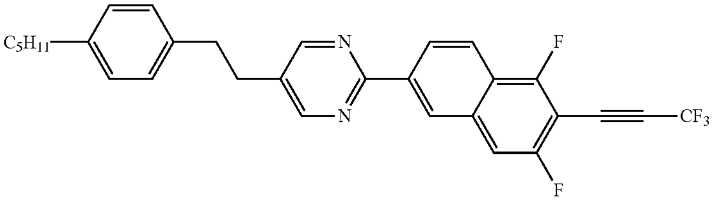
(No.307)
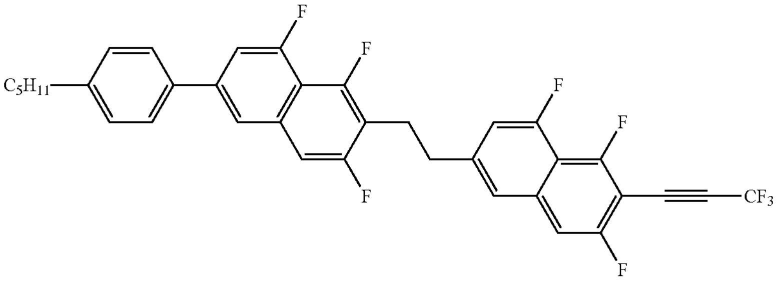
(No.308)
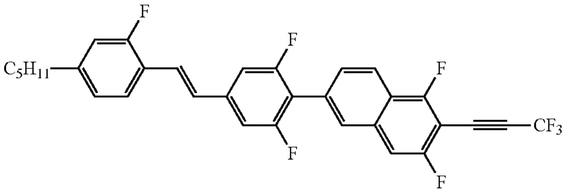
(No.309)
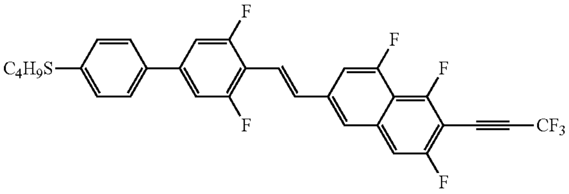
(No.310)
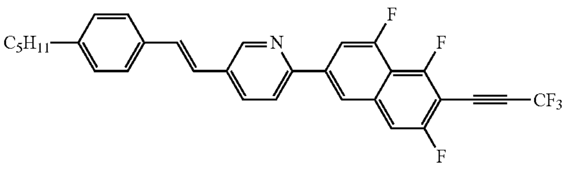
(No.311)
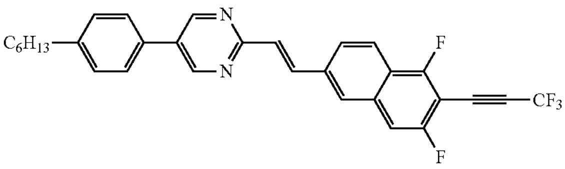

-continued
(No.312)
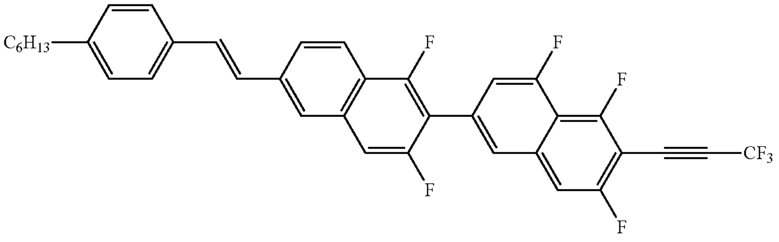
(No.313)
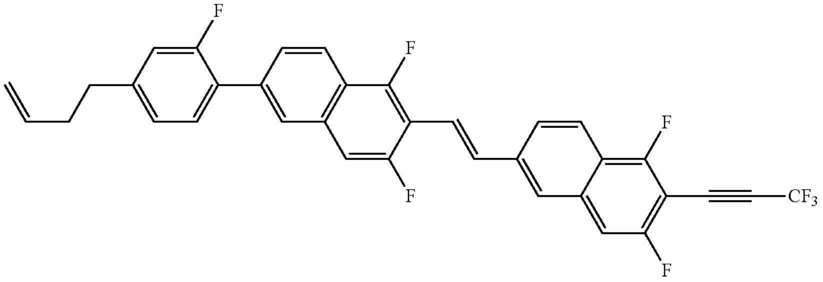
(No.314)
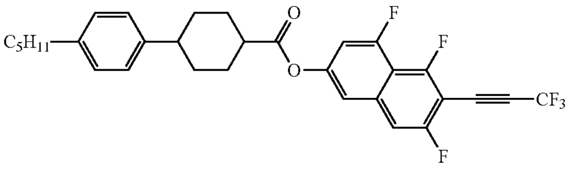
(No.315)
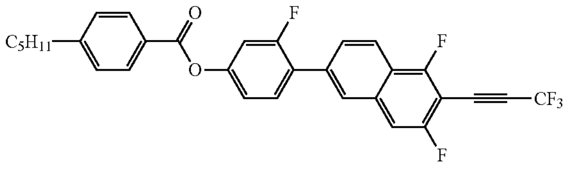
(No.316)
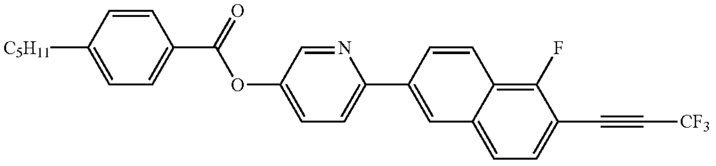
(No.317)
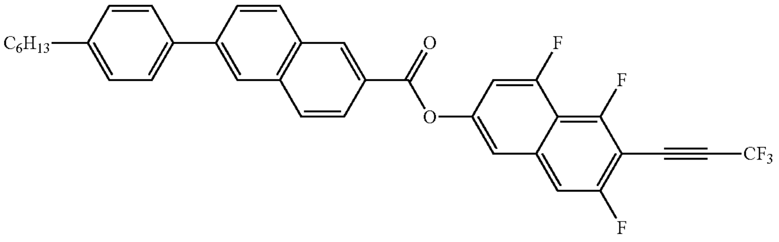
(No.318)
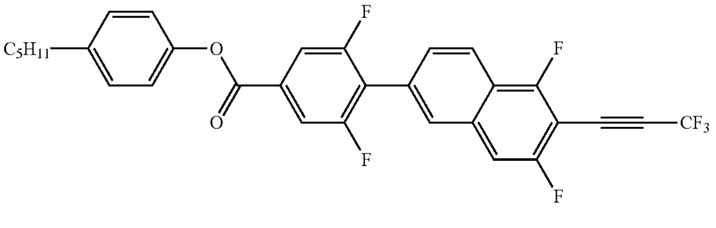
(No.319)
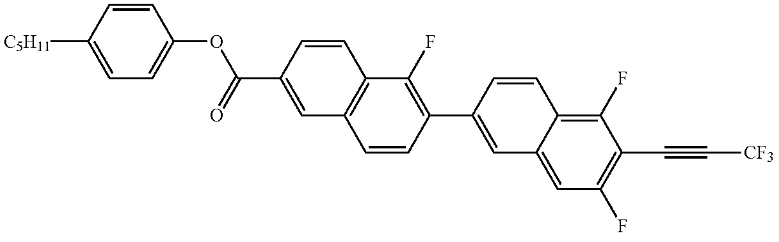

-continued
(No.320)
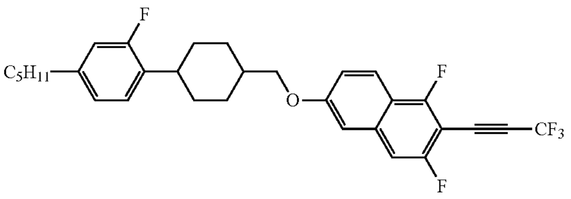
(No.321)
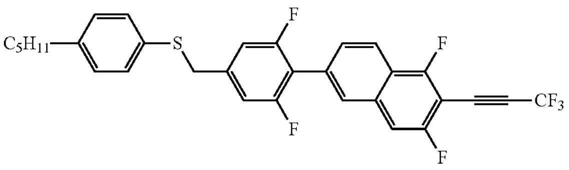
(No.322)
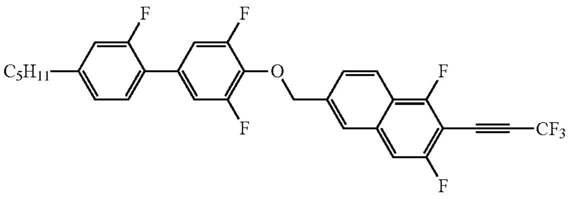
(No.323)
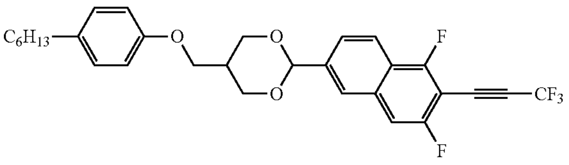
(No.324)
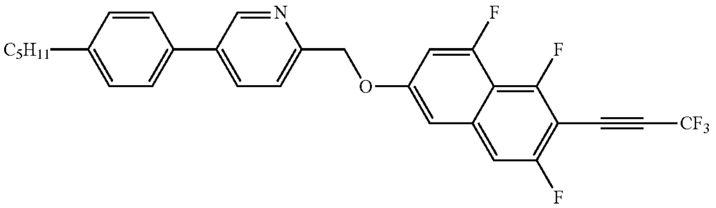
(No.325)
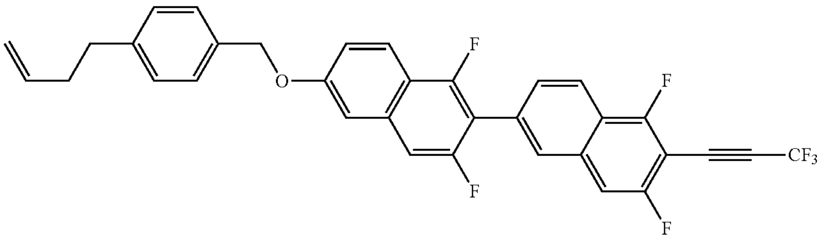
(No.326)
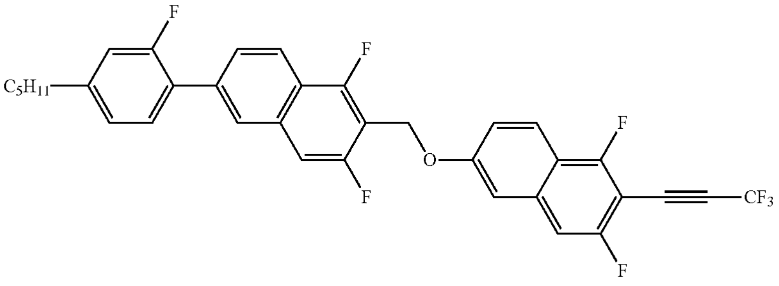
(No.327)
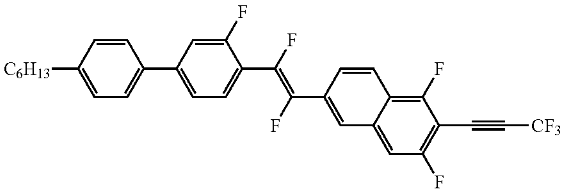
(No.328)
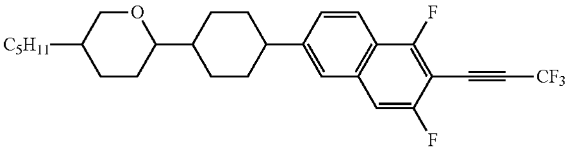
(No.329)
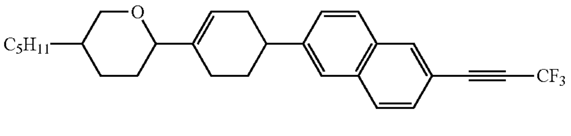
(No.330)
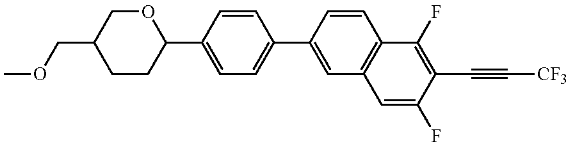

-continued
(No.331)
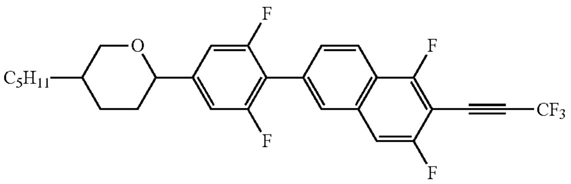
(No.332)
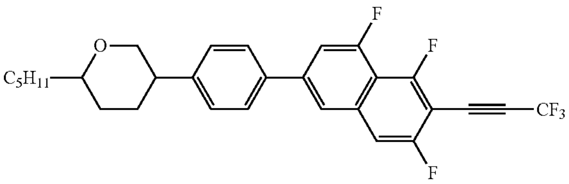
(No.333)
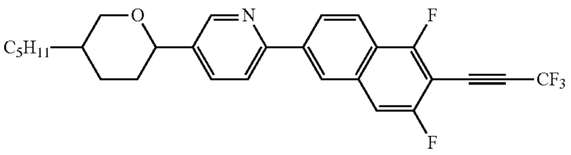
(No.334)
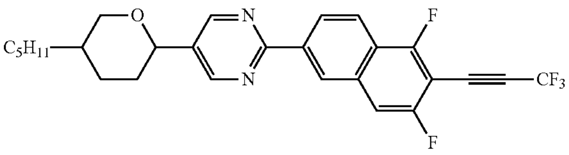
(No.335)
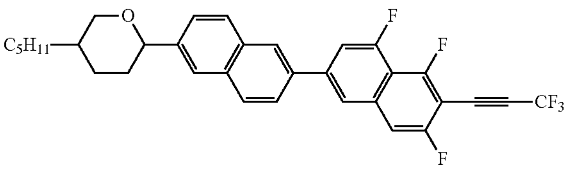
(No.336)
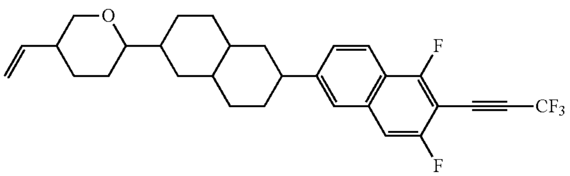
(No.337)
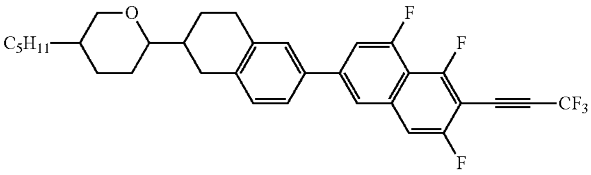
(No.338)
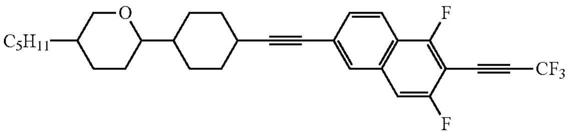
(No.339)
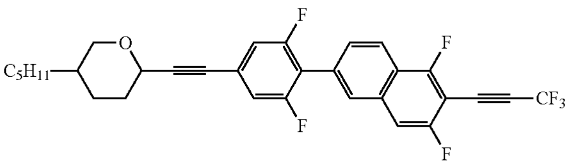
(No.340)
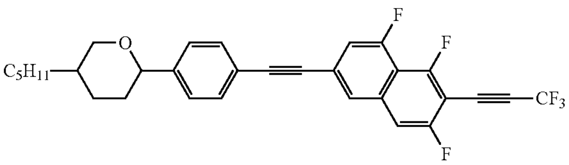
(No.341)
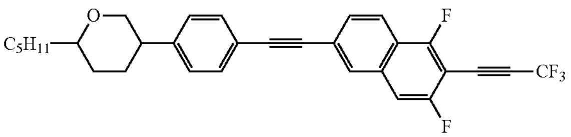
(No.342)
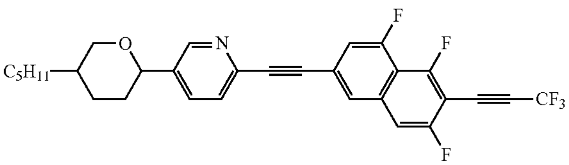
(No.343)
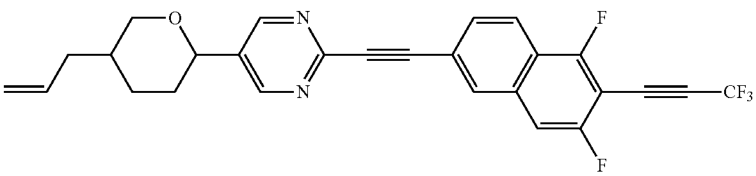
(No.344)
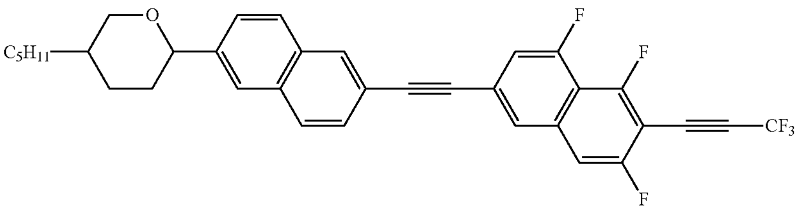

-continued
(No.345)
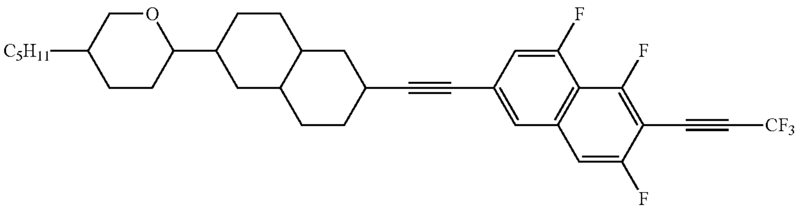
(No.346)
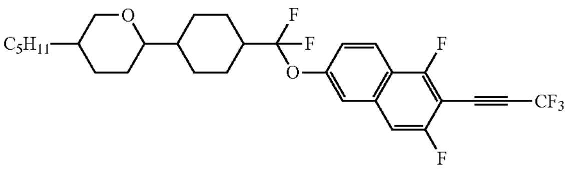
(No.347)
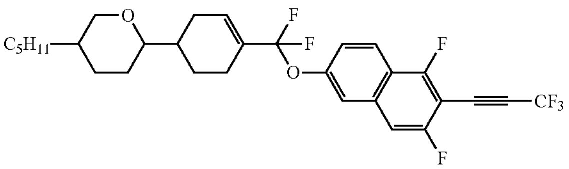
(No.348)
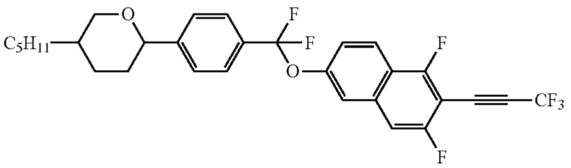
(No.349)
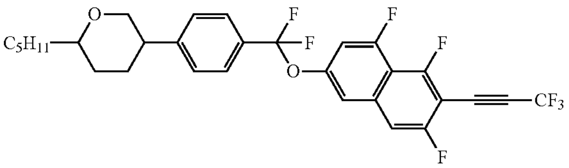
(No.350)
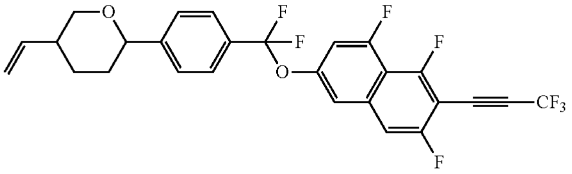
(No.351)
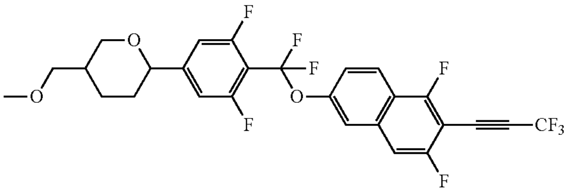
(No.352)
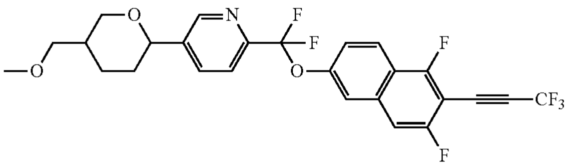
(No.353)
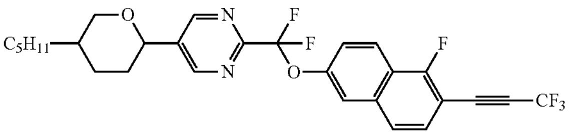
(No.354)
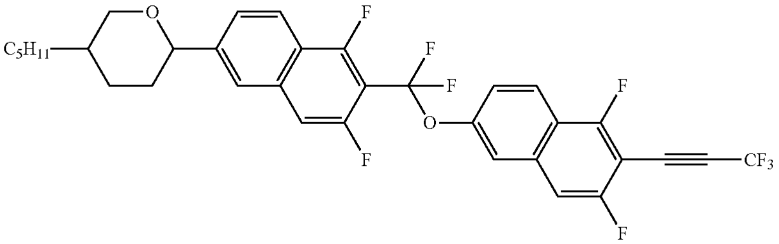
(No.355)
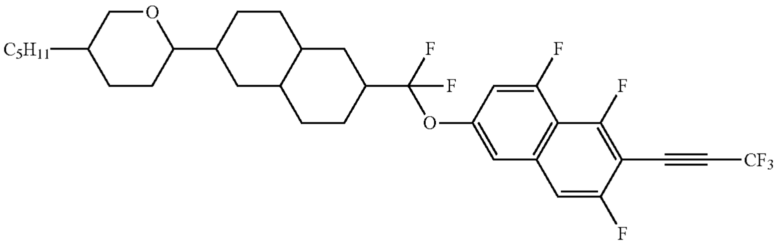

-continued
(No.356)
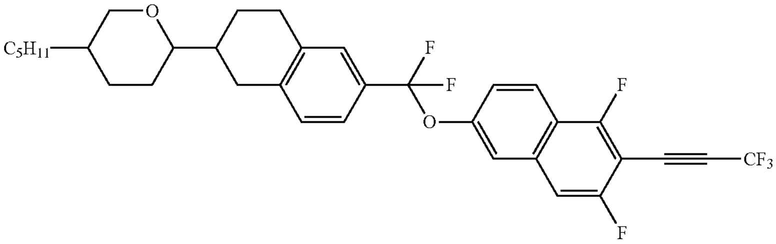
(No.357)
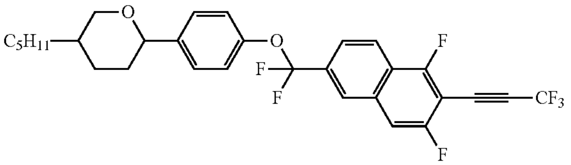
(No.358)
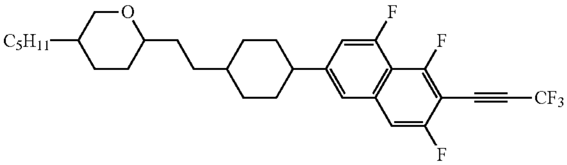
(No.359)
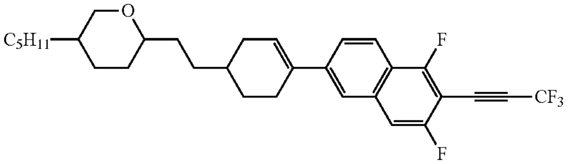
(No.360)
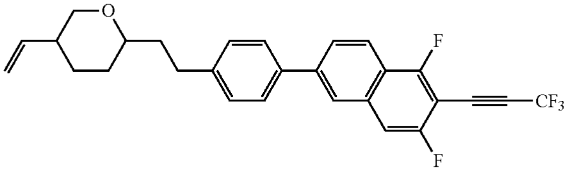
(No.361)
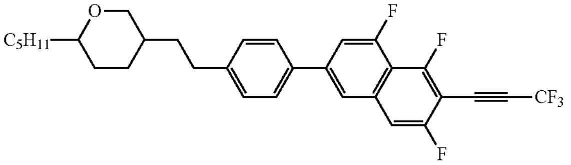
(No.362)
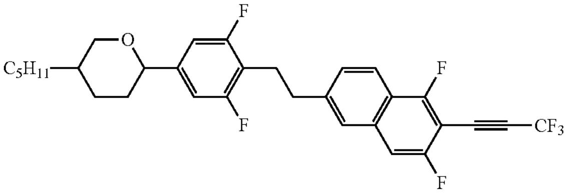
(No.363)
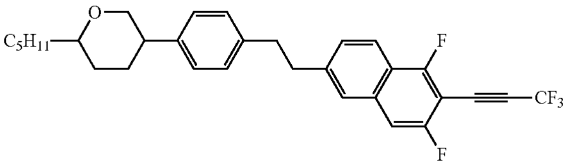
(No.364)
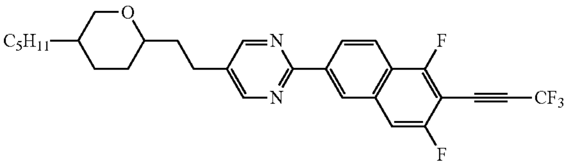
(No.365)
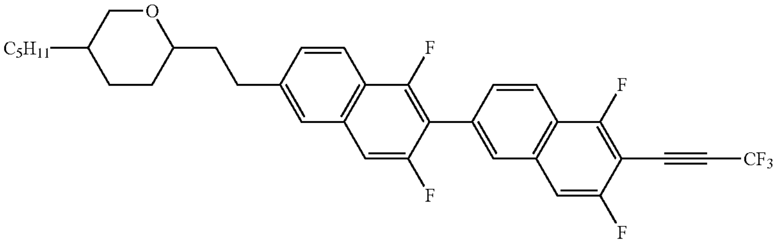
(No.366)
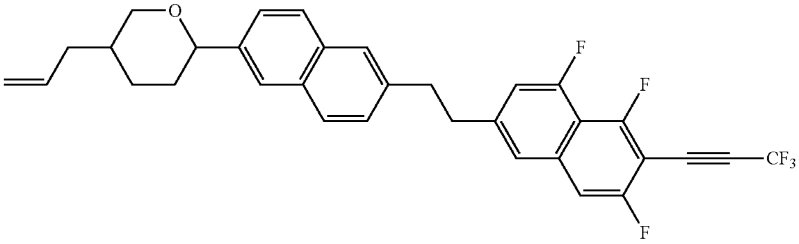

-continued
(No.367)
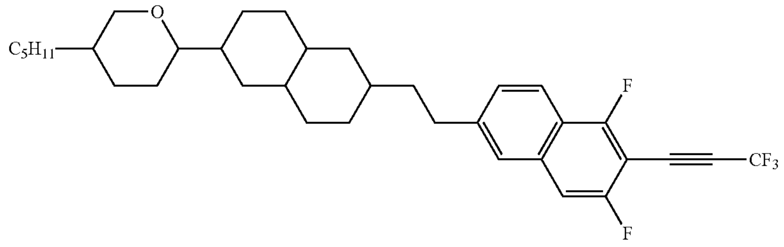
(No.368)
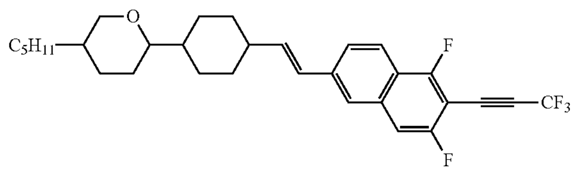
(No.369)
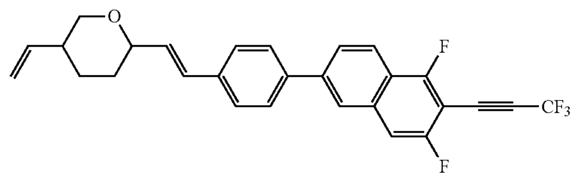
(No.370)
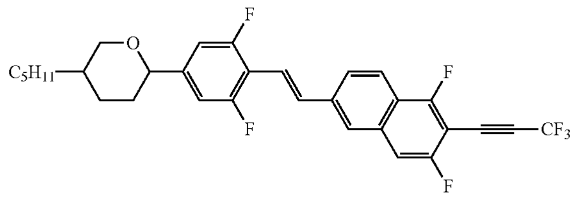
(No.371)
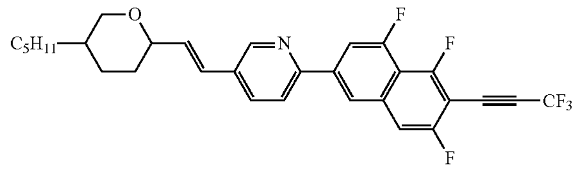
(No.372)
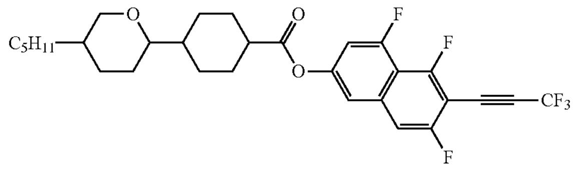
(No.373)
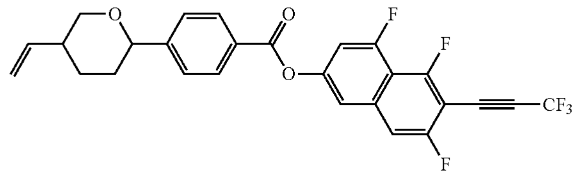
(No.374)
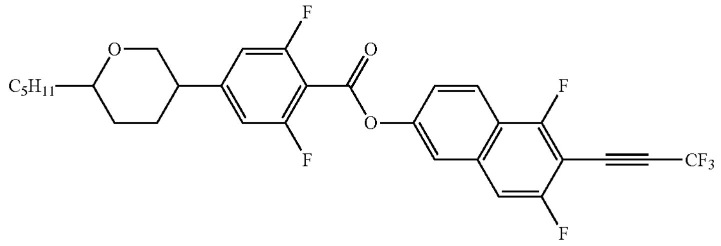
(No.375)
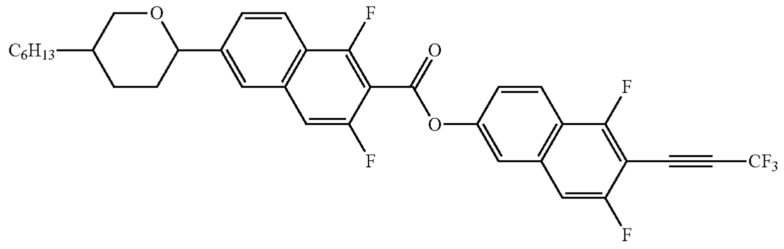
(No.376)
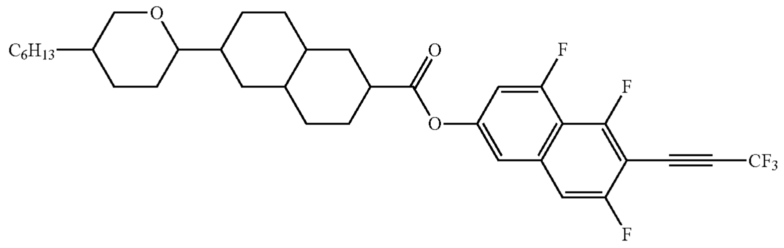

-continued
(No.377)
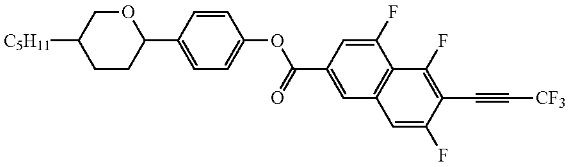
(No.378)
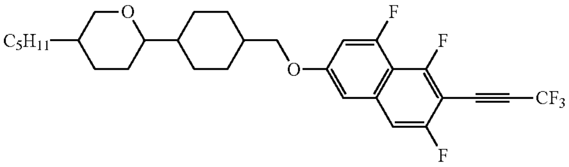
(No.379)
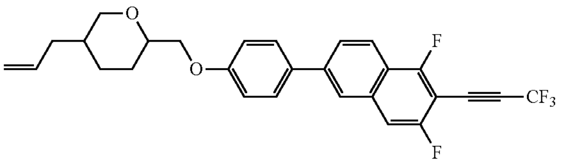
(No.380)
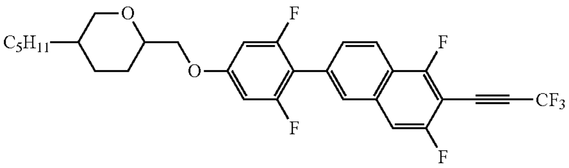
(No.381)
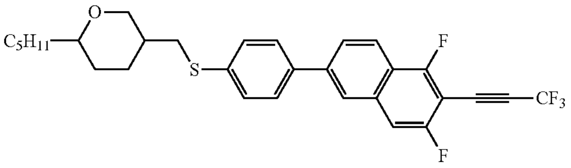
(No.382)
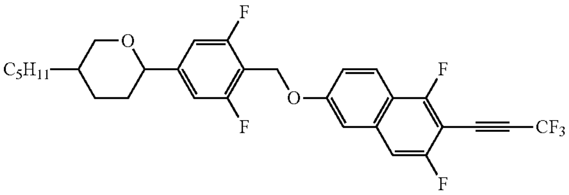
(No.383)
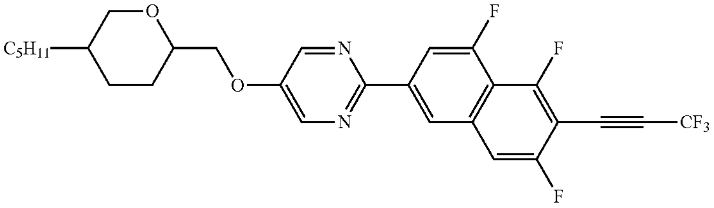
(No.384)
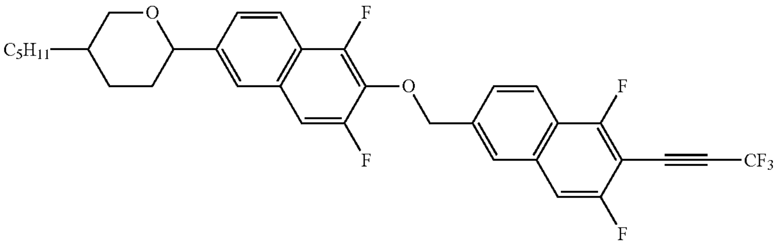
(No.385)
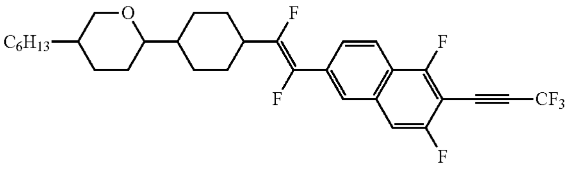
(No.386)
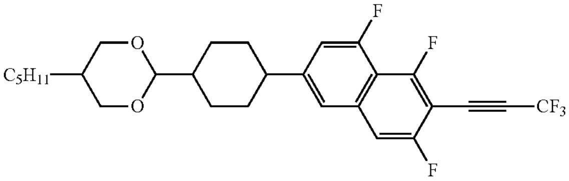
(No.387)
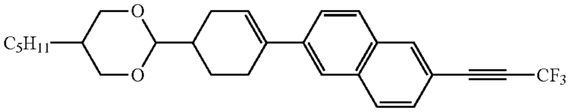
(No.388)
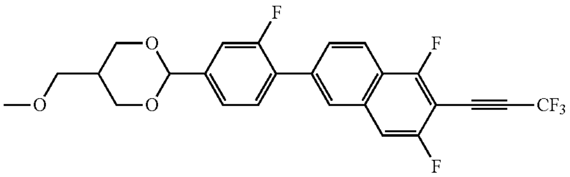

-continued
(No.389)
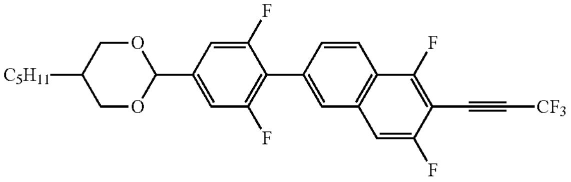
(No.390)
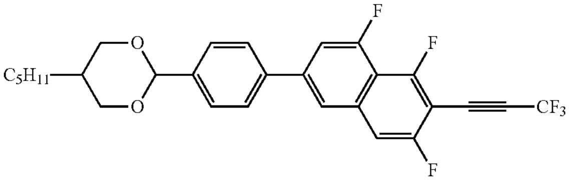
(No.391)
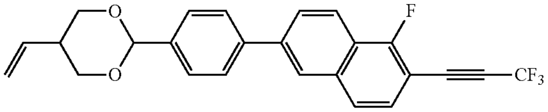
(No.392)
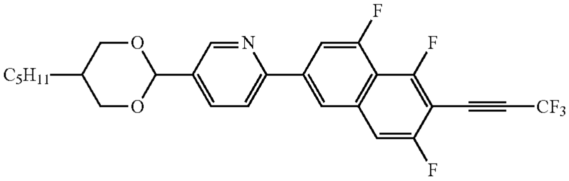
(No.393)
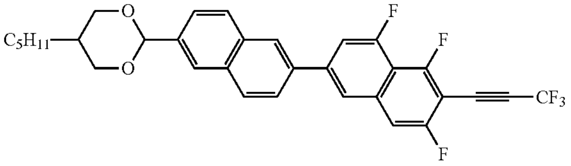
(No.394)
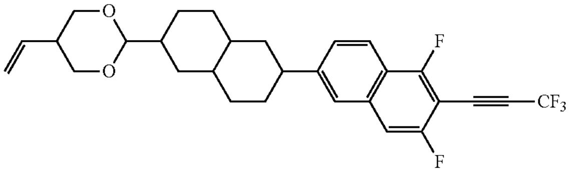
(No.395)
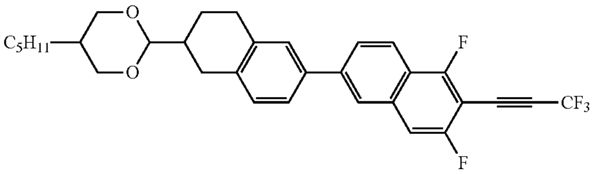
(No.396)
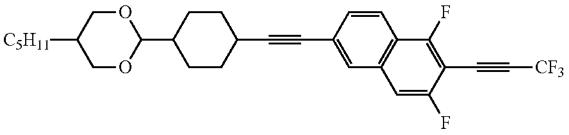
(No.397)
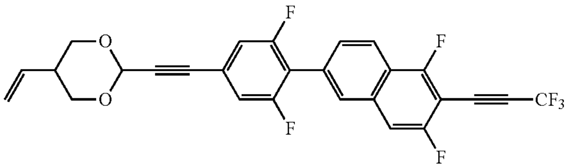
(No.398)
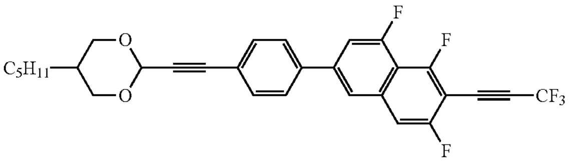
(No.399)
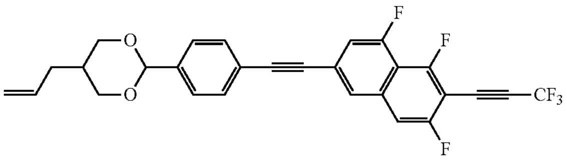
(No.400)
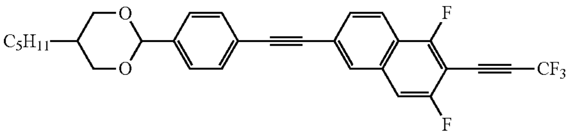
(No.401)
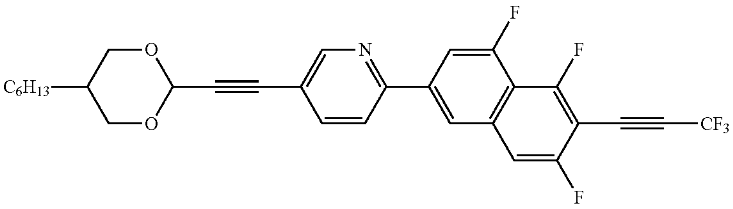
(No.402)
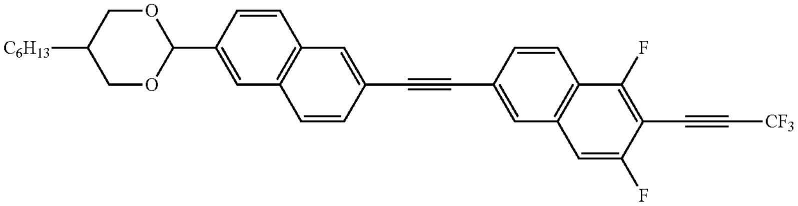

-continued
(No.403)
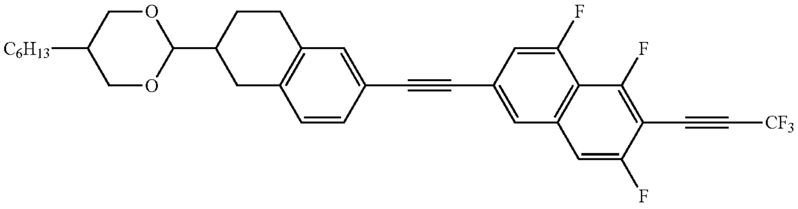
(No.404)
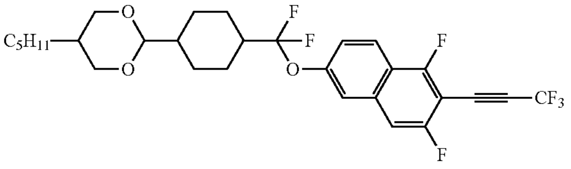
(No.405)
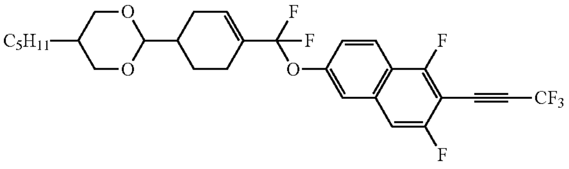
(No.406)
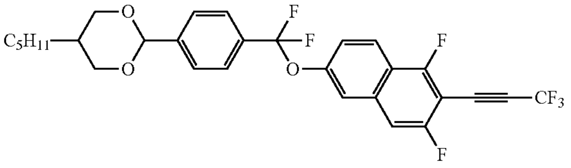
(No.407)
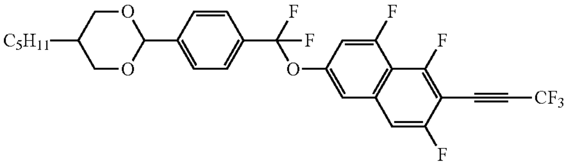
(No.408)
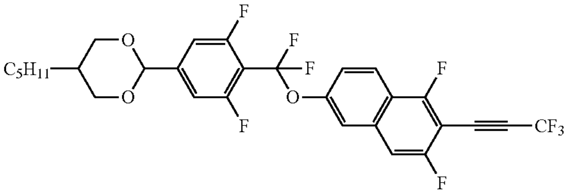
(No.409)
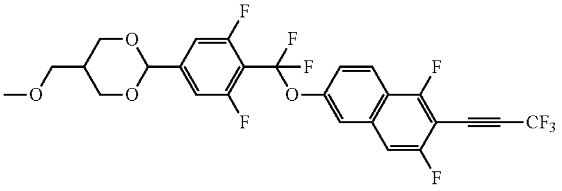
(No.410)
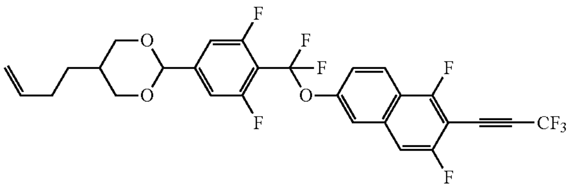
(No.411)
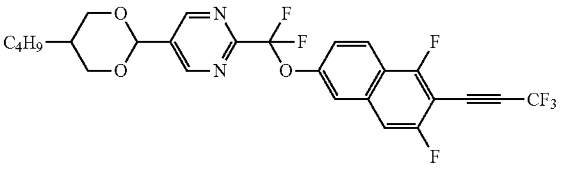
(No.412)
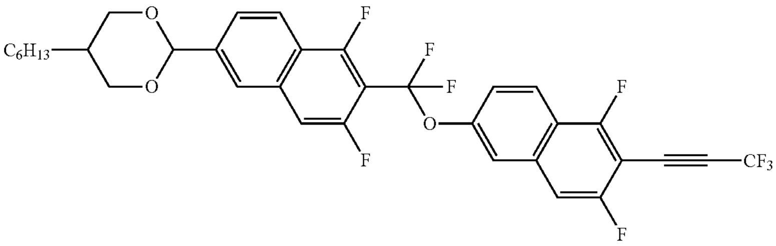
(No.413)
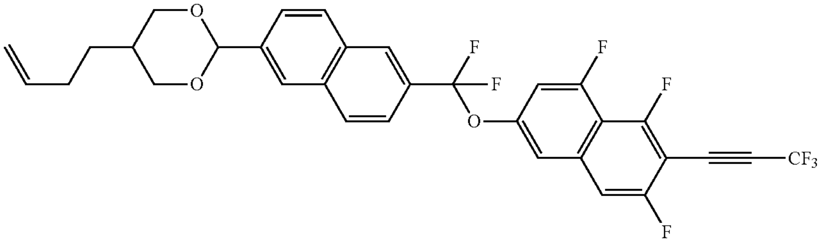

-continued
(No.414)
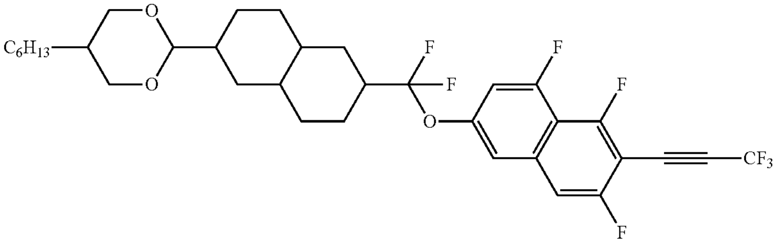
(No.415)
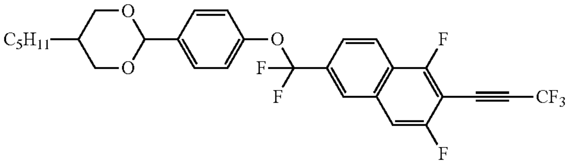
(No.416)
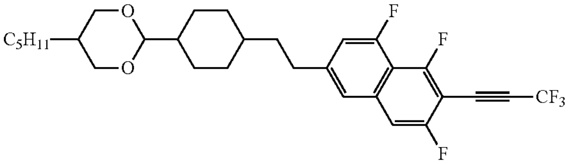
(No.417)
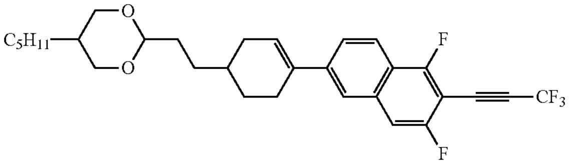
(No.418)
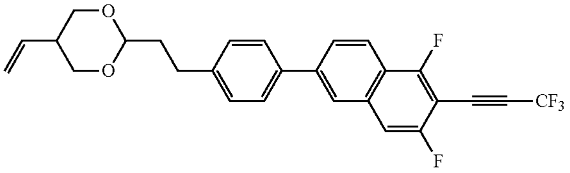
(No.419)
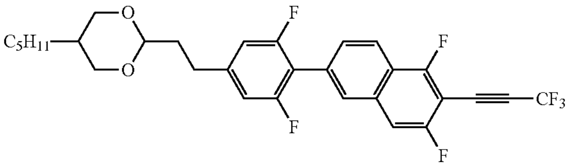
(No.420)
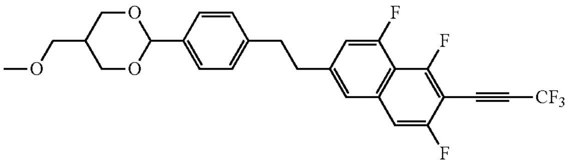
(No.421)
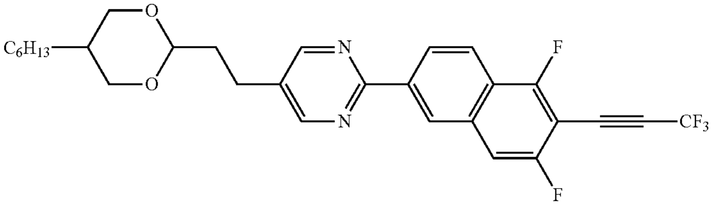
(No.422)
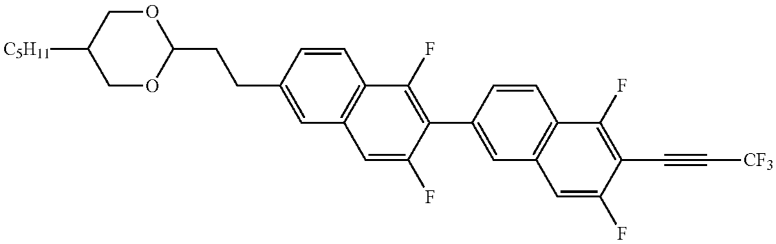
(No.423)
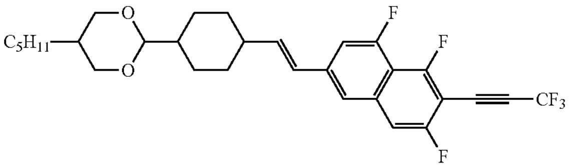
(No.424)
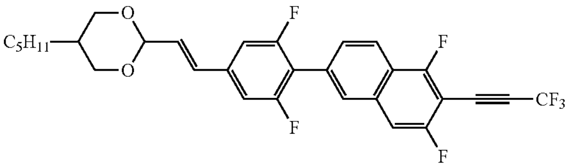

-continued
(No.425)
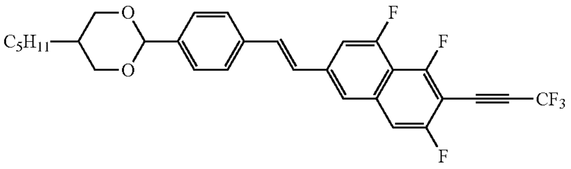
(No.426)
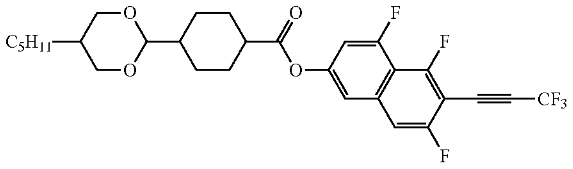
(No.427)
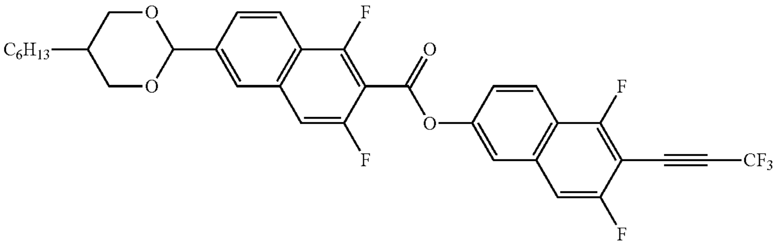
(No.428)
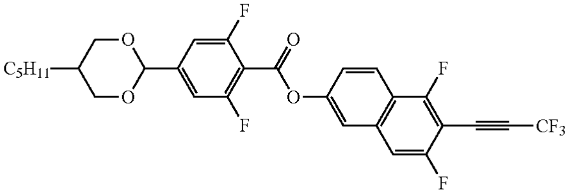
(No.429)
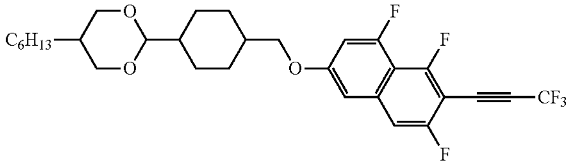
(No.430)
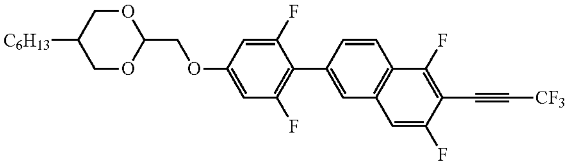
(No.431)
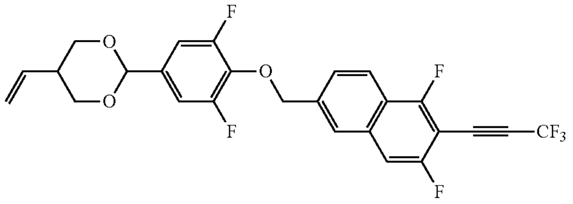
(No.432)
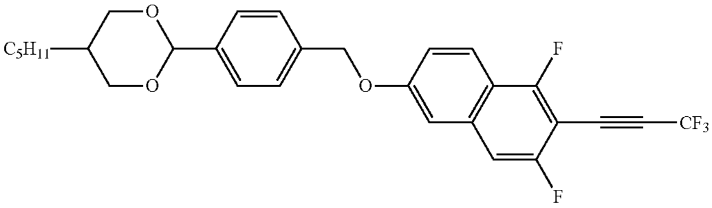
(No.433)
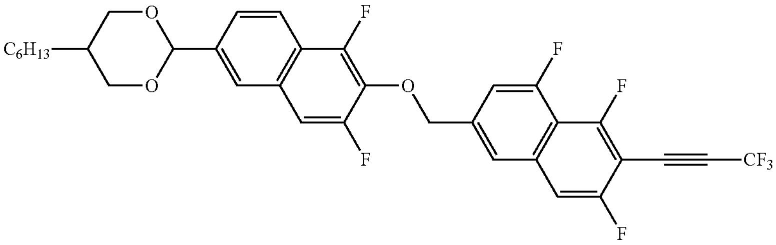
(No.434)
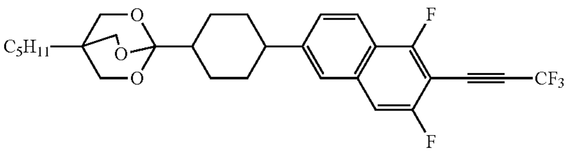
(No.435)
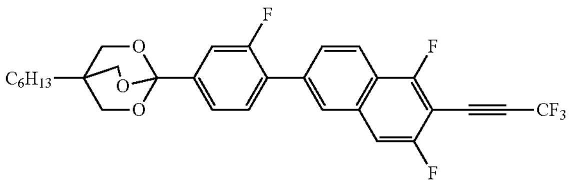

-continued
(No.436)
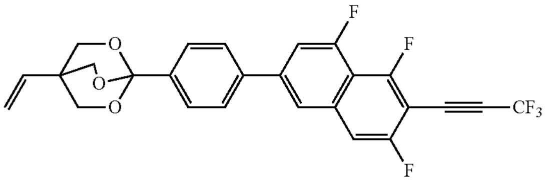
(No.437)
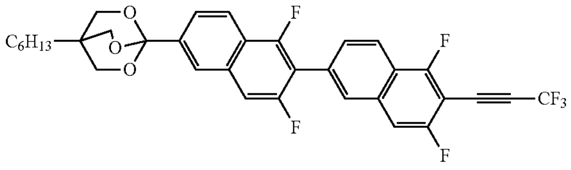
(No.438)
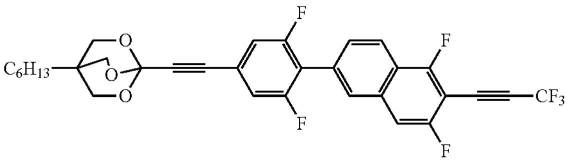
(No.439)
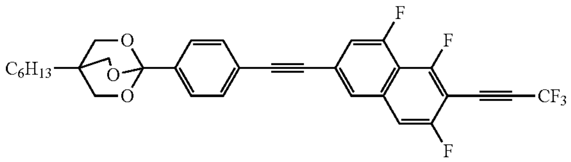
(No.440)
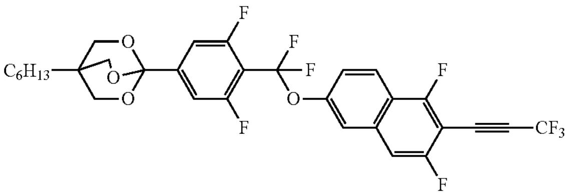
(No.441)
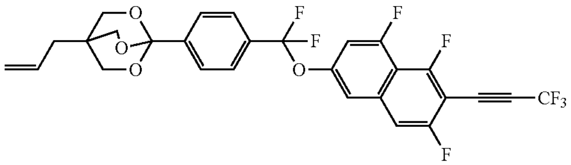
(No.442)
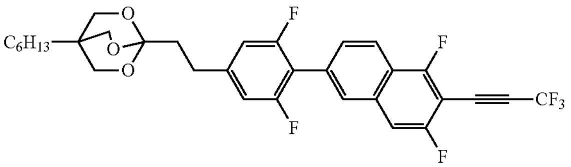
(No.443)
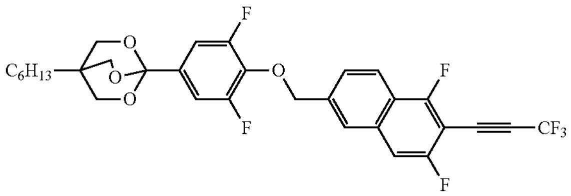
(No.444)
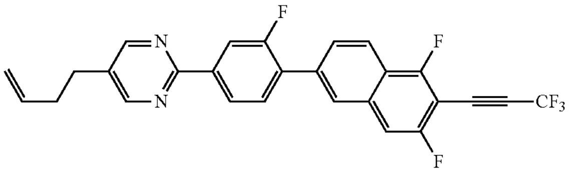
(No.445)
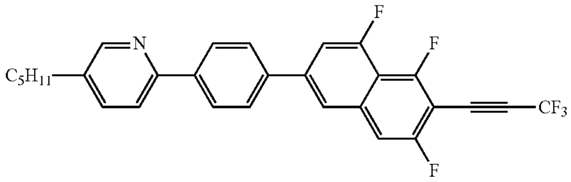
(No.446)
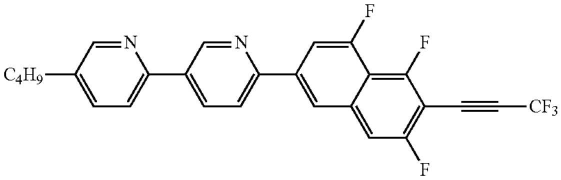
(No.447)
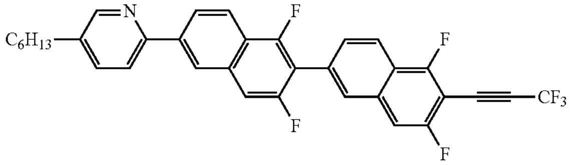
(No.448)
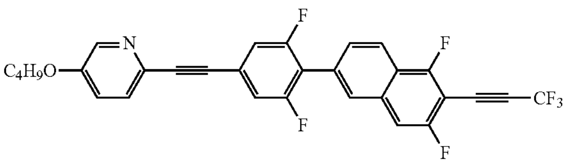
(No.449)
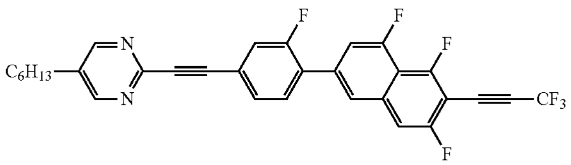

-continued
(No.450)
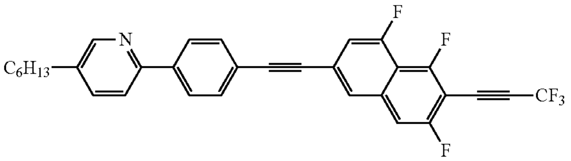
(No.451)
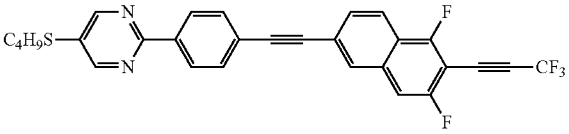
(No.452)
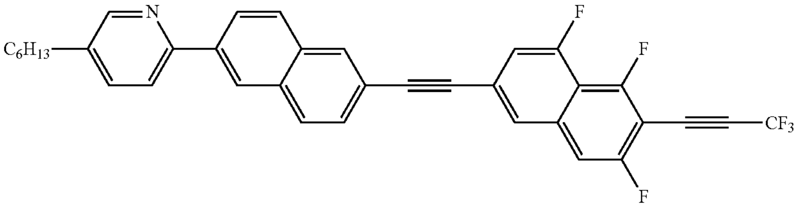
(No.453)
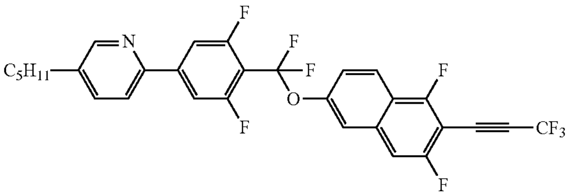
(No.454)
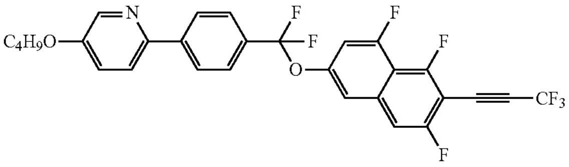
(No.455)
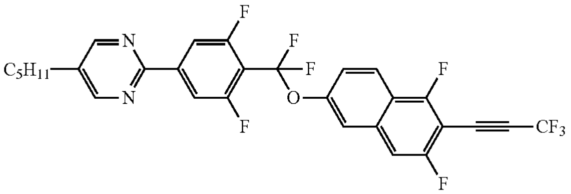
(No.456)
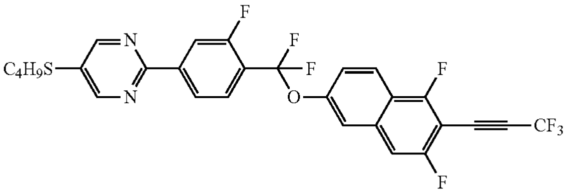
(No.457)
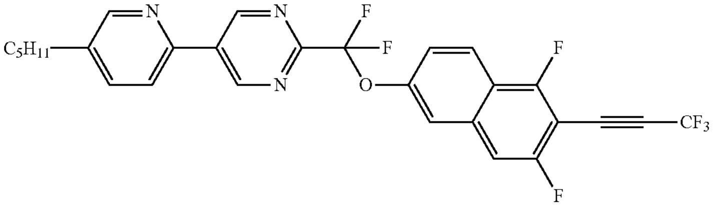
(No.458)
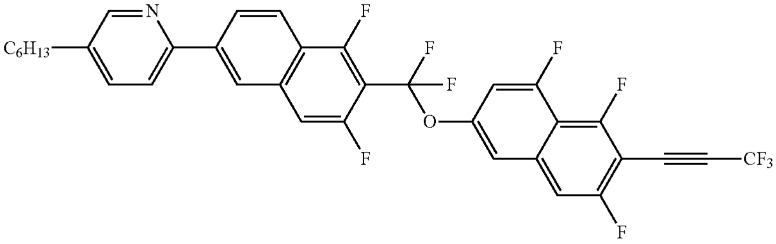
(No.459)
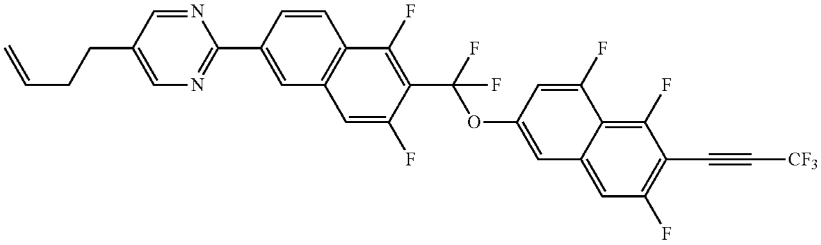

-continued
(No.460)
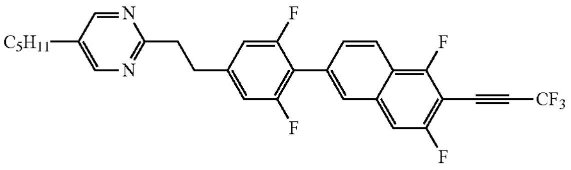
(No.461)
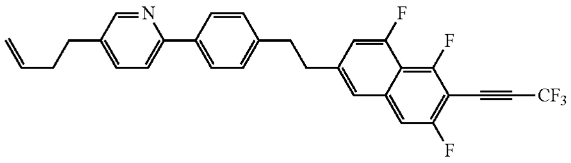
(No.462)
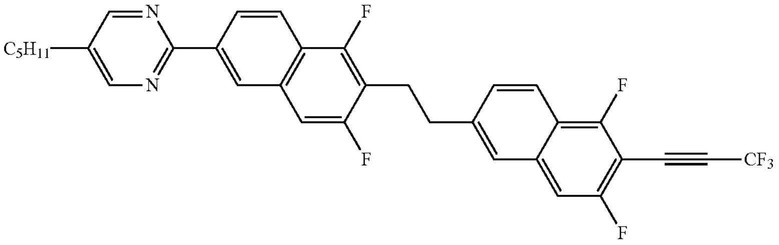
(No.463)
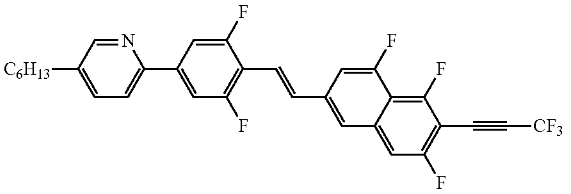
(No.464)
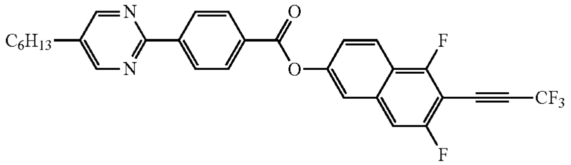
(No.465)
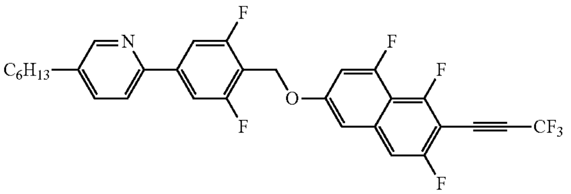
(No.488)
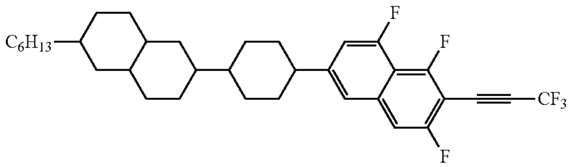
(No.489)
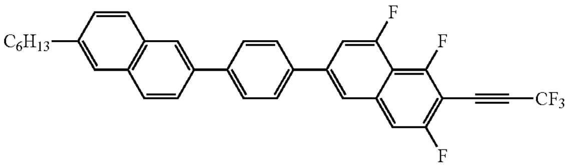
(No.490)
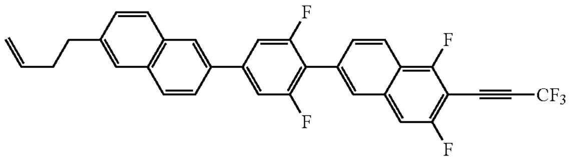
(No.491)
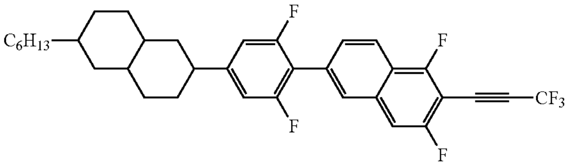
(No.492)
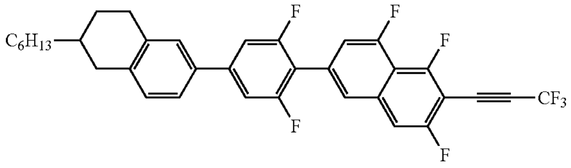
(No.493)
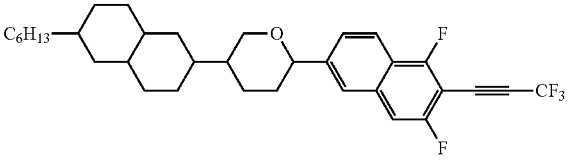
(No.494)
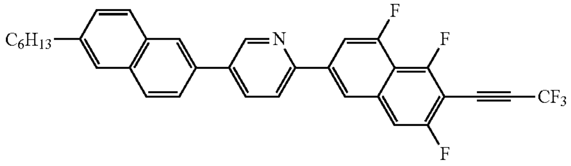

-continued
(No.495)
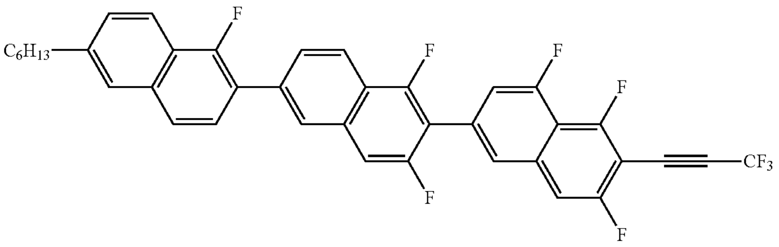
(No.496)
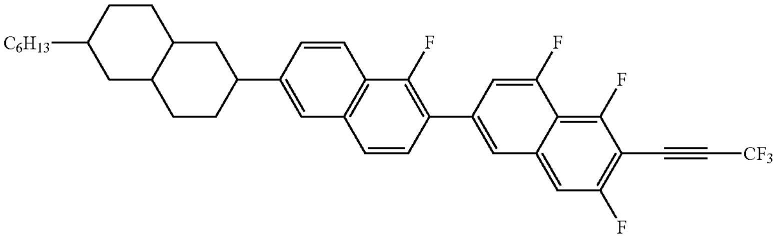
(No.497)
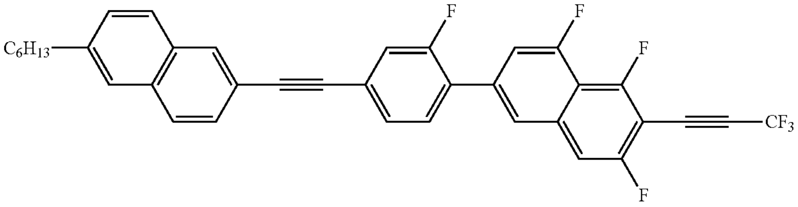
(No.498)
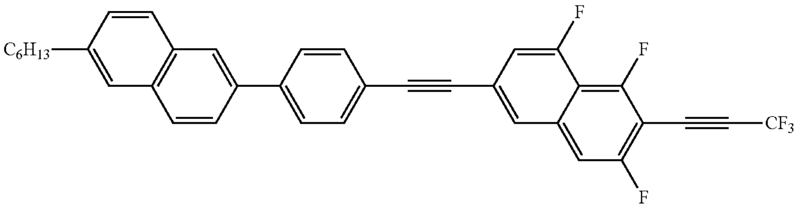
(No.499)
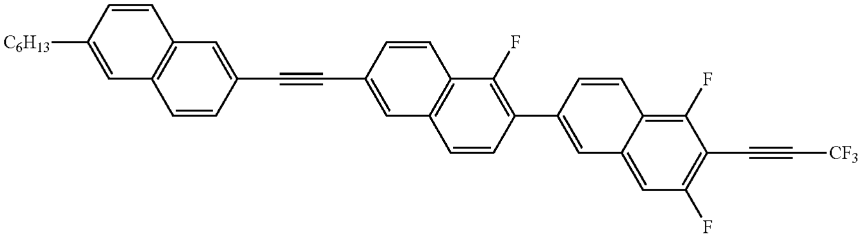
(No.500)
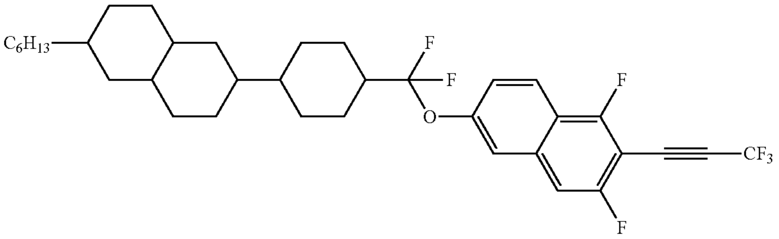

-continued
(No.501)
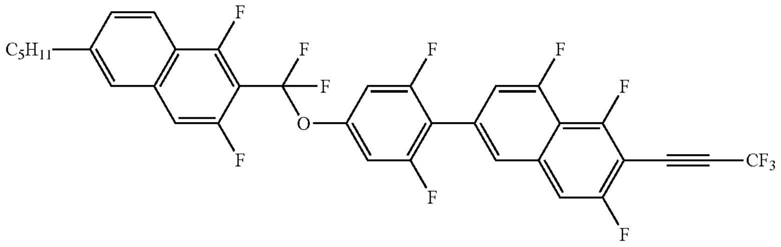
(No.502)
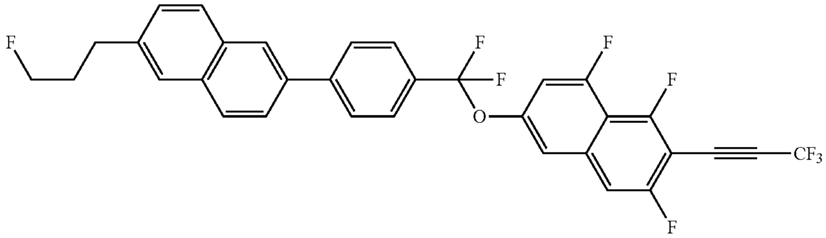
(No.503)
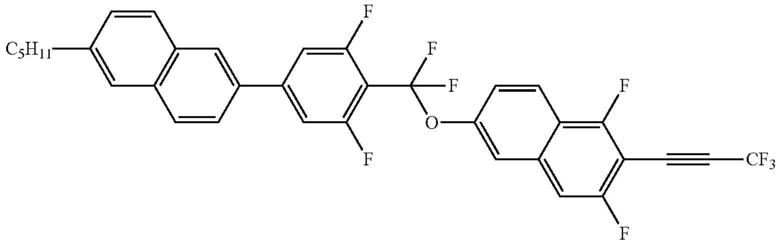
(No.504)
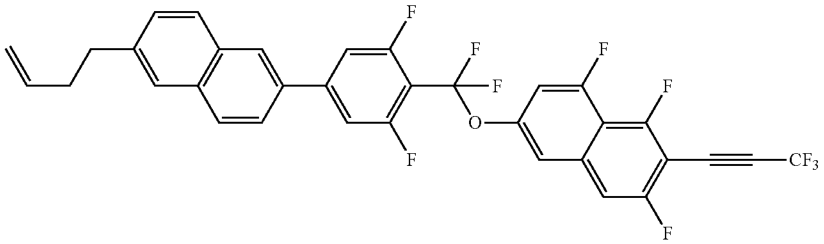
(No.505)
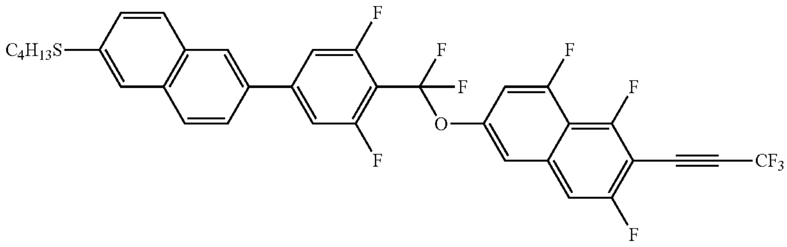
(No.506)
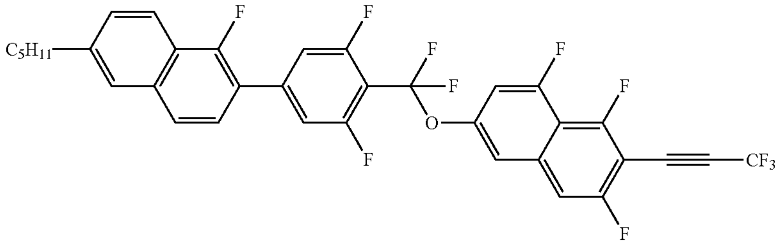

-continued
(No.507)
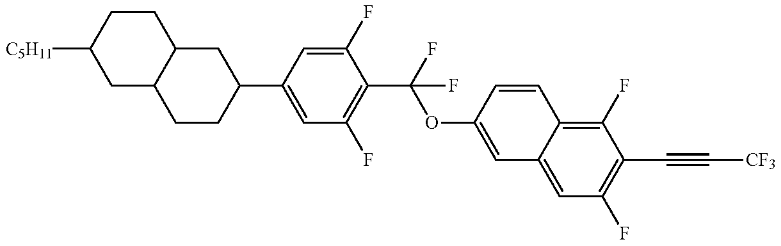
(No.508)
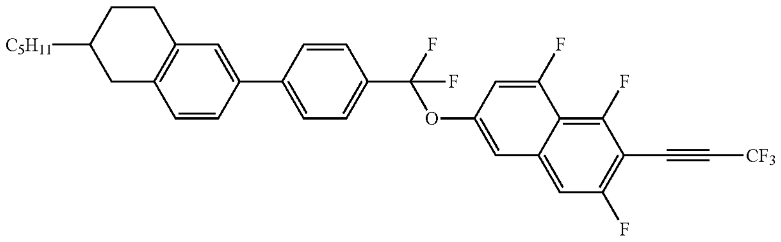
(No.509)
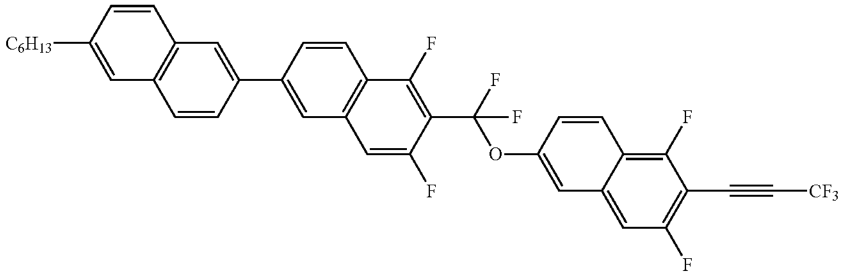
(No.510)
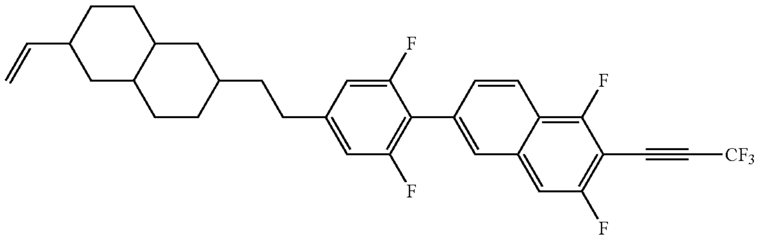
(No.511)
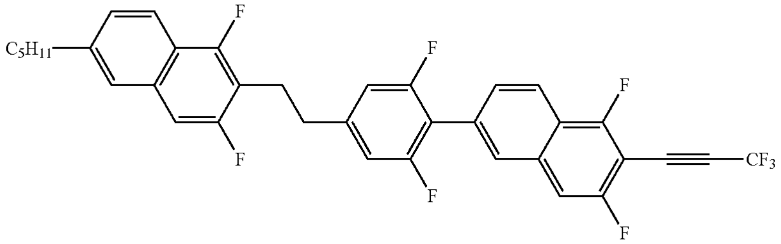
(No.512)
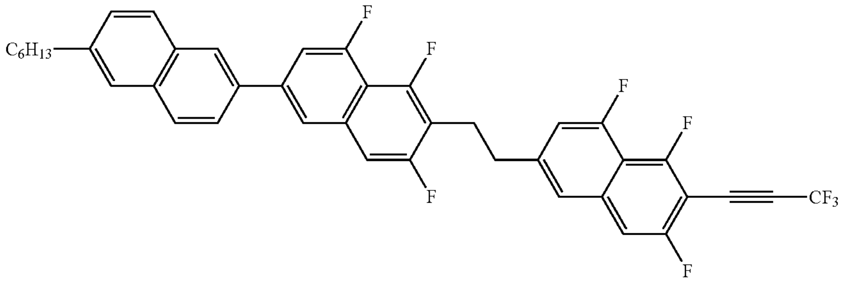

-continued
(No.513)
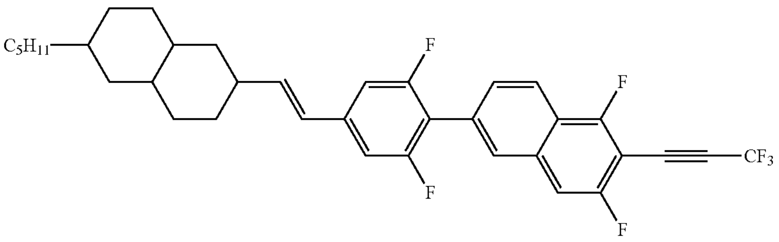
(No.514)
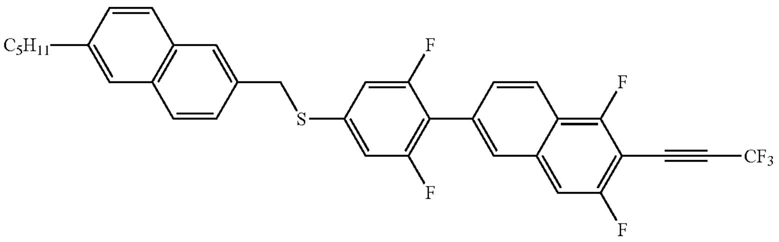
(No.515)
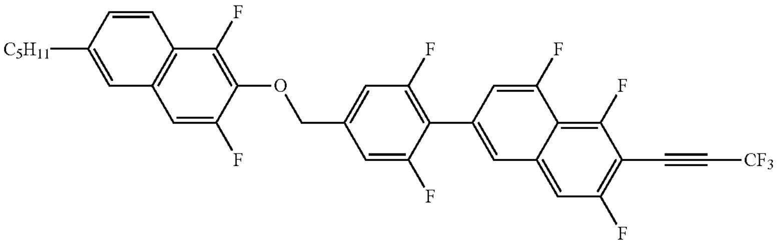
(No.516)
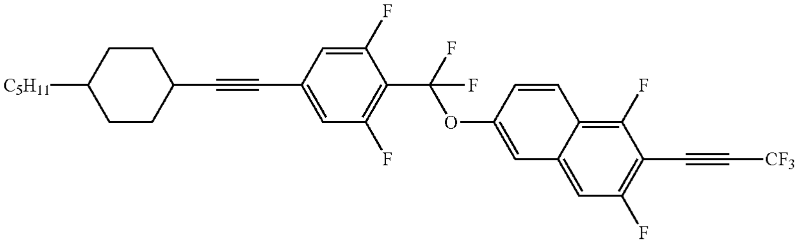
(No.517)
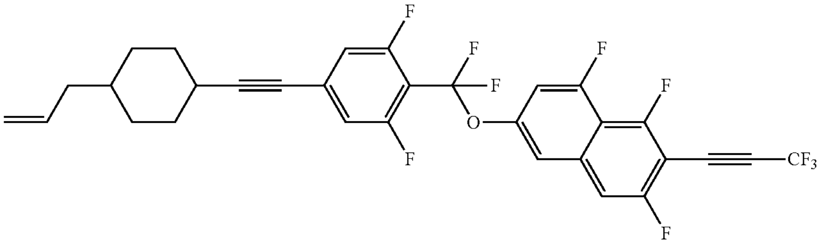
(No.518)
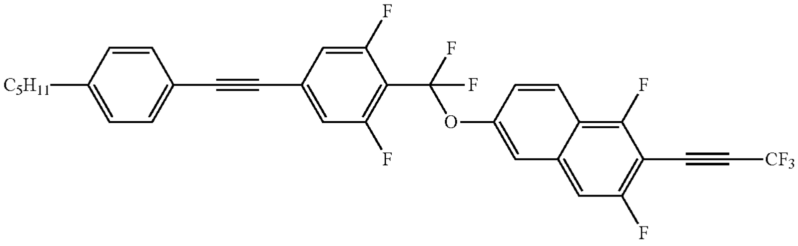
C 92.0 $S_A$ 117 N 133 I
$T_{NI}$ = 109° C., Δε = 56.1, Δn = 0.264

-continued
(No.519)
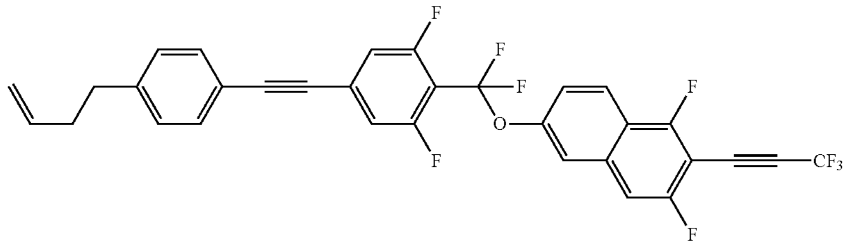
(No.520)
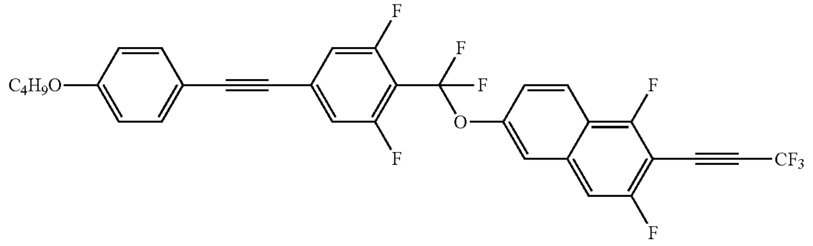
C 129 $S_A$ 161 N 165 I
$T_{NI}$ = 134° C., Δε = 57.7, Δn = 0.277
(No.521)
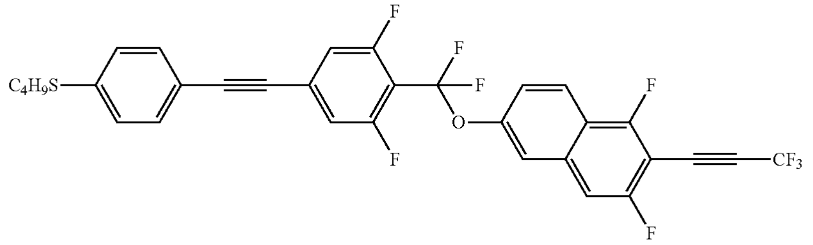
(No.522)
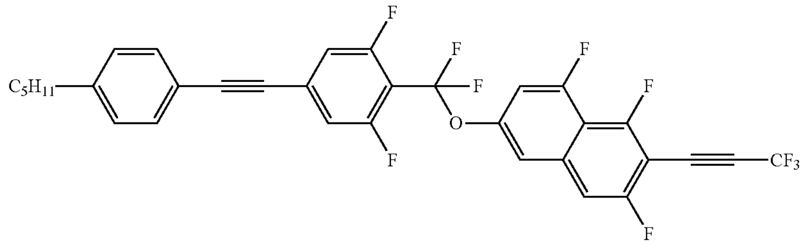
(No.523)
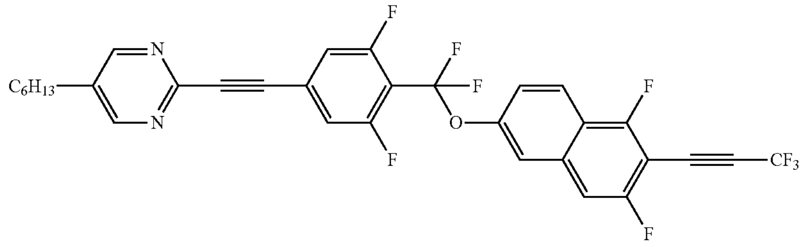
(No.524)
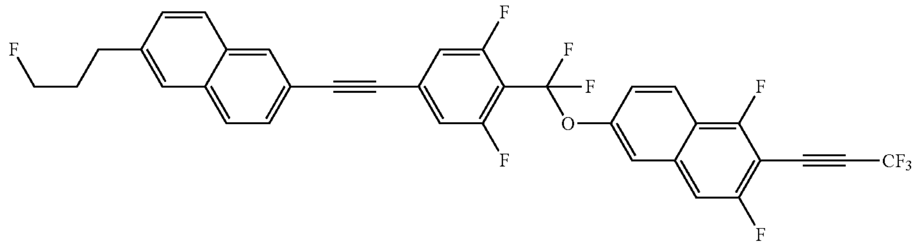

-continued
(No.525)
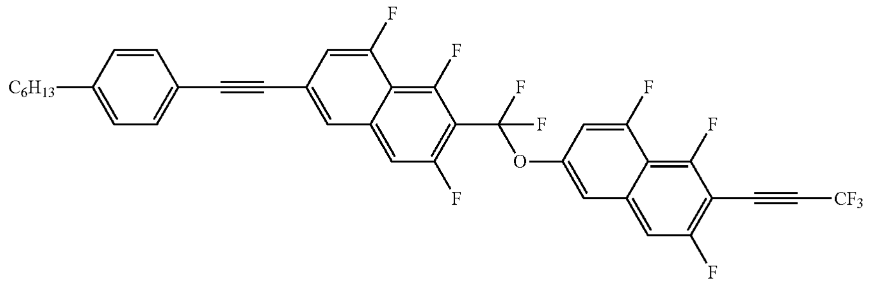
(No.526)
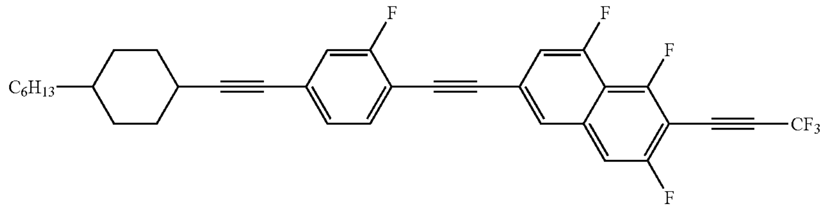
(No.527)
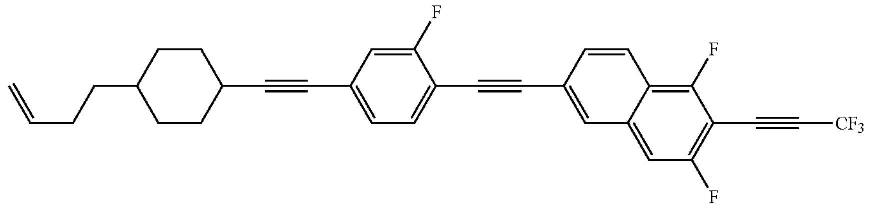
(No.528)
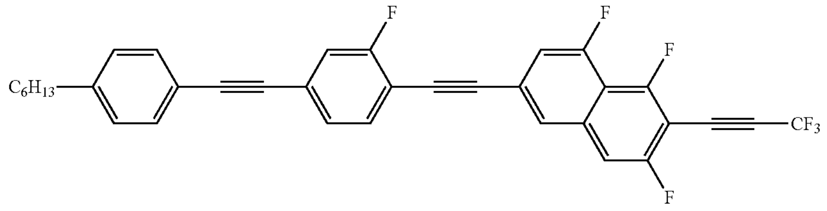
(No.529)
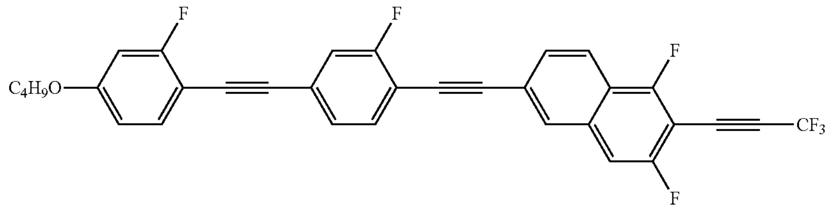
(No.530)
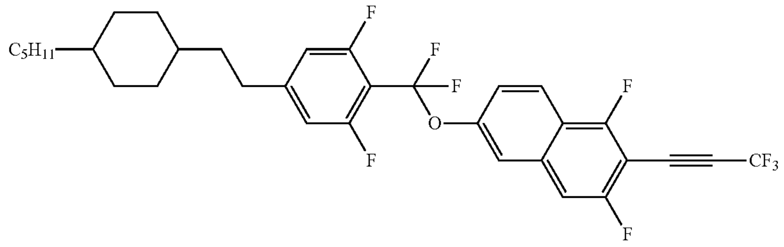

-continued
(No.531)
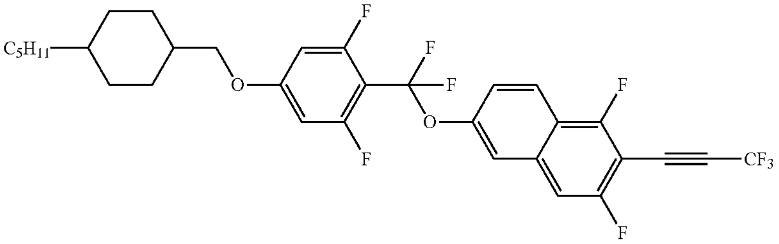
(No.532)
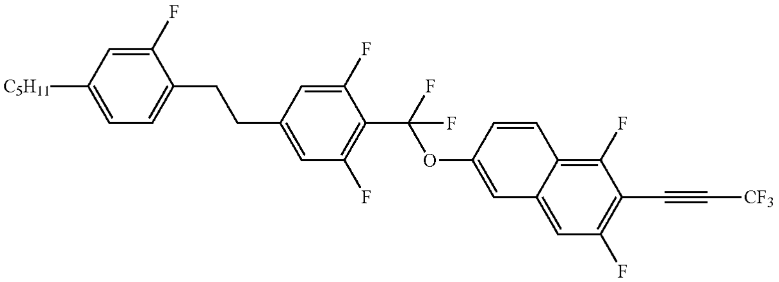
(No.533)
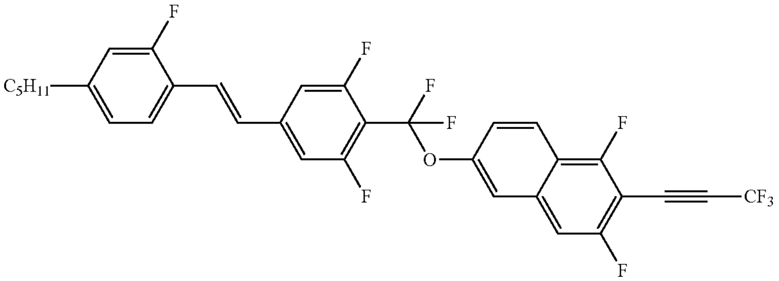
(No.534)
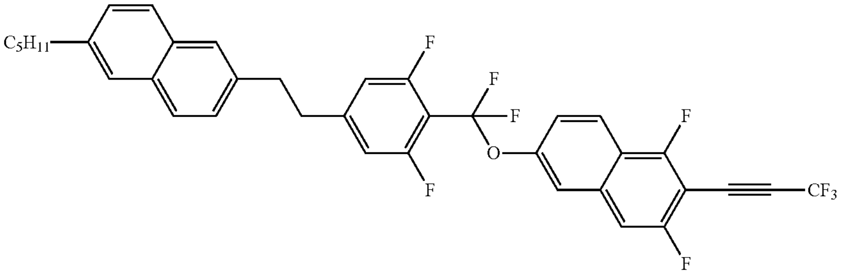
(No.535)
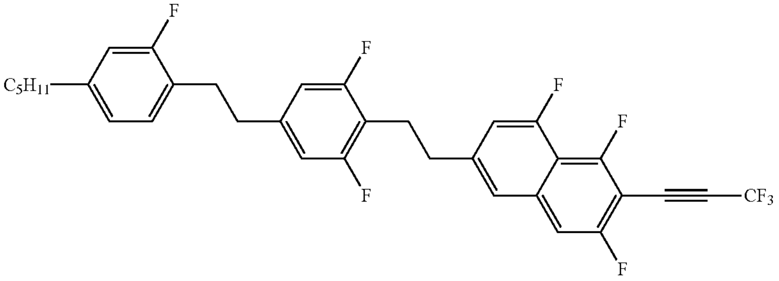

-continued
(No.536)
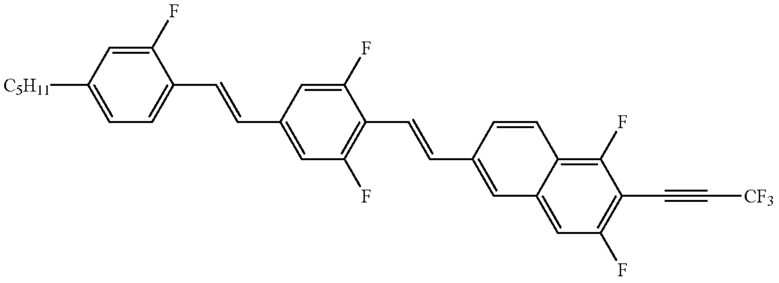
(No.537)
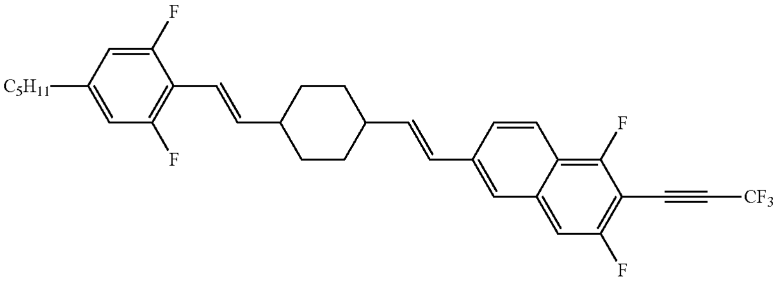
(No.538)
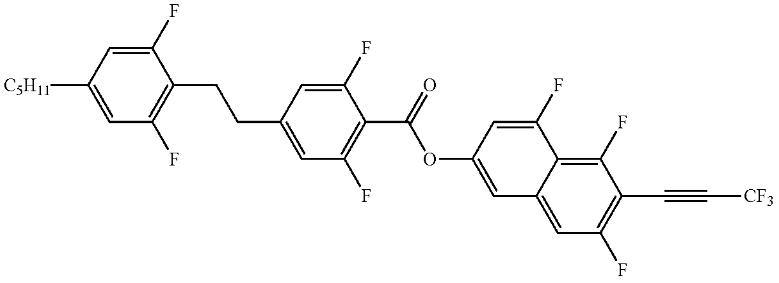
(No.539)
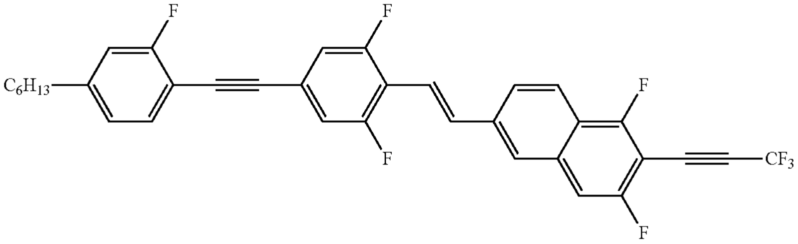
(No.550)
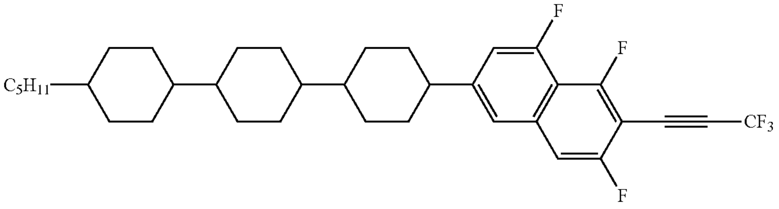
(No.551)
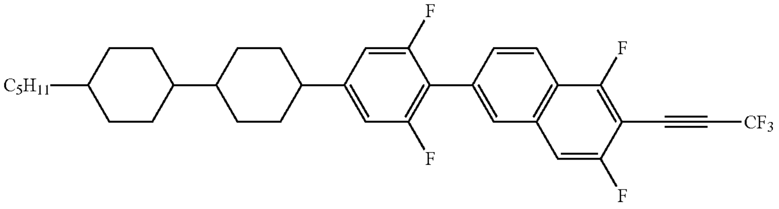

-continued
(No.552)
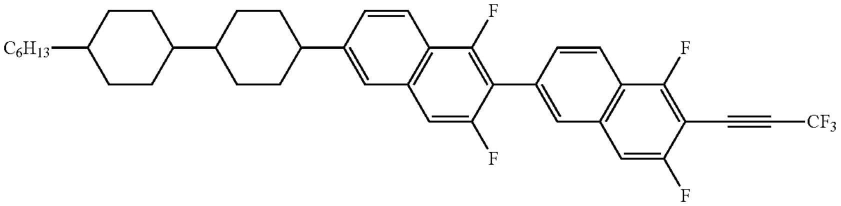
(No.553)
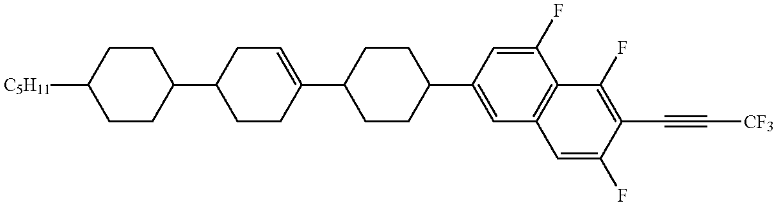
(No.554)
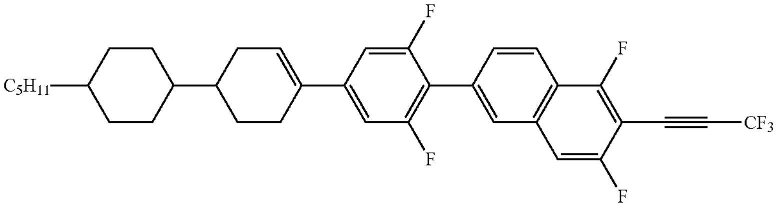
(No.555)
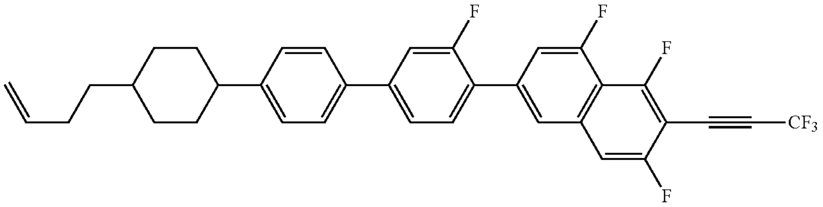
(No.556)
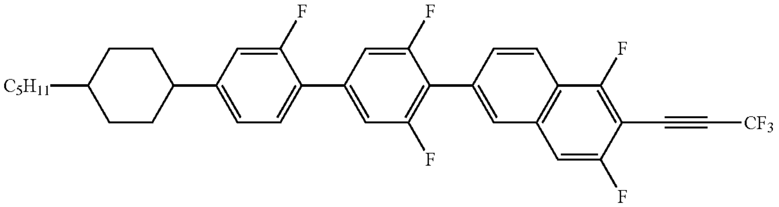
(No.557)
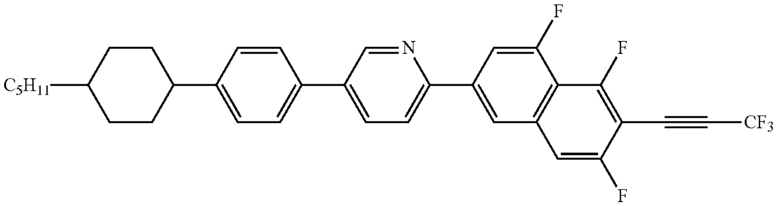
(No.558)
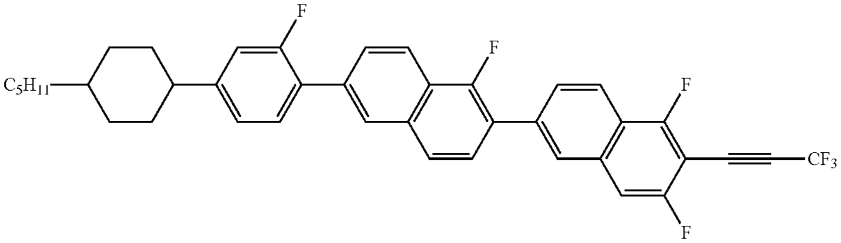

-continued
(No.559)
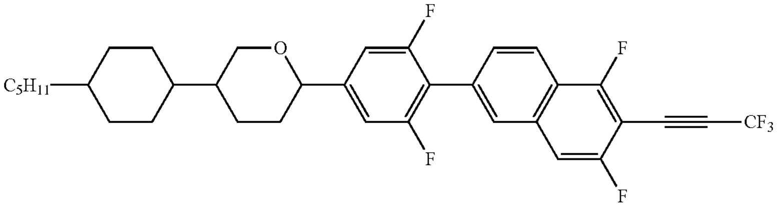
(No.560)
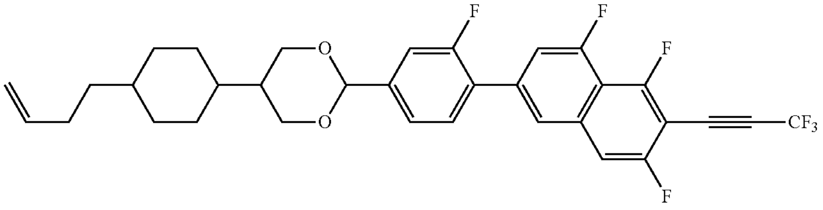
(No.561)
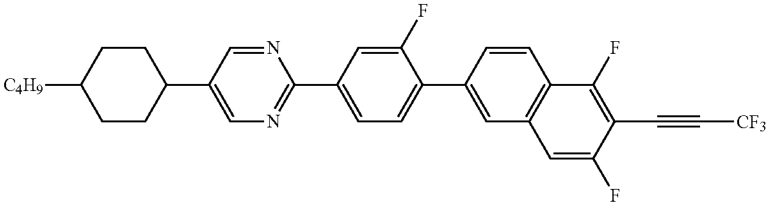
(No.562)
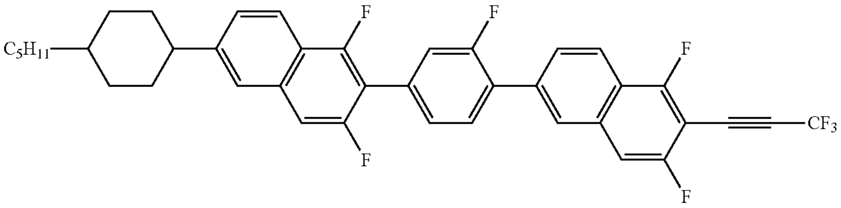
(No.563)
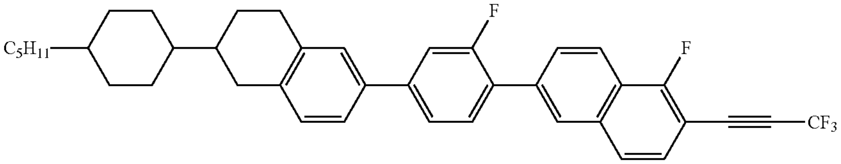
(No.564)
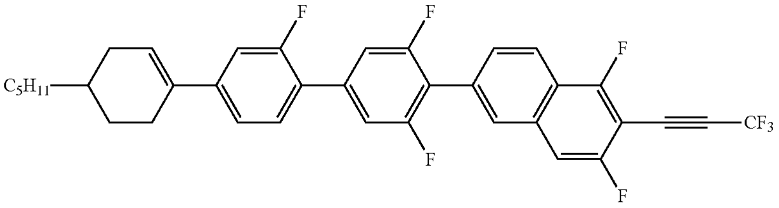
(No.565)
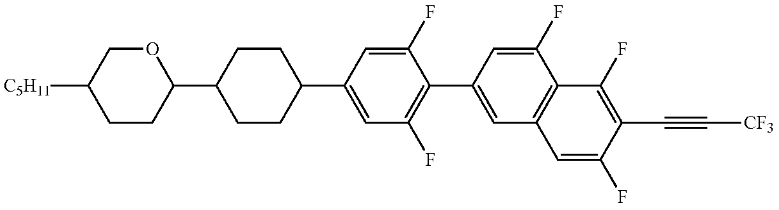

-continued
(No.566)
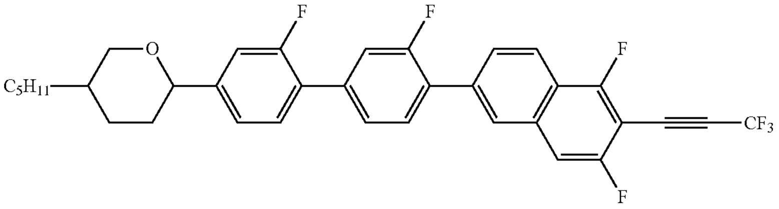
(No.567)
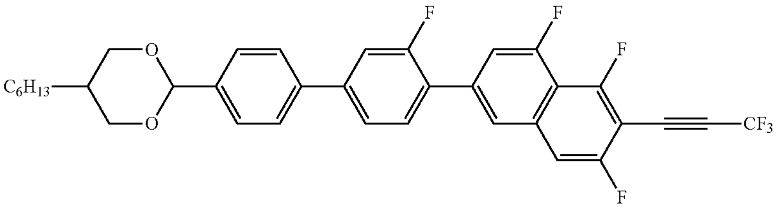
(No.568)
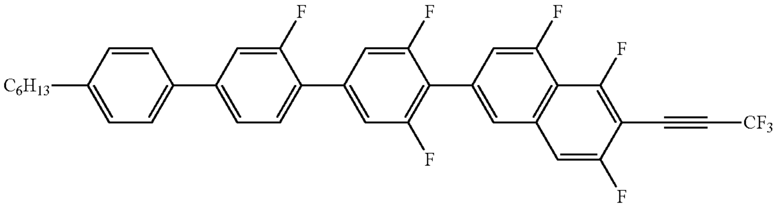
(No.569)
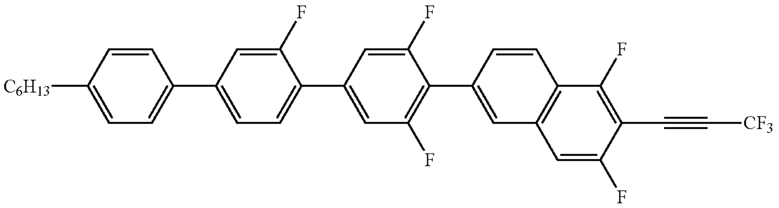
(No.570)
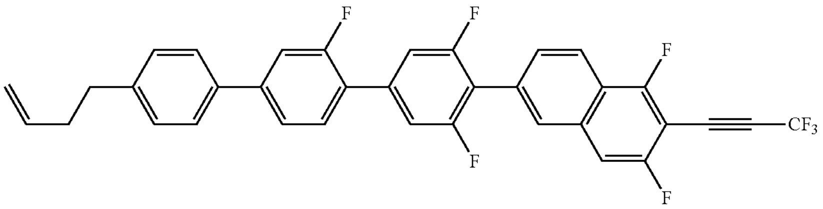
(No.571)
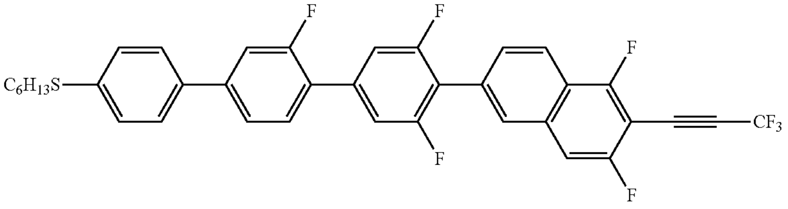
(No.572)
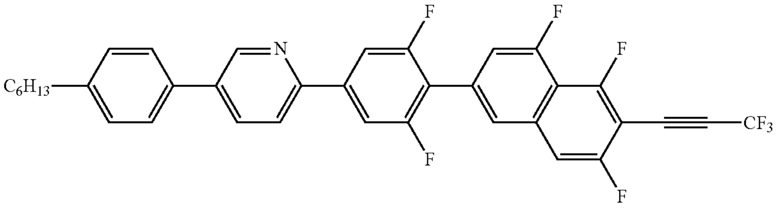

-continued
(No.573)
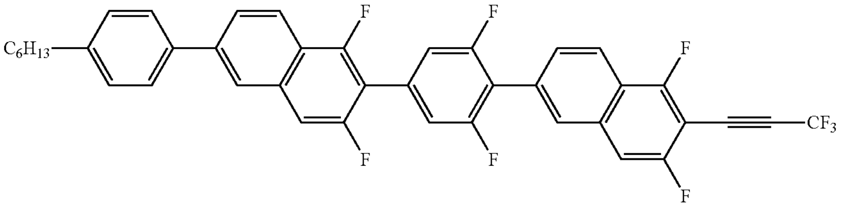
(No.574)
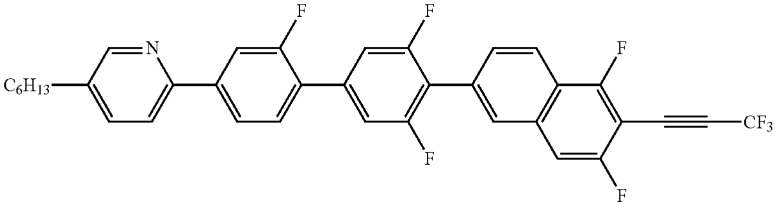
(No.575)
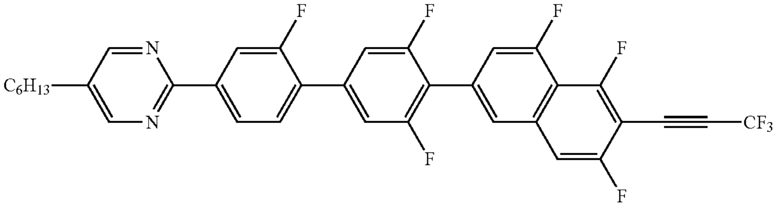
(No.576)
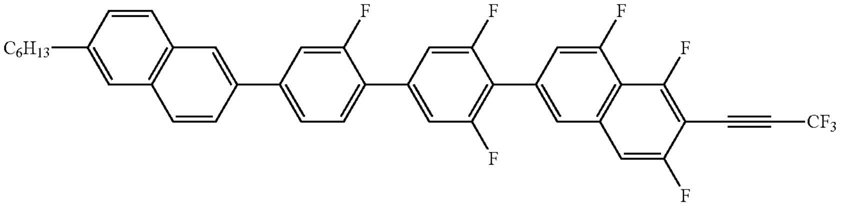
(No.577)
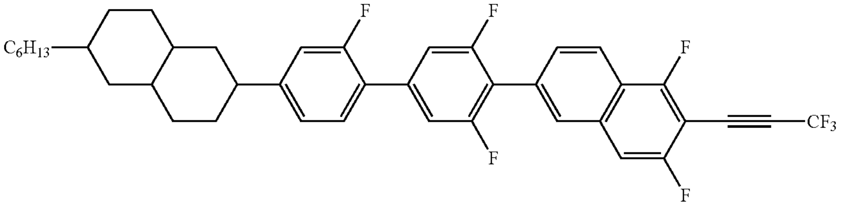
(No.578)
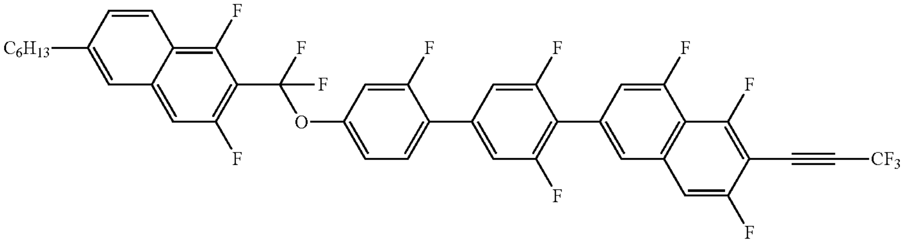
(No.579)
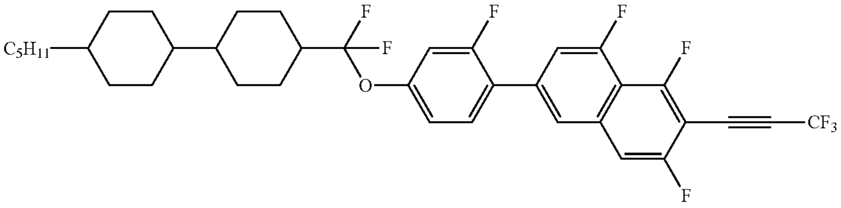

-continued
(No.580)
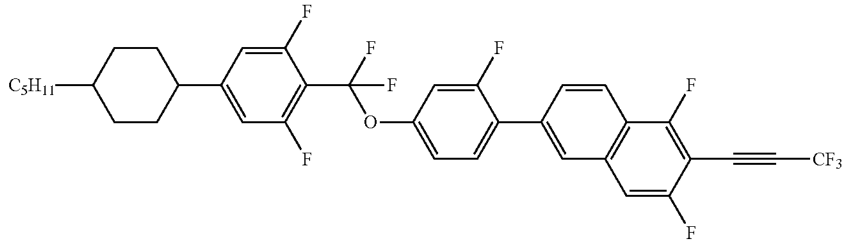
(No.581)
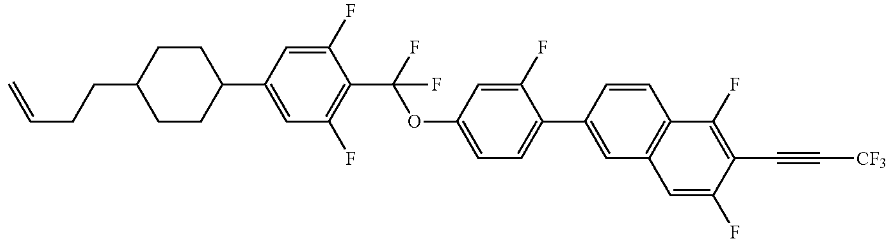
(No.582)
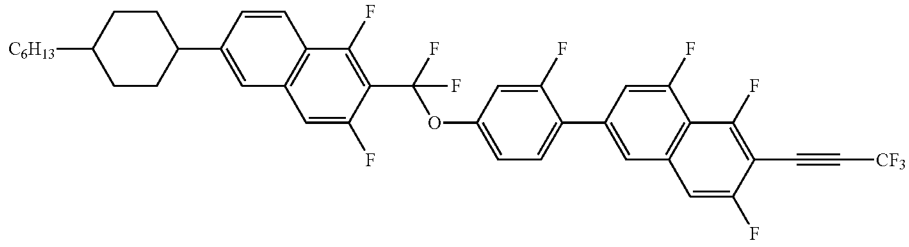
(No.583)
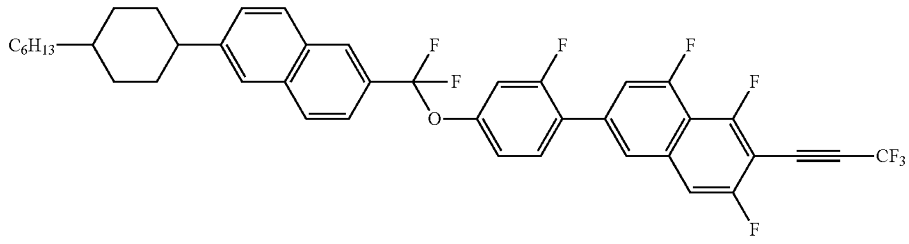
(No.584)
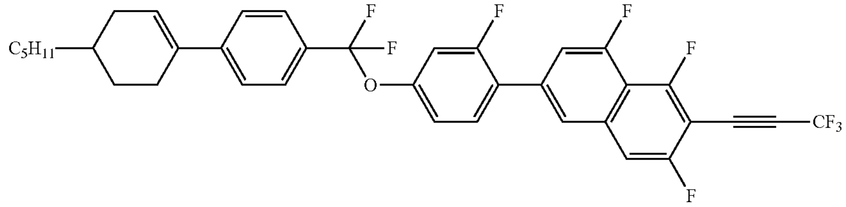
(No.585)
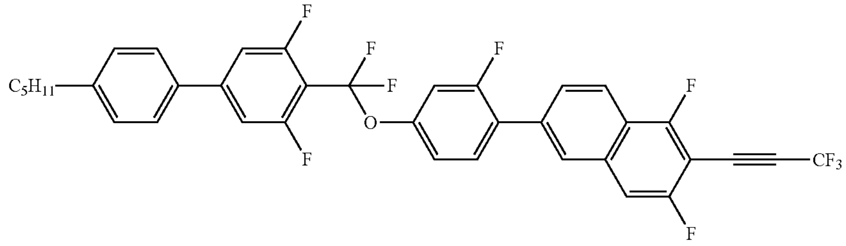

-continued
(No.586)
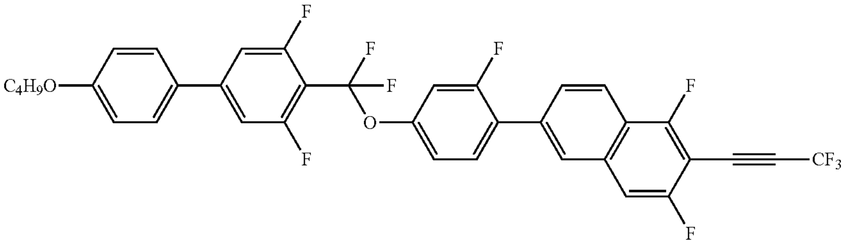
(No.587)
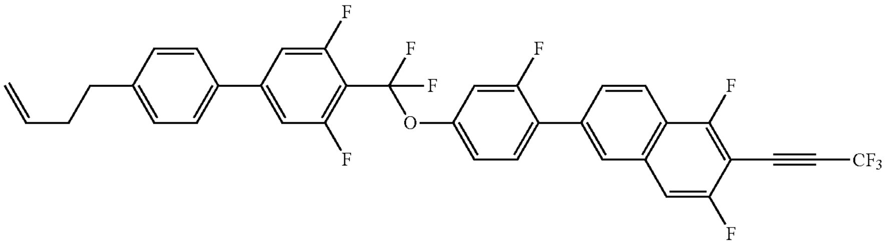
(No.588)
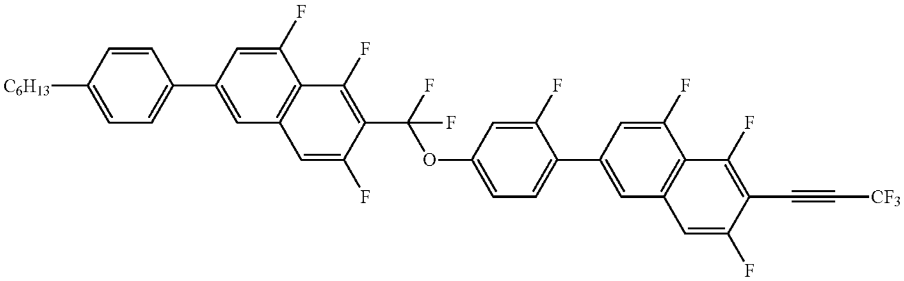
(No.589)
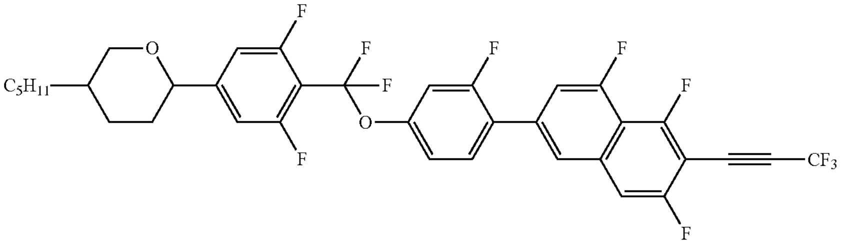
(No.590)
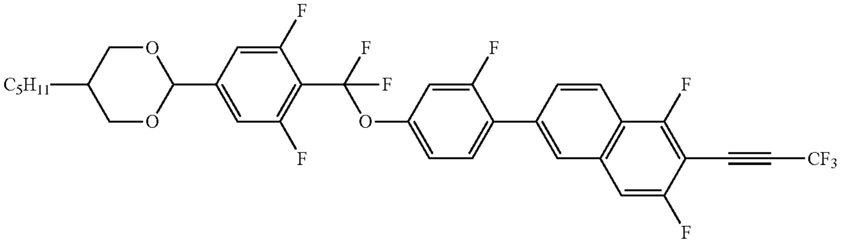
(No.591)
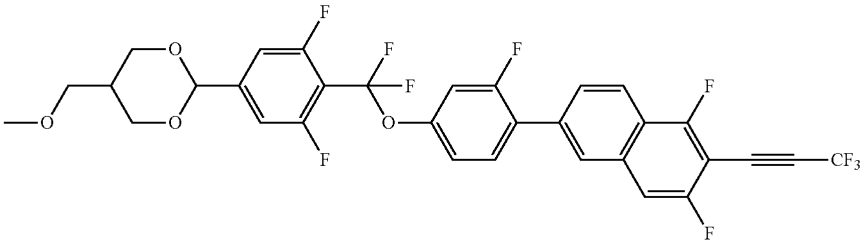

-continued
(No.592)
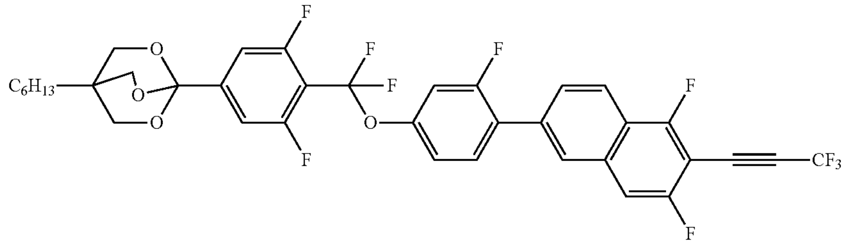
(No.593)
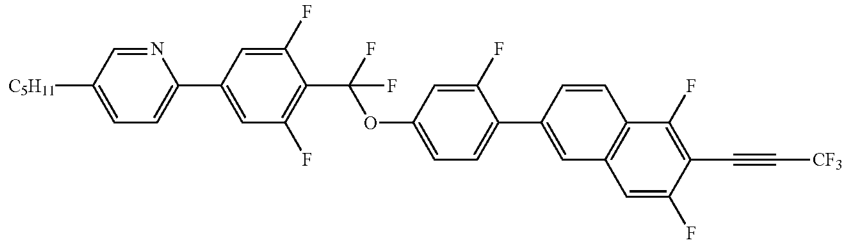
(No.594)
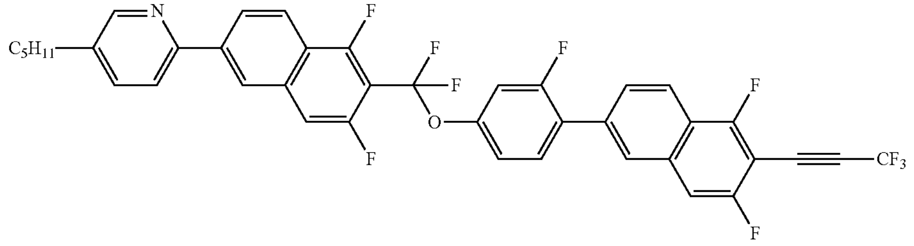
(No.595)
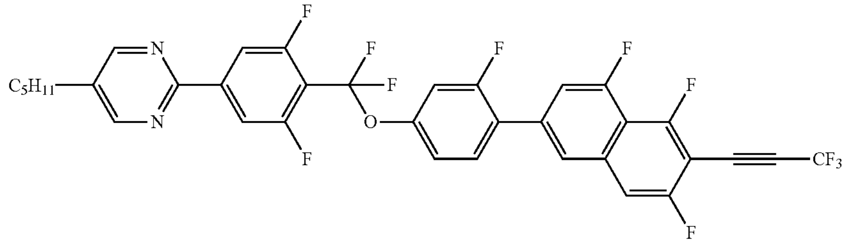
(No.596)
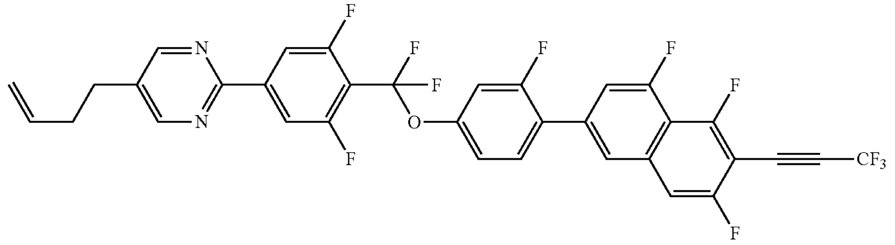
(No.597)
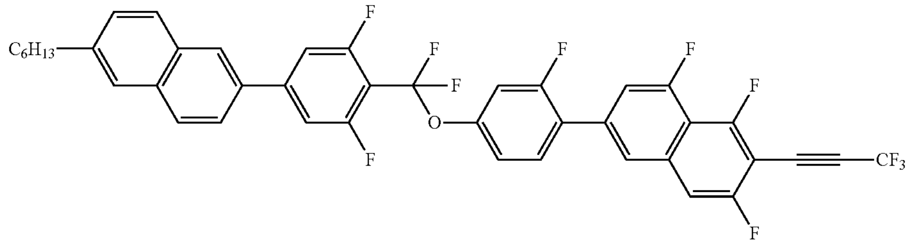

-continued
(No.598)
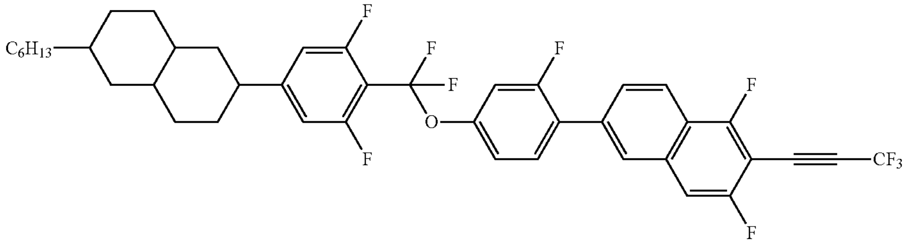
(No.599)
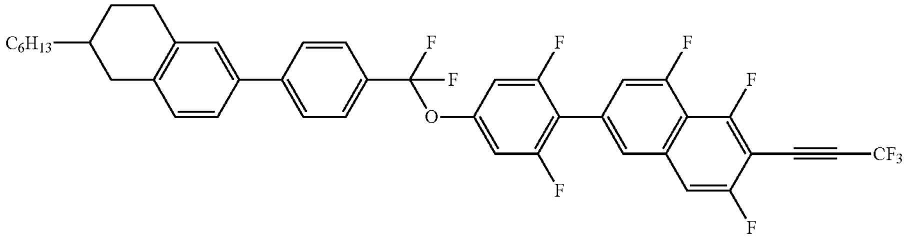
(No.600)
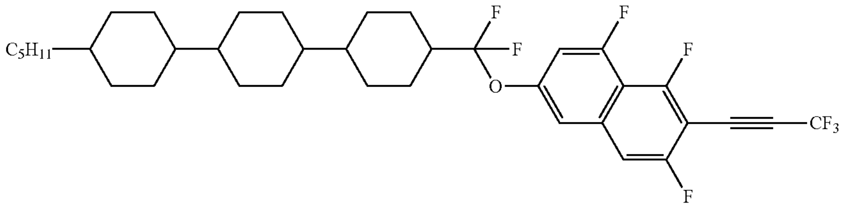
(No.601)
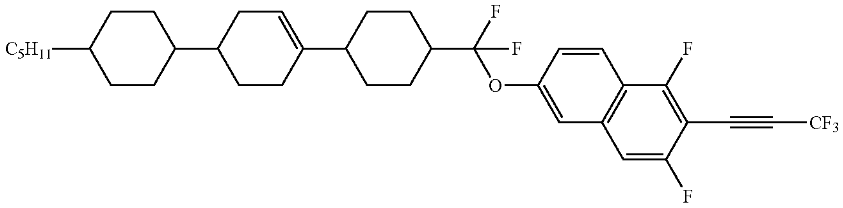
(No.602)
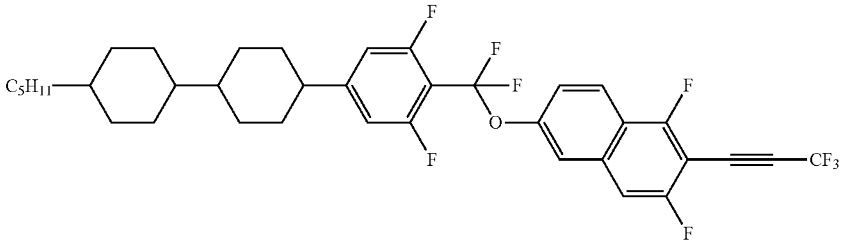
(No.603)
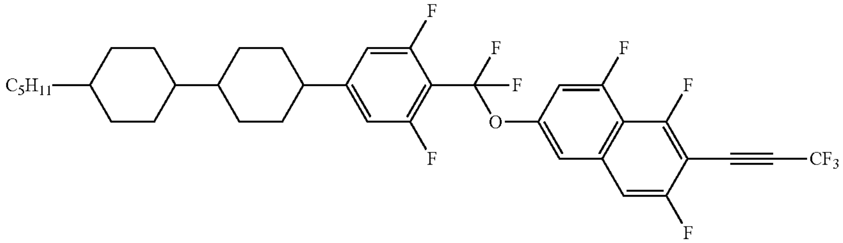

-continued
(No.604)
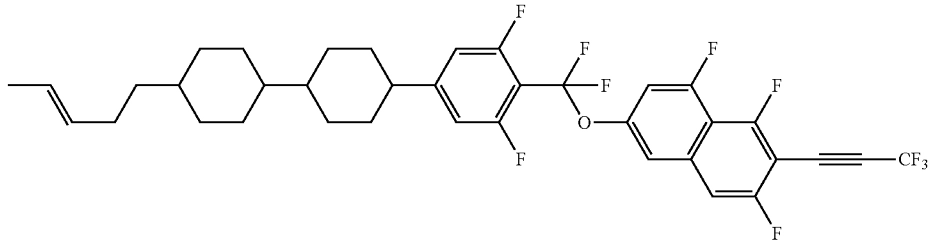
(No.605)
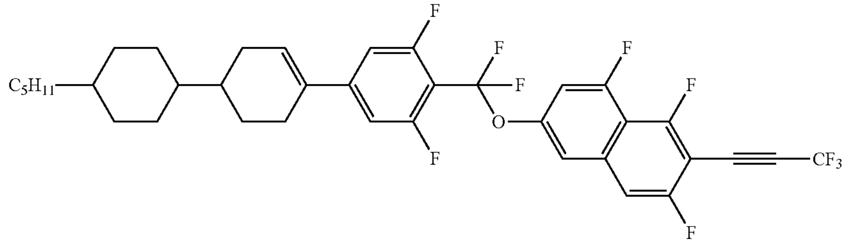
(No.606)
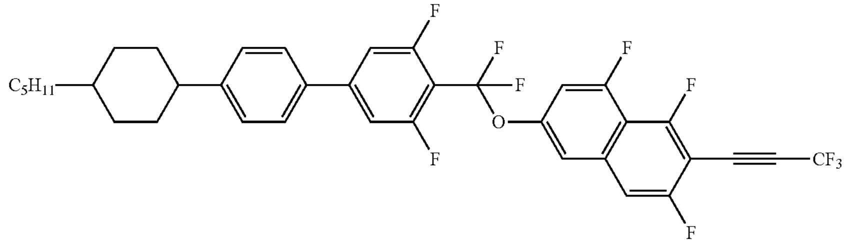
(No.607)
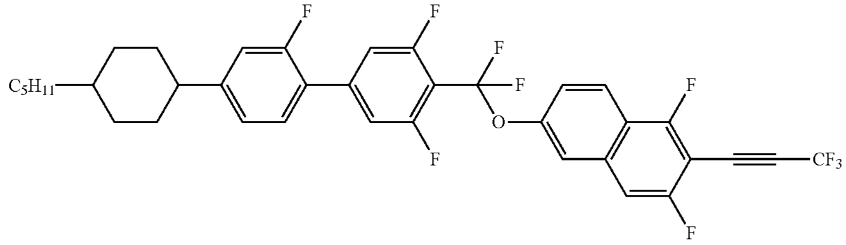
(No.608)
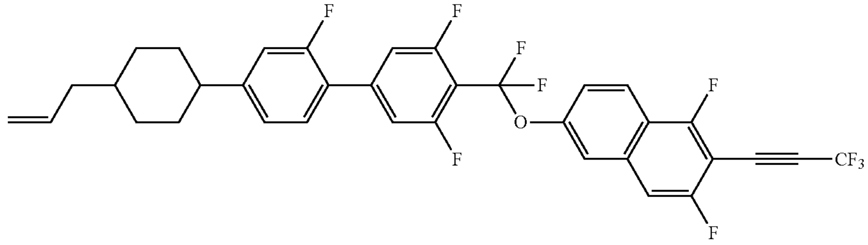
(No.609)
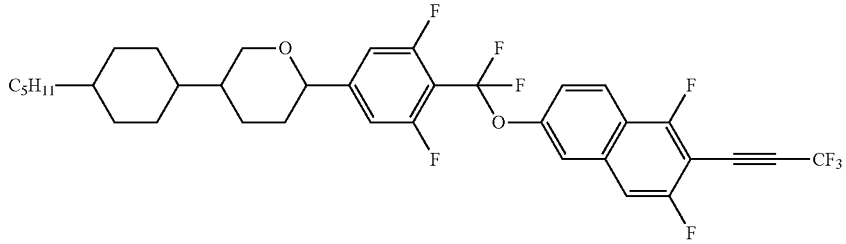

-continued
(No.610)
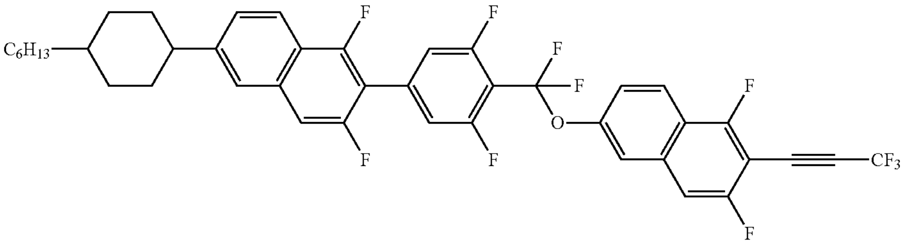
(No.611)
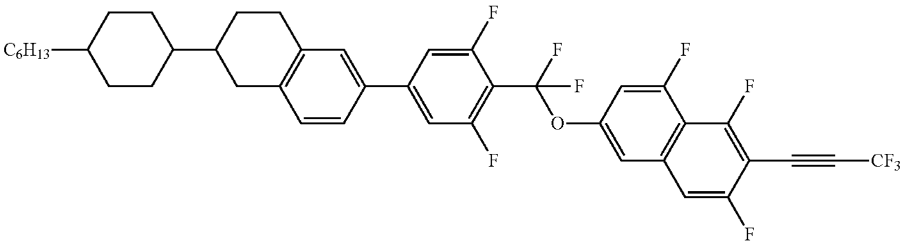
(No.612)
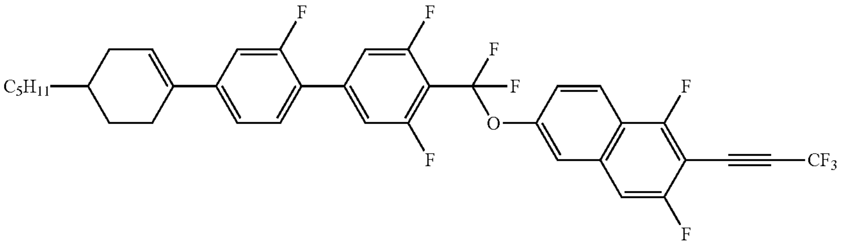
(No.613)
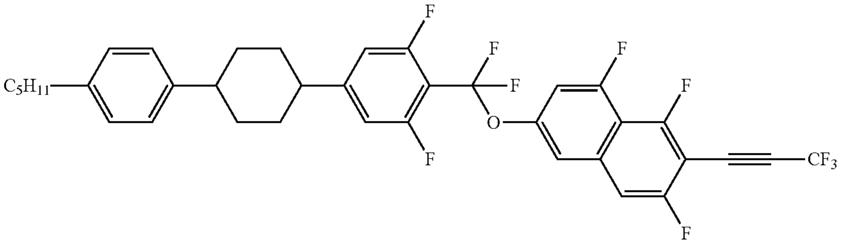
(No.614)
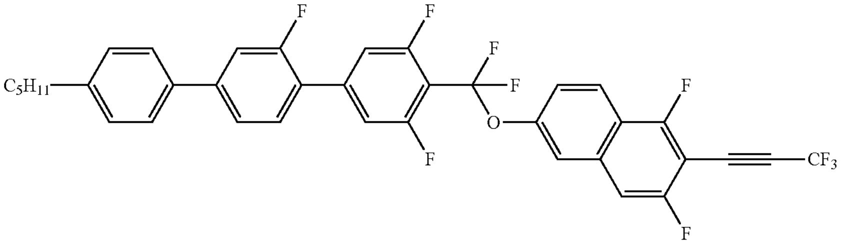
C 102 $S_A$ 205 N 212 I
$T_{NI}$ = 158° C., Δε = 52.1, Δn = 0.297
(No.615)
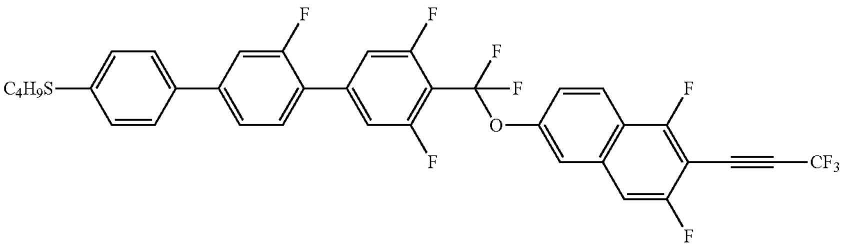

-continued
(No.616)
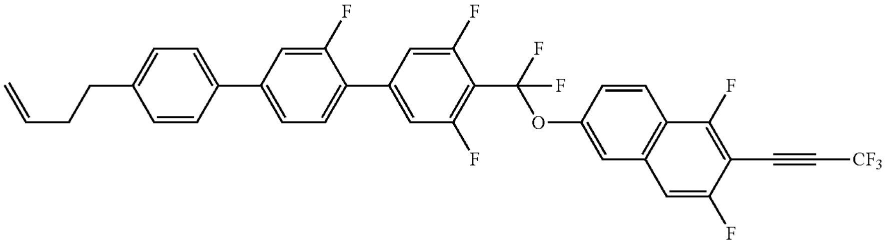
(No.617)
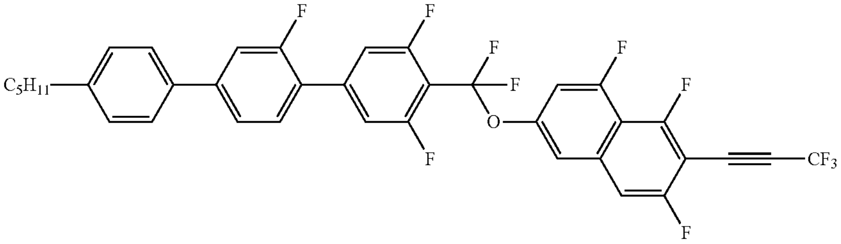
(No.618)
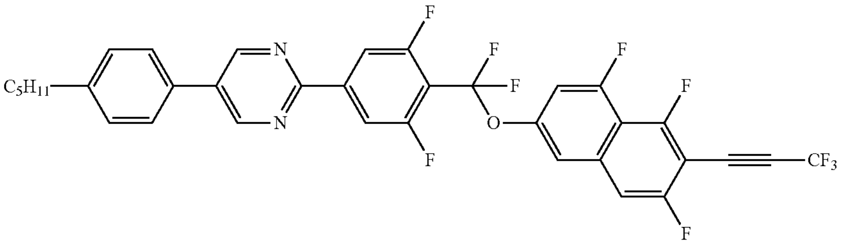
(No.619)
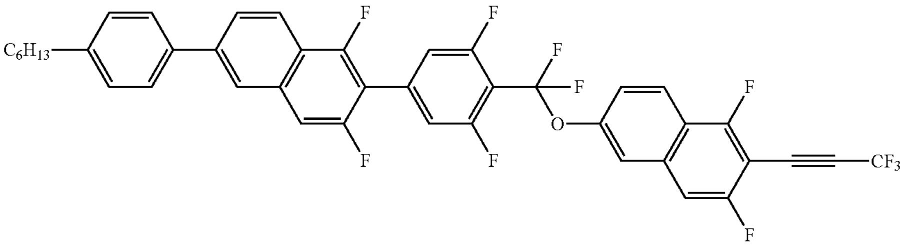
(No.620)
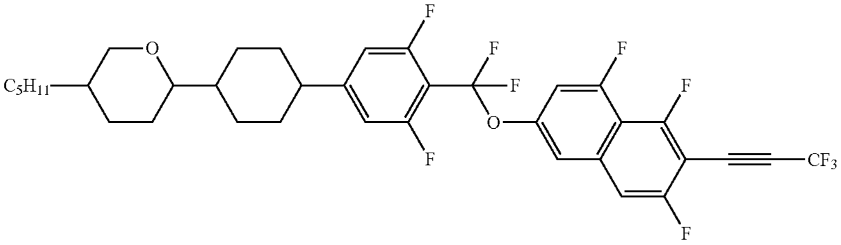
(No.621)
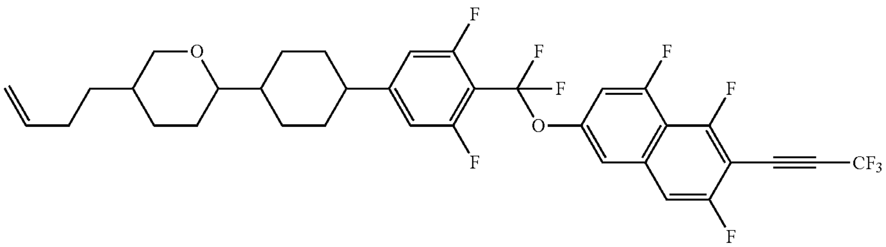

-continued
(No.622)
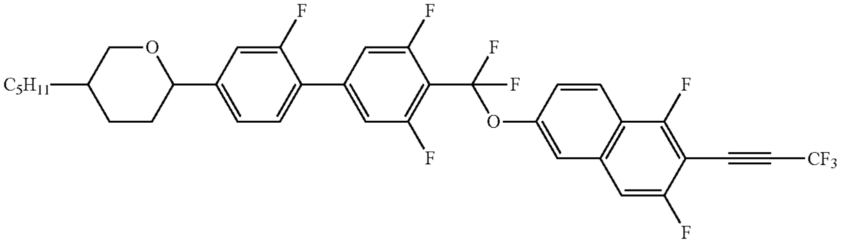
(No.623)
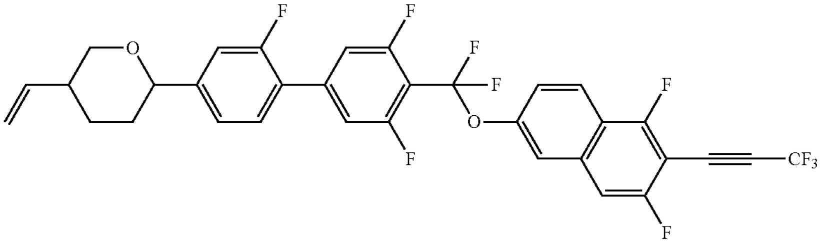
(No.624)
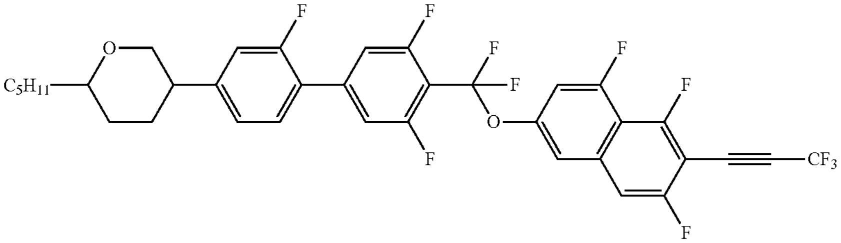
(No.625)
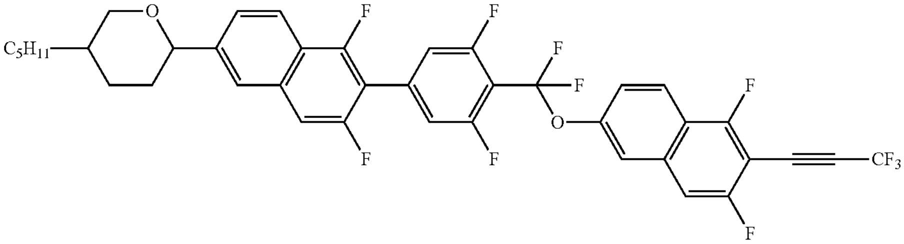
(No.626)
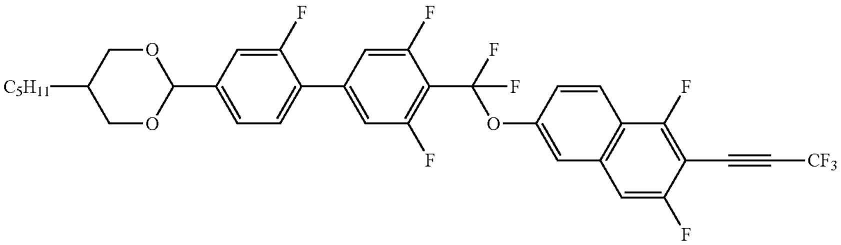
(No.627)
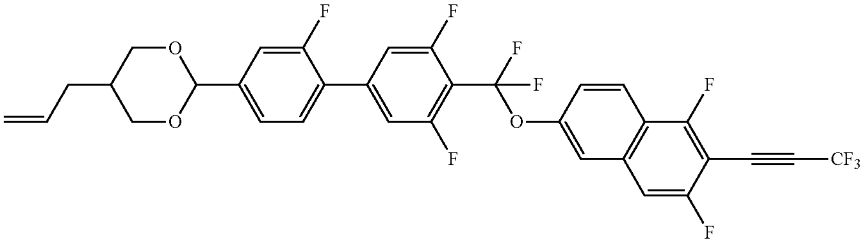

-continued
(No.628)
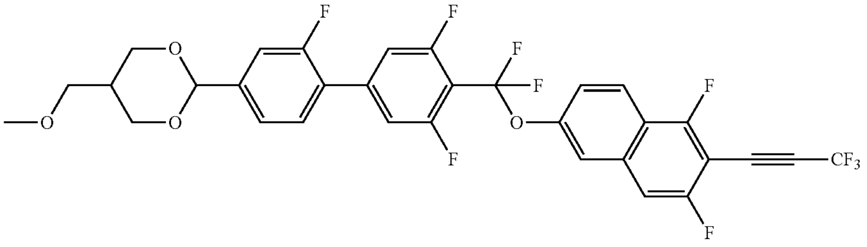
(No.629)
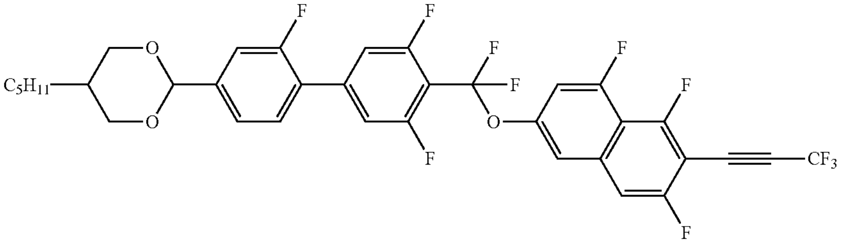
(No.630)
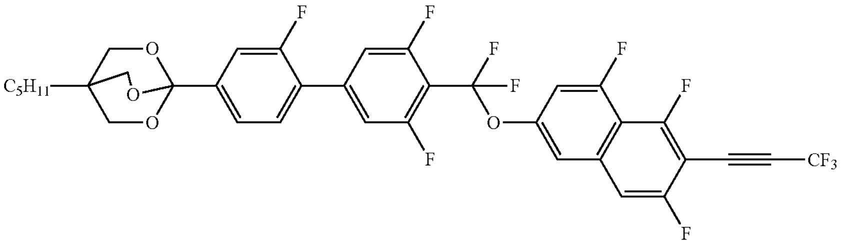
(No.631)
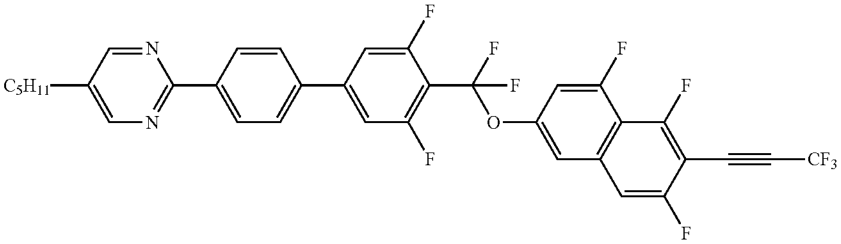
(No.632)
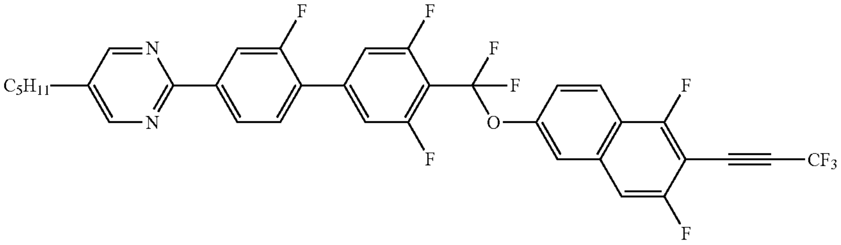
(No.633)
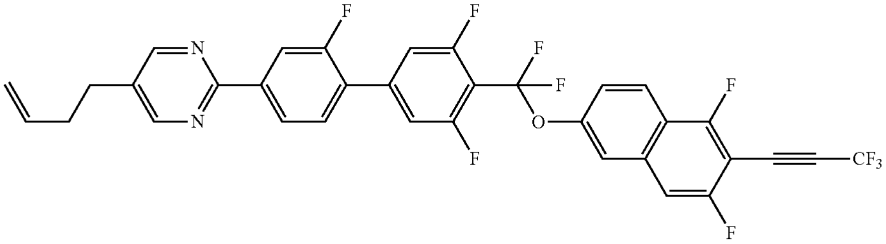

-continued
(No.634)
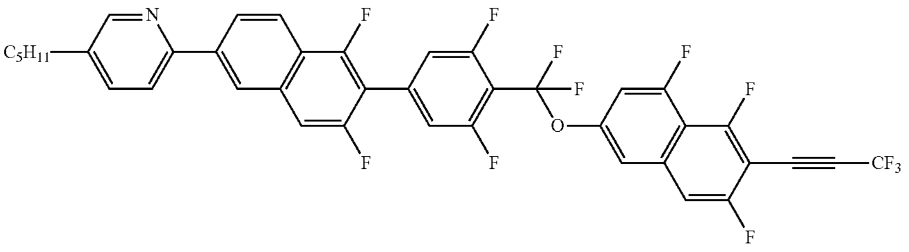
(No.635)
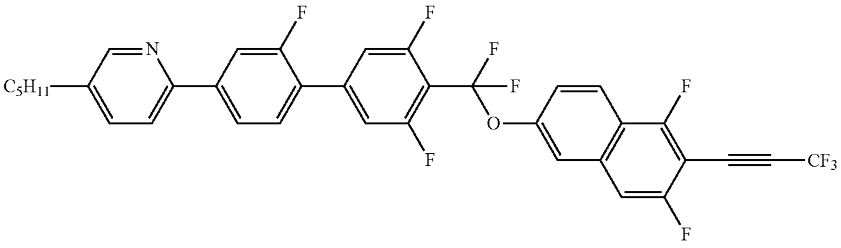
(No.636)
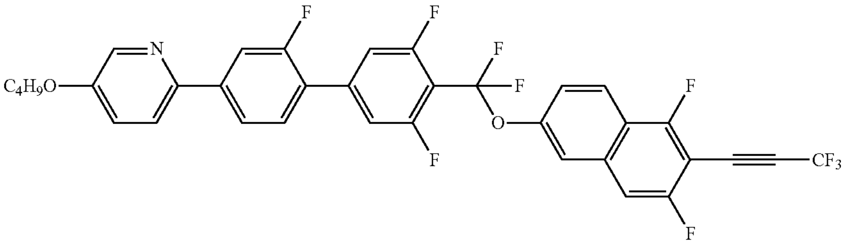
(No637)
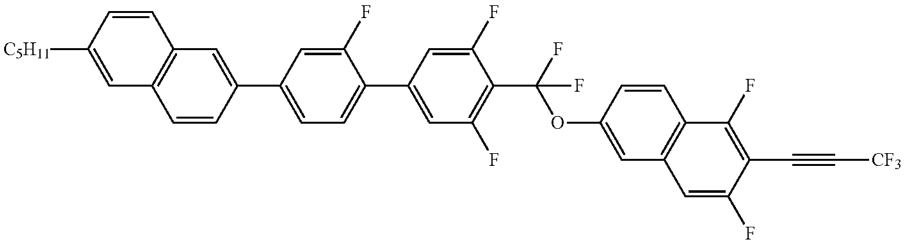
(No.638)
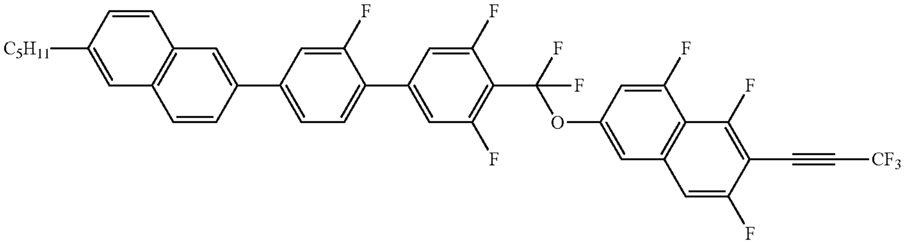
(No.639)
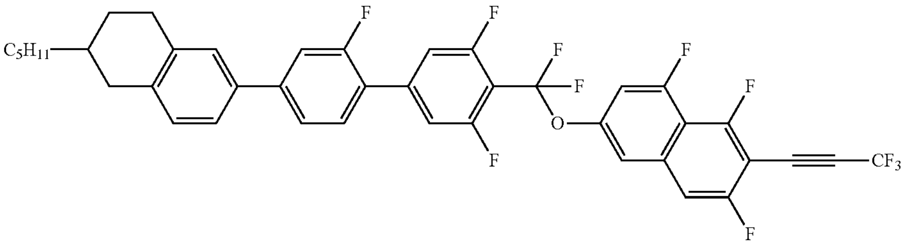

-continued
(No.640)
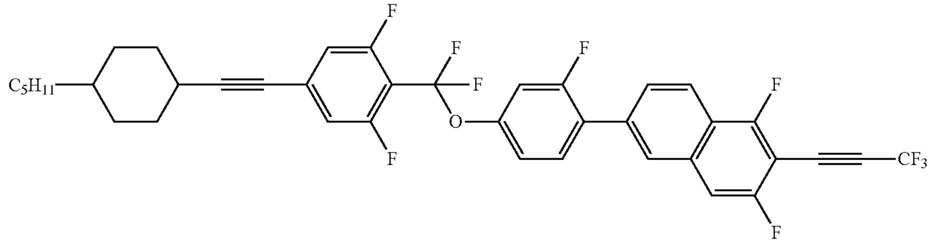
(No.641)
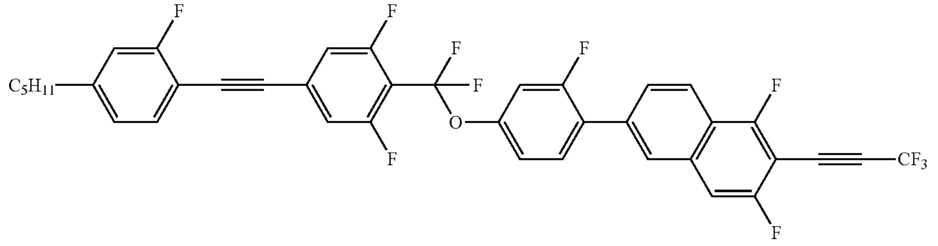
(No.642)
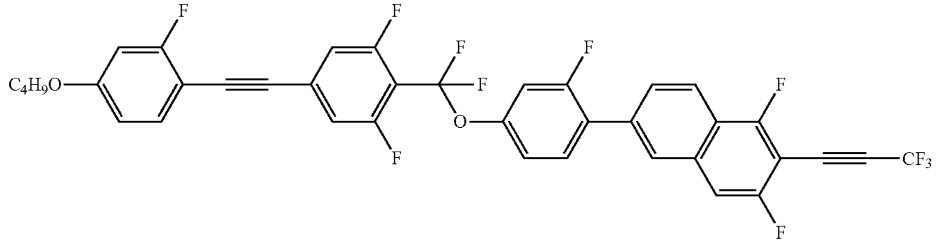
(No.643)
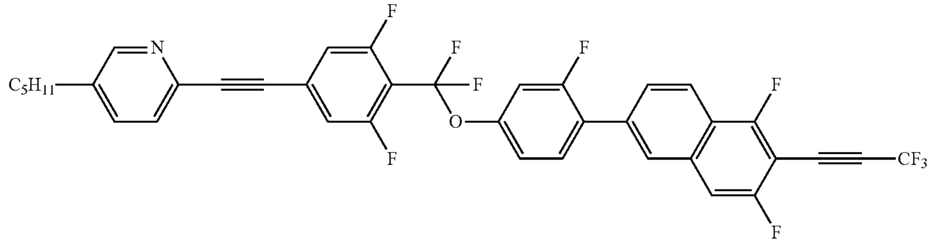
(No.644)
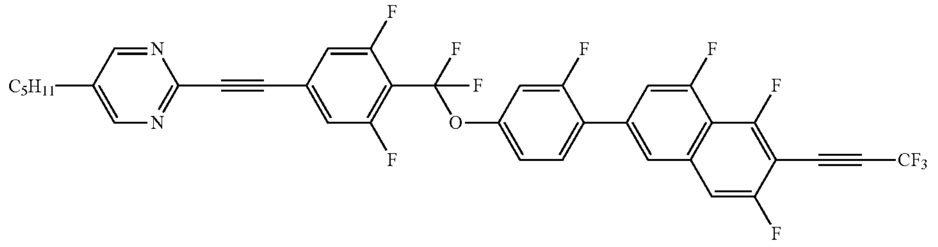
(No.645)
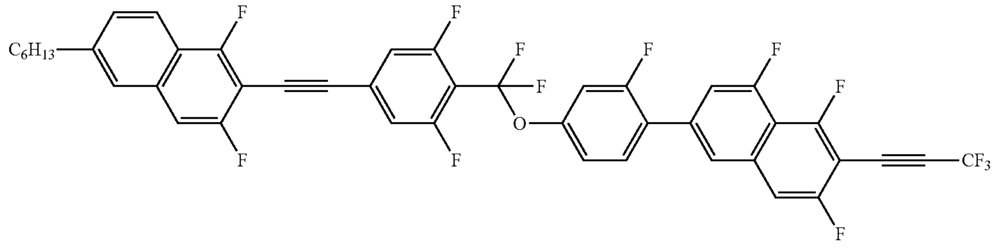

-continued
(No.646)
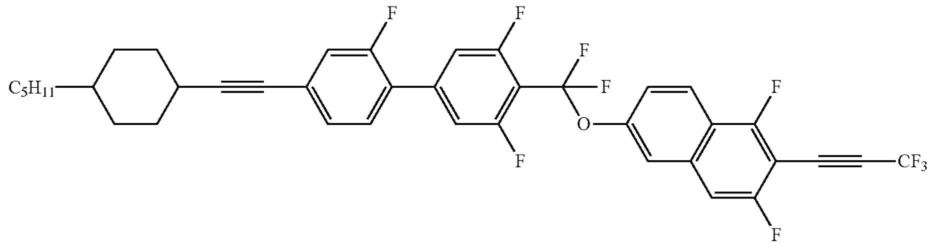
(No.647)
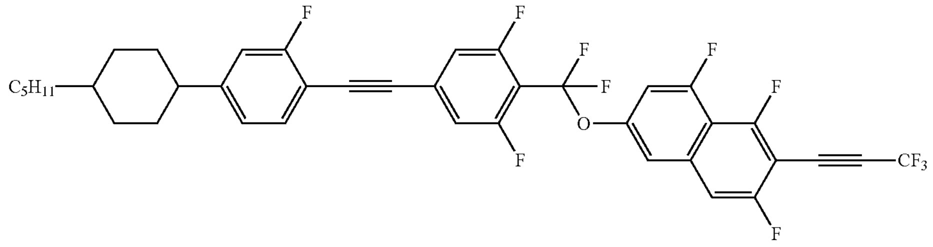
(No.648)
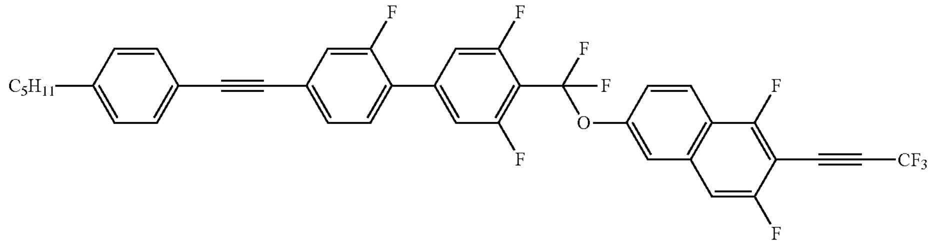
(No.649)
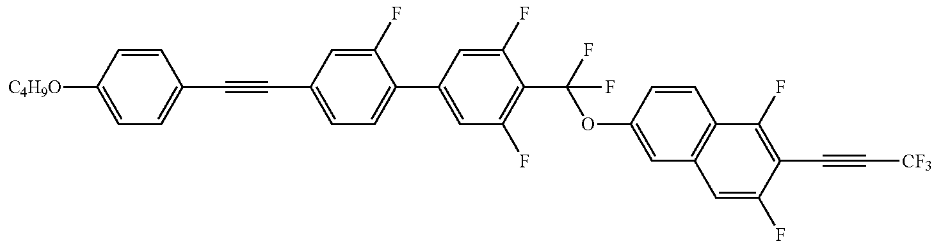
(No.650)
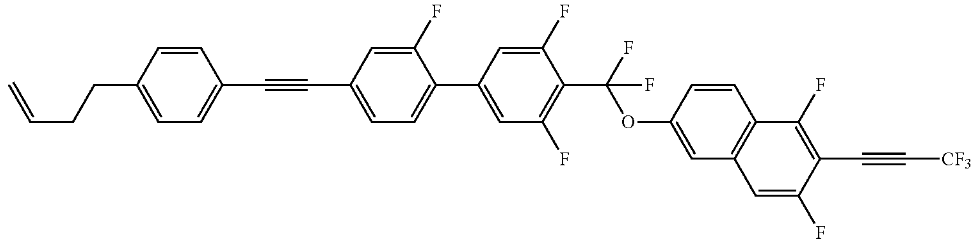
(No.651)
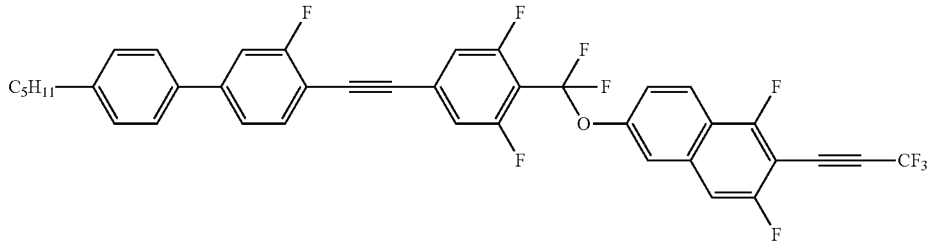

-continued
(No.652)
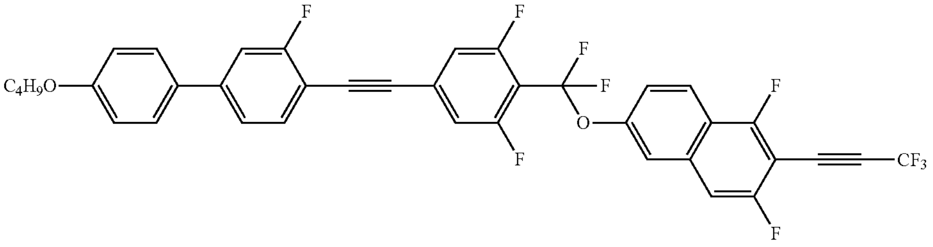
(No.653)
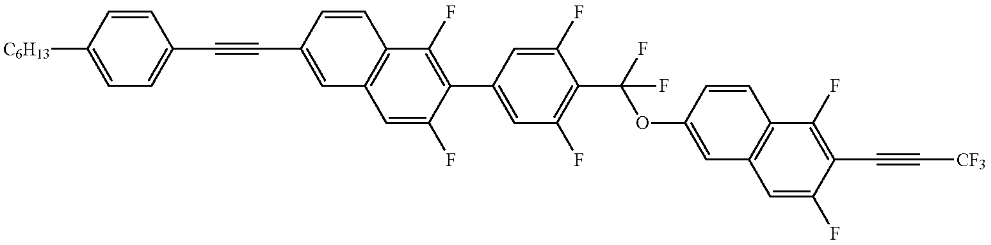
(No.654)
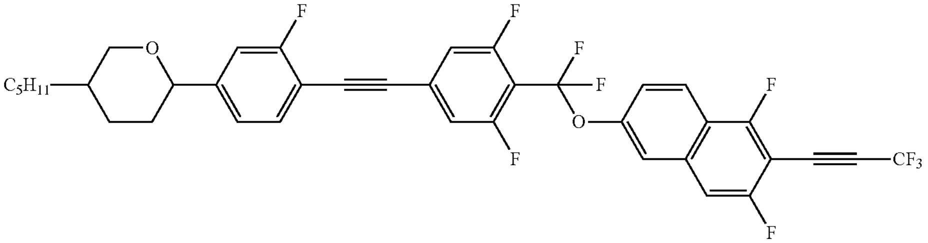
(No.655)
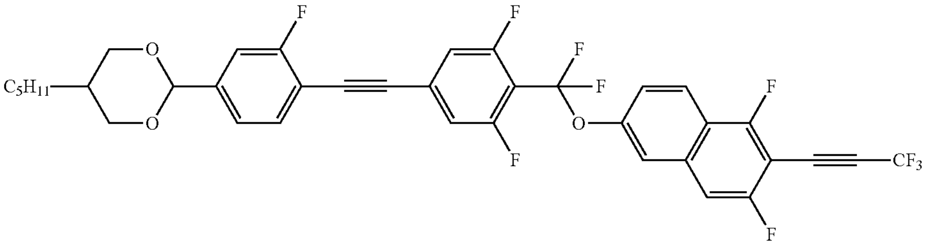
(No.656)
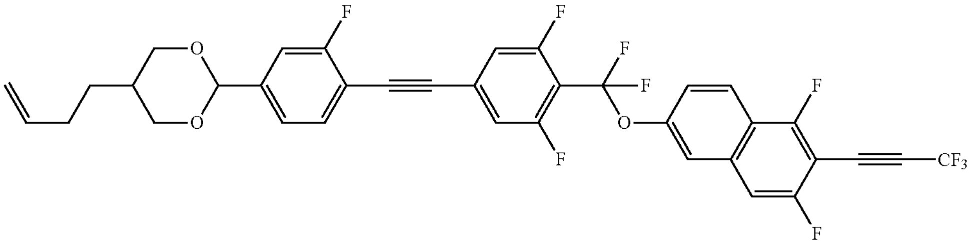
(No.657)
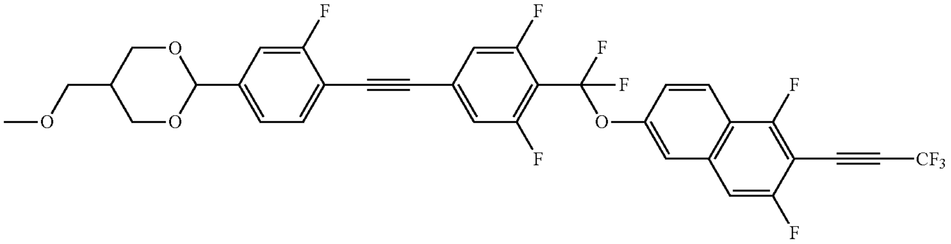

-continued
(No.658)
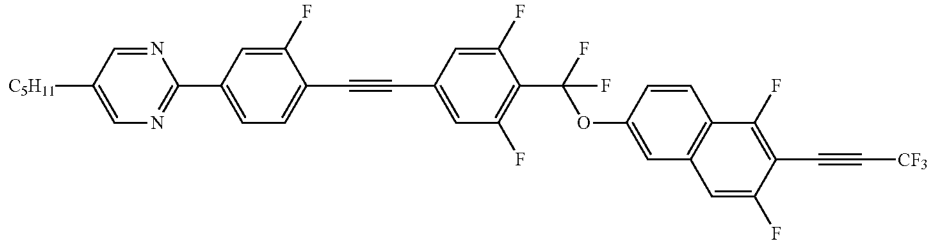
(No.659)
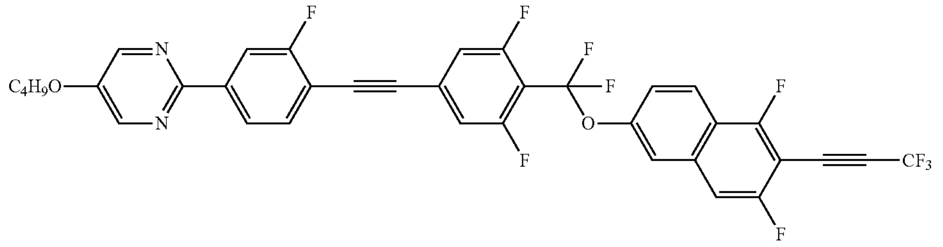
(No.660)
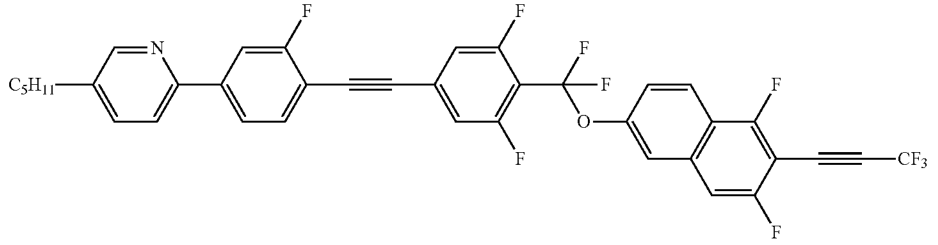
(No.661)
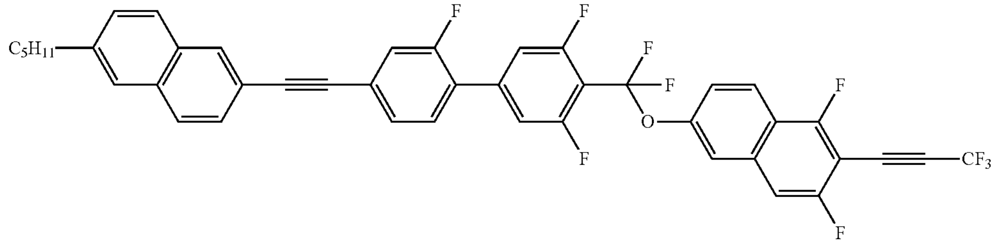
(No.662)
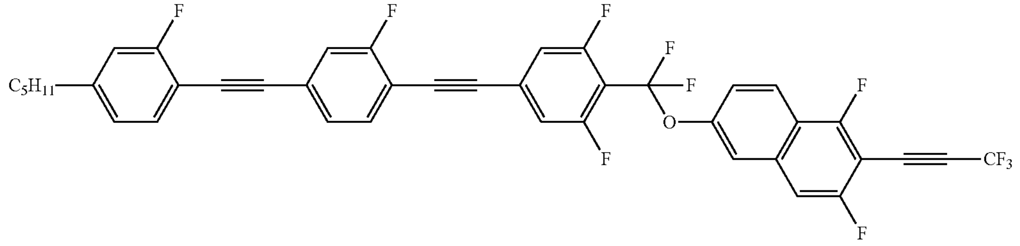
(No.663)
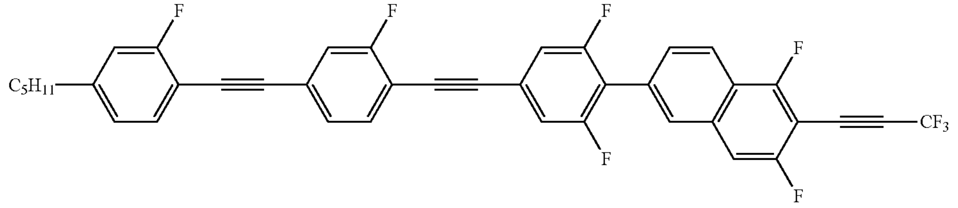

-continued
(No.664)
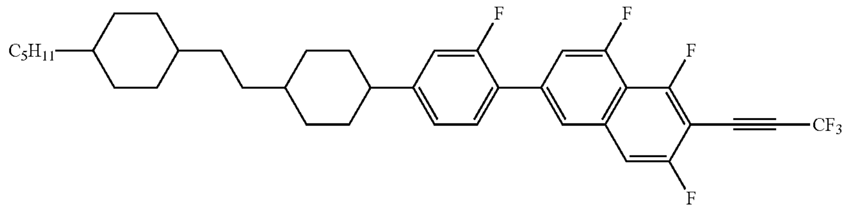
(No.665)
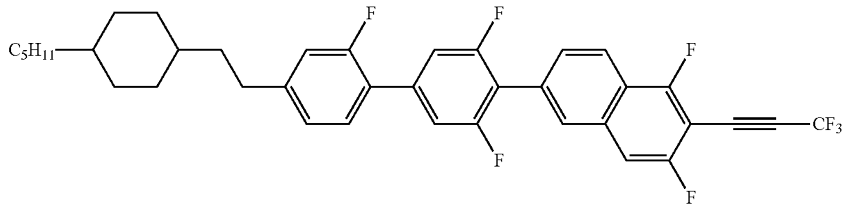
(No.666)
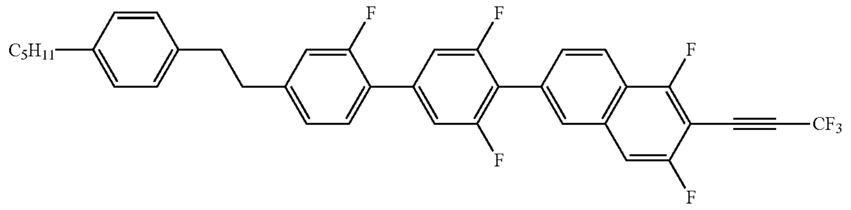
(No.667)
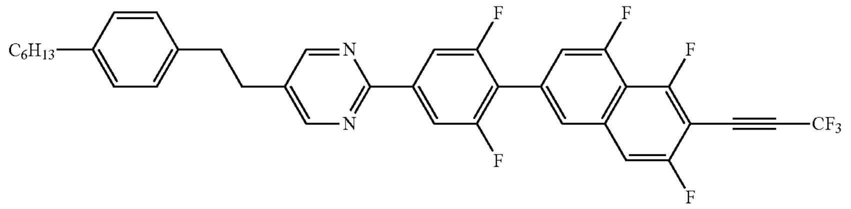
(No.668)
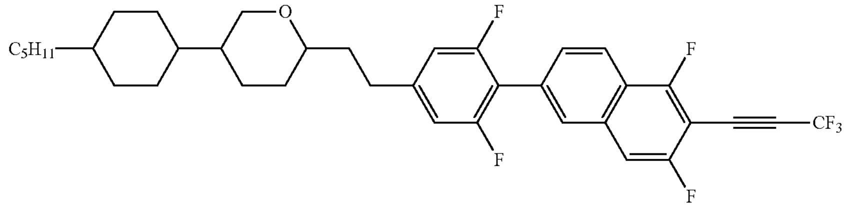
(No.669)
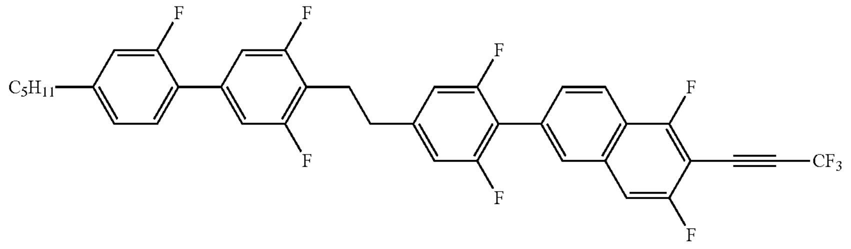
(No.670)
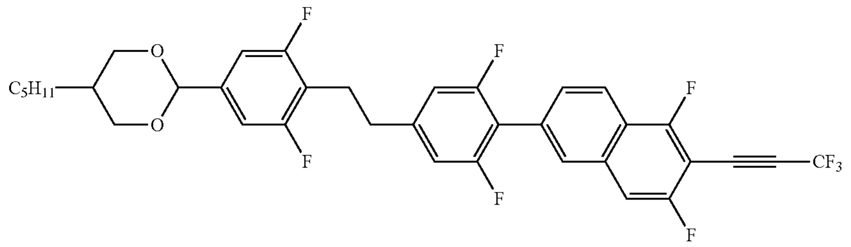

-continued
(No.671)
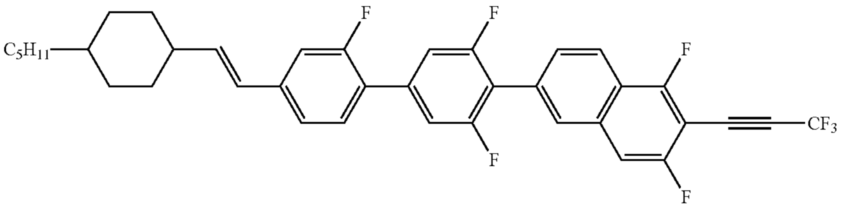
(No.672)
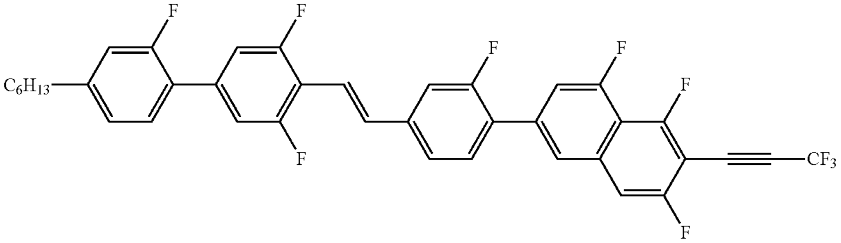
(No.673)
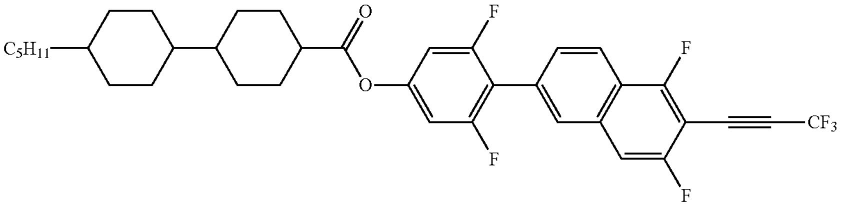
(No.674)
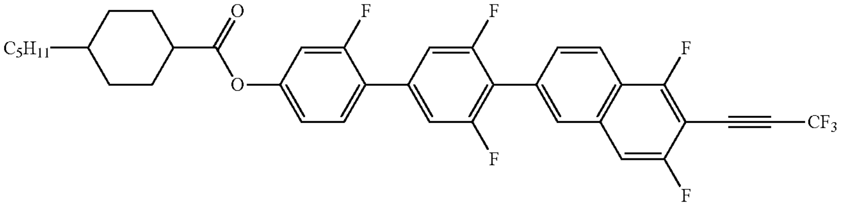
(No.675)
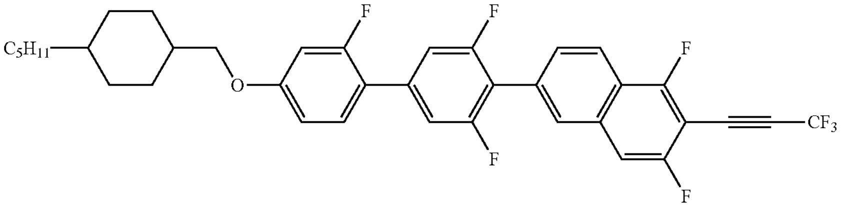
(No.676)
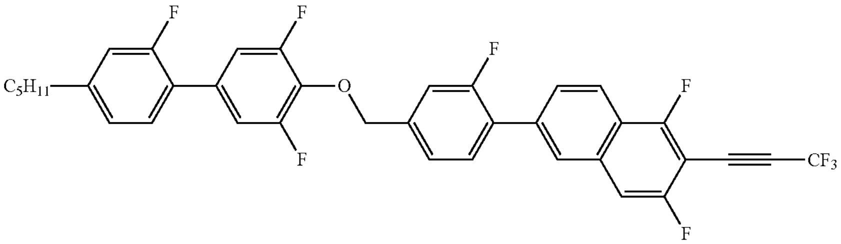
(No.677)
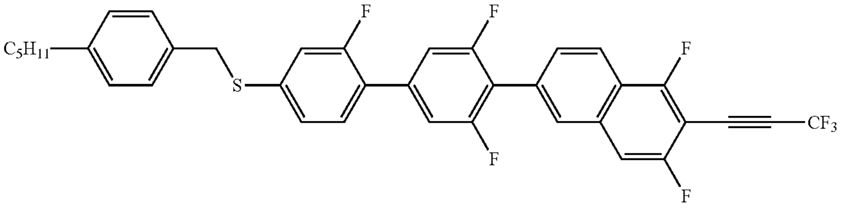

-continued (No.678)

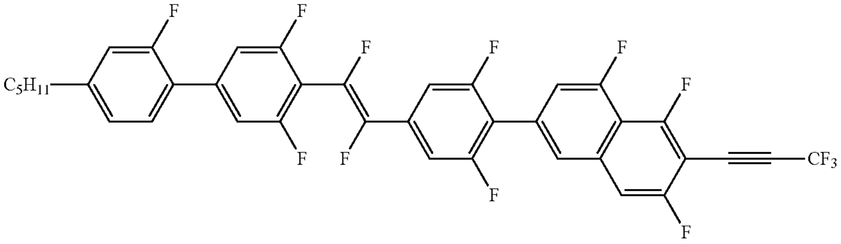

(No.679)

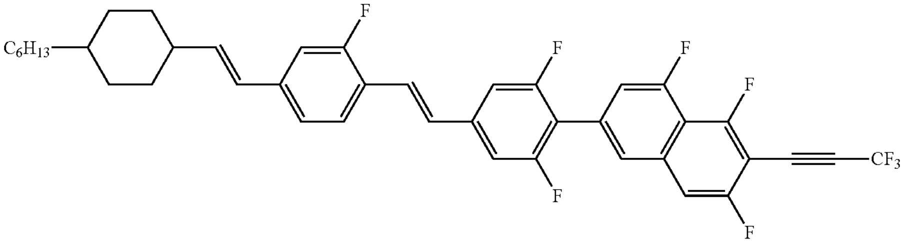

2. Examples of Compositions

The invention will be described in greater detail by way of Examples. The Examples each is a typical example, and therefore the invention is not limited by the Examples. For example, in addition to compositions in Use Examples, the invention includes a mixture of a composition in Use Example 1 and a composition in Use Example 2. The invention also includes a mixture prepared by mixing at least two of the compositions in Use Examples. Compounds in Use Examples were represented using symbols according to definitions in Table 3 described below. In Table 3, the configuration of 1,4-cyclohexylene is trans. A parenthesized number next to a symbolized compound represents a chemical formula to which the compound belongs. A symbol (-) means a liquid crystal compound different from compounds (1) to (15). A proportion (percentage) of the liquid crystal compound is expressed in terms of weight percent (% by weight) based on the weight of the liquid crystal composition containing no additives. Values of physical properties of the composition are summarized in a last part. The physical properties were measured according to the methods described above, and measured values are directly described (without extrapolation).

TABLE 3

Method for description of compounds using symbols
$R—(A_1)—Z_1— \ldots —Z_n—(A_n)—R'$

| 1) Left-terminal group R— | Symbol |
|---|---|
| $C_nH_{2n+1}$— | n- |
| $C_nH_{2n+1}O$— | nO— |
| $C_nH_{2n+1}S$— | mSn— |
| $C_mH_{2m+1}OC_nH_{2n}$— | mOn— |
| $CH_2$=CH— | V— |
| $C_nH_{2n+1}$—CH=CH— | nV— |
| $CH_2$=CH—$C_nH_{2n}$— | Vn— |
| $C_mH_{2m+1}$—CH=CH—$C_nH_{2n}$— | mVn— |
| $CF_2$=CH— | VFF— |
| $CF_2$=CH—$C_nH_{2n}$— | VFFn— |
| **2) Right-terminal group —R'** | **Symbol** |
| —$C_nH_{2n+1}$ | -n |
| —$OC_nH_{2n+1}$ | —On |
| —$COOCH_3$ | —EMe |
| —CH=$CH_2$ | —V |
| —CH=CH—$C_nH_{2n+1}$ | —Vn |
| —$C_nH_{2n}$—CH=$CH_2$ | —nV |
| —$C_mH_{2m}$—CH=CH—$C_nH_{2n+1}$ | —mVn |
| —CH=$CF_2$ | —VFF |
| —F | —F |
| —Cl | —CL |
| —$OCF_3$ | —OCF3 |
| —$OCF_2H$ | —OCF2H |
| —$CF_3$ | —CF3 |
| —OCH=CH—$CF_3$ | —OVCF3 |
| —C≡N | —C |
| —C≡C—$CF_3$ | —TCF3 |

TABLE 3-continued
| Method for description of compounds using symbols $R—(A_1)—Z_1— \ldots —Z_n—(A_n)—R'$ | |
|---|---|
| 3) Bonding group —Zn— | Symbol |
| $—C_nH_{2n}—$ | n |
| —COO— | E |
| —CH═CH— | V |
| $—CH_2O—$ | 1O |
| $—OCH_2—$ | O1 |
| $—CF_2O—$ | X |
| —C≡C— | T |
| 4) Ring structure $—A_n—$ | Symbol |
| 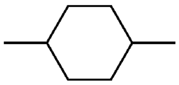 | H |
| 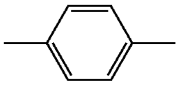 | B |
| 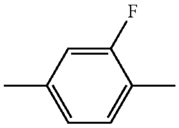 | B(F) |
| 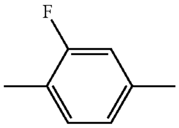 | B(2F) |
| 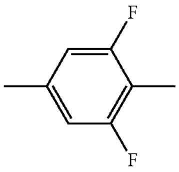 | B(F,F) |
| 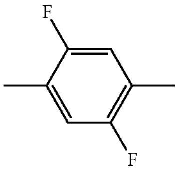 | B(2F,5F) |
| 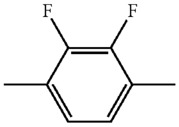 | B(2F,3F) |
| 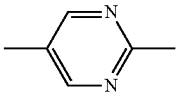 | Py |
| 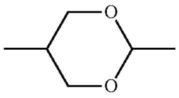 | G |
| 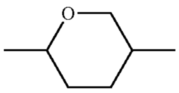 | Dh |

TABLE 3-continued
| Method for description of compounds using symbols $R—(A_1)—Z_1— . . . —Z_n—(A_n)—R'$ | |
|---|---|
| 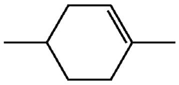 | ch |
| 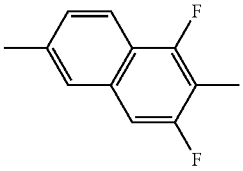 | Np(1F,3F) |
| 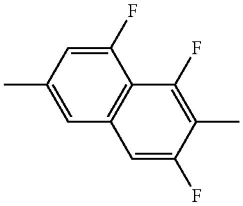 | Np(1F,3F,8F) |
5) Examples of description
Example 1 5-B(F)B(F,F)XNp(1F,3F)—TCF3
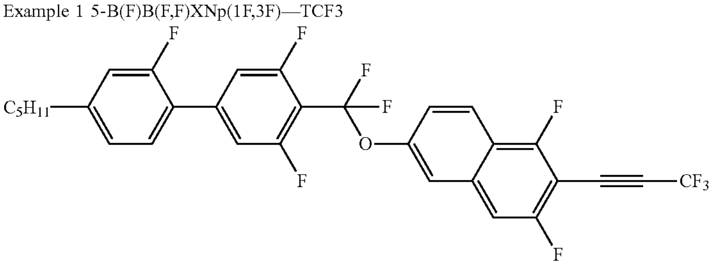
Example 2 5-HHBB(F,F)—F
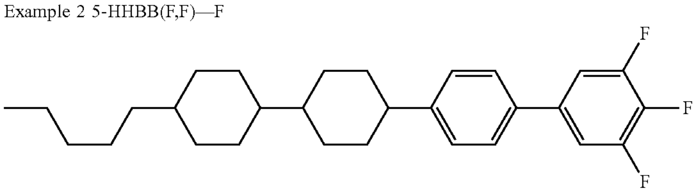
Example 3 3-HB—O2
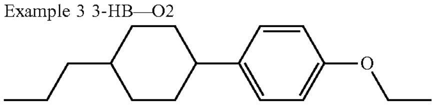
Example 4 3-HBB(F,F)—F
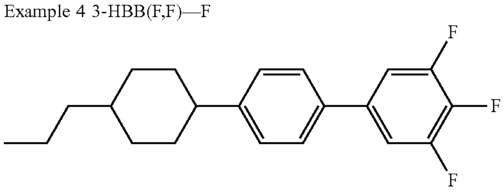
Use Example 1
| | | |
|---|---|---|
| 5-B(F)B(F,F)XNp(1F,3F)-TCF3 | (No. 290) | 3% |
| 3-HB—O1 | (2-5) | 15% |
| 3-HH-4 | (2-1) | 5% |
| 3-HB-O2 | (2-5) | 3% |
-continued
| | | |
|---|---|---|
| 3-HB(2F,3F)—O2 | (9-1) | 12% |
| 5-HB(2F,3F)—O2 | (9-1) | 12% |
| 2-HHB(2F,3F)-1 | (10-1) | 11% |
| 3-HHB(2F,3F)-1 | (10-1) | 10% |
| 3-HHB(2F,3F)—O2 | (10-1) | 12% |

-continued

| | | |
|---|---|---|
| 5-HHB(2F,3F)—O2 | (10-1) | 11% |
| 3-HHB-1 | (3-1) | 6% |

NI=80.2° C.; η=36.3 mPa·s; Δn=0.090; Δε=−1.9.

Use Example 2

| | | |
|---|---|---|
| 5-BB(F)B(F,F)XNp(1F,3F)-TCF3 | (No. 614) | 5% |
| 2-HH-5 | (2-1) | 3% |
| 3-HH-4 | (2-1) | 15% |
| 3-HH-5 | (2-1) | 5% |
| 3-HB—O2 | (2-5) | 10% |
| 3-H2B(2F,3F)—O2 | (9-4) | 13% |
| 5-H2B(2F,3F)—O2 | (9-4) | 14% |
| 3-HHB(2F,3CL)—O2 | (10-12) | 4% |
| 2-HBB(2F,3F)—O2 | (10-7) | 3% |
| 3-HBB(2F,3F)—O2 | (10-7) | 8% |
| 5-HBB(2F,3F)—O2 | (10-7) | 8% |
| 3-HBB(2F,3CL)—O2 | (10-13) | 3% |
| 3-HHB-1 | (3-1) | 3% |
| 3-HHB-3 | (3-1) | 3% |
| 3-HHB—O1 | (3-1) | 3% |

NI=81.2° C.; r=23.9 mPa·s; Δn=0.104; Δε=−1.9.

Use Example 3

| | | |
|---|---|---|
| 4O—B(F)B(F,F)XNp(1F,3F)-TCF3 | (No. 292) | 4% |
| 2-HH-3 | (2-1) | 18% |
| 3-HH-4 | (2-1) | 9% |
| 1-BB-3 | (2-8) | 9% |
| 3-HB—O2 | (2-5) | 3% |
| 3-BB(2F,3F)—O2 | (9-3) | 8% |
| 5-BB(2F,3F)—O2 | (9-3) | 6% |
| 2-HH1OB(2F,3F)—O2 | (10-5) | 12% |
| 3-HH1OB(2F,3F)—O2 | (10-5) | 20% |
| 3-HHB-1 | (3-1) | 5% |
| 3-HHB—O1 | (3-1) | 3% |
| 2-BBB(2F)-5 | (3-8) | 3% |

Use Example 4

| | | |
|---|---|---|
| 5-BTB(F,F)XNp(1F,3F)-TCF3 | (No. 518) | 5% |
| 2-HH-3 | (2-1) | 13% |
| 3-HH-4 | (2-1) | 3% |
| 7-HB-1 | (2-5) | 8% |
| 5-HB—O2 | (2-5) | 7% |
| 3-HB(2F,3F)—O2 | (9-1) | 16% |
| 5-HB(2F,3F)—O2 | (9-1) | 15% |
| 3-HHB(2F,3CL)—O2 | (10-12) | 3% |
| 4-HHB(2F,3CL)—O2 | (10-12) | 3% |
| 5-HHB(2F,3CL)—O2 | (10-12) | 3% |
| 3-HBB(2F,3CL)—O2 | (10-13) | 3% |
| 3-HH1OCro(7F,8F)-5 | (13-6) | 3% |
| 5-HBB(F)B-2 | (4-5) | 9% |
| 5-HBB(F)B-3 | (4-5) | 9% |

Use Example 5

| | | |
|---|---|---|
| 5-PyB(F)B(F,F)XNp(1F,3F)-TCF3 | (No. 632) | 3% |
| 1-BB-3 | (2-8) | 8% |
| 3-HH—V | (2-1) | 29% |
| 3-BB(2F,3F)—O2 | (9-3) | 12% |
| 2-HH1OB(2F,3F)—O2 | (10-5) | 19% |
| 3-HH1OB(2F,3F)—O2 | (10-5) | 15% |
| 5-HBB(2F,3F)—O2 | (10-7) | 5% |
| 3-HHB-1 | (3-1) | 3% |
| 2-BBB(2F)-5 | (3-8) | 6% |

Use Example 6

| | | |
|---|---|---|
| V2-BB(F)B(F,F)XNp(1F,3F)-TCF3 | (No. 616) | 4% |
| 2-HH-3 | (2-1) | 5% |
| 3-HH—V1 | (2-1) | 10% |
| 1V2-HH-1 | (2-1) | 8% |
| 1V2-HH-3 | (2-1) | 7% |
| 3-BB(2F,3F)—O2 | (9-3) | 7% |
| 5-BB(2F,3F)—O2 | (9-3) | 3% |
| 3-H1OB(2F,3F)—O2 | (9-5) | 6% |
| 2-HH1OB(2F,3F)—O2 | (10-5) | 9% |
| 3-HH1OB(2F,3F)—O2 | (10-5) | 18% |
| 3-HDhB(2F,3F)—O2 | (10-3) | 6% |
| 3-HHB-1 | (3-1) | 3% |
| 3-HHB-3 | (3-1) | 3% |
| 2-BB(2F,3F)B-3 | (11-1) | 11% |

Use Example 7

| | | |
|---|---|---|
| 4S—BB(F)B(F,F)XNp(1F,3F)-TCF3 | (No. 615) | 5% |
| 2-HH-5 | (2-1) | 3% |
| 3-HH-4 | (2-1) | 15% |
| 3-HH-5 | (2-1) | 4% |
| 3-HB—O2 | (2-5) | 10% |
| 3-H2B(2F,3F)—O2 | (9-4) | 12% |
| 5-H2B(2F,3F)—O2 | (9-4) | 14% |
| 3-HHB(2F,3CL)—O2 | (10-12) | 5% |
| 2-HBB(2F,3F)—O2 | (10-7) | 4% |
| 3-HBB(2F,3F)—O2 | (10-7) | 8% |
| 5-HBB(2F,3F)—O2 | (10-7) | 9% |
| 3-HHB-1 | (3-1) | 4% |
| 3-HHB-3 | (3-1) | 4% |
| 3-HHB—O1 | (3-1) | 3% |

Use Example 8

| | | |
|---|---|---|
| 5-BB(F)B(F,F)XNp(1F,3F,8F)-TCF3 | (No. 617) | 4% |
| 2-HH-3 | (2-1) | 16% |
| 7-HB-1 | (2-5) | 10% |
| 5-HB—O2 | (2-5) | 7% |
| 3-HB(2F,3F)—O2 | (9-1) | 10% |
| 5-HB(2F,3F)—O2 | (9-1) | 11% |
| 3-HHB(2F,3CL)—O2 | (10-12) | 8% |
| 4-HHB(2F,3CL)—O2 | (10-12) | 5% |
| 5-HBB(2F,3F)—O2 | (10-7) | 7% |
| 3-HH1OCro(7F,8F)-5 | (13-6) | 5% |
| 5-HBB(F)B-2 | (4-5) | 10% |
| 5-HBB(F)B-3 | (4-5) | 7% |

Use Example 9

| | | |
|---|---|---|
| 5-BB(F)Np(1F,3F)-TCF3 | (No. 270) | 3% |
| 1-BB-3 | (2-8) | 8% |

-continued

| | | |
|---|---|---|
| 3-HH—V | (2-1) | 25% |
| 3-BB(2F,3F)—O2 | (9-3) | 10% |
| 5-BB(2F,3F)—O2 | (9-3) | 10% |
| 2-HH1OB(2F,3F)—O2 | (10-5) | 15% |
| 3-HH1OB(2F,3F)—O2 | (10-5) | 10% |
| 5-HBB(2F,3F)—O2 | (10-7) | 5% |
| 3-HHB-1 | (3-1) | 8% |
| 3-HHB—O1 | (3-1) | 3% |
| 2-BBB(2F)-5 | (3-8) | 3 |

Use Example 10

| | | |
|---|---|---|
| 5-BTB(F)Np(1F,3F)-TCF3 | (No. 278) | 5% |
| 3-HB—O1 | (2-5) | 14% |
| 3-HH-4 | (2-1) | 4% |
| 3-HB—O2 | (2-5) | 4% |
| 3-HB(2F,3F)—O2 | (9-1) | 11% |
| 5-HB(2F,3F)—O2 | (9-1) | 11% |
| 2-HHB(2F,3F)-1 | (10-1) | 11% |
| 3-HHB(2F,3F)-1 | (10-1) | 11% |
| 3-HHB(2F,3F)—O2 | (10-1) | 12% |
| 5-HHB(2F,3F)—O2 | (10-1) | 12% |
| 3-HHB-1 | (3-1) | 5% |

Use Example 11

| | | |
|---|---|---|
| 5-BB(F)B(F,F)XNp(1F,3F)-TCF3 | (No. 614) | 10% |
| 3-BB(F)B(F,F)XB(F,F)—F | (7-47) | 2% |
| 4-BB(F)B(F,F)XB(F,F)—F | (7-47) | 7% |
| 5-BB(F)B(F,F)XB(F,F)—F | (7-47) | 7% |
| 3-BB(F)B(F,F)XB(F)—F | (7-46) | 3% |
| 3-BB(F,F)XB(F)B(F,F)—F | (7-56) | 6% |
| 3-BB(F)B(F,F)—F | (6-69) | 3% |
| 3-BB(F,F)XB(F,F)—F | (6-97) | 9% |
| 3-H2BTB-2 | (3-17) | 3% |
| 3-HB(F)TB-2 | (3-18) | 5% |
| 3-HB(F)TB-3 | (3-18) | 5% |
| 3-HB(F)TB-4 | (3-18) | 2% |
| 2-BTB—O1 | (2-10) | 7.6% |
| 3-BTB—O1 | (2-10) | 7.6% |
| 4-BTB—O1 | (2-10) | 7.6% |
| 4-BTB—O2 | (2-10) | 7.6% |
| 5-BTB—O1 | (2-10) | 7.6% |

NI=91.7° C.; Δn=0.250; Δε=14.5; V10=1.55: V90=2.16.

Use Example 12

| | | |
|---|---|---|
| 5-B(F)B(F,F)XNp(1F,3F)-TCF3 | (No. 290) | 10% |
| 3-BB(F)B(F,F)XB(F,F)—F | (7-47) | 2% |
| 4-BB(F)B(F,F)XB(F,F)—F | (7-47) | 9% |
| 5-BB(F)B(F,F)XB(F,F)—F | (7-47) | 5% |
| 3-BB(F)B(F,F)XB(F)—F | (7-46) | 3% |
| 3-BB(F,F)XB(F)B(F,F)—F | (7-56) | 6% |
| 3-HB(F)TB-2 | (3-18) | 5% |
| 3-BB(F)TB-2 | (4-8) | 6% |
| 3-BB(F)TB-3 | (4-8) | 6% |
| 3-BB(F)TB-4 | (4-8) | 5% |
| 2-BTB—O1 | (2-10) | 8.6% |
| 3-BTB—O1 | (2-10) | 8.6% |

-continued

| | | |
|---|---|---|
| 4-BTB—O1 | (2-10) | 8.6% |
| 4-BTB—O2 | (2-10) | 8.6% |
| 5-BTB—O1 | (2-10) | 8.6% |

NI=95.0° C.; Δn=0.275; Δε=11.8; V10=1.81: V90=2.62.

Use Example 13

| | | |
|---|---|---|
| 5-BB(F)B(F,F)XNp(1F,3F)-TCF3 | (No. 614) | 10% |
| 3-BB(F)B(F,F)XB(F,F)—F | (7-47) | 2% |
| 4-BB(F)B(F,F)XB(F,F)—F | (7-47) | 9% |
| 5-BB(F)B(F,F)XB(F,F)—F | (7-47) | 5% |
| 4-BTB(F)B(F,F)XB(F,F)—F | (7-58) | 3% |
| 5-BTB(F)B(F,F)XB(F,F)—F | (7-58) | 3% |
| 3-BB(F,F)XB(F)B(F,F)—F | (7-56) | 3% |
| 3-HB(F)TB-2 | (3-18) | 5% |
| 3-BB(F)TB-2 | (4-8) | 6% |
| 3-BB(F)TB-3 | (4-8) | 6% |
| 3-BB(F)TB-4 | (4-8) | 5% |
| 2-BTB—O1 | (2-10) | 8.6% |
| 3-BTB—O1 | (2-10) | 8.6% |
| 4-BTB—O1 | (2-10) | 8.6% |
| 4-BTB—O2 | (2-10) | 8.6% |
| 5-BTB—O1 | (2-10) | 8.6% |

NI=105.2° C.; Δn=0.290; Δε=12.1; V10=2.05: V90=2.86.

Use Example 14

| | | |
|---|---|---|
| 40-BTB(F,F)XNp(1F,3F)-TCF3 | (No. 520) | 5% |
| 3-BB(F)B(F,F)XB(F,F)—F | (7-47) | 2% |
| 4-BB(F)B(F,F)XB(F,F)—F | (7-47) | 7% |
| 5-BB(F)B(F,F)XB(F,F)—F | (7-47) | 7% |
| 3-BB(F)B(F,F)XB(F)—F | (7-46) | 3% |
| 3-BB(F,F)XB(F)B(F,F)—F | (7-56) | 6% |
| 3-BB(F)B(F,F)—F | (6-69) | 3% |
| 3-BB(F,F)XB(F,F)—F | (6-97) | 9% |
| 3-H2BTB-2 | (3-17) | 3% |
| 3-H2BTB-3 | (3-17) | 3% |
| 3-HB(F)TB-2 | (3-18) | 5% |
| 3-HB(F)TB-3 | (3-18) | 5% |
| 3-HB(F)TB-4 | (3-18) | 5% |
| 2-BTB—O1 | (2-10) | 7.4% |
| 3-BTB—O1 | (2-10) | 7.4% |
| 4-BTB—O1 | (2-10) | 7.4% |
| 4-BTB—O2 | (2-10) | 7.4% |
| 5-BTB—O1 | (2-10) | 7.4% |

NI=90.9° C.; η=48.6 mPa's; Δn=0.249; Δε=11.9; V10=1.74: V90=2.53.

Use Example 15

| | | |
|---|---|---|
| 40-BTB(F,F)XNp(1F,3F)-TCF3 | (No. 520) | 10% |
| 3-BB(F)B(F,F)XB(F,F)—F | (7-47) | 2% |
| 4-BB(F)B(F,F)XB(F,F)—F | (7-47) | 7% |
| 5-BB(F)B(F,F)XB(F,F)—F | (7-47) | 7% |
| 3-BB(F,F)XB(F)B(F,F)—F | (7-56) | 6% |
| 3-BB(F,F)XB(F,F)—F | (6-97) | 9% |
| 3-HHEBH-3 | (4-6) | 3% |
| 3-HHEBH-4 | (4-6) | 3% |
| 3-HB(F)TB-2 | (3-18) | 5% |

-continued

| | | |
|---|---|---|
| 3-HB(F)TB-3 | (3-18) | 5% |
| 3-HB(F)TB-4 | (3-18) | 5% |
| 3-BB(F)TB-2 | (4-8) | 3% |
| 3-BB(F)TB-3 | (4-8) | 3% |
| 3-BB(F)TB-4 | (4-8) | 3% |
| 2-BTB—O1 | (2-10) | 5.8% |
| 3-BTB—O1 | (2-10) | 5.8% |
| 4-BTB—O1 | (2-10) | 5.8% |
| 4-BTB—O2 | (2-10) | 5.8% |
| 5-BTB—O1 | (2-10) | 5.8% |

NI=108.0° C.; Δn=0.252; Δε=13.7; V10=1.62: V90=2.39.

INDUSTRIAL APPLICABILITY

A liquid crystal compound of the invention has good physical properties. A liquid crystal composition containing the compound can be widely applied to a liquid crystal display device used in a personal computer, a television and so forth.

What is claimed is:

1. A compound, represented by formula (1):

(1)

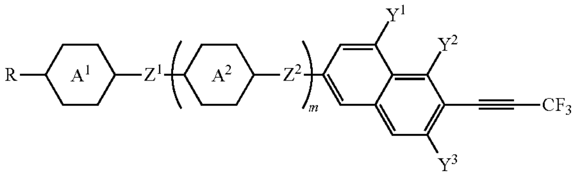

wherein, in formula (1),

R is alkyl having 1 to 15 carbons, and in the alkyl, at least one $—CH_2—$ may be replaced by —O— or —S—, and at least one $—CH_2CH_2—$ may be replaced by —CH=CH—, and in the groups, at least one hydrogen may be replaced by fluorine or chlorine;

ring $A^1$ and ring $A^2$ are independently 1,4-cyclohexylene, 1,4-cyclohexenylene, 1,4-phenylene, tetrahydropyran-2,5-diyl, 1,3-dioxane-2,5-diyl, 2,6,7-trioxabicyclo[2.2.2]octane-1,4-diyl, naphthalene-2,6-diyl, decahydronaphthalene-2,6-diyl, 1,2,3,4-tetrahydronaphthalene-2,6-diyl, pyridine-2,5-diyl or pyrimidine-2,5-diyl, and in the rings, at least one hydrogen may be replaced by fluorine or chlorine;

$Z^1$ and $Z^2$ are independently a single bond, $—CH_2CH_2—$, —CH=CH—, —C≡C—, —COO—, —OCO—, $—CH_2O—$, $—OCH_2—$, $—CH_2S—$, $—SCH_2—$, $—CF_2O—$, $—OCF_2—$ or —CF=CF—;

$Y^1$, $Y^2$ and $Y^3$ are independently hydrogen, fluorine or chlorine; and m is 0, 1 or 2.

2. The compound according to claim 1, represented by formula (1A):

(1A)

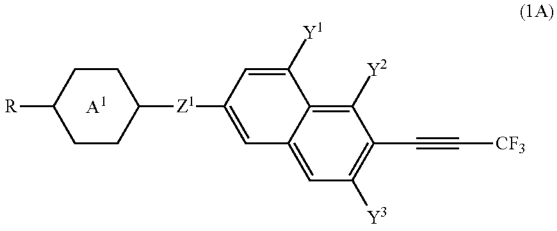

wherein, in formula (IA),

R is alkyl having 1 to 15 carbons, alkoxy having 1 to 14 carbons, alkenyl having 2 to 15 carbons, alkenyloxy having 2 to 14 carbons, alkylthio having 1 to 14 carbons or alkenylthio having 2 to 14 carbons;

ring $A^1$ is 1,4-cyclohexylene, 1,4-cyclohexenylene, 1,4-phenylene, 2-fluoro-1,4-phenylene, 2,6-difluoro-1,4-phenylene, tetrahydropyran-2,5-diyl, 1,3-dioxane-2,5-diyl, 2,6,7-trioxabicyclo[2.2.2]octane-1,4-diyl, pyridine-2,5-diyl, pyrimidine-2,5-diyl, naphthalene-2,6-diyl, 1-fluoronaphthalene-2,6-diyl, 1,3-difluoronaphthalene-2,6-diyl or 1,3,8-trifluoronaphthalene-2,6-diyl;

$Z^1$ is a single bond, $—CH_2CH_2—$, —CH=CH—, —C≡C—, —COO—, —OCO—, $—CH_2O—$, $—OCH_2—$, $—CH_2S—$, $—SCH_2—$, $—CF_2O—$ or $—OCF_2—$; and $Y^1$, $Y^2$ and $Y^3$ are independently hydrogen or fluorine.

3. The compound according to claim 1, represented by any one of formulas (1A-1) to (1A-3):

(1A-1)

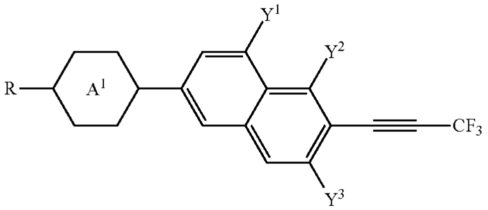

(1A-2)

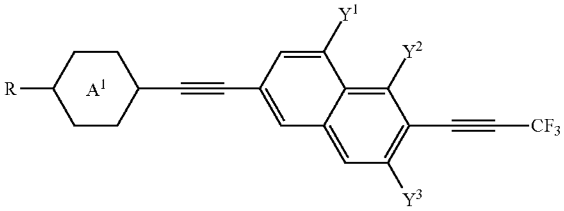

(1A-3)

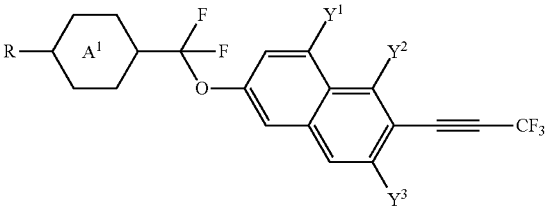

wherein, in formulas (1A-1) to (1A-3),

R is alkyl having 1 to 15 carbons, alkoxy having 1 to 14 carbons, alkenyl having 2 to 15 carbons or alkenyloxy having 2 to 14 carbons;

ring $A^1$ is 1,4-cyclohexylene, 1,4-phenylene, 2-fluoro-1,4-phenylene, 2,6-difluoro-1,4-phenylene, 1,3-dioxane-2,5-diyl, 2,6,7-trioxabicyclo[2.2.2]octane-1,4-diyl, pyridine-2,5-diyl, pyrimidine-2,5-diyl, naphthalene-2,6-diyl, 1-fluoronaphthalene-2,6-diyl, 1,3-difluoronaphthalene-2,6-diyl or 1,3,8-trifluoronaphthalene-2,6-diyl; and $Y^1$, $Y^2$ and $Y^3$ are independently hydrogen or fluorine.

4. The compound according to claim 1, represented by any one of formulas (1A-4) to (1A-15):

(1A-4)

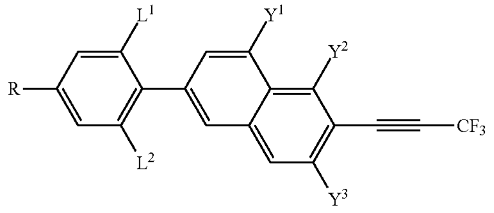

(1A-5)

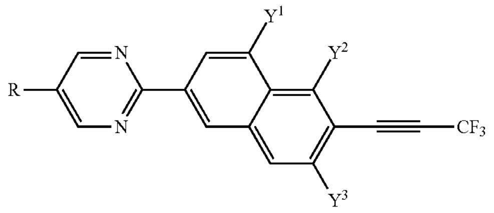

(1A-6)

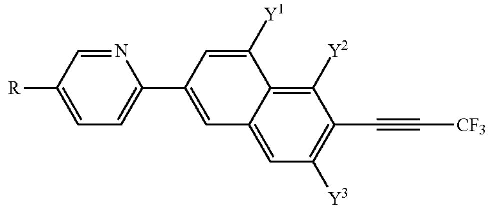

(1A-7)

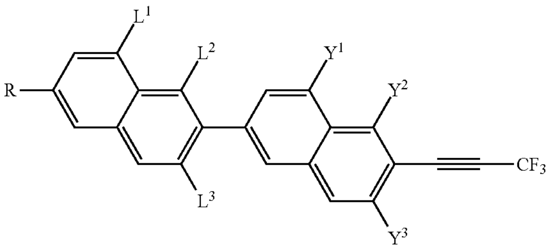

(1A-8)

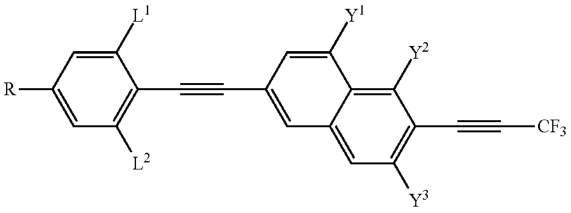

-continued (1A-9)

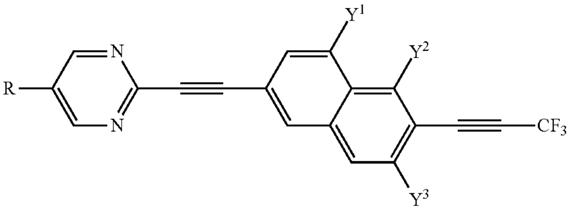

(1A-10)

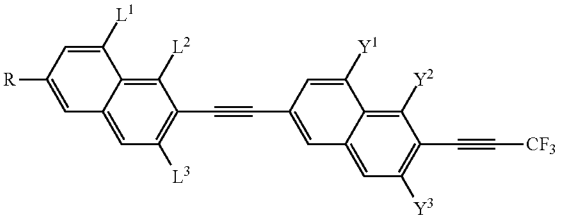

(1A-11)

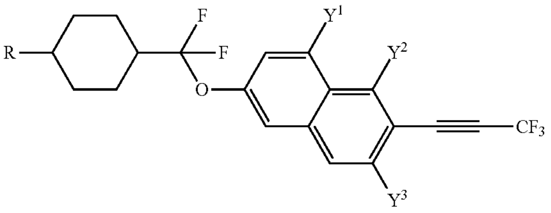

(1A-12)

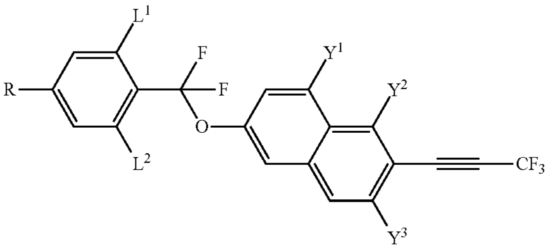

(1A-13)

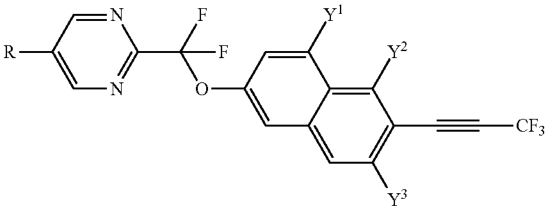

(1A-14)

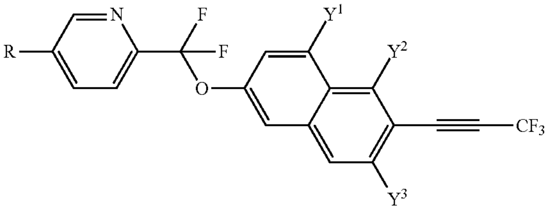

-continued (1A-15)

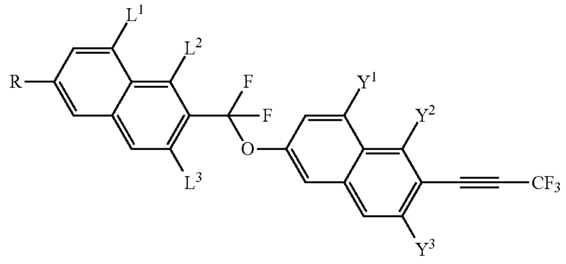

wherein, in formulas (1A-4) to (1A-15),

R is alkyl having 1 to 10 carbons, alkoxy having 1 to 9 carbons, alkenyl having 2 to 10 carbons or alkenyloxy having 2 to 9 carbons; and $Y^1$, $Y^2$, $Y^3$, $L^1$, $L^2$ and $L^3$ are independently hydrogen or fluorine.

5. The compound according to claim 1, represented by formula (1B):

(1B)

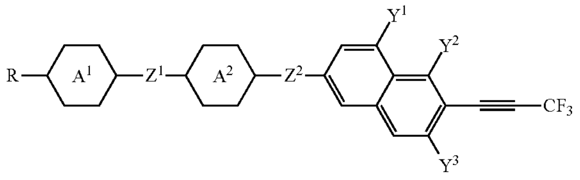

wherein, in formula (1B),

R is alkyl having 1 to 15 carbons, alkoxy having 1 to 14 carbons, alkenyl having 2 to 15 carbons, alkenyloxy having 2 to 14 carbons, alkylthio having 1 to 14 carbons or alkenylthio having 2 to 14 carbons;

ring $A^1$ is 1,4-cyclohexylene, 1,4-cyclohexenylene, 1,4-phenylene, 2-fluoro-1,4-phenylene, 2,6-difluoro-1,4-phenylene, tetrahydropyran-2,5-diyl, 1,3-dioxane-2,5-diyl, 2,6,7-trioxabicyclo[2.2.2]octane-1,4-diyl, pyridine-2,5-diyl, pyrimidine-2,5-diyl, naphthalene-2,6-diyl, 1-fluoronaphthalene-2,6-diyl, 1,3-difluoronaphthalene-2,6-diyl or 1,3,8-trifluoronaphthalene-2,6-diyl; and ring $A^2$ is 1,4-phenylene, 2-fluoro-1,4-phenylene, 2,6-difluoro-1,4-phenylene, pyridine-2,5-diyl, pyrimidine-2,5-diyl, naphthalene-2,6-diyl, 1-fluoronaphthalene-2,6-diyl, 1,3-difluoronaphthalene-2,6-diyl or 1,3,8-trifluoronaphthalene-2,6-diyl;

$Z^1$ and $Z^2$ are independently a single bond, $—CH_2CH_2—$, $—CH{=}CH—$, $—C{\equiv}C—$, $—COO—$, $—OCO—$, $—CH_2O—$, $—OCH_2—$, $—CH_2S—$, $—SCH_2—$, $—CF_2O—$ or $—OCF_2—$; and $Y^1$, $Y^2$ and $Y^3$ are independently hydrogen or fluorine.

6. The compound according to claim 1, represented by any one of formulas (1B-1) to (1B-5):

(1B-1)

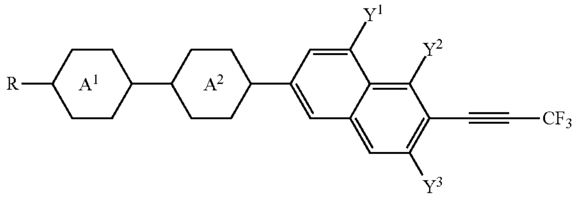

(1B-2)

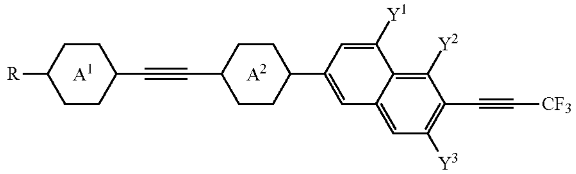

(1B-3)

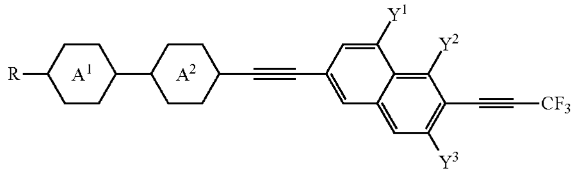

(1B-4)

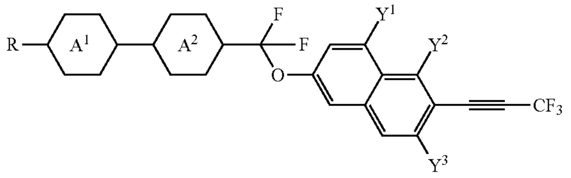

(1B-5)

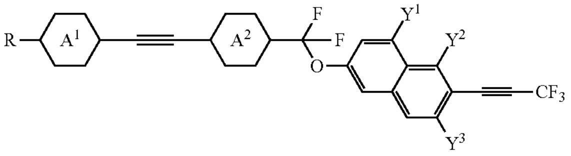

wherein, in formulas (1B-1) to (1B-5),

R is alkyl having 1 to 15 carbons, alkoxy having 1 to 14 carbons, alkenyl having 2 to 15 carbons or alkenyloxy having 2 to 14 carbons;

ring $A^1$ is 1,4-cyclohexylene, 1,4-phenylene, 2-fluoro-1,4-phenylene, 2,6-difluoro-1,4-phenylene, 1,3-dioxane-2,5-diyl, pyridine-2,5-diyl, pyrimidine-2,5-diyl, naphthalene-2,6-diyl, 1-fluoronaphthalene-2,6-diyl, 1,3-difluoronaphthalene-2,6-diyl or 1,3,8-trifluoronaphthalene-2,6-diyl; and ring $A^2$ is 1,4-phenylene, 2-fluoro-1,4-phenylene, 2,6-difluoro-1,4-phenylene, naphthalene-2,6-diyl, 1-fluoronaphthalene-2,6-diyl, 1,3-difluoronaphthalene-2,6-diyl or 1,3,8-trifluoronaphthalene-2,6-diyl; and $Y^1$, $Y^2$ and $Y^3$ are independently hydrogen or fluorine.

7. The compound according to claim 1, represented by any one of formulas (1B-6) to (1B-31):

(1B-6)
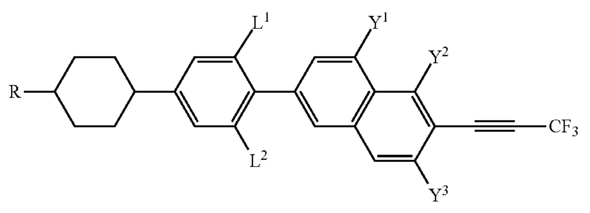
(1B-7)
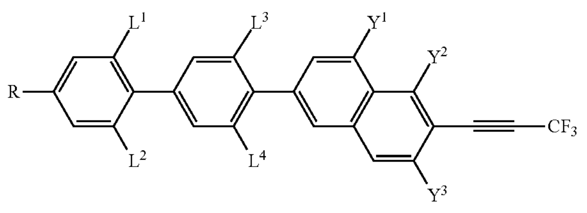
(1B-8)
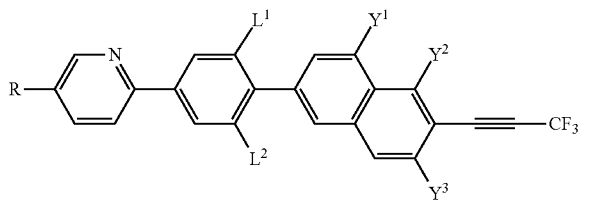
(1B-9)
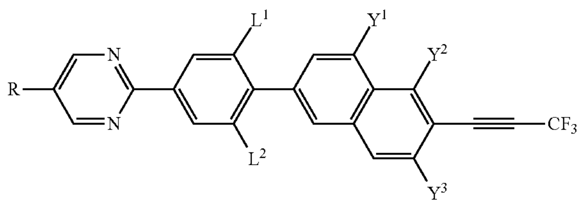
(1B-10)
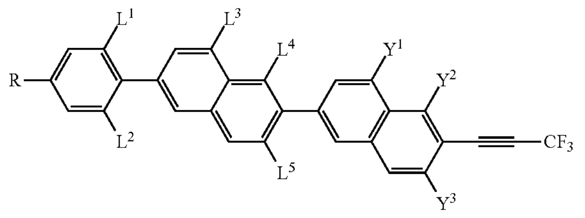
(1B-11)
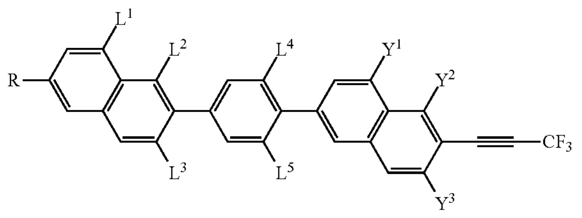
(1B-12)
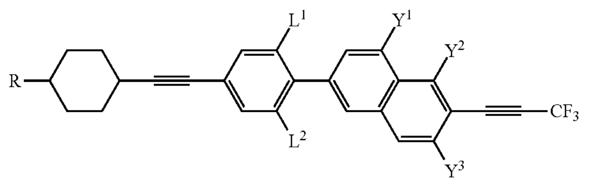
(1B-13)
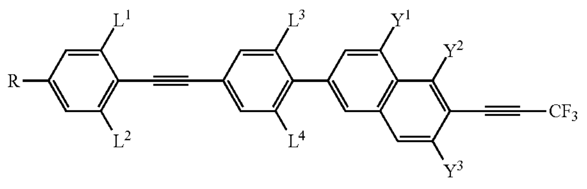
(1B-14)
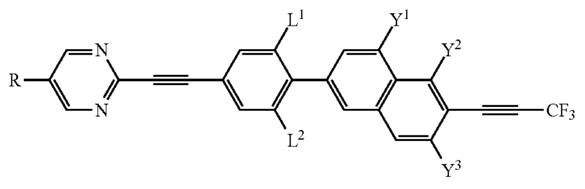
(1B-15)
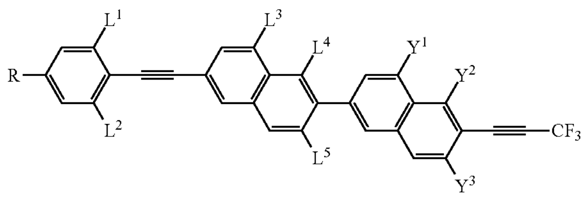
(1B-16)
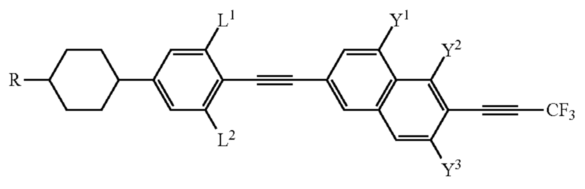
(1B-17)
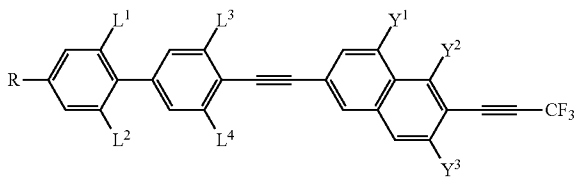
(1B-18)
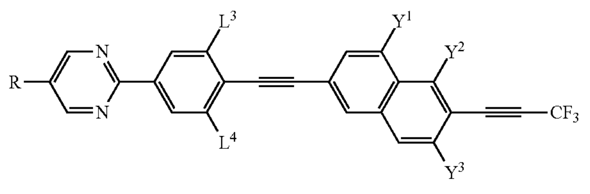
(1B-19)
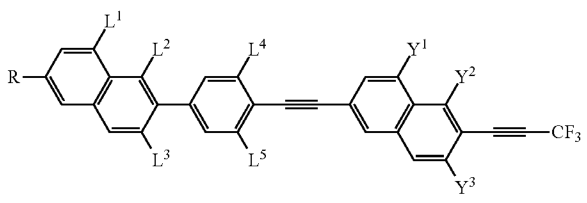

-continued
(1B-20)
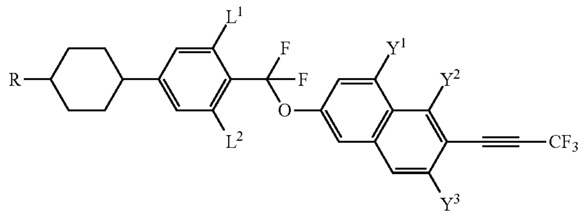
(1B-21)
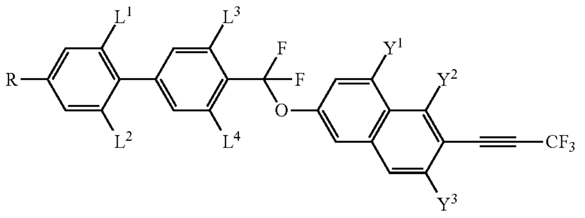
(1B-22)
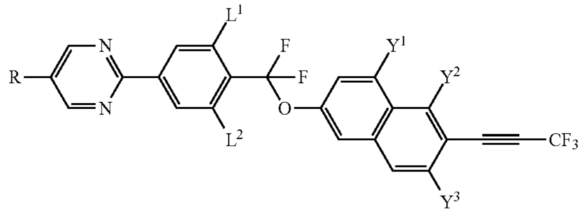
(1B-23)
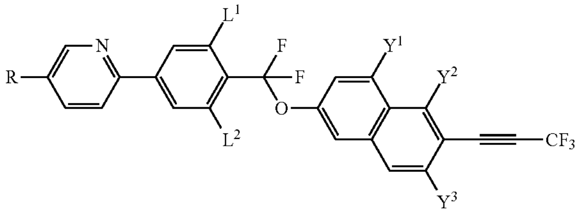
(1B-24)
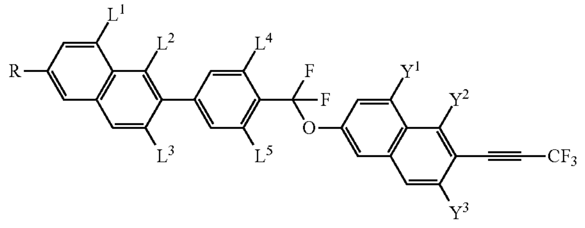
(1B-25)
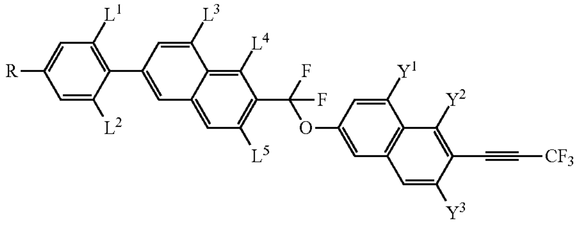
(1B-26)
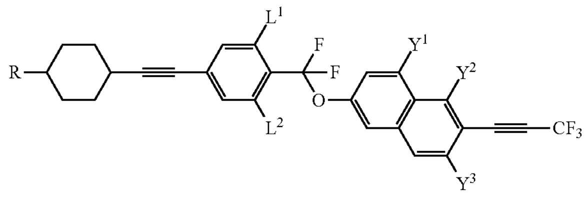
(1B-27)
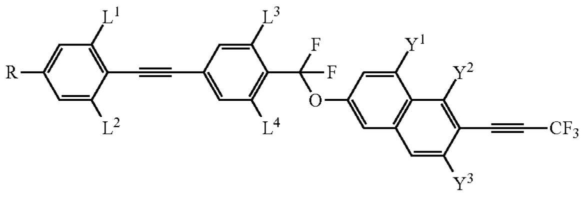
(1B-28)
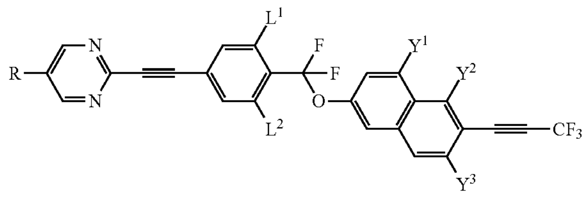
(1B-29)
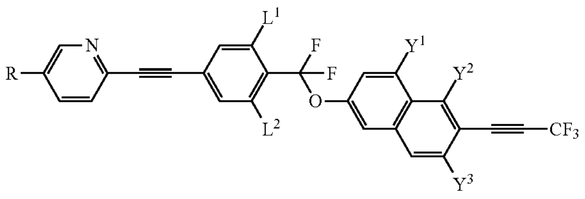
(1B-30)
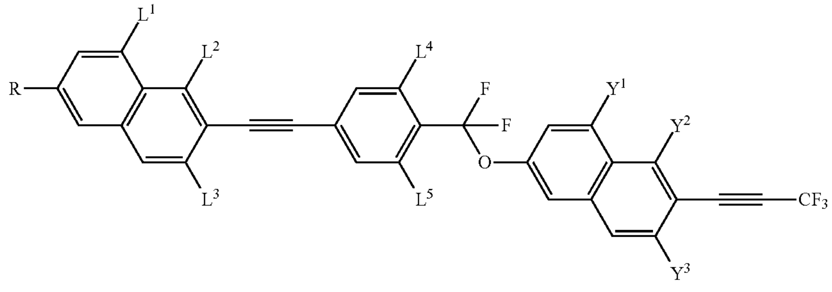

-continued (1B-31)

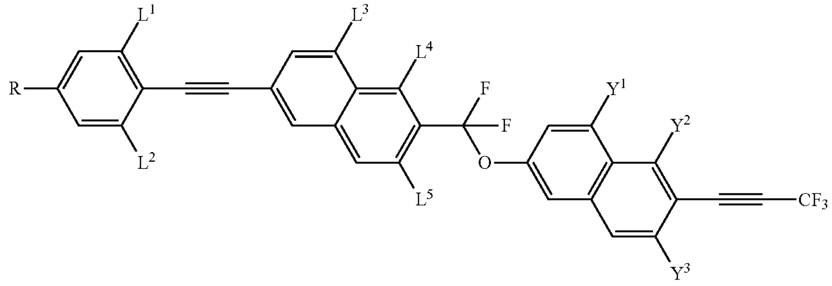

wherein, in formulas (1B-6) to (1B-31),

R is alkyl having 1 to 10 carbons, alkoxy having 1 to 9 carbons, alkenyl having 2 to 10 carbons or alkenyloxy having 2 to 9 carbons; and $Y^1$, $Y^3$, $L^1$, $L^2$, $L^3$, $L^4$ and $L^5$ are independently hydrogen or fluorine.

8. The compound according to claim 1, represented by formula (IC):

(1C)

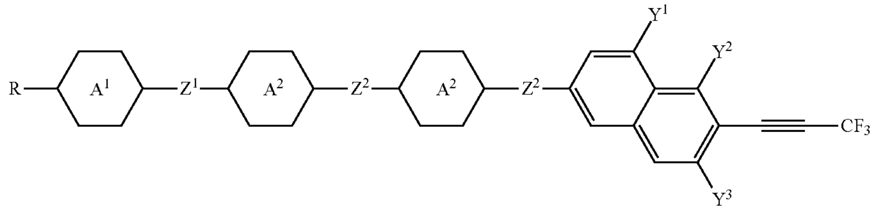

wherein, in formula (1C),

R is alkyl having 1 to 15 carbons, alkoxy having 1 to 14 carbons, alkenyl having 2 to 15 carbons, alkenyloxy having 2 to 14 carbons, alkylthio having 1 to 14 carbons or alkenylthio having 2 to 14 carbons;

ring $A^1$ is 1,4-cyclohexylene, 1,4-cyclohexenylene, 1,4-phenylene, 2-fluoro-1,4-phenylene, 2,6-difluoro-1,4-phenylene, tetrahydropyran-2,5-diyl, 1,3-dioxane-2,5-diyl, 2,6,7-trioxabicyclo[2.2.2]octane-1,4-diyl, pyridine-2,5-diyl, pyrimidine-2,5-diyl, naphthalene-2,6-diyl, 1-fluoronaphthalene-2,6-diyl, 1,3-difluoronaphthalene-2,6-diyl or 1,3,8-trifluoronaphthalene-2,6-diyl, and ring $A^2$ is 1,4-cyclohexylene, 1,4-cyclohexenylene, 1,4-phenylene, 2-fluoro-1,4-phenylene, 2,6-difluoro-1,4-phenylene, pyridine-2,5-diyl, naphthalene-2,6-diyl, pyrimidine-2,5-diyl, 1-fluoronaphthalene-2,6-diyl, 1,3-difluoronaphthalene-2,6-diyl or 1,3,8-trifluoronaphthalene-2,6-diyl;

$Z^1$ and $Z^2$ are independently a single bond, $—CH_2CH_2—$, —CH═CH—, —C≡C—, —C≡C—, —COO—, —OCO—, $—CH_2O—$, $—OCH_2—$, $—CH_2S—$, $—SCH_2—$, $—CF_2O—$ or $—OCF_2—$; and $Y^1$, $Y^2$ and $Y^3$ are independently hydrogen or fluorine.

9. The compound according to claim 1, represented by any one of formulas (1C-1) to (1C-6):

(1C-1)

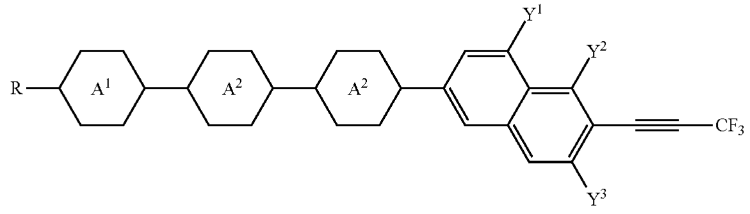

-continued (1C-2)

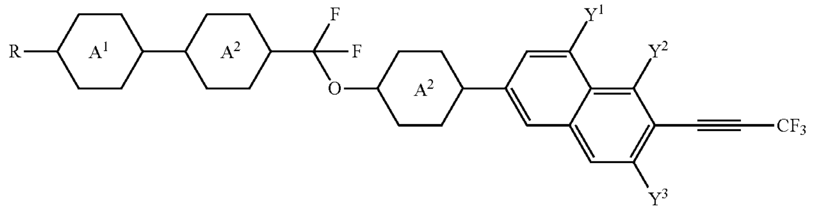

(1C-3)

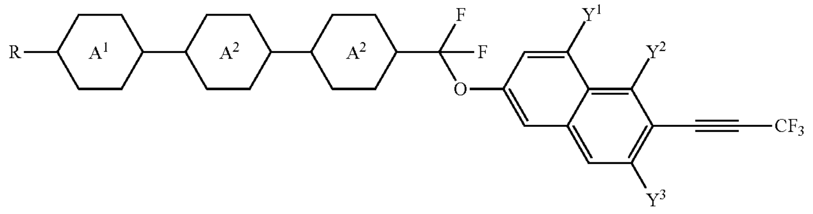

(1C-4)

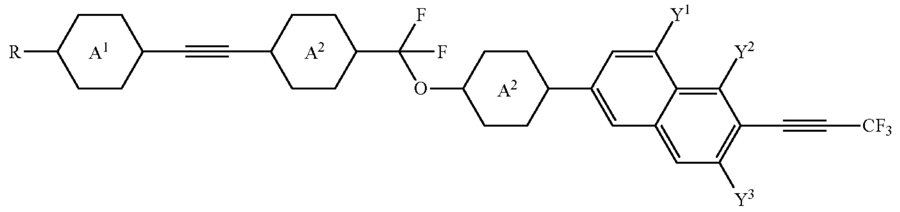

(1C-5)

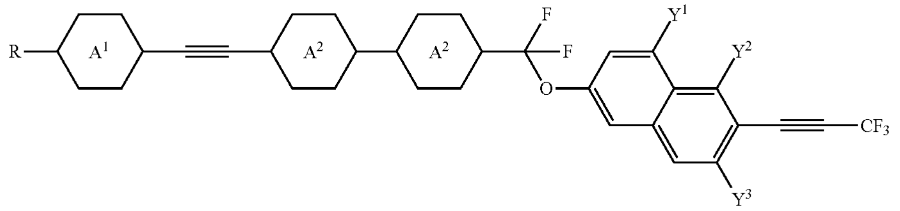

(1C-6)

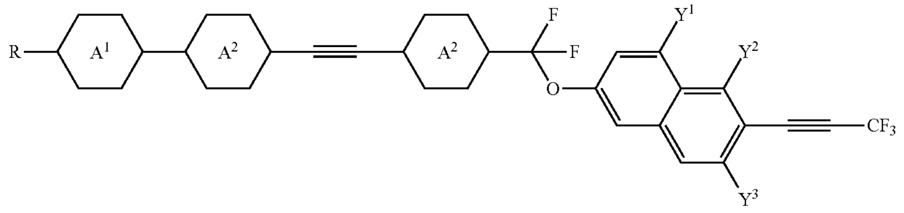

wherein, in formulas (1C-1) to (1C-6),

R is alkyl having 1 to 15 carbons, alkoxy having 1 to 14 carbons, alkenyl having 2 to 15 carbons or alkenyloxy having 2 to 14 carbons;

ring $A^1$ is 1,4-cyclohexylene, 1,4-phenylene, 2-fluoro-1,4-phenylene, 2,6-difluoro-1,4-phenylene, 1,3-dioxane-2,5-diyl, pyridine-2,5-diyl, pyrimidine-2,5-diyl, naphthalene-2,6-diyl, 1-fluoronaphthalene-2,6-diyl, 1,3-difluoronaphthalene-2,6-diyl or 1,3,8-trifluoronaphthalene-2,6-diyl, and ring $A^2$ is 1,4-cyclohexylene, 1,4-phenylene, 2-fluoro-1,4-phenylene, 2,6-difluoro-1,4-phenylene, naphthalene-2,6-diyl, 1-fluoronaphthalene-2,6-diyl, 1,3-difluoronaphthalene-2,6-diyl or 1,3,8-trifluoronaphthalene-2,6-diyl; and $Y^1$, $Y^2$ and $Y^3$ are independently hydrogen or fluorine.

10. The compound according to claim 1, represented by any one of formulas (1C-7) to (1C-32):

(1C-7)

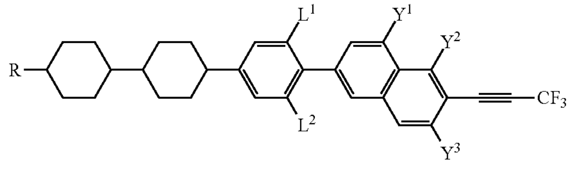

(1C-8)

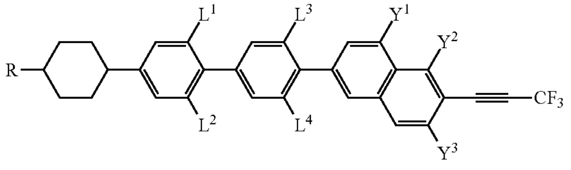

-continued
(1C-9)
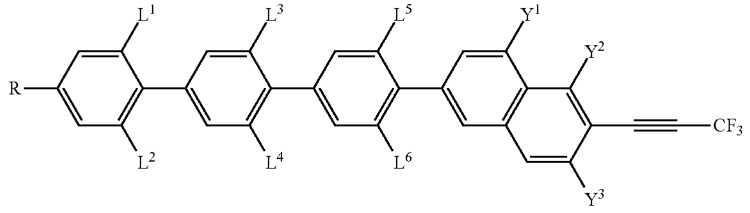
(1C-10)
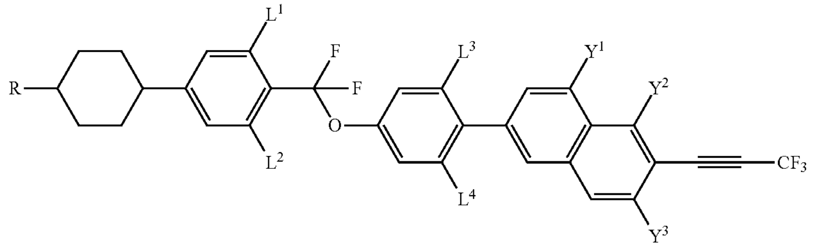
(1C-11)
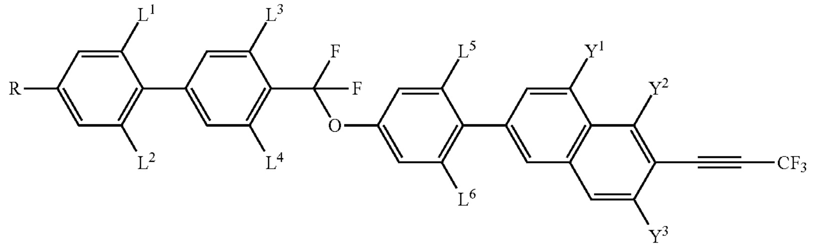
(1C-12)
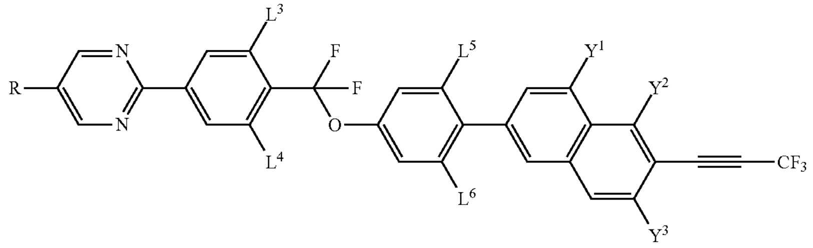
(1C-13)
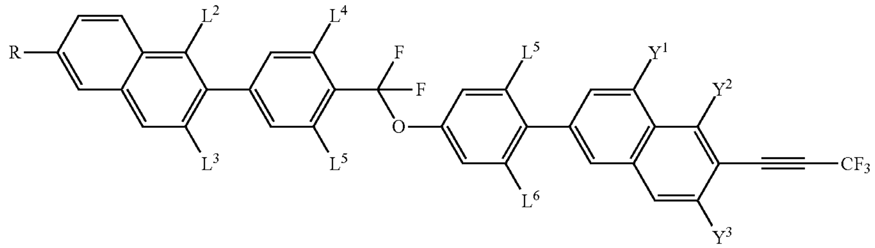
(1C-14)
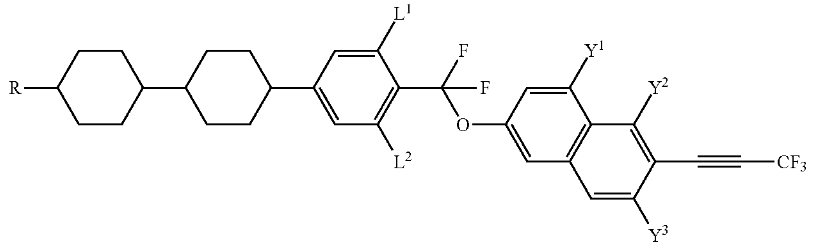

-continued
(1C-15)
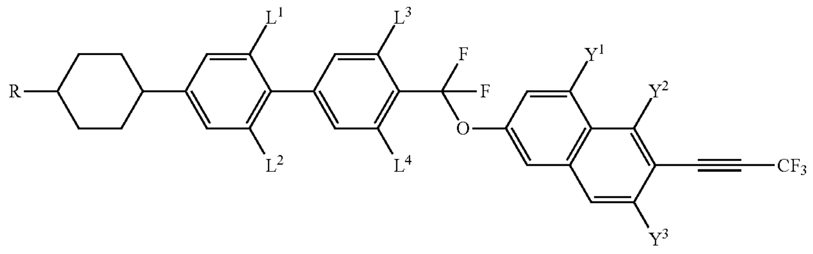
(1C-16)
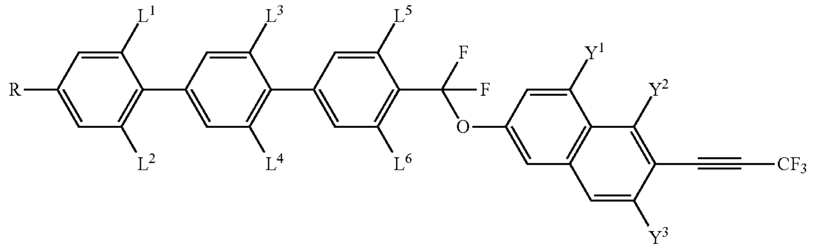
(1C-17)
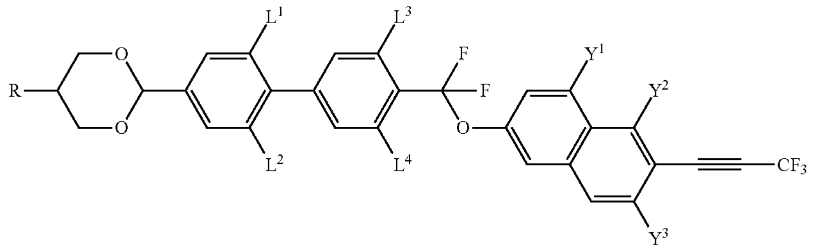
(1C-18)
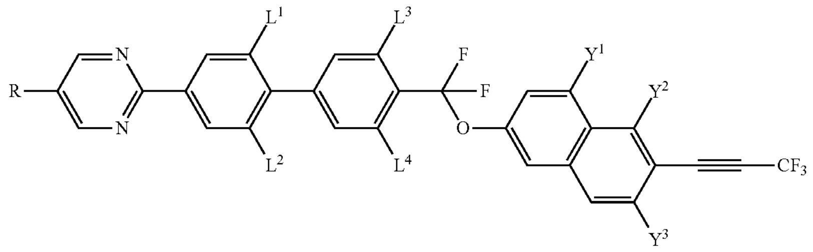
(1C-19)
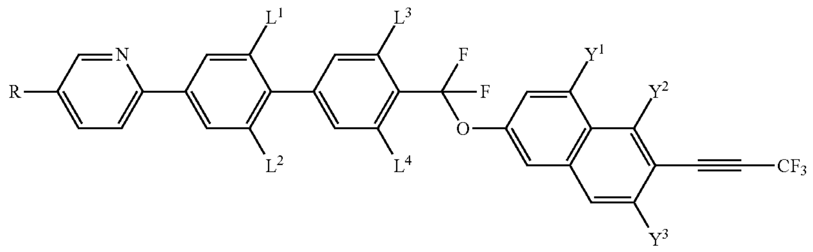
(1C-20)
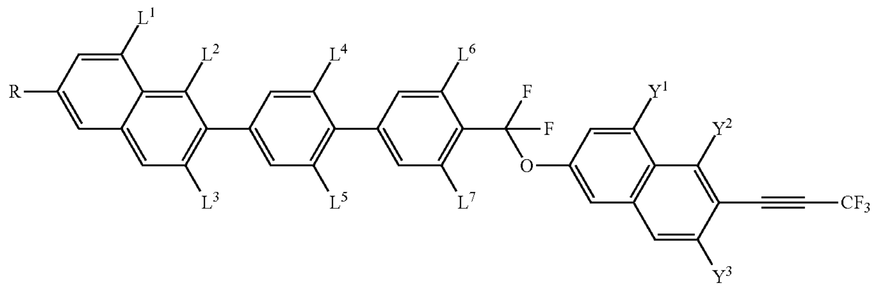

-continued
(1C-21)
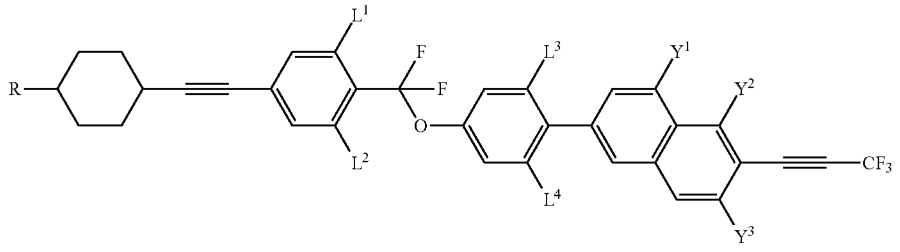
(1C-22)
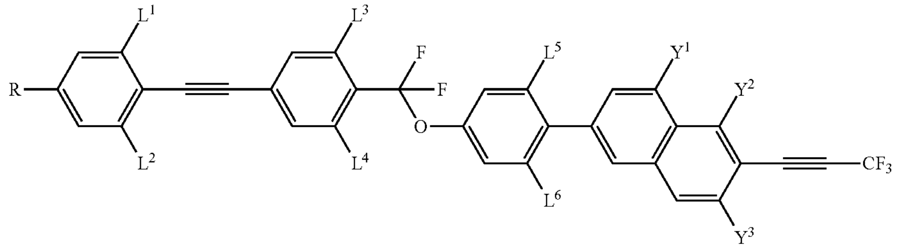
(1C-23)
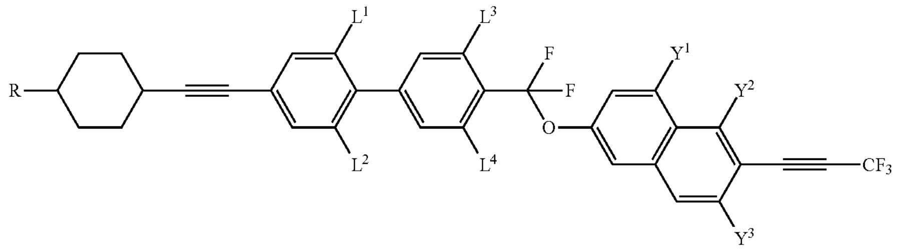
(1C-24)
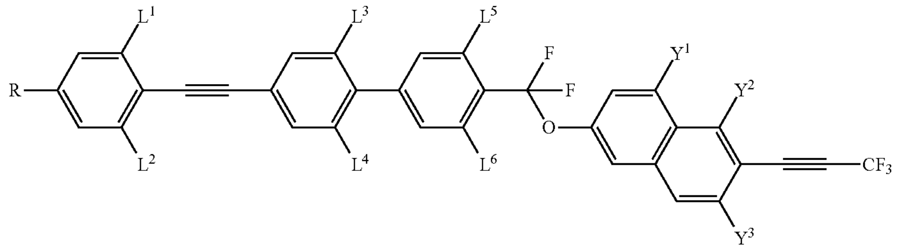
(1C-25)
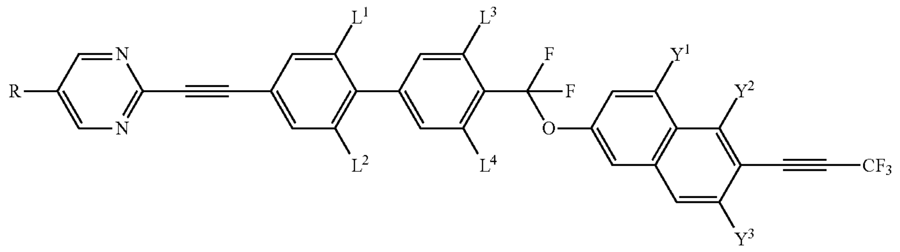
(1C-26)
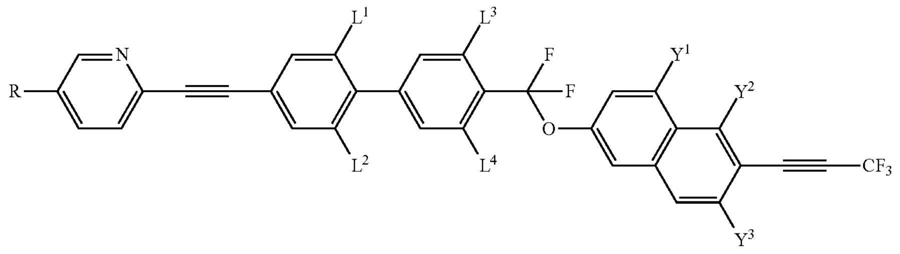

-continued
(1C-27)
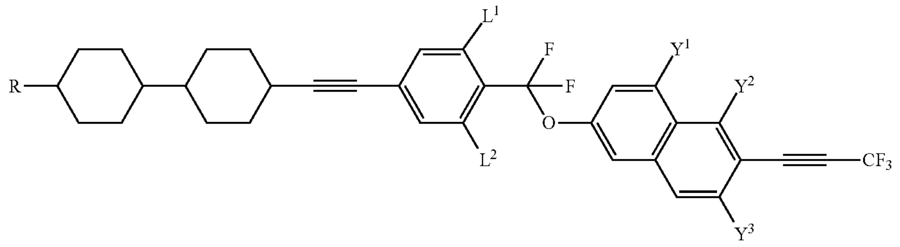
(1C-28)
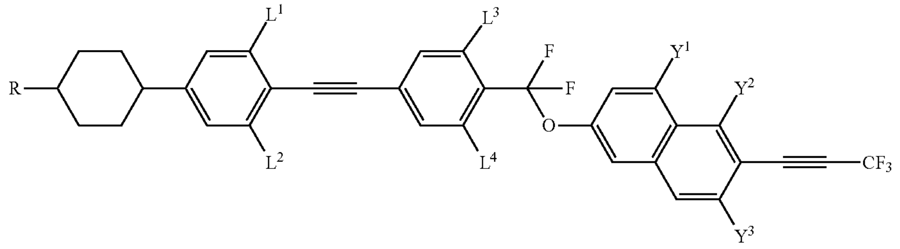
(1C-29)
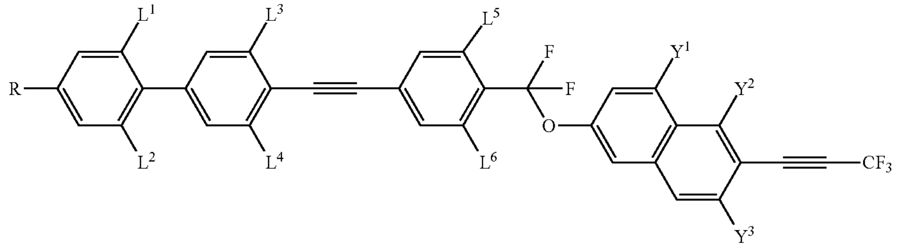
(1C-30)
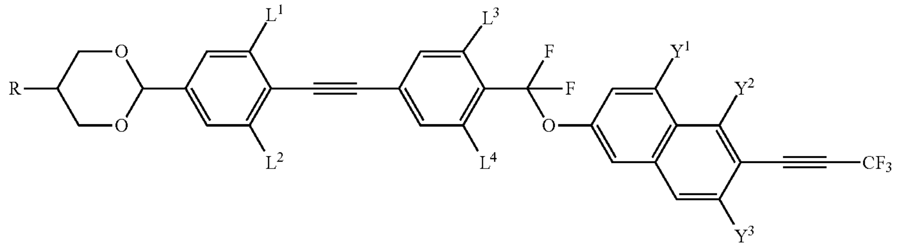
(1C-31)
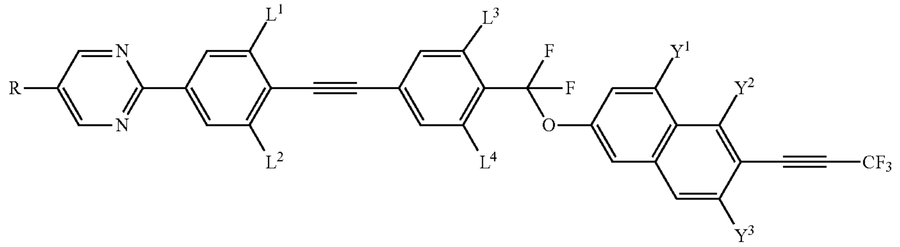
(1C-32)
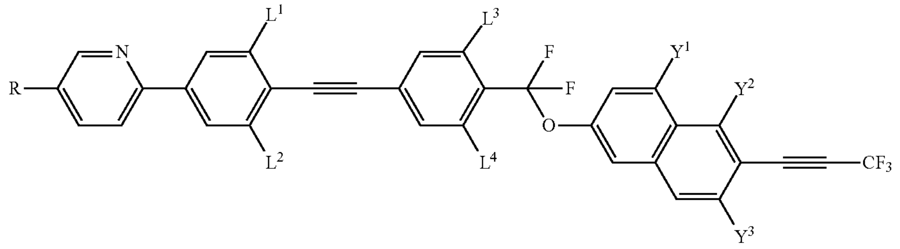

wherein, in formulas (1C-7) to (1C-32),
R is alkyl having 1 to 10 carbons, alkoxy having 1 to 9 carbons, alkenyl having 2 to 10 carbons or alkenyloxy having 2 to 9 carbons; and
$Y^1$, $Y^2$, $Y^3$, $L^1$, $L^2$, $L^3$, $L^4$, $L^5$, $L^6$ and $L^7$ are independently hydrogen or fluorine.
11. The compound according to claim 1, represented by any one of formulas (1A-12), (1B-21) to (1B-23), (1B-27), (1C-15) to (1C-19), (1C-22), (1C-24) and (1C-29):
(1A-12)
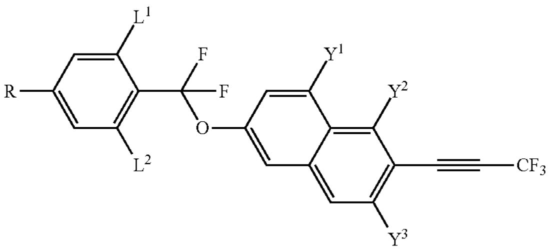
(1B-21)
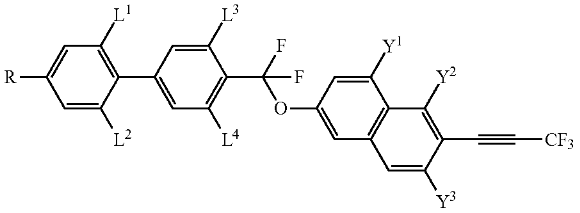
(1B-22)
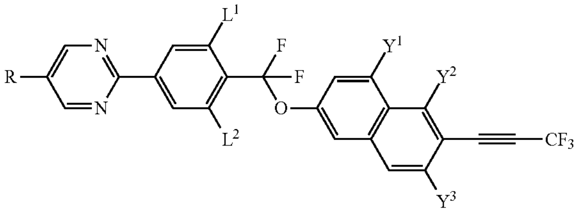
(1B-23)
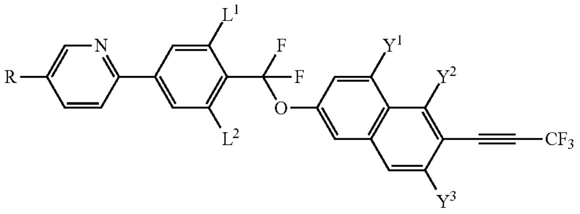
(1B-27)
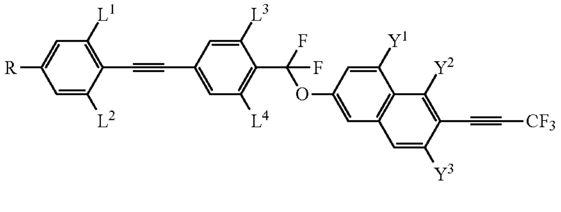
-continued
(1C-15)
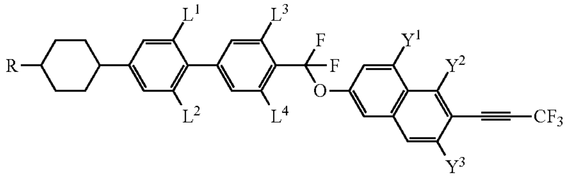
(1C-16)
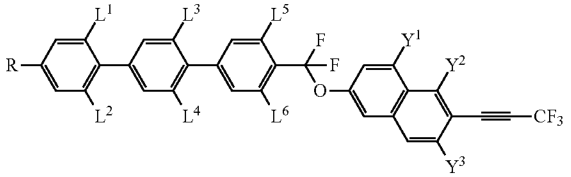
(1C-17)
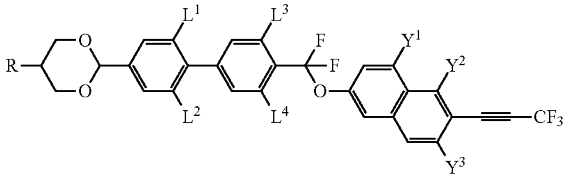
(1C-18)
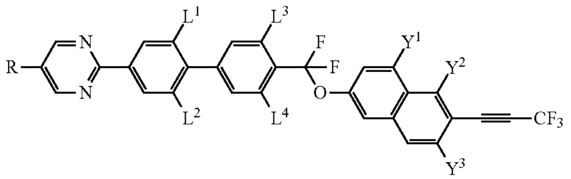
(1C-19)
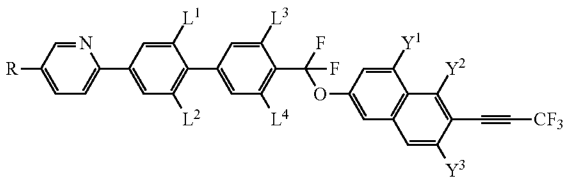
(1C-22)
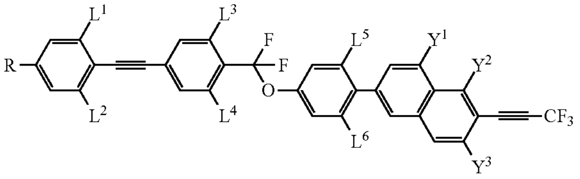
(1C-24)
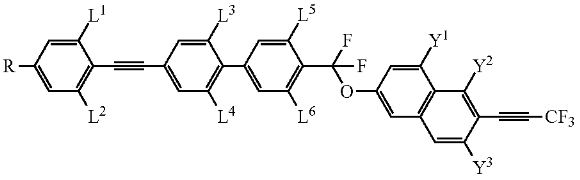

-continued (1C-29)

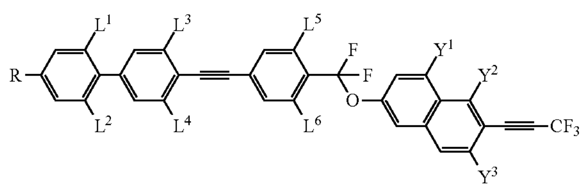

wherein, in formulas (1A-12), (1B-21) to (1B-23), (1B-27), (1C-15) to (1C-19), (1C-22), (1C-24) and (1C-29), R is alkyl having 1 to 10 carbons, alkoxy having 1 to 9 carbons, alkenyl having 2 to 10 carbons, alkenyloxy having 2 to 9 carbons, alkylthio having 1 to 9 carbons or alkenylthio having 2 to 9 carbons; and $Y^1$, $Y^2$, $Y^3$, $L^1$, $L^2$, $L^3$, $L^4$, $L^5$ and $L^6$ are independently hydrogen or fluorine.

12. The compound according to claim 11, wherein, in formulas (1A-12), (1B-21) to (1B-23), (1B-27), (1C-15) to (1C-19), (1C-22), (1C-24) and (1C-29), R is alkyl having 1 to 10 carbons, alkoxy having 1 to 9 carbons or alkenyl having 2 to 10 carbons; and $Y^1$, $Y^2$, $Y^3$, $L^1$, $L^2$, $L^3$, $L^4$, $L^5$ and $L^6$ are independently hydrogen or fluorine.

13. A liquid crystal composition, containing at least one compound according to claim 1.

14. The liquid crystal composition according to claim 13, further containing at least one compound selected from the group of compounds represented by formulas (2) to (4):

(2)

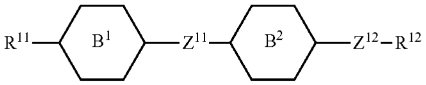

(3)

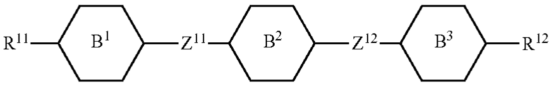

(4)

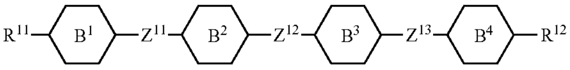

wherein, in formulas (2) to (4), $R^{11}$ and $R^{12}$ are independently alkyl having 1 to 10 carbons or alkenyl having 2 to 10 carbons, and in the alkyl and the alkenyl, at least one $—CH_2—$ may be replaced by —O—, and in the groups, at least one hydrogen may be replaced by fluorine;

ring $B^1$, ring $B^2$, ring $B^3$ and ring $B^4$ are independently 1,4-cyclohexylene, 1,4-phenylene, 2-fluoro-1,4-phenylene, 2,5-difluoro-1,4-phenylene or pyrimidine-2,5-diyl; and $Z^{11}$, $Z^{12}$ and $Z^{13}$ are independently a single bond, —COO—, $—CH_2CH_2—$, —CH═CH— or —C≡C—.

15. The liquid crystal composition according to claim 13, further containing at least one compound selected from the group of compounds represented by formulas (5) to (7):

(5)

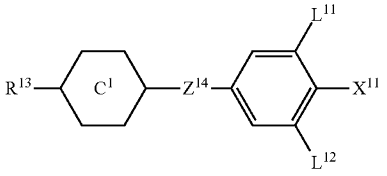

(6)

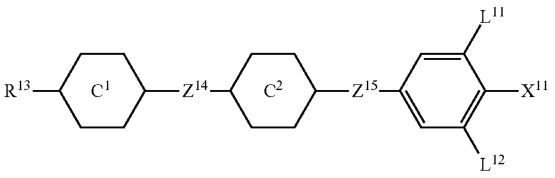

(7)

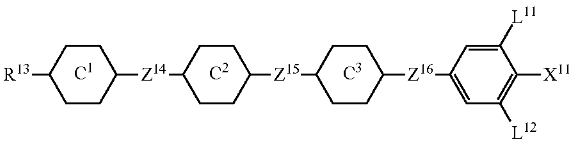

wherein, in formulas (5) to (7), $R^{13}$ is alkyl having 1 to 10 carbons or alkenyl having 2 to 10 carbons, and in the alkyl and the alkenyl, at least one $—CH_2—$ may be replaced by —O—, and in the groups, at least one hydrogen may be replaced by fluorine;

$X^{11}$ is fluorine, chlorine, $—OCF_3$, $—OCHF_2$, $—CF_3$, $—CHF_2$, $—CH_2F$, $—OCF_2CHF_2$ or $—OCF_2CHFCF_3$;

ring $C^1$, ring $C^2$ and ring $C^3$ are independently 1,4-cyclohexylene, 1,4-phenylene, 1,4-phenylene in which at least one hydrogen is replaced by fluorine, tetrahydropyran-2,5-diyl, 1,3-dioxane-2,5-diyl or pyrimidine-2,5-diyl;

$Z^{14}$, $Z^{15}$ and $Z^{16}$ are independently a single bond, —COO—, —OCO—, $—CH_2O—$, $—OCH_2—$, $—CF_2O—$, $—OCF_2—$, $—CH_2CH_2—$, —CH═CH—, —C≡C— or $—(CH_2)_4—$; and $L^{11}$ and $L^{12}$ are independently hydrogen or fluorine.

16. The liquid crystal composition according to claim 13, further containing at least one compound selected from compounds represented by formula (8):

(8)

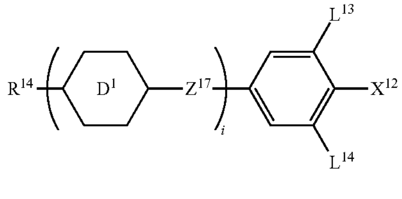

wherein, in formula (8), $R^{14}$ is alkyl having 1 to 10 carbons or alkenyl having 2 to 10 carbons, and in the alkyl and the alkenyl, at least one $—CH_2—$ may be replaced by —O—, and in the groups, at least one hydrogen may be replaced by fluorine;

$X^{12}$ is —C≡N or —C≡C—C≡N;

ring $D^1$ is 1,4-cyclohexylene, 1,4-phenylene, 1,4-phenylene in which at least one hydrogen is replaced by fluorine, tetrahydropyran-2,5-diyl, 1,3-dioxane-2,5-diyl or pyrimidine-2,5-diyl;

$Z^{17}$ is a single bond, —COO—, —OCO—, —$CH_2O$—, —$OCH_2$—, —$CF_2O$—, —$OCF_2$—, —$CH_2CH_2$— or —C≡C—;

$L^{13}$ and $L^{14}$ are independently hydrogen or fluorine; and i is 1, 2, 3 or 4.

17. The liquid crystal composition according to claim 13, further containing at least one compound selected from the group of compounds represented by formulas (9) to (15):

(9)

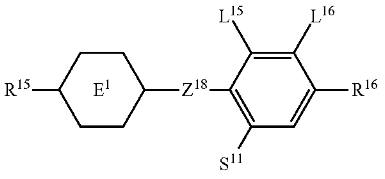

(10)

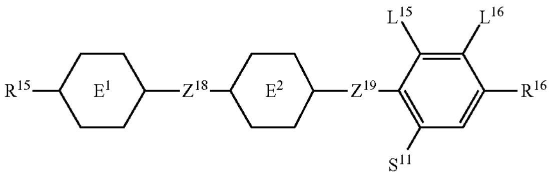

(11)

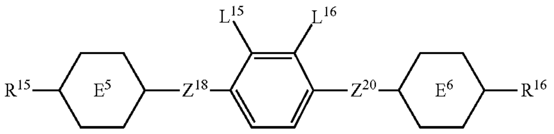

(12)

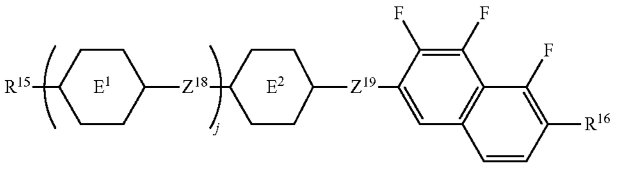

(13)

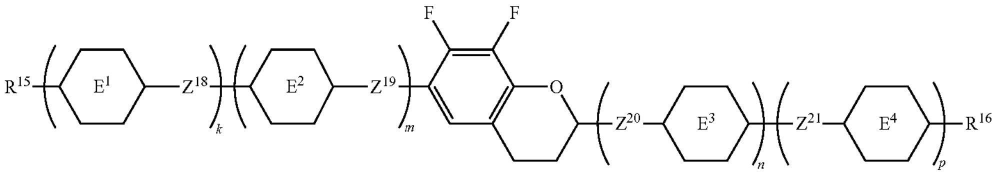

(14)

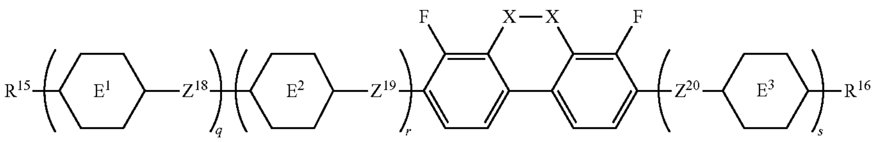

(15)

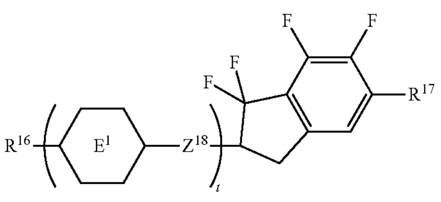

wherein, in formulas (9) to (15), $R^{15}$, $R^{16}$ and $R^{17}$ are independently alkyl having 1 to 10 carbons or alkenyl having 2 to 10 carbons, and in the alkyl and the alkenyl, at least one —$CH_2$— may be replaced by —O—, and in the groups, at least one hydrogen may be replaced by fluorine, and $R^{17}$ may be hydrogen or fluorine;

ring $E^1$, ring $E^2$, ring $E^3$ and ring $E^4$ are independently 1,4-cyclohexylene, 1,4-cyclohexenylene, 1,4-phenylene, 1,4-phenylene in which at least one hydrogen is replaced by fluorine, tetrahydropyran-2,5-diyl or decahydronaphthalene-2,6-diyl;

ring $E^5$ and ring $E^6$ are independently 1,4-cyclohexylene, 1,4-cyclohexenylene, 1,4-phenylene, tetrahydropyran-2,5-diyl or decahydronaphthalene-2,6-diyl;

$Z^{18}$, $Z^{19}$, $Z^{20}$ and $Z^{21}$ are independently a single bond, —COO—, —OCO—, —$CH_2O$—, —$OCH_2$—, —$CF_2O$—, —$OCF_2$—, —$CH_2CH_2$—, —$CF_2OCH_2CH_2$— or —$OCF_2CH_2CH_2$—;

$L^{15}$ and $L^{16}$ are independently fluorine or chlorine;

$S^{11}$ is hydrogen or methyl;

X is —CHF— or —$CF_2$—; and j, k, m, n, p, q, r and s are independently 0 or 1, a sum of k, m, n and p is 1 or 2, a sum of q, r and s is 0, 1,2 or 3, and t is 1,2 or 3.

18. A liquid crystal display device, including the liquid crystal composition according to claim 13.

19. The liquid crystal display device according to claim 18, wherein the liquid crystal composition is encapsulated.

20. The liquid crystal display device according to claim 18, wherein the liquid crystal composition is used in a lens to be utilized in switching between 2D and 3D.

* * * * *